United States Patent [19]

Yazawa et al.

[11] Patent Number: 5,683,898
[45] Date of Patent: Nov. 4, 1997

[54] GENE CODING FOR EICOSAPENTAENOIC ACID SYNTHESIZING ENZYMES AND PROCESS FOR PRODUCTION OF EICOSAPENTAENOIC ACID

[75] Inventors: Kazunaga Yazawa; Akiko Yamada; Seishi Kato, all of Sagamihara; Kiyosi Kondo, Yamato, all of Japan

[73] Assignee: Sagami Chemical Research Center, Tokyo, Japan

[21] Appl. No.: 375,709

[22] Filed: Jan. 20, 1995

Related U.S. Application Data

[63] Continuation-in-part of Ser. No. 178,251, Jan. 10, 1994, abandoned.

[30] Foreign Application Priority Data

May 15, 1992 [JP] Japan ..................................... 4-147945

[51] Int. Cl.$^6$ .................... C12P 7/64; C12N 1/20; C12N 15/00; C07H 19/00
[52] U.S. Cl. .................... 435/136; 435/134; 435/69.1; 435/183; 435/240.2; 435/252.3; 435/320.1; 536/22.1; 536/23.1; 536/23.2; 536/23.7
[58] Field of Search ..................... 435/69.1, 134, 435/183, 240.2, 252.3, 320.1, 136; 536/22.1, 23.1, 23.2, 23.7

[56] References Cited

FOREIGN PATENT DOCUMENTS

| 223 877 | 1/1990 | Japan . |
| 297 393 | 4/1990 | Japan . |
| 228 023 | 11/1990 | Japan . |

OTHER PUBLICATIONS

Yazawa et al., "Production of Eicosapentaenoic Acid by Marine Bacteria," J. Biochem. vol. 103, pp. 5-7 (1988).

*Primary Examiner*—Vasu S. Jagannathan
*Assistant Examiner*—Hyosuk Kim
*Attorney, Agent, or Firm*—Foley & Lardner

[57] ABSTRACT

There is provided an advantageous process for production of EPA by a gene recombinant technique wherein genes coding for biosynthesis enzymes for eicosapentaenoic acid (EPA) useful as pharmaceuticals, agrochemicals, foods, feeds or the like is obtained from microorganisms.

EPA is produced by obtaining genes coding for eicosapentaenoic acid (EPA) biosynthesis enzymes, constructing a plasmid by joining the genes to a vector, transforming *E. coli* with the plasmid, and culturing the transformed *E. coli*.

9 Claims, 2 Drawing Sheets

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 37895 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Shewanella putrefaciens SCRC-2874 (FERM BP- 1625)

( x i ) SEQUENCE DESCRIPTION: SEQ ID NO:1:

```
GATCTCTTAC AAAGAAACTA TCTCAATGTG AATTTAACCT TAATTCCGTT TAATTACGGC    60
CTGATAGAGC ATCACCCAAT CAGCCATAAA ACTGTAAAGT GGGTACTCAA AGGTGGCTGG   120
GCGATTCTTC TCAAATACAA AGTGCCCAAC CCAAGCAAAT CCATATCCGA TAACAGGTAA   180
AAGTAGCAAT AAACCCCAGC GCTGAGTTAG TAATACATAA GCGAATAATA GGATCACTAA   240
ACTACTGCCG AAATAGTGTA ATATTCGACA GTTTCTATGC TGATGTTGAG ATAAATAAAA   300
AGGGTAAAAT TCAGCAAAAG AACGATAGCG CTTACTCATT ACTCACACCT CGGTAAAAAA   360
GCAACTCGCC ATTAACTTGG CCAATCGTCA GTTGTTCTAT CGTCTCAAAG TTATGCCGAC   420
TAAATAACTC TATATGTGCA TTATGATTAG CAAAAACTCC GATACCATCA AGATGAAGTT   480
GTTCATCACA CCAACTCAAA ACTGCGTCGA TAAGCTTACT GCCATAGCCC TTGCCTTGCT   540
CCACATTTGC GATAGCAATA AACTGTAAAA TGCCACATTG GCCACTTGGT AAGCTCTCTA   600
TAATCTGATT TTCTTTGTTA ATAAGTGCCT GAGTTGAATA CCAACCAGTA CTTAACAACA   660
TCTTTAAACG CCAATGCCAA AAACGCGCTT CACCTAAGGG AACCTGCTGA GTCACTATGC   720
AGGCTACGCC TATCAATCTA TCCCCAACGA ACATACCAAT AAGTGCTTGC TCCTGTTGCC   780
AGAGCTCATT GAGTTCTTCT CGAATAGCCC CGCGAAGCTT TTGCTCATAC TGCGCTTGAT   840
CACCACTAAA AAGTGTTTCG ATAAAAAAGG GATCATCATG ATAGGCGTTA TAGAGAATAG   900
AGGCTGCTAT GCGTAAATCT TCTGCCGTGA GATAAACTGC ACGACACTCT TCCATGGCTT   960
GATCTTCCAT TGTTATTGTC CTTGACCTTG ATCACACAAC ACCAATGTAA CAAGACTGTA  1020
TAGAAGTGCA ATTAATAATC AATTCGTGCA TTAAGCAGGT CAGCATTTCT TTGCTAAACA  1080
AGCTTTATTG GCTTTGACAA AACTTTGCCT AGACTTTAAC GATAGAAATC ATAATGAAAG  1140
AGAAAAGCTA CAACCTAGAG GGGAATAATC AAACAACTGC TAAGATCTAG ATAATGTAAT  1200
AAACACCGAG TTATCGACC ATACTTAGAT AGAGTCATAG CAACGAGAAT AGTTATGGAT  1260
ACAACGCCGC AAGATCTATC ACACCTGTTT TTACAGCTAG GATTAGCAAA TGATCAACCC  1320
GCAATTGAAC AGTTTATCAA TGACCATCAA TTAGCGGACA ATATATTGCT ACATCAAGCA  1380
AGCTTTTGGA GCCCATCGCA AAAGCACTTC TTAATTGAGT CATTTAATGA AGATGCCCAG  1440
TGGACCGAAG TCATCGACCA CTTAGACACC TTATTAAGAA AAAACTAACC ATTACAACAG  1500
CAACTTTAAA TTTTGCCGTA AGCCATCTCC CCCCACCCCA CAACAGCGTT GTTGCTTATG  1560
ACCACTGGAG TACATTCGTC TTTAGTCGTT TTACCATCAC CATGGGTACG TTGAGTGCGA  1620
TAAAAAAGCA CATAAACTTC TTTATCGGCC TGAATATAGG CTTCGTTAAA ATCAGCTGTT  1680
```

```
CCCATTAAAG TAACCACTTG CTCTTTACTC ATGCCTAGAG ATATCTTTGT CAAATTGTCA     1740
CGGTTTTTAT CTTGAGTTTT CTCCCAAGCA CCGTGATTAT CCCAGTCAGA TTCCCCATCA     1800
CCAACATTGA CCACACAGCC CGTTAGCCCT AAGCTTGCAA TCCCAAAACA TGCTAAACCT     1860
AATAATTTAT TTTTCATTTT AACTTCCTGT TATGACATTA TTTTTGCTTA GAAGAAAAGC     1920
AACTTACATG CCAAAACACA AGCTGTTGTT TTAAATGACT TTATTTATTA TTAGCCTTTT     1980
AGGATATGCC TAGAGCAATA ATAATTACCA ATGTTAAGG AATTTGACTA ACTATGAGTC      2040
CGATTGAGCA AGTGCTAACA GCTGCTAAAA AAATCAATGA ACAAGGTAGA GAACCAACAT     2100
TAGCATTGAT TAAAACCAAA CTTGGTAATA GCATCCCAAT GCGCGAGTTA ATCCAAGGTT     2160
TGCAACAGTT TAAGTCTATG AGTGCAGAAG AAAGACAAGC AATACCTAGC AGCTTAGCAA     2220
CAGCAAAAGA AACTCAATAT GGTCAATCAA GCTTATCTCA ATCTGAACAA GCTGATAGGA     2280
TCCTCCAGCT AGAAACGCC CTCAATGAAT TAAGAAACGA ATTTAATGGG CTAAAAAGTC      2340
AATTTGATAA CTTACAACAA AACCTGATGA ATAAGAGCC TGACACCAAA TGCATGTAAT      2400
TGAACTACGA TTTGAATGTT TTGATAACAC CACGATTACT GCAGCAGAAA AAGCCATTAA     2460
TGGTTTGCTT GAAGCTTATC GAGCCAATGG CCAGGTTCTA GGTCGTGAAT TTGCCGTTGC     2520
ATTTAACGAT GGTGAGTTTA AAGCACGCAT GTTAACCCCA GAAAAAGCA GCTTATCTAA      2580
ACGCTTTAAT AGTCCTTGGG TAAATAGTGC ACTCGAAGAG CTAACCGAAG CCAAATTGCT     2640
TGCGCCACGT GAAAAGTATA TTGGCCAAGA TATTAATTCT GAAGCATCTA GCCAAGACAC     2700
ACCAAGTTGG CAGCTACTTT ACACAAGTTA TGTGCACATG TGCTCACCAC TAAGAAATGG     2760
CGACACCTTG CAGCCTATTC CACTGTATCA AATTCCAGCA ACTGCCAACG GCGATCATAA     2820
ACGAATGATC CGTTGGCAAA CAGAATGGCA AGCTTGTGAT GAATTGCAAA TGGCCGCAGC     2880
TACTAAAGCT GAATTTGCCG CACTTGAAGA GCTAACCAGT CATCAGAGTG ATCTATTTAG     2940
GCGTGGTTGG GACTTACGTG GCAGAGTCGA ATACTTGACG AAAATTCCGA CCTATTACTA     3000
TTTATACCGT GTTGGCGGTG AAAGCTTAGC AGTAGAAAAG CAGCGCTCTT GTCCTAAGTG     3060
TGGCAGTCAA GAATGGCTGC TCGATAAACC ATTATTGGAT ATGTTCCATT TTCGCTGTGA     3120
CACCTGCCGC ATCGTATCTA ATATCTCTTG GGACCATTTA TAACTCTTCC GAGTCTTATC     3180
ACACTAGAGT TTAGTCAGCA TAAAAATGGC GCTTATATTT CAATTAAAAG AAATATAAGC     3240
GCCATTTTCA TCGATACTAT ATATCAGCAG ACTATTTTCC GCGTAAATTA GCCCACATTA     3300
ATTTCATTCT TTGCCAGATC CCTGGATGAT CTAGTTGTGG CATCGACTCT TCAATAGGTT     3360
TAACCGCAGG TGTAACCCTT GGAGTCAATT CGTTATAAA CTCGTTTAAA CTGTCACTTA      3420
ATTTAACGCT TTGTACTTCA CCTGGAATTT CAATCCATAC GCTGCCATCA CTATTATTAA     3480
CCGTCAACAT TTTATCTTCA TCATCAAGAA TACCAATAAA CCAAGTCGGC TCTTGCTTAA     3540
GCTTTCTCTT CATCATTAAA TGACCAATGA TGTTTTGTTG TAAGTATTCA AAATCAGTTT     3600
GATCCCACAC TTGGATTAGC TCACCTTGGC CCCATTGTGA GTCAAAAAAT AGCGGTGCAG     3660
AAAAATGACT GCCAAAAAAT GGATTAATTT CTGCAGATAA TGTCATTTCA AGTGCTGTTT     3720
CAACATTAGC AAATTCACCA GGTTGTTGAC GTACAACCGA TTGCCAAAAC ACTGCGCCAT     3780
CGGAGCCCGC TTCGGCGACA ACACACTCAG ACTTTTGTCC TTGCGCATAA TATCTTGGCT     3840
GTTCACCAAG CTTATCCATG TAGGCTTGTT GATATTTAGA TAAAAAAAGA TCTAAAGCAG     3900
GTAAAGAAGA CACTTAAGCC AGTTCCAAAA TCAGTTATAA TAGGGGTCTA TTTTGACATG     3960
GAAACCGTAT TGATGACACA ACATCATGAT CCCTACAGTA ACGCCCCGA ACTTTCTGAA      4020
TTAACTTTAG GAAAGTCGAC CGGTTATCAA GAGCAGTATG ATGCATCTTT ACTACAAGCG     4080
```

| | | | | | |
|---|---|---|---|---|---|
| TGCCGCGTAA | ATTAAACCGT | GATGCTATCG | GTCTAACCAA | TGAGCTACCT | TTTCATGGCT | 4140 |
| GTGATATTTG | GACTGGCTAC | GAACTGTCTT | GGCTAAATGC | TAAAGGCAAG | CCAATGATTG | 4200 |
| CTATTGCAGA | CTTTAACCTA | AGTTTGATA | GTAAAATCT | GATCGAGTCT | AAGTCGTTTA | 4260 |
| AGCTGTATTT | AAACAGCTAT | AACCAAACAC | GATTGATAG | CGTTCAAGCG | GTTCAAGAAC | 4320 |
| GTTAACTGA | AGACTTAAGC | GCCTGTGCCC | AAGGCACAGT | TACGGTAAAA | GTGATTGAAC | 4380 |
| CTAAGCAATT | TAACCACCTG | AGAGTGGTTG | ATATGCCAGG | TACCTGCATT | GACGATTTAG | 4440 |
| ATATTGAAGT | TGATGACTAT | AGCTTTAACT | CTGACTATCT | CACCGACAGT | GTTGATGACA | 4500 |
| AAGTCATGGT | TGCTGAAACG | CTAACGTCAA | ACTTATTGAA | ATCAAACTGC | CTAATCACTT | 4560 |
| CTCAGCCTGA | CTGGGGTACA | GTGATGATCC | GTTATCAAGG | GCCTAAGATA | GACCGTGAAA | 4620 |
| AGCTACTTAG | ATATCTGATT | TCATTAGAC | AGCACAATGA | ATTCATGAG | CAGTGTGTTG | 4680 |
| AGCGTATATT | TGTTGATTTA | AAGCACTATT | GCCAATGTGC | CAAACTTACT | GTCTATGCAC | 4740 |
| GTTATACCCG | CCGTGGTGGT | TTAGATATCA | ACCCATATCG | TAGCGACTTT | GAAAACCCTG | 4800 |
| CAGAAAATCA | GCGCCTAGCG | AGACAGTAAT | TGATTGCAGT | ACCTACAAAA | AACAATGCCT | 4860 |
| ATAAGCCAAG | CTTATGGGCA | TTTTTATATT | ATCAACTTGT | CATCAAACCT | CAGCCGCCAA | 4920 |
| GCCTTTTAGT | TTTATCGCTA | AATTAAGCCG | CTCTCTCAGC | CAAATATTTG | CAGGATTTTG | 4980 |
| CTGTAATTTA | TGGCTCCACA | CCATGAAATA | CTCTATCGGC | TCTACCGCAA | AAGGTAAGTC | 5040 |
| AAATACCTGT | AAGCCAAACA | GCTTGGCATA | TTCGTCAGTG | TGGGCTTTTG | ACGCGATAGC | 5100 |
| TAACGCATCA | CTTTTGAGG | CAACCGACAT | CATACTTAAT | ATTGATGATT | GCTCGCTGTG | 5160 |
| CATTTGCCTT | GCCGGTAACA | CCTGTTTAGT | CAGCAAGTCG | GCAACACTTA | AATTGTAGCG | 5220 |
| GCGCATCTTA | AAAATAATAT | GCTTTTCATT | AAAGTATTGC | TCTTGCGTCA | ACCCACCTTG | 5280 |
| GATCCTTGGG | TGAGCATTTC | GTGCCACACA | AACTAATTTA | TCCTGCATTA | CTTTTTGACT | 5340 |
| CTTAAATGCC | GCAGATTCTG | GCAGCCAAAT | ATCTAAGGCT | AAATCCACCT | TTTCTAGTTG | 5400 |
| TAGGTCCATC | TGCAACTCTT | CTTCAATGAG | CGGCGGCTCA | CGAAATACAA | TATTAATTGC | 5460 |
| AGTGCCCTGT | AACACTTGCT | CAATTTGATC | TTGCAAGAGT | TGTATTGCCG | ACTCGCTGGC | 5520 |
| ATACACATAA | AAAGTTCGCT | CACTTGAAGT | GGGGTCAAAT | GCTTCAAAGC | TAGTCGCAAC | 5580 |
| TTGCTCAATT | GTTGACATAG | CGCCCGCGAG | CTGTTGATAA | AGCGTCATCG | CACTTGCGGT | 5640 |
| AGGTTTAACT | CCCCTACCCA | CTCGAGTAAA | CAACTCTTCT | CCAACAATAC | TTTTTAGCCT | 5700 |
| CGAAATCGCA | TTACTAACCG | ACGACTGAGT | CAAATCCAGC | TCTTCTGCCG | CCCGGCTAAA | 5760 |
| AGATGAGGTG | CGATACACCG | CAGTAAAAAC | GCGAAATAAA | TTAAGATCAA | AAGCTTTTG | 5820 |
| CTGCGACATA | AATCAGCTAT | CTCCTTATCC | TTATCCTTAT | CCTTATAAAA | AGTTAGCTCC | 5880 |
| AGAGCACTCT | AGCTCAAAAA | CAACTCAGCG | TATTAAGCCA | ATATTTGGG | AACTCAATTA | 5940 |
| ATATTCATAA | TAAAAGTATT | CATAATATAA | ATACCAAGTC | ATAATTTAGC | CCTAATTATT | 6000 |
| AATCAATTCA | AGTTACCTAT | ACTGGCCTCA | ATTAAGCAAA | TGTCTCATCA | GTCTCCCTGC | 6060 |
| AACTAAATGC | AATATTGAGA | CATAAAGCTT | TGAACTGATT | CAATCTTACG | AGGGTAACTT | 6120 |
| ATGAAACAGA | CTCTAATGGC | TATCTCAATC | ATGTCGCTTT | TTCATTCAA | TGCGCTAGCA | 6180 |
| GCGCAACATG | AACATGACCA | CATCACTGTT | GATTACGAAG | GGAAAGCCGC | AACAGAACAC | 6240 |
| ACCATAGCTC | ACAACCAAGC | TGTAGCTAAA | ACACTTAACT | TTGCCGACAC | GCGTGCATTT | 6300 |
| GAGCAATCGT | CTAAAAATCT | AGTCGCCAAG | TTTGATAAAG | CAACTGCCGA | TATATTACGT | 6360 |
| GCCGAATTTG | CTTTTATTAG | CGATGAAATC | CCTGACTCGG | TTAACCCGTC | TCTCTACCGT | 6420 |
| CAGGCTCAGC | TTAATATGGT | GCCTAATGGT | CTGTATAAAG | TGAGCGATGG | CATTTACCAG | 6480 |

```
GTCCGCGGTA CCGACTTATC TAACCTTACA CTTATCCGCA GTGATAACGG TTGGATAGCA    6540
TACGATGTTT TGTTAACCAA AGAAGCAGCA AAAGCCTCAC TACAATTTGC GTTAAAGAAT    6600
CTACCTAAAG ATGGCGATTT ACCCGTTGTT GCGATGATTT ACTCCCATAG CCATGCGGAC    6660
CACTTTGGCG GAGCTCGCGG TGTTCAAGAG ATGTTCCCTG ATGTCAAAGT CTACGGCTCA    6720
GATAACATCA CTAAAGAAAT TGTCGATGAG AACGTACTTG CCGGTAACGC CATGAGCCGC    6780
CGCGCAGCTT ATCAATACGG CGCAACACTG GGCAAACATG ACCACGGTAT TGTTGATGCT    6840
GCGCTAGGTA AAGGTCTATC AAAAGGTGAA ATCACTTACG TCGCCCCAGA CTACACCTTA    6900
AACAGTGAAG GCAAATGGGA AACGCTGACG ATTGATGGTC TAGAGATGGT GTTTATGGAT    6960
GCCTCGGGCA CCGAAGCTGA GTCAGAAATG ATCACTTATA TTCCCTCTAA AAAAGCGCTC    7020
TGGACGGCGG AGCTTACCTA TCAAGGTATG CACAACATTT ATACGCTGCG CGGCGCTAAA    7080
GTACGTGATG CGCTCAAGTG GTCAAAAGAT ATCAACGAAA TGATCAATGC CTTTGGTCAA    7140
GATGTCGAAG TGCTGTTTGC CTCGCACTCT GCGCCAGTGT GGGGTAACCA AGCGATCAAC    7200
GATTTCTTAC GCCTACAGCG TGATAACTAC GGCCTAGTGC ACAATCAAAC CTTGAGACTT    7260
GCCAACGATG GTGTCGGTAT ACAAGATATT GGCGATGCGA TTCAAGACAC GATTCCAGAG    7320
TCTATCTACA AGACGTGGCA TACCAATGGT TACCACGGCA CTTATAGCCA TAACGCTAAA    7380
GCGGTTTATA ACAAGTATCT AGGCTACTTC GATATGAACC CAGCCAACCT TAATCCGCTG    7440
CCAACCAAGC AAGAATCTGC CAAGTTTGTC GAATACATGG GCGGCGCAGA TGCCGCAATT    7500
AAGCGCGCTA AAGATGATTA CGCTCAAGGT GAATACCGCT TTGTTGCAAC GGCATTAAAT    7560
AAGGTGGTGA TGGCCGAGCC AGAAAATGAC TCCGCTCGTC AATTGCTAGC CGATACCTAT    7620
GAGCAACTTG GTTATCAAGC AGAAGGGGCT GGCTGGAGAA ACATTTACTT AACTGGCGCA    7680
CAAGAGCTAC GAGTAGGTAT TCAAGCTGGC GCGCCTAAAA CCGCATCGGC AGATGTCATC    7740
AGTGAAATGG ACATGCCGAC TCTATTTGAC TTCCTCGCGG TGAAGATTGA TAGTCAACAG    7800
GCGGCTAAGC ACGGCTTAGT TAAGATGAAT GTTATCACCC CTGATACTAA AGATATTCTC    7860
TATATTGAGC TAAGCAACGG TAACTTAAGC AACGCAGTGG TCGACAAAGA GCAAGCAGCT    7920
GACGCAAACC TTATGGTTAA TAAAGCTGAC GTTAACCGCA TCTTACTTGG CCAAGTAACC    7980
CTAAAAGCGT TATTAGCCAG CGGCGATGCC AAGCTCACTG GTGATAAAAC GGCATTTAGT    8040
AAAATAGCCG ATAGCATGGT CGAGTTTACA CCTGACTTCG AAATCGTACC AACGCCTGTT    8100
AAATGAGGCA TTAATCTCAA CAAGTGCAAG CTAGACATAA AAATGGGGCG ATTAGACGCC    8160
CCATTTTTTA TGCAATTTTG AACTAGCTAG TCTTAGCTGA AGCTCGAACA ACAGCTTTAA    8220
AATTCACTTC TTCTGCTGCA ATACTTATTT GCTGACACTG ACCAATACTC AGTGCAAAAC    8280
GATAACTATC ATCAAGATGG CCCAGTAAAC AATGCCAATT ATCAGCAGCG TTCATTTGCT    8340
GTTCTTTAGC CTCAATCAAA CCTAAACCAG ACTTTTGTGG CTCAGCGTTA GGCTTATTAG    8400
AACTCGACTC TAGTAAAGCA AGACCAATAT CTTGTTTTAA CAAAACCTGT CGCTGATTAA    8460
GTTGATGCTC AACCTTGTGA TCCGCAATAG CATCGGAAAT ATCAACACAA TGGCTCAAGC    8520
TTTTAGGTGC ATTAACTCCA AGAAAAGTTT CGCTCAGTGC AGAGAAGTCA AACGCAAAAG    8580
ATTTTAGCGA TAATGCCAGC CCAAGTCCTT TCGCTTTAAT GTAAGACTCC TTGAGCGCCC    8640
ACAAATCAAA AAAGCGGTCT CGCTGCAAGG CCTCTGGTAA CGCTAACAAG GCTCGCTTTT    8700
CTGATTCAGA GAAATAATGA CTAAGAATAG AGTGGATATT GGTGCTGTTA CGGCAACGCT    8760
CAATGTCGAC GCCAAACTCA ATACTAGCAG AGTCAGTTTC CTCCTTGCTT GCCTGACTGG    8820
CGCCTTTATT ATCAGCAGTG CAAATGCCTA CTAATAGCCA ATCTCCACTA TGACTCACAT    8880
```

```
TAAAGTGGAC CCCGGTTTGA GCAAATTGCG CATCACTCAA TCTAGGCTTA CCTTTGTCGC    8940
CATATTCAAA GCGCCATTCA TTGGGGCGTA TTTCACTATG TTGTGACAAT AAAGCGCGCA    9000
AATAGCCTCT TACCATTAAA CCTTGAGTTT TAGCTTCTTG TTTAATGTAG CGATTAACCT    9060
TAATTAACTC ATCTTCAGGC AGCCATGACT TAACCAACTC TGTAGTCTGG TTATCGCACT    9120
CTTGTATTGT TAACGGACAG AAGTATAAGG AAATCAATCG AGAAGTTAGC AATTTTTCAG    9180
GACACTCTTT AAAGCAACAA ACATAACCCC TATTTTACC AATTAAGAT CAAAACTAAA      9240
GCCAAAACTA ATTGAGAATA GTGTCAAACT AGCTTTAAAG GAAAAAATA TAAAAGAAC      9300
ATTATACTTG TATAAATTAT TTTACACACC AAAGCCATGA TCTTCACAAA ATTAGCTCCC    9360
TCTCCCTAAA ACAAGATTGA ATAAAAAAAT AAACCTTAAC TTTCATATAG ATAAAACAAA    9420
CCAATGGGAT AAAGTATATT GAATTCATTT TTAAGGAAAA ATTCAAATTG AATTCAAGCT    9480
CTTCAGTAAA AGCATATTTT GCCGTTAGTG TGAAAAAAAA CAAATTTAAA AACCAACATA    9540
GAACAAATAA GCAGACAATA AAACCAAGGC GCAACACAAA CAACGCGCTT ACAATTTTCA    9600
CAAAAAAGCA ACAAGAGTAA CGTTAGTAT TTGGATATGG TTATTGTAAT TGAGAATTTT     9660
ATAACAATTA TATTAAGGGA ATGAGTATGT TTTTAAATTC AAAACTTTCG CGCTCAGTCA    9720
AACTTGCCAT ATCCGCAGGC TTAACAGCCT CGCTAGCTAT GCCTGTTTTT GCAGAAGAAA    9780
CTGCTGCTGA AGAACAAATA GAAAGAGTCG CAGTGACCGG ATCGCGAATC GCTAAAGCAG    9840
AGCTAACTCA ACCAGCTCCA GTCGTCAGCC TTTCAGCCGA AGAACTGACA AAATTTGGTA    9900
ATCAAGATTT AGGTAGCGTA CTAGCAGAAT TACCTGCTAT TGGTGCAACC AACACTATTA    9960
TTGGTAATAA CAATAGCAAC TCAAGCGCAG GTGTTAGCTC AGCAGACTTG CGTCGTCTAG    10020
GTGCTAACAG AACCTTAGTA TTAGTCAACG GTAAGCGCTA CGTTGCCGGC CAACCGGGCT    10080
CAGCTGAGGT AGATTTGTCA ACTATACCAA CTAGCATGAT CTCGCGAGTT GAGATTGTAA    10140
CCGGCGGTGC TTCAGCAATT TATGGTTCGG ACGCTGTATC AGGTGTTATC AACGTTATCC    10200
TTAAAGAAGA CTTTGAAGGC TTTGAGTTTA ACGCACGTAC TAGCGGTTCT ACTGAAAGTG    10260
TAGGCACTCA AGAGCACTCT TTTGACATTT GGGTGGTGC AAACGTTGCA GATGGACGTG     10320
GTAATGTAAC CTTCTACGCA GGTTATGAAC GTACAAAAGA AGTCATGGCT ACCGACATTC    10380
GCCAATTCGA TGCTTGGGGA ACAATTAAAA ACGAAGCCGA TGGTGGTGAA GATGATGGTA    10440
TTCCAGACAG ACTACGTGTA CCACGAGTTT ATTCTGAAAT GATTAATGCT ACCGGTGTTA    10500
TCAATGCATT TGGTGGTGGA ATTGGTCGCT CAACCTTTGA CAGTAACGGC AATCCTATTG    10560
CACAACAAGA ACGTGATGGG ACTAACAGCT TTGCATTTGG TTCATTCCCT AATGGCTGTG    10620
ACACATGTTT CAACACTGAA GCATACGAAA ACTATATTCC AGGGGTAGAA AGAATAAACG    10680
TTGGCTCATC ATTCAACTTT GATTTTACCG ATAACATTCA ATTTACACT GACTTCAGAT     10740
ATGTAAAGTC AGATATTCAG CAACAATTTC AGCCTTCATT CCGTTTTGGT AACATTAATA    10800
TCAATGTTGA AGATAACGCC TTTTTGAATG ACGACTTGCG TCAGCAAATG CTCGATGCGG    10860
GTCAAACCAA TGCTAGTTTT GCCAAGTTTT TTGATGAATT AGGAAATCGC TCAGCAGAAA    10920
ATAAACGCGA ACTTTTCCGT TACGTAGGTG GCTTTAAAGG TGGCTTTGAT ATTAGCGAAA    10980
CCATATTTGA TTACGACCTT TACTATGTTT ATGGCGAGAC TAATAACCGT CGTAAAACCC    11040
TTAATGACCT AATTCCTGAT AACTTTGTCG CAGCTGTCGA CTCTGTTATT GATCCTGATA    11100
CTGGCTTAGC AGCGTGTCGC TCACAAGTAG CAAGCGCTCA AGGCGATGAC TATACAGATC    11160
CCGCGTCTGT AAATGGTAGC GACTGTGTTG CTTATAACCC ATTTGGCATG GGTCAAGCTT    11220
CAGCAGAAGC CCGCGACTGG GTTCTGCTG ATGTGACTCG TGAAGACAAA ATAACTCAAC     11280
```

```
AAGTGATTGG TGGTACTCTC GGTACCGATT CTGAAGAACT ATTTGAGCTT CAAGGTGGTG    11340
CAATCGCTAT GGTTGTTGGT TTTGAATACC GTGAAGAAAC GTCTGGTTCA ACAACCGATG    11400
AATTTACTAA AGCAGGTTTC TTGACAAGCG CTGCAACGCC AGATTCTTAT GGCGAATACG    11460
ACGTGACTGA GTATTTGTT GAGGTGAACA TCCCAGTACT AAAAGAATTA CCTTTTGCAC     11520
ATGAGTTGAG CTTTGACGGT GCATACCGTA ATGCTGATTA CTCACATGCC GGTAAGACTG    11580
AAGCATGGAA AGCTGGTATG TTCTACTCAC CATTAGAGCA ACTTGCATTA CGTGGTACGG    11640
TAGGTGAAGC AGTACGAGCA CCAAACATTG CAGAAGCCTT TAGTCCACGC TCTCCTGGTT    11700
TTGGCCGCGT TTCAGATCCA TGTGATGCAG ATAACATTAA TGACGATCCG GATCGCGTGT    11760
CAAACTGTGC AGCATTGGGG ATCCCTCCAG GATTCCAAGC TAATGATAAC GTCAGTGTAG    11820
ATACCTTATC TGGTGGTAAC CCAGATCTAA AACCTGAAAC ATCAACATCC TTTACAGGTG    11880
GTCTTGTTTG GACACCAACG TTTGCTGACA ATCTATCATT CACTGTCGAT TATTATGATA    11940
TTCAAATTGA GGATGCTATT TTGTCAGTAG CCACCCAGAC TGTGGCTGAT AACTGTGTTG    12000
ACTCAACTGG CGGACCTGAC ACCGACTTCT GTAGTCAAGT TGATCGTAAT CCAACGACCT    12060
ATGATATTGA ACTTGTTCGC TCTGGTTATC TAAATGCCGC GGCATTGAAT ACCAAAGGTA    12120
TTGAATTTCA AGCTGCATAC TCATTAGATC TAGAGTCTTT CAACGCGCCT GGTGAACTAC    12180
GCTTCAACCT ATTGGGGAAC CAATTACTTG AACTAGAACG TCTTGAATTC CAAAATCGTC    12240
CTGATGAGAT TAATGATGAA AAAGGCGAAG TAGGTGATCC AGAGCTGCAG TTCCGCCTAG    12300
GCATCGATTA CCGTCTAGAT GATCTAAGTG TTAGCTGGAA CACGCGTTAT ATTGATAGCG    12360
TAGTAACTTA TGATGTCTCT GAAAATGGTG GCTCTCCTGA AGATTTATAT CCAGGCCACA    12420
TAGGCTCAAT GACAACTCAT GACTTGAGCG CTACATACTA CATCAATGAG AACTTCATGA    12480
TTAACGGTGG TGTACGTAAC CTATTTGACG CACTTCCACC TGGATACACT AACGATGCGC    12540
TATATGATCT AGTTGGTCGC CGTGCATTCC TAGGTATTAA GGTAATGATG TAATTAATTA    12600
TTACGCCTCT AACTAATAAA AATGCAATCT CTTCGTAGAG ATTGCATTTT TTTATGAAAT    12660
CCAATCTTAA ACTGGTTCTC CGAGCATCTT ACGCCTTAAA ACCCCGCCC CTCAATGTAA     12720
CGCCAAAGTT AATTGCTTAC ACGCACTTAC ACAAACGAAC AATTTCATTA ACACGAGACA    12780
CAGCTCACGC TTTTTATTTT ACCCTTGATT TTACTACATA AAATTGCGTT TTAGCGCACA    12840
AGTGTTCTCC CAAGCTGGTC GTATCTGTAA TTATTCAGTC CCAGGTGATT GTATTGACCC    12900
ATAAGCTCAG GTAGTCTGCT CTGCCATTAG CTAAACAATA TTGACAAAAT GGCGATAAAA    12960
TGTGGCTTAG CGCTAAGTTC ACCGTAAGTT TTATCGGCAT TAAGTCCCAA CAGATTATTA    13020
ACGGAAACCC GCTAAACTGA TGGCAAAAAT AAATAGTGAA CACTTGGATG AAGCTACTAT    13080
TACTTCGAAT AAGTGTACGC AAACAGAGAC TGAGGCTCGG CATAGAAATG CCACTACAAC    13140
ACCTGAGATG CGCCGATTCA TACAAGAGTC GGATCTCAGT GTTAGCCAAC TGTCTAAAAT    13200
ATTAAATATC AGTGAAGCTA CCGTACGTAA GTGGCGCAAG CGTGACTCTG TCGAAAACTG    13260
TCCTAATACC CCGCACCATC TCAATACCAC GCTAACCCCT TTGCAAGAAT ATGTGGTTGT    13320
GGGCCTGCGT TATCAATTGA AAATGCCATT AGACAGATTG CTCAAAGCAA CCCAAGAGTT    13380
TATCAATCCA AACGTGTCGC GCTCAGGTTT AGCAAGATGT TTGAAGCGTT ATGGCGTTTC    13440
ACGGGTGAGT GATATCCAAA GCCCACACGT ACCAATGCGC TACTTTAATC AAATTCCAGT    13500
CACTCAAGGC AGCGATGTGC AAACCTACAC CCTGCACTAT GAAACGCTGG CAAAAACCTT    13560
AGCCTTACCT AGTACCGATG GTGACAATGT GGTGCAAGTG GTGTCTCTCA CCATTCCACC    13620
AAAGTTAACC GAAGAAGCAC CCAGTTCAAT TTTGCTCGGC ATTGATCCTC ATAGCGACTG    13680
```

```
GATCTATCTC GACATATACC AAGATGGCAA TACACAAGCC ACGAATAGAT ATATGGCTTA   13740
TGTGCTAAAA CACGGGCCAT TCCATTTACG AAAGTTACTC GTGCGTAACT ATCACACCTT   13800
TTTACAGCGC TTTCCTGGAG CGACGCAAAA TCGCCGCCCC TCTAAAGATA TGCCTGAAAC   13860
AATCAACAAG ACGCCTGAAA CACAGGCACC CAGTGGAGAC TCATAATGAG CCAGACCTCT   13920
AAACCTACAA ACTCAGCAAC TGAGCAAGCA CAAGACTCAC AAGCTGACTC TCGTTTAAAT   13980
AAACGACTAA AAGATATGCC AATTGCTATT GTTGGCATGG CGAGTATTTT TGCAAACTCT   14040
CGCTATTTGA ATAAGTTTTG GGACTTAATC AGCGAAAAAA TTGATGCGAT TACTGAATTA   14100
CCATCAACTC ACTGGCAGCC TGAAGAATAT TACGACGCAG ATAAAACCGC AGCAGACAAA   14160
AGCTACTGTA AACGTGGTGG CTTTTTGCCA GATGTAGACT TCAACCCAAT GGAGTTTGGC   14220
CTGCCGCCAA ACATTTTGGA ACTGACCGAT TCATCGCAAC TATTATCACT CATCGTTGCT   14280
AAAGAAGTGT TGGCTGATGC TAACTTACCT GAGAATTACG ACCGCGATAA AATTGGTATC   14340
ACCTTAGGTG TCGGCGGTGG TCAAAAAATT AGCCACAGCC TAACAGCGCG TCTGCAATAC   14400
CCAGTATTGA AGAAAGTATT CGCCAATAGC GGCATTAGTG ACACCGACAG CGAAATGCTT   14460
ATCAAGAAAT TCCAAGACCA ATATGTACAC TGGGAAGAAA ACTCGTTCCC AGGTTCACTT   14520
GGTAACGTTA TTGCGGGCCG TATCGCCAAC CGCTTCGATT TTGGCGGCAT GAACTGTGTG   14580
GTTGATGCTG CCTGTGCTGG ATCACTTGCT GCTATGCGTA TGGCGCTAAC AGAGCTAACT   14640
GAAGGTCGCT CTGAAATGAT GATCACCGGT GGTGTGTGTA CTGATAACTC ACCCTCTATG   14700
TATATGAGCT TTTCAAAAAC GCCCGCCTTT ACCACTAACG AAACCATTCA GCCATTTGAT   14760
ATCGACTCAA AAGGCATGAT GATTGGTGAA GGTATTGGCA TGGTGGCGCT AAAGCGTCTT   14820
GAAGATGCAG AGCGCGATGG CGACCGCATT TACTCTGTAA TTAAAGGTGT GGGTGCATCA   14880
TCTGACGGTA AGTTTAAATC AATCTATGCC CCTCGCCCAT CAGGCCAAGC TAAAGCACTT   14940
AACCGTGCCT ATGATGACGC AGGTTTTGCG CCGCATACCT TAGGTCTAAT TGAAGCTCAC   15000
GGAACAGGTA CTGCAGCAGG TGACGCGGCA GAGTTTGCCG GCCTTTGCTC AGTATTTGCT   15060
GAAGGCAACG ATACCAAGCA ACACATTGCG CTAGGTTCAG TTAAATCACA AATTGGTCAT   15120
ACTAAATCAA CTGCAGGTAC AGCAGGTTTA ATTAAAGCTG CTCTTGCTTT GCATCACAAG   15180
GTACTGCCGC CGACCATTAA CGTTAGTCAG CCAAGCCCTA AACTTGATAT CGAAAACTCA   15240
CCGTTTTATC TAAACACTGA GACTCGTCCA TGGTTACCAC GTGTTGATGG TACGCCGCGC   15300
CGCGCGGGTA TTAGCTCATT TGGTTTTGGT GGCACTAACT TCCATTTTGT ACTAGAAGAG   15360
TACAACCAAG AACACAGCCG TACTGATAGC GAAAAAGCTA AGTATCGTCA ACGCCAAGTG   15420
GCGCAAAGCT TCCTTGTTAG CGCAAGCGAT AAAGCATCGC TAATTAACGA GTTAAACGTA   15480
CTAGCAGCAT CTGCAAGCCA AGCTGAGTTT ATCCTCAAAG ATGCAGCAGC AAACTATGGC   15540
GTACGTGAGC TTGATAAAAA TGCACCACGG ATCGGTTTAG TTGCAAACAC AGCTGAAGAG   15600
TTAGCAGGCC TAATTAAGCA AGCACTTGCC AAACTAGCAG CTAGCGATGA TAACGCATGG   15660
CAGCTACCTG GTGGCACTAG CTACCGCGCC GCTGCAGTAG AAGGTAAAGT TGCCGCACTG   15720
TTTGCTGGCC AAGGTTCACA ATATCTCAAT ATGGGCCGTG ACCTTACTTG TTATTACCCA   15780
GAGATGCGTC AGCAATTTGT AACTGCAGAT AAAGTATTTG CCGCAAATGA TAAAACGCCG   15840
TTATCGCAAA CTCTGTATCC AAAGCCTGTA TTTAATAAAG ATGAATTAAA GGCTCAAGAA   15900
GCCATTTTGA CCAATACCGC CAATGCCCAA AGCGCAATTG GTGCGATTTC AATGGGTCAA   15960
TACGATTTGT TTACTGCGGC TGGCTTTAAT GCCGACATGG TTGCAGGCCA TAGCTTTGGT   16020
GAGCTAAGTG CACTGTGTGC TGCAGGTGTT ATTTCAGCTG ATGACTACTA CAAGCTGGCT   16080
```

-continued

```
TTTGCTCGTG GTGAGGCTAT GGCAACAAAA GCACCGGCTA AAGACGGCGT TGAAGCAGAT  16140
GCAGGAGCAA TGTTTGCAAT CATAACCAAG AGTGCTGCAG ACCTTGAAAC CGTTGAAGCC  16200
ACCATCGCTA AATTTGATGG GGTGAAAGTC GCTAACTATA ACGCGCCAAC GCAATCAGTA  16260
ATTGCAGGCC CAACAGCAAC TACCGCTGAT GCGGCTAAAG CGCTAACTGA GCTTGGTTAC  16320
AAAGCGATTA ACCTGCCAGT ATCAGGTGCA TTCCACACTG AACTTGTTGG TCACGCTCAA  16380
GCGCCATTTG CTAAAGCGAT TGACGCAGCC AAATTTACTA AACAAGCCG AGCACTTTAC  16440
TCAAATGCAA CTGGCGGACT TTATGAAAGC ACTGCTGCAA AGATTAAAGC CTCGTTTAAG  16500
AAACATATGC TTCAATCAGT GCGCTTTACT AGCCAGCTAG AAGCCATGTA CAACGACGGC  16560
GCCCGTGTAT TTGTTGAATT TGGTCCAAAG AACATCTTAC AAAAATTAGT TCAAGGCACG  16620
CTTGTCAACA CTGAAAATGA AGTTTGCACT ATCTCTATCA ACCCTAATCC TAAAGTTGAT  16680
AGTGATCTGC AGCTTAAGCA AGCAGCAATG CAGCTAGCGG TTACTGGTGT GGTACTCAGT  16740
GAAATTGACC CATACCAAGC CGATATTGCC GCACCAGCGA AAAAGTCGCC AATGAGCATT  16800
TCGCTTAATG CTGCTAACCA TATCAGCAAA GCAACTCGCG CTAAGATGGC CAAGTCTTTA  16860
GAGACAGGTA TCGTCACCTC GCAAATAGAA CATGTTATTG AAGAAAAAAT CGTTGAAGTT  16920
GAGAAACTGG TTGAAGTCGA AAAGATCGTC GAAAAAGTGG TTGAAGTAGA GAAAGTTGTT  16980
GAGGTTGAAG CTCCTGTTAA TTCAGTGCAA GCCAATGCAA TTCAAACCCG TTCAGTTGTC  17040
GCTCCAGTAA TAGAGAACCA AGTCGTGTCT AAAAACAGTA AGCCAGCAGT CCAGAGCATT  17100
AGTGGTGATG CACTCAGCAA CTTTTTTGCT GCACAGCAGC AAACCGCACA GTTGCATCAG  17160
CAGTTCTTAG CTATTCCGCA GCAATATGGT GAGACGTTCA CTACGCTGAT GACCGAGCAA  17220
GCTAAACTGG CAAGTTCTGG TGTTGCAATT CCAGAGAGTC TGCAACGCTC AATGGAGCAA  17280
TTCCACCAAC TACAAGCGCA AACACTACAA AGCCACACCC AGTTCCTTGA GATGCAAGCG  17340
GGTAGCAACA TTGCAGCGTT AAACCTACTC AATAGCAGCC AAGCAACTTA CGCTCCAGCC  17400
ATTCACAATG AAGCGATTCA AAGCCAAGTG GTTCAAAGCC AAACTGCAGT CCAGCCAGTA  17460
ATTTCAACAC AAGTTAACCA TGTGTCAGAG CAGCCAACTC AAGCTCCAGC TCCAAAAGCG  17520
CAGCCAGCAC CTGTGACAAC TGCAGTTCAA ACTGCTCCGG CACAAGTTGT TCGTCAAGCC  17580
GCACCAGTTC AAGCCGCTAT TGAACCGATT AATACAAGTG TTGCGACTAC AACGCCTTCA  17640
GCCTTCAGCG CCGAAACAGC CCTGAGCGCA ACAAAAGTCC AAGCCACTAT GCTTGAAGTG  17700
GTTGCTGAGA AAACCGGTTA CCCAACTGAA ATGCTAGAGC TTGAAATGGA TATGGAAGCC  17760
GATTTAGGCA TCGATTCTAT CAAGCGTGTA GAAATTCTTG GCACAGTACA AGATGAGCTA  17820
CCGGGTCTAC CTGAGCTTAG CCCTGAAGAT CTAGCTGAGT GTCGAACGCT AGGCGAAATC  17880
GTTGACTATA TGGGCAGTAA ACTGCCGGCT GAAGGCTCTA TGAATTCTCA GCTGTCTACA  17940
GGTTCCGCAG CTGCGACTCC TGCAGCGAAT GGTCTTTCTG CGGAGAAAGT TCAAGCGACT  18000
ATGATGTCTG TGGTTGCCGA AAAGACTGGC TACCCAACTG AAATGCTAGA GCTTGAAATG  18060
GATATGGAAG CCGATTTAGG CATAGATTCT ATCAAGCGCG TTGAAATTCT TGGCACAGTA  18120
CAAGATGAGC TACCGGGTCT ACCTGAGCTT AGCCCTGAAG ATCTAGCTGA GTGTCGTACT  18180
CTAGGCGAAA TCGTTGACTA TATGAACTCT AAACTCGCTG ACGGCTCTAA GCTGCCGGCT  18240
GAAGGCTCTA TGAATTCTCA GCTGTCTACA AGTGCCGCAG CTGCGACTCC TGCAGCGAAT  18300
GGTCTCTCTG CGGAGAAAGT TCAAGCGACT ATGATGTCTG TGGTTGCCGA AAAGACTGGC  18360
TACCCAACTG AAATGCTAGA ACTTGAAATG GATATGGAAG CTGACCTTGG CATCGATTCA  18420
ATCAAGCGCG TTGAAATTCT TGGCACAGTA CAAGATGAGC TACCGGGTTT ACCTGAGCTA  18480
```

| | | | | | | |
|---|---|---|---|---|---|---|
| AATCCAGAAG | ATTTGGCAGA | GTGTCGTACT | CTTGGCGAAA | TCGTGACTTA | TATGAACTCT | 18540 |
| AAACTCGCTG | ACGGCTCTAA | GCTGCCAGCT | GAAGGCTCTA | TGCACTATCA | GCTGTCTACA | 18600 |
| AGTACCGCTG | CTGCGACTCC | TGTAGCGAAT | GGTCTCTCTG | CAGAAAAAGT | TCAAGCGACC | 18660 |
| ATGATGTCTG | TAGTTGCAGA | TAAAACTGGC | TACCCAACTG | AAATGCTTGA | ACTTGAAATG | 18720 |
| GATATGGAAG | CCGATTTAGG | TATCGATTCT | ATCAAGCGCG | TTGAAATTCT | TGGCACAGTA | 18780 |
| CAAGATGAGC | TACCGGGTTT | ACCTGAGCTA | AATCCAGAAG | ATCTAGCAGA | GTGTCGCACC | 18840 |
| CTAGGCGAAA | TCGTTGACTA | TATGGGCAGT | AAACTGCCGG | CTGAAGGCTC | TGCTAATACA | 18900 |
| AGTGCCGCTG | CGTCTCTTAA | TGTTAGTGCC | GTTGCGGCGC | CTCAAGCTGC | TGCGACTCCT | 18960 |
| GTATCGAACG | GTCTCTCTGC | AGAGAAAGTG | CAAAGCACTA | TGATGTCAGT | AGTTGCAGAA | 19020 |
| AAGACCGGCT | ACCCAACTGA | AATGCTAGAA | CTTGGCATGG | ATATGGAAGC | CGATTTAGGT | 19080 |
| ATCGACTCAA | TTAAACGCGT | TGAGATTCTT | GGCACAGTAC | AAGATGAGCT | ACCGGGTCTA | 19140 |
| CCAGAGCTTA | ATCCTGAAGA | TTTAGCTGAG | TGCCGTACGC | TGGGCGAAAT | CGTTGACTAT | 19200 |
| ATGAACTCTA | AGCTGGCTGA | CGGCTCTAAG | CTTCCAGCTG | AAGGCTCTGC | TAATACAAGT | 19260 |
| GCCACTGCTG | CGACTCCTGC | AGTGAATGGT | CTTTCTGCTG | ACAAGGTACA | GGCGACTATG | 19320 |
| ATGTCTGTAG | TTGCTGAAAA | GACCGGCTAC | CCAACTGAAA | TGCTAGAACT | TGGCATGGAT | 19380 |
| ATGGAAGCAG | ACCTTGGTAT | TGATTCTATT | AAGCGCGTTG | AAATTCTTGG | CACAGTACAA | 19440 |
| GATGAGCTCC | CAGGTTTACC | TGAGCTTAAT | CCTGAAGATC | TCGCTGAGTG | CCGCACGCTT | 19500 |
| GGCGAAATCG | TTAGCTATAT | GAACTCTCAA | CTGGCTGATG | GCTCTAAACT | TTCTACAAGT | 19560 |
| GCGGCTGAAG | GCTCTGCTGA | TACAAGTGCT | GCAAATGCTG | CAAAGCCGGC | AGCAATTTCG | 19620 |
| GCAGAACCAA | GTGTTGAGCT | TCCTCCTCAT | AGCGAGGTAG | CGCTAAAAAA | GCTTAATGCG | 19680 |
| GCGAACAAGC | TAGAAAATTG | TTTCGCCGCA | GACGCAAGTG | TTGTGATTAA | CGATGATGGT | 19740 |
| CACAACGCAG | GCGTTTTAGC | TGAGAAACTT | ATTAAACAAG | GCCTAAAAGT | AGCCGTTGTG | 19800 |
| CGTTTACCGA | AAGGTCAGCC | TCAATCGCCA | CTTTCAAGCG | ATGTTGCTAG | CTTTGAGCTT | 19860 |
| GCCTCAAGCC | AAGAATCTGA | GCTTGAAGCC | AGTATCACTG | CAGTTATCGC | GCAGATTGAA | 19920 |
| ACTCAGGTTG | GCGCTATTGG | TGGCTTTATT | CACTTGCAAC | CAGAAGCGAA | TACAGAAGAG | 19980 |
| CAAACGGCAG | TAAACCTAGA | TGCGCAAAGT | TTTACTCACG | TTAGCAATGC | GTTCTTGTGG | 20040 |
| GCCAAATTAT | TGCAACCAAA | GCTCGTTGCT | GGAGCAGATG | CGCGTCGCTG | TTTTGTAACA | 20100 |
| GTAAGCCGTA | TCGACGGTGG | CTTTGGTTAC | CTAAATACTG | ACGCCCTAAA | AGATGCTGAG | 20160 |
| CTAAACCAAG | CAGCATTAGC | TGGTTTAACT | AAAACCTTAA | GCCATGAATG | GCCACAAGTG | 20220 |
| TTCTGTCGCG | CGCTAGATAT | TGCAACAGAT | GTTGATGCAA | CCCATCTTGC | TGATGCAATC | 20280 |
| ACCAGTGAAC | TATTTGATAG | CCAAGCTCAG | CTACCTGAAG | TGGGCTTAAG | CTTAATTGAT | 20340 |
| GGCAAAGTTA | ACCGCGTAAC | TCTAGTTGCT | GCTGAAGCTG | CAGATAAAAC | AGCAAAGCA | 20400 |
| GAGCTTAACA | GCACAGATAA | AATCTTAGTG | ACTGGTGGGG | CAAAAGGGGT | GACATTTGAA | 20460 |
| TGTGCACTGG | CATTAGCATC | TCGCAGCCAG | TCTCACTTTA | TCTTAGCTGG | GCGCAGTGAA | 20520 |
| TTACAAGCTT | TACCAAGCTG | GGCTGAGGGT | AAGCAAACTA | GCGAGCTAAA | ATCAGCTGCA | 20580 |
| ATCGCACATA | TTATTTCTAC | TGGTCAAAAG | CCAACGCCTA | AGCAAGTTGA | AGCCGCTGTG | 20640 |
| TGGCCAGTGC | AAAGCAGCAT | TGAAATTAAT | GCCGCCCTAG | CCGCCTTTAA | CAAAGTTGGC | 20700 |
| GCCTCAGCTG | AATACGTCAG | CATGGATGTT | ACCGATAGCG | CCGCAATCAC | AGCAGCACTT | 20760 |
| AATGGTCGCT | CAAATGAGAT | CACCGGTCTT | ATTCATGGCG | CAGGTGTACT | AGCCGACAAG | 20820 |
| CATATTCAAG | ACAAGACTCT | TGCTGAACTT | GCTAAAGTTT | ATGGCACTAA | AGTCAACGGC | 20880 |

```
CTAAAAGCGC TGCTCGCGGC ACTTGAGCCA AGCAAAATTA AATTACTTGC TATGTTCTCA    20940
TCTGCAGCAG GTTTTTACGG TAATATCGGC CAAAGCGATT ACGCGATGTC GAACGATATT    21000
CTTAACAAGG CAGCGCTGCA GTTCACCGCT CGCAACCCAC AAGCTAAAGT CATGAGCTTT    21060
AACTGGGGTC CTTGGGATGG CGGCATGGTT AACCCAGCGC TTAAAAAGAT GTTACCGAG     21120
CGTGGTGTGT ACGTTATTCC ACTAAAAGCA GGTGCAGAGC TATTTGCCAC TCAGCTATTG    21180
GCTGAAACTG GCGTGCAGTT GCTCATTGGT ACGTCAATGC AAGGTGGCAG CGACACTAAA    21240
GCAACTGAGA CTGCTTCTGT AAAAAAGCTT AATGCGGGTG AGGTGCTAAG TGCATCGCAT    21300
CCGCGTGCTG GTGCACAAAA AACACCACTA CAAGCTGTCA CTGCAACGCG TCTGTTAACC    21360
CCAAGTGCCA TGGTCTTCAT TGAAGATCAC CGCATTGGCG GTAACAGTGT GTTGCCAACG    21420
GTATGCGCCA TCGACTGGAT GCGTGAAGCG GCAAGCGACA TGCTTGGCGC TCAAGTTAAG    21480
GTACTTGATT ACAAGCTATT AAAAGGCATT GTATTTGAGA CTGATGAGCC GCAAGAGTTA    21540
ACACTTGAGC TAACGCCAGA CGATTCAGAC GAAGCTACGC TACAAGCATT AATCAGCTGT    21600
AATGGGCGTC CGCAATACAA GGCGACGCTT ATCAGTGATA ATGCCGATAT TAAGCAACTT    21660
AACAAGCAGT TTGATTTAAG CGCTAAGGCG ATTACCACAG CAAAAGAGCT TTATAGCAAC    21720
GGCACCTTGT TCCACGGTCC GCGTCTACAA GGGATCCAAT CTGTAGTGCA GTTCGATGAT    21780
CAAGGCTTAA TTGCTAAAGT CGCTCTGCCT AAGGTTGAAC TTAGCGATTG TGGTGAGTTC    21840
TTGCCGCAAA CCCACATGGG TGGCAGTCAA CCTTTTGCTG AGGACTTGCT ATTACAAGCT    21900
ATGCTGGTTT GGGCTCGCCT TAAAACTGGC TCGGCAAGTT TGCCATCAAG CATTGGTGAG    21960
TTTACCTCAT ACCAACCAAT GGCCTTTGGT GAAACTGGTA CCATAGAGCT TGAAGTGATT    22020
AAGCACAACA AACGCTCACT TGAAGCGAAT GTTGCGCTAT ATCGTGACAA CGGCGAGTTA    22080
AGTGCCATGT TTAAGTCAGC TAAAATCACC ATTAGCAAAA GCTTAAATTC AGCATTTTA    22140
CCTGCTGTCT TAGCAAACGA CAGTGAGGCG AATTAGTGGA ACAAACGCCT AAAGCTAGTG    22200
CGATGCCGCT GCGCATCGCA CTTATCTTAC TGCCAACACC GCAGTTTGAA GTTAACTCTG    22260
TCGACCAGTC AGTATTAGCC AGCTATCAAA CACTGCAGCC TGAGCTAAAT GCCCTGCTTA    22320
ATAGTGCGCC GACACCTGAA ATGCTCAGCA TCACTATCTC AGATGATAGC GATGCAAACA    22380
GCTTTGAGTC GCAGCTAAAT GCTGCGACCA ACGCAATTAA CAATGGCTAT ATCGTCAAGC    22440
TTGCTACGGC AACTCACGCT TTGTTAATGC TGCCTGCATT AAAAGCGGCG CAAATGCGGA    22500
TCCATCCTCA TGCGCAGCTT GCCGCTATGC AGCAAGCTAA ATCGACGCCA ATGAGTCAAG    22560
TATCTGGTGA GCTAAAGCTT GGCGCTAATG CGCTAAGCCT AGCTCAGACT AATGCGCTGT    22620
CTCATGCTTT AAGCCAAGCC AAGCGTAACT TAACTGATGT CAGCGTGAAT GAGTGTTTTG    22680
AGAACCTCAA AAGTGAACAG CAGTTCACAG AGGTTTATTC GCTTATTCAG CAACTTGCTA    22740
GCCGCACCCA TGTGAGAAAA GAGGTTAATC AAGGTGTGGA ACTTGGCCCT AAACAAGCCA    22800
AAAGCCACTA TTGGTTTAGC GAATTTCACC AAAACCGTGT TGCTGCCATC AACTTTATTA    22860
ATGGCCAACA AGCAACCAGC TATGTGCTTA CTCAAGGTTC AGGATTGTTA GCTGCGAAAT    22920
CAATGCTAAA CCAGCAAAGA TTAATGTTTA TCTTGCCGGG TAACAGTCAG CAACAAATAA    22980
CCGCATCAAT AACTCAGTTA ATGCAGCAAT TAGAGCGTTT GCAGGTAACT GAGGTTAATG    23040
AGCTTTCTCT AGAATGCCAA CTAGAGCTGC TCAGCATAAT GTATGACAAC TTAGTCAACG    23100
CAGACAAACT CACTACTCGC GATAGTAAGC CCGCTTATCA GGCTGTGATT CAAGCAAGCT    23160
CTGTTAGCGC TGCAAAGCAA GAGTTAAGCG CGCTTAACGA TGCACTCACA GCGCTGTTTG    23220
CTGAGCAAAC AAACGCCACA TCAACGAATA AAGGCTTAAT CCAATACAAA ACACCGGCGG    23280
```

| | | | | | |
|---|---|---|---|---|---|
| GCAGTTACTT | AACCCTAACA | CCGCTTGGCA | GCAACAATGA | CAACGCCCAA | GCGGGTCTTG | 23340 |
| CTTTTGTCTA | TCCGGGTGTG | GGAACGGTTT | ACGCCGATAT | GCTTAATGAG | CTGCATCAGT | 23400 |
| ACTTCCCTGC | GCTTACGCC | AAACTTGAGC | GTGAAGGCGA | TTTAAAGGCG | ATGCTACAAG | 23460 |
| CAGAAGATAT | CTATCATCTT | GACCCTAAAC | ATGCTGCCCA | AATGAGCTTA | GGTGACTTAG | 23520 |
| CCATTGCTGG | CGTGGGGAGC | AGCTACCTGT | TAACTCAGCT | GCTCACCGAT | GAGTTAATA | 23580 |
| TTAAGCCTAA | TTTTGCATTA | GGTTACTCAA | TGGGTGAAGC | ATCAATGTGG | GCAAGCTTAG | 23640 |
| GCGTATGGCA | AAACCCGCAT | GCGCTGATCA | GCAAAACCCA | AACCGACCCG | CTATTTACTT | 23700 |
| CTGCTATTTC | CGGCAAATTG | ACCGCGGTTA | GACAAGCTTG | GCAGCTTGAT | GATACCGCAG | 23760 |
| CGGAAATCCA | GTGGAATAGC | TTTGTGGTTA | GAAGTGAAGC | AGCGCCGATT | GAAGCCTTGC | 23820 |
| TAAAAGATTA | CCCACACGCT | TACCTCGCGA | TTATTCAAGG | GGATACCTGC | GTAATCGCTG | 23880 |
| GCTGTGAAAT | CCAATGTAAA | GCGCTACTTG | CAGCACTGGG | TAAACGCGGT | ATTGCAGCTA | 23940 |
| ATCGTGTAAC | GGCGATGCAT | ACGCAGCCTG | CGATGCAAGA | GCATCAAAAT | GTGATGGATT | 24000 |
| TTTATCTGCA | ACCGTTAAAA | GCAGAGCTTC | CTAGTGAAAT | AAGCTTTATC | AGCGCCGCTG | 24060 |
| ATTAACTGC | CAAGCAAACG | GTGAGTGAGC | AAGCACTTAG | CAGCCAAGTC | GTTGCTCAGT | 24120 |
| CTATTGCCGA | CACCTTCTGC | CAAACCTTGG | ACTTTACCGC | GCTAGTACAT | CACGCCCAAC | 24180 |
| ATCAAGGCGC | TAAGCTGTTT | GTTGAAATTG | GCGCGGATAG | ACAAAACTGC | ACCTTGATAG | 24240 |
| ACAAGATTGT | TAAACAAGAT | GGTGCCAGCA | GTGTACAACA | TCAACCTTGT | TGCACAGTGC | 24300 |
| CTATGAACGC | AAAAGGTAGC | CAAGATATTA | CCAGCGTGAT | TAAAGCGCTT | GGCCAATTAA | 24360 |
| TTAGCCATCA | GGTGCCATTA | TCGGTGCAAC | CATTTATTGA | TGGACTCAAG | CGCGAGCTAA | 24420 |
| CACTTTGCCA | ATTGACCAGC | CAACAGCTGG | CAGCACATGC | AAATGTTGAC | AGCAAGTTTG | 24480 |
| AGTCTAACCA | AGACCATTTA | CTTCAAGGGG | AAGTCTAATG | TCATTACCAG | ACAATGCTTC | 24540 |
| TAACCACCTT | TCTGCCAACC | AGAAAGGCGC | ATCTCAGGCA | AGTAAAACCA | GTAAGCAAAG | 24600 |
| CAAAATCGCC | ATTGTCGGTT | TAGCCACTCT | GTATCCAGAC | GCTAAAACCC | CGCAAGAATT | 24660 |
| TTGGCAGAAT | TTGCTGGATA | AACGCGACTC | TCGCAGCACC | TTAACTAACG | AAAAACTCGG | 24720 |
| CGCTAACAGC | CAAGATTATC | AAGGTGTGCA | AGGCCAATCT | GACCGTTTTT | ATTGTAATAA | 24780 |
| AGGCGGCTAC | ATTGAGAACT | TCAGCTTTAA | TGCTGCAGGC | TACAAATTGC | CGGAGCAAAG | 24840 |
| CTTAAATGGC | TTGGACGACA | GCTTCCTTTG | GGCGCTCGAT | ACTAGCCGTA | ACGCACTAAT | 24900 |
| TGATGCTGGT | ATTGATATCA | ACGGCGCTGA | TTTAAGCCGC | GCAGGTGTAG | TCATGGGCGC | 24960 |
| GCTGTCGTTC | CCAACTACCC | GCTCAAACGA | TCTGTTTTTG | CCAATTTATC | ACAGCGCCGT | 25020 |
| TGAAAAAGCC | CTGCAAGATA | AACTAGGCGT | AAAGGCATTT | AAGCTAAGCC | CAACTAATGC | 25080 |
| TCATACCGCT | CGCGCGGCAA | ATGAGAGCAG | CCTAAATGCA | GCCAATGGTG | CCATTGCCCA | 25140 |
| TAACAGCTCA | AAAGTGGTGG | CCGATGCACT | TGGCCTTGGC | GGCGCACAAC | TAAGCCTAGA | 25200 |
| TGCTGCCTGT | GCTAGTTCGG | TTTACTCATT | AAAGCTTGCC | TGCGATTACC | TAAGCACTGG | 25260 |
| CAAAGCCGAT | ATCATGCTAG | CAGGCGCAGT | ATCTGGCGCG | GATCCTTTCT | TTATTAATAT | 25320 |
| GGGATTCTCA | ATCTTCCACG | CCTACCCAGA | CCATGGTATC | TCAGTACCGT | TGATGCCAG | 25380 |
| CAGTAAAGGT | TTGTTTGCTG | GCGAAGGCGC | TGGCGTATTA | GTGCTTAAAC | GTCTTGAAGA | 25440 |
| TGCCGAGCGC | GACAATGACA | AAATCTATGC | GGTTGTTAGC | GGCGTAGGTC | TATCAAACGA | 25500 |
| CGGTAAAGGC | CAGTTTGTAT | TAAGCCCTAA | TCCAAAAGGT | CAGGTGAAGG | CCTTTGAACG | 25560 |
| TGCTTATGCT | GCCAGTGACA | TTGAGCCAAA | AGACATTGAA | GTGATTGAGT | GCCACGCAAC | 25620 |
| AGGCACACCG | CTTGGCGATA | AAATTGAGCT | CACTTCAATG | GAAACCTTCT | TGAAGACAA | 25680 |

```
GCTGCAAGGC ACCGATGCAC CGTTAATTGG CTCAGCTAAG TCTAACTTAG GCCACCTATT   25740
AACTGCAGCG CATGCGGGGA TCATGAAGAT GATCTTCGCC ATGAAAGAAG GTTACCTGCC   25800
GCCAAGTATC AATATTAGTG ATGCTATCGC TTCGCCGAAA AAACTCTTCG GTAAACCAAC   25860
CCTGCCTAGC ATGGTTCAAG GCTGGCCAGA TAAGCCATCG AATAATCATT TTGGTGTAAG   25920
AACCCGTCAC GCAGGCGTAT CGGTATTTGG CTTTGGTGGC TGTAACGCCC ATCTGTTGCT   25980
TGAGTCATAC AACGGCAAAG GAACAGTAAA GGCAGAAGCC ACTCAAGTAC CGCGTCAAGC   26040
TGAGCCGCTA AAAGTGGTTG GCCTTGCCTC GCACTTTGGG CCTCTTAGCA GCATTAATGC   26100
ACTCAACAAT GCTGTGACCC AAGATGGGAA TGGCTTTATC GAACTGCCGA AAAAGCGCTG   26160
GAAAGGCCTT GAAAAGCACA GTGAACTGTT AGCTGAATTT GGCTTAGCAT CTGCGCCAAA   26220
AGGTGCTTAT GTTGATAACT TCGAGCTGGA CTTTTTACGC TTTAAACTGC CGCCAAACGA   26280
AGATGACCGT TTGATCTCAC AGCAGCTAAT GCTAATGCGA GTAACAGACG AAGCCATTCG   26340
TGATGCCAAG CTTGAGCCGG GGCAAAAAGT AGCTGTATTA GTGGCAATGG AAACTGAGCT   26400
TGAACTGCAT CAGTTCCGCG GCCGGGTTAA CTTGCATACT CAATTAGCGC AAAGTCTTGC   26460
CGCCATGGGC GTGAGTTTAT CAACGGATGA ATACCAAGCG CTTGAAGCCA TCGCCATGGA   26520
CAGCGTGCTT GATGCTGCCA AGCTCAATCA GTACACCAGC TTTATTGGTA ATATTATGGC   26580
GTCACGCGTG GCGTCACTAT GGGACTTTAA TGGCCCAGCC TTCACTATTT CAGCAGCAGA   26640
GCAATCTGTG AGCCGCTGTA TCGATGTGGC GCAAAACCTC ATCATGGAGG ATAACCTAGA   26700
TGCGGTGGTG ATTGCAGCGG TCGATCTCTC TGGTAGCTTT GAGCAAGTCA TTCTTAAAAA   26760
TGCCATTGCA CCTGTAGCCA TTGAGCCAAA CCTCGAAGCA AGCCTTAATC CAACATCAGC   26820
AAGCTGGAAT GTCGGTGAAG GTGCTGGCGC GGTCGTGCTT GTTAAAAATG AAGCTACATC   26880
GGGCTGCTCA TACGGCCAAA TTGATGCACT TGGCTTTGCT AAAACTGCCG AAACAGCGTT   26940
GGCTACCGAC AAGCTACTGA GCCAAACTGC CACAGACTTT AATAAGGTTA AGTGATTGA    27000
AACTATGGCA GCGCCTGCTA GCCAAATTCA ATTAGCGCCA ATAGTTAGCT CTCAAGTGAC   27060
TCACACTGCT GCAGAGCAGC GTGTTGGTCA CTGCTTTGCT GCAGCGGGTA TGGCAAGCCT   27120
ATTACACGGC TTACTTAACT TAAATACTGT AGCCCAAACC AATAAAGCCA ATTGCGCGCT   27180
TATCAACAAT ATCAGTGAAA ACCAATTATC ACAGCTGTTG ATTAGCCAAA CAGCGAGCGA   27240
ACAACAAGCA TTAACCGCGC GTTTAAGCAA TGAGCTTAAA TCCGATGCTA AACACCAACT   27300
GGTTAAGCAA GTCACCTTAG GTGGCCGTGA TATCTACCAG CATATTGTTG ATACACCGCT   27360
TGCAAGCCTT GAAAGCATTA CTCAGAAATT GGCGCAAGCG ACAGCATCGA CAGTGGTCAA   27420
CCAAGTTAAA CCTATTAAGG CCGCTGGCTC AGTCGAAATG GCTAACTCAT TCGAAACGGA   27480
AAGCTCAGCA GAGCCACAAA TAACAATTGC AGCACAACAG ACTGCAAACA TTGGCGTCAC   27540
CGCTCAGGCA ACCAAACGTG AATTAGGTAC CCCACCAATG ACAACAAATA CCATTGCTAA   27600
TACAGCAAAT AATTTAGACA AGACTCTTGA GACTGTTGCT GGCAATACTG TTGCTAGCAA   27660
GGTTGGCTCT GGCGACATAG TCAATTTTCA ACAGAACCAA CAATTGGCTC AACAAGCTCA   27720
CCTCGCCTTT CTTGAAAGCC GCAGTGCGGG TATGAAGGTG GCTGATGCTT TATTGAAGCA   27780
ACAGCTAGCT CAAGTAACAG GCCAAACTAT CGATAATCAG GCCCTCGATA CTCAAGCCGT   27840
CGATACTCAA ACAAGCGAGA ATGTAGCGAT TGCCGCAGAA TCACCAGTTC AAGTTACAAC   27900
ACCTGTTCAA GTTACAACAC CTGTTCAAAT CAGTGTTGTG GAGTTAAAAC CAGATCACGC   27960
TAATGTGCCA CCATACACGC CGCCAGTGCC TGCATTAAAG CCGTGTATCT GGAACTATGC   28020
CGATTTAGTT GAGTACGCAG AAGGCGATAT CGCCAAGGTA TTTGGCAGTG ATTATGCCAT   28080
```

| | | | | | |
|---|---|---|---|---|---|
| TATCGACAGC | TACTCGCGCC | GCGTACGTCT | ACCGACCACT | GACTACCTGT | TGGTATCGCG | 28140 |
| CGTGACCAAA | CTTGATGCGA | CCATCAATCA | ATTAAGCCA | TGCTCAATGA | CCACTGAGTA | 28200 |
| CGACATCCCT | GTTGATGCGC | CGTACTTAGT | AGACGGACAA | ATCCCTTGGG | CGGTAGCAGT | 28260 |
| AGAATCAGGC | CAATGTGACT | TGATGCTTAT | TAGCTATCTC | GGTATCGACT | TTGAGAACAA | 28320 |
| AGGCGAGCGG | GTTATCGAC | TACTCGATTG | TACCCTCACC | TTCCTAGGCG | ACTTGCCACG | 28380 |
| TGGCGGAGAT | ACCCTACGTT | ACGACATTAA | GATCAATAAC | TATGCTCGCA | ACGGCGACAC | 28440 |
| CCTGCTGTTC | TTCTTCTCGT | ATGAGTGTTT | TGTTGGCGAC | AAGATGATCC | TCAAGATGGA | 28500 |
| TGGCGGCTGC | GCTGGCTTCT | TCACTGATGA | AGAGCTTGCC | GACGGTAAAG | GCGTGATTCG | 28560 |
| CACAGAAGAA | GAGATTAAAG | CTCGCAGCCT | AGTGCAAAAG | CAACGCTTTA | ATCCGTTACT | 28620 |
| AGATTGTCCT | AAAACCCAAT | TTAGTTATGG | TGATATTCAT | AAGCTATTAA | CTGCTGATAT | 28680 |
| TGAGGGTTGT | TTTGGCCCAA | GCCACAGTGG | CGTCCACCAG | CCGTCACTTT | GTTTCGCATC | 28740 |
| TGAAAAATTC | TTGATGATTG | AACAAGTCAG | CAAGGTTGAT | CGCACTGGCG | GTACTTGGGG | 28800 |
| ACTTGGCTTA | ATTGAGGGTC | ATAAGCAGCT | TGAAGCAGAC | CACTGGTACT | TCCCATGTCA | 28860 |
| TTTCAAGGGC | GACCAAGTGA | TGGCTGGCTC | GCTAATGGCT | GAAGGTTGTG | GCCAGTTATT | 28920 |
| GCAGTTCTAT | ATGCTGCACC | TTGGTATGCA | TACCCAAACT | AAAAATGGTC | GTTCCAACC | 28980 |
| TCTTGAAAAC | GCCTCACAGC | AAGTACGCTG | TCGCGGTCAA | GTGCTGCCAC | AATCAGGCGT | 29040 |
| GCTAACTTAC | CGTATGGAAG | TGACTGAAAT | CGGTTTCAGT | CCACGCCCAT | ATGCTAAAGC | 29100 |
| TAACATCGAT | ATCTTGCTTA | ATGGCAAAGC | GGTAGTGGAT | TTCCAAAACC | TAGGGGTGAT | 29160 |
| GATAAAGAG | GAAGATGAGT | GTACTCGTTA | TCCACTTTTG | ACTGAATCAA | CAACGGCTAG | 29220 |
| CACTGCACAA | GTAAACGCTC | AAACAAGTGC | GAAAAGGTA | TACAAGCCAG | CATCAGTCAA | 29280 |
| TGCGCCATTA | ATGGCACAAA | TTCCTGATCT | GACTAAAGAG | CCAAACAAGG | GCGTTATTCC | 29340 |
| GATTTCCCAT | GTTGAAGCAC | CAATTACGCC | AGACTACCCG | AACCGTGTAC | CTGATACAGT | 29400 |
| GCCATTCACG | CCGTATCACA | TGTTTGAGTT | TGCTACAGGC | AATATCGAAA | ACTGTTTCGG | 29460 |
| GCCAGAGTTC | TCAATCTATC | GCGGCATGAT | CCCACCACGT | ACACCATGCG | GTGACTTACA | 29520 |
| AGTGACCACA | CGTGTGATTG | AAGTTAACGG | TAAGCGTGGC | GACTTAAAA | AGCCATCATC | 29580 |
| GTGTATCGCT | GAATATGAAG | TGCCTGCAGA | TGCGTGGTAT | TTCGATAAAA | ACAGCCACGG | 29640 |
| CGCAGTGATG | CCATATTCAA | TTTTAATGGA | GATCTCACTG | CAACCTAACG | GCTTTATCTC | 29700 |
| AGGTTACATG | GGCACAACCC | TAGGCTTCCC | TGGCCTTGAG | CTGTTCTTCC | GTAACTTAGA | 29760 |
| CGGTAGCGGT | GAGTTACTAC | GTGAAGTAGA | TTTACGTGGT | AAAACCATCC | GTAACGACTC | 29820 |
| ACGTTTATTA | TCAACAGTGA | TGGCCGGCAC | TAACATCATC | CAAAGCTTTA | GCTTCGAGCT | 29880 |
| AAGCACTGAC | GGTGAGCCTT | TCTATCGCGG | CACTGCGGTA | TTTGGCTATT | TTAAAGGTGA | 29940 |
| CGCACTTAAA | GATCAGCTAG | GCCTAGATAA | CGGTAAAGTC | ACTCAGCCAT | GGCATGTAGC | 30000 |
| TAACGGCGTT | GCTGCAAGCA | CTAAGGTGAA | CCTGCTTGAT | AAGAGCTGCC | GTCACTTTAA | 30060 |
| TGCGCCAGCT | AACCAGCCAC | ACTATCGTCT | AGCCGGTGGT | CAGCTGAACT | TTATCGACAG | 30120 |
| TGTTGAAATT | GTTGATAATG | GCGGCACCGA | AGGTTTAGGT | TACTTGTATG | CCGAGCGCAC | 30180 |
| CATTGACCCA | AGTGATTGGT | TCTTCCAGTT | CCACTTCCAC | CAAGATCCGG | TTATGCCAGG | 30240 |
| CTCCTTAGGT | GTTGAAGCAA | TTATTGAAAC | CATGCAAGCT | TACGCTATTA | GTAAAGACTT | 30300 |
| GGGCGCAGAT | TTCAAAAATC | CTAAGTTTGG | TCAGATTTTA | TCGAACATCA | AGTGGAAGTA | 30360 |
| TCGCGGTCAA | ATCAATCCGC | TGAACAAGCA | GATGTCTATG | GATGTCAGCA | TTACTTCAAT | 30420 |
| CAAAGATGAA | GACGGTAAGA | AAGTCATCAC | AGGTAATGCC | AGCTTGAGTA | AAGATGGTCT | 30480 |

-continued

| | | | | | |
|---|---|---|---|---|---|
|GCGCATATAC|GAGGTCTTCG|ATATAGCTAT|CAGCATCGAA|GAATCTGTAT|AAATCGGAGT|30540|
|GACTGTCTGG|CTATTTTACT|CAATTTCTGT|GTCAAAAGTG|CTCACCTATA|TTCATAGGCT|30600|
|GCGCGCTTTT|TTCTGGAAAT|TGAGCAAAAG|TATCTGCGTC|CTAACTCGAT|TTATAAGAAT|30660|
|GGTTTAATTG|AAAAGAACAA|CAGCTAAGAG|CCGCAAGCTC|AATATAAATA|ATTAAGGGTC|30720|
|TTACAAATAA|TGAATCCTAC|AGCAACTAAC|GAAATGCTTT|CTCCGTGGCC|ATGGGCTGTG|30780|
|ACAGAGTCAA|ATATCAGTTT|TGACGTGCAA|GTGATGGAAC|AACAACTTAA|AGATTTTAGC|30840|
|CGGGCATGTT|ACGTGGTCAA|TCATGCCGAC|CACGGCTTTG|GTATTGCGCA|AACTGCCGAT|30900|
|ATCGTGACTG|AACAAGCGGC|AAACAGCACA|GATTACCTG|TTAGTGCTTT|TACTCCTGCA|30960|
|TTAGGTACCG|AAAGCCTAGG|CGACAATAAT|TTCCGCCGCG|TTCACGGCGT|TAAATACGCT|31020|
|TATTACGCAG|GCGCTATGGC|AAACGGTATT|TCATCTGAAG|AGCTAGTGAT|TGCCCTAGGT|31080|
|CAAGCTGGCA|TTTTGTGTGG|TTCGTTTGGA|GCAGCCGGTC|TTATTCCAAG|TCGCGTTGAA|31140|
|GCGGCAATTA|ACCGTATTCA|AGCAGCGCTG|CCAAATGGCC|CTTATATGTT|TAACCTTATC|31200|
|CATAGTCCTA|GCGAGCCAGC|ATTAGAGCGT|GGCAGCGTAG|AGCTATTTT|AAAGCATAAG|31260|
|GTACGCACCG|TTGAAGCATC|AGCTTTCTTA|GGTCTAACAC|CACAAATCGT|CTATTACCGT|31320|
|GCAGCAGGAT|TGAGCCGAGA|CGCACAAGGT|AAAGTTGTGG|TTGGTAACAA|GGTTATCGCT|31380|
|AAAGTAAGTC|GCACCGAAGT|GGCTGAAAAG|TTTATGATGC|CAGCGCCCGC|AAAAATGCTA|31440|
|CAAAAACTAG|TTGATGACGG|TTCAATTACC|GCTGAGCAAA|TGGAGCTGGC|GCAACTTGTA|31500|
|CCTATGGCTG|ACGACATCAC|TGCAGAGGCC|GATTCAGGTG|GCCATACTGA|TAACCGTCCA|31560|
|TTAGTAACAT|TGCTGCCAAC|CATTTTAGCG|CTGAAAGAAG|AAATTCAAGC|TAAATACCAA|31620|
|TACGACACTC|CTATTCGTGT|CGGTTGTGGT|GGCGGTGTGG|GTACGCCTGA|TGCAGCGCTG|31680|
|GCAACGTTTA|ACATGGGCGC|GGCGTATATT|GTTACCGGCT|CTATCAACCA|AGCTTGTGTT|31740|
|GAAGCGGGCG|CAAGTGATCA|CACTCGTAAA|TTACTTGCCA|CCACTGAAAT|GGCCGATGTG|31800|
|ACTATGGCAC|CAGCTGCAGA|TATGTTCGAG|ATGGGCGTAA|AACTGCAGGT|GGTTAAGCGC|31860|
|GGCACGCTAT|TCCCAATGCG|CGCTAACAAG|CTATATGAGA|TCTACACCCG|TTACGATTCA|31920|
|ATCGAAGCGA|TCCCATTAGA|CGAGCGTGAA|AAGCTTGAGA|AACAAGTATT|CCGCTCAAGC|31980|
|CTAGATGAAA|TATGGGCAGG|TACAGTGGCG|CACTTTAACG|AGCGCGACCC|TAAGCAAATC|32040|
|GAACGCGCAG|AGGGTAACCC|TAAGCGTAAA|ATGGCATTGA|TTTTCCGTTG|GTACTTAGGT|32100|
|CTTTCTAGTC|GCTGGTCAAA|CTCAGGCGAA|GTGGGTCGTG|AAATGGATTA|TCAAATTTGG|32160|
|GCTGGCCCTG|CTCTCGGTGC|ATTTAACCAA|TGGGCAAAAG|GCAGTTACTT|AGATAACTAT|32220|
|CAAGACCGAA|ATGCCGTCGA|TTTGGCAAAG|CACTTAATGT|ACGGCGCGGC|TTACTTAAAT|32280|
|CGTATTAACT|CGCTAACGGC|TCAAGGCGTT|AAAGTGCCAG|CACAGTTACT|TCGCTGGAAG|32340|
|CCAAACCAAA|GAATGGCCTA|ATACACTTAC|AAAGCACCAG|TCTAAAAAGC|CACTAATCTT|32400|
|GATTAGTGGC|TTTTTTTATT|GTGGTCAATA|TGAGGCTATT|TAGCCTGTAA|GCCTGAAAAT|32460|
|ATCAGCACTC|TGACTTTACA|AGCAAATTAT|AATTAAGGCA|GGGCTCTACT|CATTTATACT|32520|
|GCTAGCAAAC|AAGCAAGTTG|CCCAGTAAAA|CAACAAGGTA|CCTGATTTAT|ATCGTCATAA|32580|
|AAGTTGGCTA|GAGATTCGTT|ATTGATCTTT|ACTGATTAGA|GTCGCTCTGT|TTGGAAAAAG|32640|
|GTTTCTCGTT|ATCATCAAAA|TACACTCTCA|AACCTTTAAT|CAATTACAAC|TTAGGCTTTC|32700|
|TGCGGGCATT|TTTATCTTAT|TTGCCACAGC|TGTATTTGCC|TTTAGGTTTT|GGGTGCAACT|32760|
|ACCATTAATT|GAGGCCTCAT|TAGTTAAATT|ATCTGAGCAA|GAGCTCACCT|CTTTAAATTA|32820|
|CGCTTTTCAG|CAAATGAGAA|AGCCACTACA|AACCATTAAT|TACGACTATG|CGGTGTGGGA|32880|

```
CAGAACCTAC AGCTATATGA AATCAAACTC AGCGAGCGCT AAAAGGTACT ATGAAAAACA    32940
TGAGTACCCA GATGATACGT TCAAGAGTTT AAAAGTCGAC GGAGTATTTA TATTCAACCG    33000
TACAAATCAG CCAGTTTTTA GTAAAGGTTT TAATCATAGA AATGATATAC CGCTGGTCTT    33060
TGAATTAACT GACTTTAAAC AACATCCACA AAACATCGCA TTATCTCCAC AAACCAAACA    33120
GGCACACCCA CCGGCAAGTA AGCCGTTAGA CTCCCTGAT GATGTGCCTT CTACCCATGG    33180
GGTTATCGCC ACACGATACG GTCCAGCAAT TTATAGCTCT ACCAGCATTT TAAAATCTGA    33240
TCGTAGCGGC TCCCAACTTG GTTATTTAGT CTTCATTAGG TTAATTGATG AATGGTTCAT    33300
CGCTGAGCTA TCGCAATACA CTGCCGCAGG TGTTGAAATC GCTATGGCTG ATGCCGCAGA    33360
CGCACAATTA GCGAGATTAG GCGCAAACAC TAAGCTTAAT AAAGTAACCG CTACATCCGA    33420
ACGGTTAATA ACTAATGTCG ATGGTAAGCC TCTGTTGAAG TTAGTGCTTT ACCATACCAA    33480
TAACCAACCG CCGCCGATGC TAGATTACAG TATAATAATT CTATTAGTTG AGATGTCATT    33540
TTACTGATC CTCGCTTATT TCCTTTACTC CTACTTCTTA GTCAGGCCAG TTAGAAAGCT    33600
GGCTTCAGAT ATTAAAAAAA TGGATAAAAG TCGTGAAATT AAAAAGCTAA GGTATCACTA    33660
CCCTATTACT GAGCTAGTCA AAGTTGCGAC TCACTTCAAC GCCCTAATGG GACGATTCA     33720
GGAACAAACT AAACAGCTTA ATGAACAAGT TTTTATTGAT AAATTAACCA ATATTCCCAA    33780
TCGTCGCGCT TTGAGCAGC GACTTGAAAC CTATTGCCAA CTGCTAGCCC GGCAACAAAT    33840
TGGCTTTACT CTCATCATTG CCGATGTGGA TCATTTAAA GAGTACAACG ATACTCTTGG    33900
GCACCTTGCT GGGGATGAAG CATTAATAAA AGTGGCACAA ACACTATCGC AACAGTTTTA    33960
CCGTGCAGAA GATATTTGTG CCCGTTTTGG TGGTGAAGAA TTTATTATGT TATTCGAGA    34020
CATACCTGAT GAGCCCTTGC AGAGAAAGCT CGATGCGATG CTGCACTCTT TTGCAGAGCT    34080
CAACCTACCT CATCCAAACT CATCAACCGC TAATTACGTT ACTGTGAGCC TTGGGGTTTG    34140
CACAGTTGTT GCTGTTGATG ATTTTGAATT TAAAAGTGAG TCGCATATTA TTGGCAGTCA    34200
GGCTGCATTA ATCGCAGATA AGGCGCTTTA TCATGCTAAA GCCTGTGGTC GTAACCAGTT    34260
GTCAAAAACT ACTATTACTG TTGATGAGAT TGAGCAATTA GAAGCAAATA AAATCGGTCA    34320
TCAAGCCTAA ACTCGTTCGA GTACTTTCCC CTAAGTCAGA GCTATTTGCC ACTTCAAGAT    34380
GTGGCTACAA GGCTTACTCT TTCAAAACCT GCATCAATAG AACACAGCAA AATACAATAA    34440
TTTAAGTCAA TTTAGCCTAT TAAACAGAGT TAATGACAGC TCATGGTCGC AACTTATTAG    34500
CTATTTCTAG CAATATAAAA ACTTATCCAT TAGTAGTAAC CAATAAAAAA ACTAATATAT    34560
AAAACTATTT AATCATTATT TTACAGATGA TTAGCTACCA CCCACCTTAA GCTGGCTATA    34620
TTCGCACTAG TAAAAATAAA CATTAGATCG GGTTCAGATC AATTTACGAG TCTCGTATAA    34680
AATGTACAAT AATTCACTTA ATTTAATACT GCATATTTTT ACAAGTAGAG AGCGGTGATG    34740
AAACAAAATA CGAAAGGCTT TACATTAATT GAATTAGTCA TCGTGATTAT TATTCTCGGT    34800
ATACTTGCTG CTGTGGCACT GCCGAAATTC ATCAATGTTC AAGATGACGC TAGGATCTCT    34860
GCGATGAGCG GTCAGTTTTC ATCATTTGAA AGTGCCGTAA AACTATACCA TAGCGGTTGG    34920
TTAGCCAAAG GCTACAACAC TGCGGTTGAA AAGCTCTCAG GCTTTGGCCA AGGTAATGTT    34980
GCATCAAGTG ACACAGGTTT TCCGTACTCA ACATCAGGCA CGAGTACTGA TGTGCATAAA    35040
GCTTGTGGTG AACTATGGCA TGGCATTACC GATACAGACT TCACAATTGG TGCGGTTAGT    35100
GATGGCGATC TAATGACTGC AGATGTCGAT ATTGCTTACA CCTATCGTGG TGATATGTGT    35160
ATCTATCGCG ATCTGTATTT TATTCAGCGC TCATTACCTA CTAAGGTGAT GAACTACAAA    35220
TTTAAAACTG GTGAAATAGA AATTATTGAT GCTTTCTACA ACCCTGACGG CTCAACTGGT    35280
```

```
CAATTACCAT AAATTTGGCG CTTATCTAAG TTGTACTTGC TCTGACCGAC ACAAATAATG   35340
TCGTTTCTCA GCATATATCA AAATACACAG CAAAAATTTG GGGTTAGCTA TATAGCTAAC   35400
CCCAAATCAT ATCTAACTTT ACACTGCATC TAATTCCAAA CAGTATCCAG CCAAAAGCCT   35460
AAACTATTGT TGACTCAGCG CTAAAATATG CGATGCAACA AACAAGTCTT GGATCGCAAT   35520
ACCTGAGCTA TCAAAAATGG TCACCTCATC AGCACTTTGA CGTCCTGTTG CGGACTCGTT   35580
TATCACCTGA CCAATCTCAA TTATCGGCGT ATTTCTGCTA TGTTGAAACT CACCAATAAC   35640
AATAGATTGA GAAGCAAAGT CGCAAAACAA GCGAGCATGA CTATATAGGT CAGTTGGCAA   35700
CTCTTGCTTA CCCACTTTAT CAGCGCCCAT TGCAGAAATA TGCGTTCCTG CTTGTACCCA   35760
CTGCGCTTCA AATAAAGGCG CTTGAGCTGT GGTTGCTGTG ATAATAATAT CTGCTTGTTC   35820
ACAAGCAGCT TGTGCATCAC AAGCTTCGGC ATTAATGCCT TTTCTAATA AACGCTTAAC    35880
CAAGTTTTCA GTTTGCTAG CACTACGGCC AACTACCAAT ACCTTAGTTA ATGAACGAAC    35940
CTTGCTCACT GCTAGCACTT CATATTCAGC CTGATGACCG GTACCAAAAA CAGTTAATAC   36000
CGTAGCATCT TCTCTCGCGA GGTAACTCAC TGCTACTGCA TCGGCAGCAC CAGTGCGGTA   36060
AGCATTAACG GTAGTGGCAG CAATCACCGN CTGCAACATA CCGGTTAATG GATCGAGTAA   36120
AAATACGTTA GTGCCGTGGC ATGGTAAACC ATGTTTATGG TTATCAGGCC AATAGCTGCC   36180
TGTTTTCCAG CCGACAAGGT TTGGCGTTGA AGCCGACTTT AATGAGAACA TTTCATTAAG   36240
GTTCGCGCCC TGTGCATTAA CTACCGGGAA CAAGGTTGCT TTATCATCTA CGGCAGCGAC   36300
AAACGCTTCT TAACAGCGA TATAAGCCAG CTCATGGGAG ATGAGCTTTG ATGTTTGCGC    36360
TTCAGTTAAA TAGATCATAT TACCACCCCT GCACTCGATT CCAGATCTCA TAGCCACCAT   36420
TATCACCATC AGTATCAAAT ACATGGTACT GAGCGTGCAT TGAAGCTGTT GCACAGGCGT   36480
GGTTCGGCAA AATATGTAGA CGACTACCTA CCGGGAACTG CGCTAAATCA ATAACGCCGC   36540
CATCAACTGC TTCAATAATG CCGTGCTCTT GATTAACAGT TATAACCTGT AGACCTGATA   36600
ACACGTGACC GCTGTCGTCA CACACTAAAC CATAACCACA ATCTTTGGC TGCTCTGCAG    36660
TACCTCTATC ACCCGAAAGA GCCATCCAAC CCGCATCAAT GAAAATCCAG TTTTTATCAG   36720
GATTATGACC AATAACACTG GTCACTACCG TTGCGGCAAT ATCAGTTAAC TGACACACGT   36780
TTAGCCCTGC CATGACTAAA TCGAAGAAGG TGTACACACC CGCTCTAACC TCGGTGATCC   36840
CATCAAGGTT TTGATAGCTT TGCGCTGTTG GTGTTGAACC AATACTAACG ATGTCACATT   36900
GCATACCCGC TGCGCGAATG CGTCAGCAGC TTGTACAGCC GCTGCAACTT CATTTGCGC    36960
CGCATCAATT AATTGCTGTT TTTCAAAACA TTGATATGAC TCACCAGCGT GAGTGAGTAC   37020
GCCGTGAAAA CTCGCTGCGC CAGACGTTAG TATCTGAGCA ATTTCAATCA ACTTATCGGC   37080
TTCCGGTGGA ATACCACCAC GATGGCCATC ACAATCAATT TCAATTAATG CTGGTATTTG   37140
GCAGTCATAA GAACCACAGA AATGATTTAG CTGATGCGCT TGCTCAACAC TATCAAGTAA   37200
AACTCTTGCA TTAATACCTT GGTCCAACAT TTTAGCAATA CGCGGCAACT TACCATCGGC   37260
AATACCTACT GCATAAATAA TGTCTGTGTA ACCTTTAGAT GCTAAGGCCT CGGCCTCTTT   37320
TACCGTTGAT ACAGTGACTG GTGAGTTTTT AGTGGGTAAT AAAAACTCGG CTGCTTCAAG   37380
TGATCTTAAC GTTTTAAAAT GCGGTCTTAG GTTTGCACCT AATCCTTCAA TTTTTTGGCG   37440
TAGTTGACTG AGGTTATTAA TAAATACTGG CTTATTTACA TATAAAAACG GTGTATCAAT   37500
TGCTTGATAC TGACTTTGCT GAGTCGTGGA AAGTATTTGA GTAGATGGCA TCTTTAATAT   37560
CCTAGTTCAT CAATCAATCT AACAAGTTTG ATGCCTAGCC ACAGTGGCTT GTATTCATGA   37620
TGCTTTGGAA AATGCTTATA TTCAAAGTAT TTGAAAGACA TCAAACTTCT TGTTTAATGC   37680
```

|       |       |       |       |       |       |       |
|---|---|---|---|---|---|---|
| TCAGTATCCA | CCAGCACGCA | TTTATTTTAT | ATTAACTATT | ATCAAGATAT | AGATTAGGTT | 37740 |
| CAAACCAAAT | GATTAGTACT | GAAGATCTAC | GTTTATCAG  | CGTAATCGCC | AGTCATCGCA | 37800 |
| CCTTAGCTGA | TGCCGCTAGA | ACACTAAATA | TCACGCCACC | ATCAGTGACA | TTAAGGTTGC | 37860 |
| AGCATATTGA | AAAGAAACTA | TCGATTAGCC | TGATC      |            |            | 37895 |

( 2 ) INFORMATION FOR SEQ ID NO:2:

( i ) SEQUENCE CHARACTERISTICS:
        ( A ) LENGTH: 1983 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Shewanella putrefaciens SCRC-2874 (FERM BP- 1625)

( i x ) FEATURE:
        ( A ) NAME/KEY: CDS
        ( B ) LOCATION: 1..1983

( i x ) FEATURE:
        ( A ) NAME/KEY: mat_peptide
        ( B ) LOCATION: 1..1983

( x i ) SEQUENCE DESCRIPTION: SEQ ID NO:2:

| ATG | AAA | CAG | ACT | CTA | ATG | GCT | ATC | TCA | ATC | ATG | TCG | CTT | TTT | TCA | TTC | 48 |
|---|---|---|---|---|---|---|---|---|---|---|---|---|---|---|---|---|
| Met | Lys | Gln | Thr | Leu | Met | Ala | Ile | Ser | Ile | Met | Ser | Leu | Phe | Ser | Phe |  |
| 1 |  |  |  | 5 |  |  |  |  | 10 |  |  |  |  | 15 |  |  |
| AAT | GCG | CTA | GCA | GCG | CAA | CAT | GAA | CAT | GAC | CAC | ATC | ACT | GTT | GAT | TAC | 96 |
| Asn | Ala | Leu | Ala | Ala | Gln | His | Glu | His | Asp | His | Ile | Thr | Val | Asp | Tyr |  |
|  |  |  | 20 |  |  |  |  | 25 |  |  |  |  | 30 |  |  |  |
| GAA | GGG | AAA | GCC | GCA | ACA | GAA | CAC | ACC | ATA | GCT | CAC | AAC | CAA | GCT | GTA | 144 |
| Glu | Gly | Lys | Ala | Ala | Thr | Glu | His | Thr | Ile | Ala | His | Asn | Gln | Ala | Val |  |
|  |  | 35 |  |  |  |  | 40 |  |  |  |  | 45 |  |  |  |  |
| GCT | AAA | ACA | CTT | AAC | TTT | GCC | GAC | ACG | CGT | GCA | TTT | GAG | CAA | TCG | TCT | 192 |
| Ala | Lys | Thr | Leu | Asn | Phe | Ala | Asp | Thr | Arg | Ala | Phe | Glu | Gln | Ser | Ser |  |
|  | 50 |  |  |  |  | 55 |  |  |  |  | 60 |  |  |  |  |  |
| AAA | AAT | CTA | GTC | GCC | AAG | TTT | GAT | AAA | GCA | ACT | GCC | GAT | ATA | TTA | CGT | 240 |
| Lys | Asn | Leu | Val | Ala | Lys | Phe | Asp | Lys | Ala | Thr | Ala | Asp | Ile | Leu | Arg |  |
| 65 |  |  |  | 70 |  |  |  |  | 75 |  |  |  |  |  | 80 |  |
| GCC | GAA | TTT | GCT | TTT | ATT | AGC | GAT | GAA | ATC | CCT | GAC | TCG | GTT | AAC | CCG | 288 |
| Ala | Glu | Phe | Ala | Phe | Ile | Ser | Asp | Glu | Ile | Pro | Asp | Ser | Val | Asn | Pro |  |
|  |  |  |  | 85 |  |  |  |  | 90 |  |  |  |  | 95 |  |  |
| TCT | CTC | TAC | CGT | CAG | GCT | CAG | CTT | AAT | ATG | GTG | CCT | AAT | GGT | CTG | TAT | 336 |
| Ser | Leu | Tyr | Arg | Gln | Ala | Gln | Leu | Asn | Met | Val | Pro | Asn | Gly | Leu | Tyr |  |
|  |  |  | 100 |  |  |  |  | 105 |  |  |  |  | 110 |  |  |  |
| AAA | GTG | AGC | GAT | GGC | ATT | TAC | CAG | GTC | CGC | GGT | ACC | GAC | TTA | TCT | AAC | 384 |
| Lys | Val | Ser | Asp | Gly | Ile | Tyr | Gln | Val | Arg | Gly | Thr | Asp | Leu | Ser | Asn |  |
|  |  | 115 |  |  |  |  | 120 |  |  |  |  | 125 |  |  |  |  |
| CTT | ACA | CTT | ATC | CGC | AGT | GAT | AAC | GGT | TGG | ATA | GCA | TAC | GAT | GTT | TTG | 432 |
| Leu | Thr | Leu | Ile | Arg | Ser | Asp | Asn | Gly | Trp | Ile | Ala | Tyr | Asp | Val | Leu |  |
|  | 130 |  |  |  |  | 135 |  |  |  |  | 140 |  |  |  |  |  |
| TTA | ACC | AAA | GAA | GCA | GCA | AAA | GCC | TCA | CTA | CAA | TTT | GCG | TTA | AAG | AAT | 480 |
| Leu | Thr | Lys | Glu | Ala | Ala | Lys | Ala | Ser | Leu | Gln | Phe | Ala | Leu | Lys | Asn |  |
| 145 |  |  |  | 150 |  |  |  |  | 155 |  |  |  |  |  | 160 |  |
| CTA | CCT | AAA | GAT | GGC | GAT | TTA | CCC | GTT | GTT | GCG | ATG | ATT | TAC | TCC | CAT | 528 |
| Leu | Pro | Lys | Asp | Gly | Asp | Leu | Pro | Val | Val | Ala | Met | Ile | Tyr | Ser | His |  |
|  |  |  | 165 |  |  |  |  | 170 |  |  |  |  | 175 |  |  |  |
| AGC | CAT | GCG | GAC | CAC | TTT | GGC | GGA | GCT | CGC | GGT | GTT | CAA | GAG | ATG | TTC | 576 |
| Ser | His | Ala | Asp | His | Phe | Gly | Gly | Ala | Arg | Gly | Val | Gln | Glu | Met | Phe |  |
|  |  |  | 180 |  |  |  |  | 185 |  |  |  |  | 190 |  |  |  |

```
CCT GAT GTC AAA GTC TAC GGC TCA GAT AAC ATC ACT AAA GAA ATT GTC         624
Pro Asp Val Lys Val Tyr Gly Ser Asp Asn Ile Thr Lys Glu Ile Val
        195                 200                 205

GAT GAG AAC GTA CTT GCC GGT AAC GCC ATG AGC CGC CGC GCA GCT TAT         672
Asp Glu Asn Val Leu Ala Gly Asn Ala Met Ser Arg Arg Ala Ala Tyr
210                 215                 220

CAA TAC GGC GCA ACA CTG GGC AAA CAT GAC CAC GGT ATT GTT GAT GCT         720
Gln Tyr Gly Ala Thr Leu Gly Lys His Asp His Gly Ile Val Asp Ala
225                 230                 235                 240

GCG CTA GGT AAA GGT CTA TCA AAA GGT GAA ATC ACT TAC GTC GCC CCA         768
Ala Leu Gly Lys Gly Leu Ser Lys Gly Glu Ile Thr Tyr Val Ala Pro
            245                 250                 255

GAC TAC ACC TTA AAC AGT GAA GGC AAA TGG GAA ACG CTG ACG ATT GAT         816
Asp Tyr Thr Leu Asn Ser Glu Gly Lys Trp Glu Thr Leu Thr Ile Asp
                260                 265                 270

GGT CTA GAG ATG GTG TTT ATG GAT GCC TCG GGC ACC GAA GCT GAG TCA         864
Gly Leu Glu Met Val Phe Met Asp Ala Ser Gly Thr Glu Ala Glu Ser
        275                 280                 285

GAA ATG ATC ACT TAT ATT CCC TCT AAA AAA GCG CTC TGG ACG GCG GAG         912
Glu Met Ile Thr Tyr Ile Pro Ser Lys Lys Ala Leu Trp Thr Ala Glu
290                 295                 300

CTT ACC TAT CAA GGT ATG CAC AAC ATT TAT ACG CTG CGC GGC GCT AAA         960
Leu Thr Tyr Gln Gly Met His Asn Ile Tyr Thr Leu Arg Gly Ala Lys
305                 310                 315                 320

GTA CGT GAT GCG CTC AAG TGG TCA AAA GAT ATC AAC GAA ATG ATC AAT        1008
Val Arg Asp Ala Leu Lys Trp Ser Lys Asp Ile Asn Glu Met Ile Asn
            325                 330                 335

GCC TTT GGT CAA GAT GTC GAA GTG CTG TTT GCC TCG CAC TCT GCG CCA        1056
Ala Phe Gly Gln Asp Val Glu Val Leu Phe Ala Ser His Ser Ala Pro
                340                 345                 350

GTG TGG GGT AAC CAA GCG ATC AAC GAT TTC TTA CGC CTA CAG CGT GAT        1104
Val Trp Gly Asn Gln Ala Ile Asn Asp Phe Leu Arg Leu Gln Arg Asp
        355                 360                 365

AAC TAC GGC CTA GTG CAC AAT CAA ACC TTG AGA CTT GCC AAC GAT GGT        1152
Asn Tyr Gly Leu Val His Asn Gln Thr Leu Arg Leu Ala Asn Asp Gly
370                 375                 380

GTC GGT ATA CAA GAT ATT GGC GAT GCG ATT CAA GAC ACG ATT CCA GAG        1200
Val Gly Ile Gln Asp Ile Gly Asp Ala Ile Gln Asp Thr Ile Pro Glu
385                 390                 395                 400

TCT ATC TAC AAG ACG TGG CAT ACC AAT GGT TAC CAC GGC ACT TAT AGC        1248
Ser Ile Tyr Lys Thr Trp His Thr Asn Gly Tyr His Gly Thr Tyr Ser
            405                 410                 415

CAT AAC GCT AAA GCG GTT TAT AAC AAG TAT CTA GGC TAC TTC GAT ATG        1296
His Asn Ala Lys Ala Val Tyr Asn Lys Tyr Leu Gly Tyr Phe Asp Met
                420                 425                 430

AAC CCA GCC AAC CTT AAT CCG CTG CCA ACC AAG CAA GAA TCT GCC AAG        1344
Asn Pro Ala Asn Leu Asn Pro Leu Pro Thr Lys Gln Glu Ser Ala Lys
        435                 440                 445

TTT GTC GAA TAC ATG GGC GGC GCA GAT GCC GCA ATT AAG CGC GCT AAA        1392
Phe Val Glu Tyr Met Gly Gly Ala Asp Ala Ala Ile Lys Arg Ala Lys
450                 455                 460

GAT GAT TAC GCT CAA GGT GAA TAC CGC TTT GTT GCA ACG GCA TTA AAT        1440
Asp Asp Tyr Ala Gln Gly Glu Tyr Arg Phe Val Ala Thr Ala Leu Asn
465                 470                 475                 480

AAG GTG GTG ATG GCC GAG CCA GAA AAT GAC TCC GCT CGT CAA TTG CTA        1488
Lys Val Val Met Ala Glu Pro Glu Asn Asp Ser Ala Arg Gln Leu Leu
            485                 490                 495

GCC GAT ACC TAT GAG CAA CTT GGT TAT CAA GCA GAA GGG GCT GGC TGG        1536
Ala Asp Thr Tyr Glu Gln Leu Gly Tyr Gln Ala Glu Gly Ala Gly Trp
                500                 505                 510
```

| | | | | | | | | | | | | | | | | |
|---|---|---|---|---|---|---|---|---|---|---|---|---|---|---|---|---|
| AGA | AAC | ATT | TAC | TTA | ACT | GGC | GCA | CAA | GAG | CTA | CGA | GTA | GGT | ATT | CAA | 1584 |
| Arg | Asn | Ile | Tyr | Leu | Thr | Gly | Ala | Gln | Glu | Leu | Arg | Val | Gly | Ile | Gln | |
| | | 515 | | | | 520 | | | | | 525 | | | | | |
| GCT | GGC | GCG | CCT | AAA | ACC | GCA | TCG | GCA | GAT | GTC | ATC | AGT | GAA | ATG | GAC | 1632 |
| Ala | Gly | Ala | Pro | Lys | Thr | Ala | Ser | Ala | Asp | Val | Ile | Ser | Glu | Met | Asp | |
| 530 | | | | | 535 | | | | | 540 | | | | | | |
| ATG | CCG | ACT | CTA | TTT | GAC | TTC | CTC | GCG | GTG | AAG | ATT | GAT | AGT | CAA | CAG | 1680 |
| Met | Pro | Thr | Leu | Phe | Asp | Phe | Leu | Ala | Val | Lys | Ile | Asp | Ser | Gln | Gln | |
| 545 | | | | | 550 | | | | | 555 | | | | | 560 | |
| GCG | GCT | AAG | CAC | GGC | TTA | GTT | AAG | ATG | AAT | GTT | ATC | ACC | CCT | GAT | ACT | 1728 |
| Ala | Ala | Lys | His | Gly | Leu | Val | Lys | Met | Asn | Val | Ile | Thr | Pro | Asp | Thr | |
| | | | | 565 | | | | | 570 | | | | | 575 | | |
| AAA | GAT | ATT | CTC | TAT | ATT | GAG | CTA | AGC | AAC | GGT | AAC | TTA | AGC | AAC | GCA | 1776 |
| Lys | Asp | Ile | Leu | Tyr | Ile | Glu | Leu | Ser | Asn | Gly | Asn | Leu | Ser | Asn | Ala | |
| | | | 580 | | | | | 585 | | | | | 590 | | | |
| GTG | GTC | GAC | AAA | GAG | CAA | GCA | GCT | GAC | GCA | AAC | CTT | ATG | GTT | AAT | AAA | 1824 |
| Val | Val | Asp | Lys | Glu | Gln | Ala | Ala | Asp | Ala | Asn | Leu | Met | Val | Asn | Lys | |
| | | 595 | | | | 600 | | | | | 605 | | | | | |
| GCT | GAC | GTT | AAC | CGC | ATC | TTA | CTT | GGC | CAA | GTA | ACC | CTA | AAA | GCG | TTA | 1872 |
| Ala | Asp | Val | Asn | Arg | Ile | Leu | Leu | Gly | Gln | Val | Thr | Leu | Lys | Ala | Leu | |
| | 610 | | | | | 615 | | | | | 620 | | | | | |
| TTA | GCC | AGC | GGC | GAT | GCC | AAG | CTC | ACT | GGT | GAT | AAA | ACG | GCA | TTT | AGT | 1920 |
| Leu | Ala | Ser | Gly | Asp | Ala | Lys | Leu | Thr | Gly | Asp | Lys | Thr | Ala | Phe | Ser | |
| 625 | | | | 630 | | | | | 635 | | | | | 640 | | |
| AAA | ATA | GCC | GAT | AGC | ATG | GTC | GAG | TTT | ACA | CCT | GAC | TTC | GAA | ATC | GTA | 1968 |
| Lys | Ile | Ala | Asp | Ser | Met | Val | Glu | Phe | Thr | Pro | Asp | Phe | Glu | Ile | Val | |
| | | | | 645 | | | | | 650 | | | | | 655 | | |
| CCA | ACG | CCT | GTT | AAA | | | | | | | | | | | | 1983 |
| Pro | Thr | Pro | Val | Lys | | | | | | | | | | | | |
| | | | 660 | | | | | | | | | | | | | |

( 2 ) INFORMATION FOR SEQ ID NO:3:

( i ) SEQUENCE CHARACTERISTICS:
      ( A ) LENGTH: 661 amino acids
      ( B ) TYPE: amino acid
      ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Met | Lys | Gln | Thr | Leu | Met | Ala | Ile | Ser | Ile | Met | Ser | Leu | Phe | Phe |
| 1 | | | | 5 | | | | | 10 | | | | | 15 |
| Asn | Ala | Leu | Ala | Ala | Gln | His | Glu | His | Asp | His | Ile | Thr | Val | Asp | Tyr |
| | | | 20 | | | | | 25 | | | | | 30 | | |
| Glu | Gly | Lys | Ala | Ala | Thr | Glu | His | Thr | Ile | Ala | His | Asn | Gln | Ala | Val |
| | | 35 | | | | | 40 | | | | | 45 | | | |
| Ala | Lys | Thr | Leu | Asn | Phe | Ala | Asp | Thr | Arg | Ala | Phe | Glu | Gln | Ser | Ser |
| | 50 | | | | | 55 | | | | | 60 | | | | |
| Lys | Asn | Leu | Val | Ala | Lys | Phe | Asp | Lys | Ala | Thr | Ala | Asp | Ile | Leu | Arg |
| 65 | | | | | 70 | | | | | 75 | | | | | 80 |
| Ala | Glu | Phe | Ala | Phe | Ile | Ser | Asp | Glu | Ile | Pro | Asp | Ser | Val | Asn | Pro |
| | | | | 85 | | | | | 90 | | | | | 95 | |
| Ser | Leu | Tyr | Arg | Gln | Ala | Gln | Leu | Asn | Met | Val | Pro | Asn | Gly | Leu | Tyr |
| | | | 100 | | | | | 105 | | | | | 110 | | |
| Lys | Val | Ser | Asp | Gly | Ile | Tyr | Gln | Val | Arg | Gly | Thr | Asp | Leu | Ser | Asn |
| | | 115 | | | | | 120 | | | | | 125 | | | |
| Leu | Thr | Leu | Ile | Arg | Ser | Asp | Asn | Gly | Trp | Ile | Ala | Tyr | Asp | Val | Leu |
| | 130 | | | | | 135 | | | | | 140 | | | | |

| Leu | Thr | Lys | Glu | Ala | Ala | Lys | Ala | Ser | Leu | Gln | Phe | Ala | Leu | Lys | Asn |
| 145 | | | | 150 | | | | | 155 | | | | | | 160 |

| Leu | Pro | Lys | Asp | Gly | Asp | Leu | Pro | Val | Val | Ala | Met | Ile | Tyr | Ser | His |
| | | | | 165 | | | | 170 | | | | | | 175 | |

| Ser | His | Ala | Asp | His | Phe | Gly | Gly | Ala | Arg | Gly | Val | Gln | Glu | Met | Phe |
| | | | 180 | | | | | 185 | | | | | 190 | | |

| Pro | Asp | Val | Lys | Val | Tyr | Gly | Ser | Asp | Asn | Ile | Thr | Lys | Glu | Ile | Val |
| | | 195 | | | | | 200 | | | | | 205 | | | |

| Asp | Glu | Asn | Val | Leu | Ala | Gly | Asn | Ala | Met | Ser | Arg | Arg | Ala | Ala | Tyr |
| | 210 | | | | | 215 | | | | | 220 | | | | |

| Gln | Tyr | Gly | Ala | Thr | Leu | Gly | Lys | His | Asp | His | Gly | Ile | Val | Asp | Ala |
| 225 | | | | | 230 | | | | | 235 | | | | | 240 |

| Ala | Leu | Gly | Lys | Gly | Leu | Ser | Lys | Gly | Glu | Ile | Thr | Tyr | Val | Ala | Pro |
| | | | | 245 | | | | | 250 | | | | | 255 | |

| Asp | Tyr | Thr | Leu | Asn | Ser | Glu | Gly | Lys | Trp | Glu | Thr | Leu | Thr | Ile | Asp |
| | | | 260 | | | | | 265 | | | | | 270 | | |

| Gly | Leu | Glu | Met | Val | Phe | Met | Asp | Ala | Ser | Gly | Thr | Glu | Ala | Glu | Ser |
| | | 275 | | | | | 280 | | | | | 285 | | | |

| Glu | Met | Ile | Thr | Tyr | Ile | Pro | Ser | Lys | Lys | Ala | Leu | Trp | Thr | Ala | Glu |
| | 290 | | | | | 295 | | | | | 300 | | | | |

| Leu | Thr | Tyr | Gln | Gly | Met | His | Asn | Ile | Tyr | Thr | Leu | Arg | Gly | Ala | Lys |
| 305 | | | | | 310 | | | | | 315 | | | | | 320 |

| Val | Arg | Asp | Ala | Leu | Lys | Trp | Ser | Lys | Asp | Ile | Asn | Glu | Met | Ile | Asn |
| | | | | 325 | | | | | 330 | | | | | 335 | |

| Ala | Phe | Gly | Gln | Asp | Val | Glu | Val | Leu | Phe | Ala | Ser | His | Ser | Ala | Pro |
| | | | 340 | | | | | 345 | | | | | 350 | | |

| Val | Trp | Gly | Asn | Gln | Ala | Ile | Asn | Asp | Phe | Leu | Arg | Leu | Gln | Arg | Asp |
| | | | 355 | | | | | 360 | | | | | 365 | | |

| Asn | Tyr | Gly | Leu | Val | His | Asn | Gln | Thr | Leu | Arg | Leu | Ala | Asn | Asp | Gly |
| | | 370 | | | | | 375 | | | | | 380 | | | |

| Val | Gly | Ile | Gln | Asp | Ile | Gly | Asp | Ala | Ile | Gln | Asp | Thr | Ile | Pro | Glu |
| 385 | | | | | 390 | | | | | 395 | | | | | 400 |

| Ser | Ile | Tyr | Lys | Thr | Trp | His | Thr | Asn | Gly | Tyr | His | Gly | Thr | Tyr | Ser |
| | | | | 405 | | | | | 410 | | | | | 415 | |

| His | Asn | Ala | Lys | Ala | Val | Tyr | Asn | Lys | Tyr | Leu | Gly | Tyr | Phe | Asp | Met |
| | | | 420 | | | | | 425 | | | | | 430 | | |

| Asn | Pro | Ala | Asn | Leu | Asn | Pro | Leu | Pro | Thr | Lys | Gln | Glu | Ser | Ala | Lys |
| | | 435 | | | | | 440 | | | | | 445 | | | |

| Phe | Val | Glu | Tyr | Met | Gly | Gly | Ala | Asp | Ala | Ala | Ile | Lys | Arg | Ala | Lys |
| | 450 | | | | | 455 | | | | | 460 | | | | |

| Asp | Asp | Tyr | Ala | Gln | Gly | Glu | Tyr | Arg | Phe | Val | Ala | Thr | Ala | Leu | Asn |
| 465 | | | | | 470 | | | | | 475 | | | | | 480 |

| Lys | Val | Val | Met | Ala | Glu | Pro | Glu | Asn | Asp | Ser | Ala | Arg | Gln | Leu | Leu |
| | | | | 485 | | | | | 490 | | | | | 495 | |

| Ala | Asp | Thr | Tyr | Glu | Gln | Leu | Gly | Tyr | Gln | Ala | Glu | Gly | Ala | Gly | Trp |
| | | | 500 | | | | | 505 | | | | | 510 | | |

| Arg | Asn | Ile | Tyr | Leu | Thr | Gly | Ala | Gln | Glu | Leu | Arg | Val | Gly | Ile | Gln |
| | | 515 | | | | | 520 | | | | | 525 | | | |

| Ala | Gly | Ala | Pro | Lys | Thr | Ala | Ser | Ala | Asp | Val | Ile | Ser | Glu | Met | Asp |
| | 530 | | | | | 535 | | | | | 540 | | | | |

| Met | Pro | Thr | Leu | Phe | Asp | Phe | Leu | Ala | Val | Lys | Ile | Asp | Ser | Gln | Gln |
| 545 | | | | | 550 | | | | | 555 | | | | | 560 |

| Ala | Ala | Lys | His | Gly | Leu | Val | Lys | Met | Asn | Val | Ile | Thr | Pro | Asp | Thr |
| | | | | 565 | | | | | 570 | | | | | 575 | |

```
Lys  Asp  Ile  Leu  Tyr  Ile  Glu  Leu  Ser  Asn  Gly  Asn  Leu  Ser  Asn  Ala
               580                      585                     590

Val  Val  Asp  Lys  Glu  Gln  Ala  Ala  Asp  Ala  Asn  Leu  Met  Val  Asn  Lys
          595                      600                     605

Ala  Asp  Val  Asn  Arg  Ile  Leu  Leu  Gly  Gln  Val  Thr  Leu  Lys  Ala  Leu
     610                      615                     620

Leu  Ala  Ser  Gly  Asp  Ala  Lys  Leu  Thr  Gly  Asp  Lys  Thr  Ala  Phe  Ser
625                      630                     635                          640

Lys  Ile  Ala  Asp  Ser  Met  Val  Glu  Phe  Thr  Pro  Asp  Phe  Glu  Ile  Val
               645                      650                     655

Pro  Thr  Pro  Val  Lys
               660
```

( 2 ) INFORMATION FOR SEQ ID NO:4:

( i ) SEQUENCE CHARACTERISTICS:
        ( A ) LENGTH: 831 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Shewanella putrefaciens SCRC-2874 (FERM BP- 1625)

( i x ) FEATURE:
        ( A ) NAME/KEY: CDS
        ( B ) LOCATION: 1..831

( i x ) FEATURE:
        ( A ) NAME/KEY: mat_peptide
        ( B ) LOCATION: 1..831

( x i ) SEQUENCE DESCRIPTION: SEQ ID NO:4:

```
ATG  GTA  AGA  GGC  TAT  TTG  CGC  GCT  TTA  TTG  TCA  CAA  CAT  AGT  GAA  ATA        48
Met  Val  Arg  Gly  Tyr  Leu  Arg  Ala  Leu  Leu  Ser  Gln  His  Ser  Glu  Ile
 1                    5                        10                       15

CGC  CCC  AAT  GAA  TGG  CGC  TTT  GAA  TAT  GGC  GAC  AAA  GGT  AAG  CCT  AGA        96
Arg  Pro  Asn  Glu  Trp  Arg  Phe  Glu  Tyr  Gly  Asp  Lys  Gly  Lys  Pro  Arg
                     20                       25                       30

TTG  AGT  GAT  GCG  CAA  TTT  GCT  CAA  ACC  GGG  GTC  CAC  TTT  AAT  GTG  AGT       144
Leu  Ser  Asp  Ala  Gln  Phe  Ala  Gln  Thr  Gly  Val  His  Phe  Asn  Val  Ser
               35                       40                       45

CAT  AGT  GGA  GAT  TGG  CTA  TTA  GTA  GGC  ATT  TGC  ACT  GCT  GAT  AAT  AAA       192
His  Ser  Gly  Asp  Trp  Leu  Leu  Val  Gly  Ile  Cys  Thr  Ala  Asp  Asn  Lys
          50                       55                       60

GGC  GCC  AGT  CAG  GCA  AGC  AAG  GAG  GAA  ACT  GAC  TCT  GCT  AGT  ATT  GAG       240
Gly  Ala  Ser  Gln  Ala  Ser  Lys  Glu  Glu  Thr  Asp  Ser  Ala  Ser  Ile  Glu
65                       70                       75                          80

TTT  GGC  GTC  GAC  ATT  GAG  CGT  TGC  CGT  AAC  AGC  ACC  AAT  ATC  CAC  TCT       288
Phe  Gly  Val  Asp  Ile  Glu  Arg  Cys  Arg  Asn  Ser  Thr  Asn  Ile  His  Ser
                    85                       90                       95

ATT  CTT  AGT  CAT  TAT  TTC  TCT  GAA  TCA  GAA  AAG  CGA  GCC  TTG  TTA  GCG       336
Ile  Leu  Ser  His  Tyr  Phe  Ser  Glu  Ser  Glu  Lys  Arg  Ala  Leu  Leu  Ala
              100                      105                      110

TTA  CCA  GAG  GCC  TTG  CAG  CGA  GAC  CGC  TTT  TTT  GAT  TTG  TGG  GCG  CTC       384
Leu  Pro  Glu  Ala  Leu  Gln  Arg  Asp  Arg  Phe  Phe  Asp  Leu  Trp  Ala  Leu
         115                      120                      125

AAG  GAG  TCT  TAC  ATT  AAA  GCG  AAA  GGA  CTT  GGG  CTG  GCA  TTA  TCG  CTA       432
Lys  Glu  Ser  Tyr  Ile  Lys  Ala  Lys  Gly  Leu  Gly  Leu  Ala  Leu  Ser  Leu
              130                      135                      140
```

```
AAA  TCT  TTT  GCG  TTT  GAC  TTC  TCT  GCA  CTG  AGC  GAA  ACT  TTT  CTT  GGA    480
Lys  Ser  Phe  Ala  Phe  Asp  Phe  Ser  Ala  Leu  Ser  Glu  Thr  Phe  Leu  Gly
145            150                 155                 160

GTT  AAT  GCA  CCT  AAA  AGC  TTG  AGC  CAT  TGT  GTT  GAT  ATT  TCC  GAT  GCT    528
Val  Asn  Ala  Pro  Lys  Ser  Leu  Ser  His  Cys  Val  Asp  Ile  Ser  Asp  Ala
               165                 170                 175

ATT  GCG  GAT  CAC  AAG  GTT  GAG  CAT  CAA  CTT  AAT  CAG  CGA  CAG  GTT  TTG    576
Ile  Ala  Asp  His  Lys  Val  Glu  His  Gln  Leu  Asn  Gln  Arg  Gln  Val  Leu
               180                 185                 190

TTA  AAA  CAA  GAT  ATT  GGT  CTT  GCT  TTA  CTA  GAG  TCG  AGT  TCT  AAT  AAG    624
Leu  Lys  Gln  Asp  Ile  Gly  Leu  Ala  Leu  Leu  Glu  Ser  Ser  Ser  Asn  Lys
          195                 200                 205

CCT  AAC  GCT  GAG  CCA  CAA  AAG  TCT  GGT  TTA  GGT  TTG  ATT  GAG  GCT  AAA    672
Pro  Asn  Ala  Glu  Pro  Gln  Lys  Ser  Gly  Leu  Gly  Leu  Ile  Glu  Ala  Lys
     210                 215                 220

GAA  CAG  CAA  ATG  AAC  GCT  GCT  GAT  AAT  TGG  CAT  TGT  TTA  CTG  GGC  CAT    720
Glu  Gln  Gln  Met  Asn  Ala  Ala  Asp  Asn  Trp  His  Cys  Leu  Leu  Gly  His
225                 230                 235                 240

CTT  GAT  GAT  AGT  TAT  CGT  TTT  GCA  CTG  AGT  ATT  GGT  CAG  TGT  CAG  CAA    768
Leu  Asp  Asp  Ser  Tyr  Arg  Phe  Ala  Leu  Ser  Ile  Gly  Gln  Cys  Gln  Gln
               245                 250                 255

ATA  AGT  ATT  GCA  GCA  GAA  GAA  GTG  AAT  TTT  AAA  GCT  GTT  GTT  CGA  GCT    816
Ile  Ser  Ile  Ala  Ala  Glu  Glu  Val  Asn  Phe  Lys  Ala  Val  Val  Arg  Ala
               260                 265                 270

TCA  GCT  AAG  ACT  AGC                                                           831
Ser  Ala  Lys  Thr  Ser
               275
```

( 2 ) INFORMATION FOR SEQ ID NO:5:

( i ) SEQUENCE CHARACTERISTICS:
        ( A ) LENGTH: 277 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Val  Arg  Gly  Tyr  Leu  Arg  Ala  Leu  Leu  Ser  Gln  His  Ser  Glu  Ile
1              5                   10                  15

Arg  Pro  Asn  Glu  Trp  Arg  Phe  Glu  Tyr  Gly  Asp  Lys  Gly  Lys  Pro  Arg
               20                  25                  30

Leu  Ser  Asp  Ala  Gln  Phe  Ala  Gln  Thr  Gly  Val  His  Phe  Asn  Val  Ser
          35                  40                  45

His  Ser  Gly  Asp  Trp  Leu  Leu  Val  Gly  Ile  Cys  Thr  Ala  Asp  Asn  Lys
     50                  55                  60

Gly  Ala  Ser  Gln  Ala  Ser  Lys  Glu  Glu  Thr  Asp  Ser  Ala  Ser  Ile  Glu
65                  70                  75                  80

Phe  Gly  Val  Asp  Ile  Glu  Arg  Cys  Arg  Asn  Ser  Thr  Asn  Ile  His  Ser
               85                  90                  95

Ile  Leu  Ser  His  Tyr  Phe  Ser  Glu  Ser  Glu  Lys  Arg  Ala  Leu  Leu  Ala
               100                 105                 110

Leu  Pro  Glu  Ala  Leu  Gln  Arg  Asp  Arg  Phe  Phe  Asp  Leu  Trp  Ala  Leu
          115                 120                 125

Lys  Glu  Ser  Tyr  Ile  Lys  Ala  Lys  Gly  Leu  Gly  Leu  Ala  Leu  Ser  Leu
     130                 135                 140

Lys  Ser  Phe  Ala  Phe  Asp  Phe  Ser  Ala  Leu  Ser  Glu  Thr  Phe  Leu  Gly
145            150                 155                 160

Val  Asn  Ala  Pro  Lys  Ser  Leu  Ser  His  Cys  Val  Asp  Ile  Ser  Asp  Ala
               165                 170                 175
```

```
Ile Ala Asp His Lys Val Glu His Gln Leu Asn Gln Arg Gln Val Leu
            180                 185                 190

Leu Lys Gln Asp Ile Gly Leu Ala Leu Leu Glu Ser Ser Ser Asn Lys
        195                 200                 205

Pro Asn Ala Glu Pro Gln Lys Ser Gly Leu Gly Leu Ile Glu Ala Lys
    210                 215                 220

Glu Gln Gln Met Asn Ala Ala Asp Asn Trp His Cys Leu Leu Gly His
225                 230                 235                 240

Leu Asp Asp Ser Tyr Arg Phe Ala Leu Ser Ile Gly Gln Cys Gln Gln
                245                 250                 255

Ile Ser Ile Ala Ala Glu Glu Val Asn Phe Lys Ala Val Val Arg Ala
            260                 265                 270

Ser Ala Lys Thr Ser
            275
```

( 2 ) INFORMATION FOR SEQ ID NO:6:

( i ) SEQUENCE CHARACTERISTICS:
        ( A ) LENGTH: 2910 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Shewanella putrefaciens SCRC-2874 (FERM
            BP- 1625)

( i x ) FEATURE:
        ( A ) NAME/KEY: CDS
        ( B ) LOCATION: 1..2910

( i x ) FEATURE:
        ( A ) NAME/KEY: mat_peptide
        ( B ) LOCATION: 1..2910

( x i ) SEQUENCE DESCRIPTION: SEQ ID NO:6:

```
ATG AGT ATG TTT TTA AAT TCA AAA CTT TCG CGC TCA GTC AAA CTT GCC        48
Met Ser Met Phe Leu Asn Ser Lys Leu Ser Arg Ser Val Lys Leu Ala
1               5                   10                  15

ATA TCC GCA GGC TTA ACA GCC TCG CTA GCT ATG CCT GTT TTT GCA GAA        96
Ile Ser Ala Gly Leu Thr Ala Ser Leu Ala Met Pro Val Phe Ala Glu
            20                  25                  30

GAA ACT GCT GCT GAA GAA CAA ATA GAA AGA GTC GCA GTG ACC GGA TCG       144
Glu Thr Ala Ala Glu Glu Gln Ile Glu Arg Val Ala Val Thr Gly Ser
        35                  40                  45

CGA ATC GCT AAA GCA GAG CTA ACT CAA CCA GCT CCA GTC GTC AGC CTT       192
Arg Ile Ala Lys Ala Glu Leu Thr Gln Pro Ala Pro Val Val Ser Leu
    50                  55                  60

TCA GCC GAA GAA CTG ACA AAA TTT GGT AAT CAA GAT TTA GGT AGC GTA       240
Ser Ala Glu Glu Leu Thr Lys Phe Gly Asn Gln Asp Leu Gly Ser Val
65                  70                  75                  80

CTA GCA GAA TTA CCT GCT ATT GGT GCA ACC AAC ACT ATT ATT GGT AAT       288
Leu Ala Glu Leu Pro Ala Ile Gly Ala Thr Asn Thr Ile Ile Gly Asn
                85                  90                  95

AAC AAT AGC AAC TCA AGC GCA GGT GTT AGC TCA GCA GAC TTG CGT CGT       336
Asn Asn Ser Asn Ser Ser Ala Gly Val Ser Ser Ala Asp Leu Arg Arg
            100                 105                 110

CTA GGT GCT AAC AGA ACC TTA GTA TTA GTC AAC GGT AAG CGC TAC GTT       384
Leu Gly Ala Asn Arg Thr Leu Val Leu Val Asn Gly Lys Arg Tyr Val
        115                 120                 125

GCC GGC CAA CCG GGC TCA GCT GAG GTA GAT TTG TCA ACT ATA CCA ACT       432
```

-continued

| | | | | | | | | | | | | | | |
|---|---|---|---|---|---|---|---|---|---|---|---|---|---|---|
| Ala | Gly | Gln | Pro | Gly | Ser | Ala | Glu | Val | Asp | Leu | Ser | Thr | Ile | Pro | Thr |
| | 130 | | | | 135 | | | | | 140 | | | | | |

| AGC | ATG | ATC | TCG | CGA | GTT | GAG | ATT | GTA | ACC | GGC | GGT | GCT | TCA | GCA | ATT | 480 |
|---|---|---|---|---|---|---|---|---|---|---|---|---|---|---|---|---|
| Ser | Met | Ile | Ser | Arg | Val | Glu | Ile | Val | Thr | Gly | Gly | Ala | Ser | Ala | Ile | |
| 145 | | | | | 150 | | | | | 155 | | | | | 160 | |

| TAT | GGT | TCG | GAC | GCT | GTA | TCA | GGT | GTT | ATC | AAC | GTT | ATC | CTT | AAA | GAA | 528 |
|---|---|---|---|---|---|---|---|---|---|---|---|---|---|---|---|---|
| Tyr | Gly | Ser | Asp | Ala | Val | Ser | Gly | Val | Ile | Asn | Val | Ile | Leu | Lys | Glu | |
| | | | | 165 | | | | | 170 | | | | | 175 | | |

| GAC | TTT | GAA | GGC | TTT | GAG | TTT | AAC | GCA | CGT | ACT | AGC | GGT | TCT | ACT | GAA | 576 |
|---|---|---|---|---|---|---|---|---|---|---|---|---|---|---|---|---|
| Asp | Phe | Glu | Gly | Phe | Glu | Phe | Asn | Ala | Arg | Thr | Ser | Gly | Ser | Thr | Glu | |
| | | | 180 | | | | | 185 | | | | | 190 | | | |

| AGT | GTA | GGC | ACT | CAA | GAG | CAC | TCT | TTT | GAC | ATT | TTG | GGT | GGT | GCA | AAC | 624 |
|---|---|---|---|---|---|---|---|---|---|---|---|---|---|---|---|---|
| Ser | Val | Gly | Thr | Gln | Glu | His | Ser | Phe | Asp | Ile | Leu | Gly | Gly | Ala | Asn | |
| | | 195 | | | | | 200 | | | | | 205 | | | | |

| GTT | GCA | GAT | GGA | CGT | GGT | AAT | GTA | ACC | TTC | TAC | GCA | GGT | TAT | GAA | CGT | 672 |
|---|---|---|---|---|---|---|---|---|---|---|---|---|---|---|---|---|
| Val | Ala | Asp | Gly | Arg | Gly | Asn | Val | Thr | Phe | Tyr | Ala | Gly | Tyr | Glu | Arg | |
| | 210 | | | | | 215 | | | | | 220 | | | | | |

| ACA | AAA | GAA | GTC | ATG | GCT | ACC | GAC | ATT | CGC | CAA | TTC | GAT | GCT | TGG | GGA | 720 |
|---|---|---|---|---|---|---|---|---|---|---|---|---|---|---|---|---|
| Thr | Lys | Glu | Val | Met | Ala | Thr | Asp | Ile | Arg | Gln | Phe | Asp | Ala | Trp | Gly | |
| 225 | | | | | 230 | | | | | 235 | | | | | 240 | |

| ACA | ATT | AAA | AAC | GAA | GCC | GAT | GGT | GGT | GAA | GAT | GAT | GGT | ATT | CCA | GAC | 768 |
|---|---|---|---|---|---|---|---|---|---|---|---|---|---|---|---|---|
| Thr | Ile | Lys | Asn | Glu | Ala | Asp | Gly | Gly | Glu | Asp | Asp | Gly | Ile | Pro | Asp | |
| | | | | 245 | | | | | 250 | | | | | 255 | | |

| AGA | CTA | CGT | GTA | CCA | CGA | GTT | TAT | TCT | GAA | ATG | ATT | AAT | GCT | ACC | GGT | 816 |
|---|---|---|---|---|---|---|---|---|---|---|---|---|---|---|---|---|
| Arg | Leu | Arg | Val | Pro | Arg | Val | Tyr | Ser | Glu | Met | Ile | Asn | Ala | Thr | Gly | |
| | | | 260 | | | | | 265 | | | | | 270 | | | |

| GTT | ATC | AAT | GCA | TTT | GGT | GGT | GGA | ATT | GGT | CGC | TCA | ACC | TTT | GAC | AGT | 864 |
|---|---|---|---|---|---|---|---|---|---|---|---|---|---|---|---|---|
| Val | Ile | Asn | Ala | Phe | Gly | Gly | Gly | Ile | Gly | Arg | Ser | Thr | Phe | Asp | Ser | |
| | | 275 | | | | | 280 | | | | | 285 | | | | |

| AAC | GGC | AAT | CCT | ATT | GCA | CAA | CAA | GAA | CGT | GAT | GGG | ACT | AAC | AGC | TTT | 912 |
|---|---|---|---|---|---|---|---|---|---|---|---|---|---|---|---|---|
| Asn | Gly | Asn | Pro | Ile | Ala | Gln | Gln | Glu | Arg | Asp | Gly | Thr | Asn | Ser | Phe | |
| | 290 | | | | | 295 | | | | | 300 | | | | | |

| GCA | TTT | GGT | TCA | TTC | CCT | AAT | GGC | TGT | GAC | ACA | TGT | TTC | AAC | ACT | GAA | 960 |
|---|---|---|---|---|---|---|---|---|---|---|---|---|---|---|---|---|
| Ala | Phe | Gly | Ser | Phe | Pro | Asn | Gly | Cys | Asp | Thr | Cys | Phe | Asn | Thr | Glu | |
| 305 | | | | | 310 | | | | | 315 | | | | | 320 | |

| GCA | TAC | GAA | AAC | TAT | ATT | CCA | GGG | GTA | GAA | AGA | ATA | AAC | GTT | GGC | TCA | 1008 |
|---|---|---|---|---|---|---|---|---|---|---|---|---|---|---|---|---|
| Ala | Tyr | Glu | Asn | Tyr | Ile | Pro | Gly | Val | Glu | Arg | Ile | Asn | Val | Gly | Ser | |
| | | | | 325 | | | | | 330 | | | | | 335 | | |

| TCA | TTC | AAC | TTT | GAT | TTT | ACC | GAT | AAC | ATT | CAA | TTT | TAC | ACT | GAC | TTC | 1056 |
|---|---|---|---|---|---|---|---|---|---|---|---|---|---|---|---|---|
| Ser | Phe | Asn | Phe | Asp | Phe | Thr | Asp | Asn | Ile | Gln | Phe | Tyr | Thr | Asp | Phe | |
| | | | 340 | | | | | 345 | | | | | 350 | | | |

| AGA | TAT | GTA | AAG | TCA | GAT | ATT | CAG | CAA | CAA | TTT | CAG | CCT | TCA | TTC | CGT | 1104 |
|---|---|---|---|---|---|---|---|---|---|---|---|---|---|---|---|---|
| Arg | Tyr | Val | Lys | Ser | Asp | Ile | Gln | Gln | Gln | Phe | Gln | Pro | Ser | Phe | Arg | |
| | | 355 | | | | | 360 | | | | | 365 | | | | |

| TTT | GGT | AAC | ATT | AAT | ATC | AAT | GTT | GAA | GAT | AAC | GCC | TTT | TTG | AAT | GAC | 1152 |
|---|---|---|---|---|---|---|---|---|---|---|---|---|---|---|---|---|
| Phe | Gly | Asn | Ile | Asn | Ile | Asn | Val | Glu | Asp | Asn | Ala | Phe | Leu | Asn | Asp | |
| | 370 | | | | | 375 | | | | | 380 | | | | | |

| GAC | TTG | CGT | CAG | CAA | ATG | CTC | GAT | GCG | GGT | CAA | ACC | AAT | GCT | AGT | TTT | 1200 |
|---|---|---|---|---|---|---|---|---|---|---|---|---|---|---|---|---|
| Asp | Leu | Arg | Gln | Gln | Met | Leu | Asp | Ala | Gly | Gln | Thr | Asn | Ala | Ser | Phe | |
| 385 | | | | | 390 | | | | | 395 | | | | | 400 | |

| GCC | AAG | TTT | TTT | GAT | GAA | TTA | GGA | AAT | CGC | TCA | GCA | GAA | AAT | AAA | CGC | 1248 |
|---|---|---|---|---|---|---|---|---|---|---|---|---|---|---|---|---|
| Ala | Lys | Phe | Phe | Asp | Glu | Leu | Gly | Asn | Arg | Ser | Ala | Glu | Asn | Lys | Arg | |
| | | | | 405 | | | | | 410 | | | | | 415 | | |

| GAA | CTT | TTC | CGT | TAC | GTA | GGT | GGC | TTT | AAA | GGT | GGC | TTT | GAT | ATT | AGC | 1296 |
|---|---|---|---|---|---|---|---|---|---|---|---|---|---|---|---|---|
| Glu | Leu | Phe | Arg | Tyr | Val | Gly | Gly | Phe | Lys | Gly | Gly | Phe | Asp | Ile | Ser | |
| | | | 420 | | | | | 425 | | | | | 430 | | | |

| GAA | ACC | ATA | TTT | GAT | TAC | GAC | CTT | TAC | TAT | GTT | TAT | GGC | GAG | ACT | AAT | 1344 |
|---|---|---|---|---|---|---|---|---|---|---|---|---|---|---|---|---|
| Glu | Thr | Ile | Phe | Asp | Tyr | Asp | Leu | Tyr | Tyr | Val | Tyr | Gly | Glu | Thr | Asn | |
| | | 435 | | | | | 440 | | | | | 445 | | | | |

| AAC | CGT | CGT | AAA | ACC | CTT | AAT | GAC | CTA | ATT | CCT | GAT | AAC | TTT | GTC | GCA | 1392 |

| | | | | | | | | | | | | | | | |
|---|---|---|---|---|---|---|---|---|---|---|---|---|---|---|---|
| Asn | Arg | Arg | Lys | Thr | Leu | Asn | Asp | Leu | Ile | Pro | Asp | Asn | Phe | Val | Ala |
| | 450 | | | | 455 | | | | | 460 | | | | | |

| GCT | GTC | GAC | TCT | GTT | ATT | GAT | CCT | GAT | ACT | GGC | TTA | GCA | GCG | TGT | CGC | 1440 |
|---|---|---|---|---|---|---|---|---|---|---|---|---|---|---|---|---|
| Ala | Val | Asp | Ser | Val | Ile | Asp | Pro | Asp | Thr | Gly | Leu | Ala | Ala | Cys | Arg | |
| 465 | | | | | 470 | | | | | 475 | | | | | 480 | |

| TCA | CAA | GTA | GCA | AGC | GCT | CAA | GGC | GAT | GAC | TAT | ACA | GAT | CCC | GCG | TCT | 1488 |
|---|---|---|---|---|---|---|---|---|---|---|---|---|---|---|---|---|
| Ser | Gln | Val | Ala | Ser | Ala | Gln | Gly | Asp | Asp | Tyr | Thr | Asp | Pro | Ala | Ser | |
| | | | | 485 | | | | | 490 | | | | | 495 | | |

| GTA | AAT | GGT | AGC | GAC | TGT | GTT | GCT | TAT | AAC | CCA | TTT | GGC | ATG | GGT | CAA | 1536 |
|---|---|---|---|---|---|---|---|---|---|---|---|---|---|---|---|---|
| Val | Asn | Gly | Ser | Asp | Cys | Val | Ala | Tyr | Asn | Pro | Phe | Gly | Met | Gly | Gln | |
| | | | 500 | | | | | 505 | | | | | 510 | | | |

| GCT | TCA | GCA | GAA | GCC | CGC | GAC | TGG | GTT | TCT | GCT | GAT | GTG | ACT | CGT | GAA | 1584 |
|---|---|---|---|---|---|---|---|---|---|---|---|---|---|---|---|---|
| Ala | Ser | Ala | Glu | Ala | Arg | Asp | Trp | Val | Ser | Ala | Asp | Val | Thr | Arg | Glu | |
| | | 515 | | | | | 520 | | | | | 525 | | | | |

| GAC | AAA | ATA | ACT | CAA | CAA | GTG | ATT | GGT | GGT | ACT | CTC | GGT | ACC | GAT | TCT | 1632 |
|---|---|---|---|---|---|---|---|---|---|---|---|---|---|---|---|---|
| Asp | Lys | Ile | Thr | Gln | Gln | Val | Ile | Gly | Gly | Thr | Leu | Gly | Thr | Asp | Ser | |
| 530 | | | | | 535 | | | | | 540 | | | | | | |

| GAA | GAA | CTA | TTT | GAG | CTT | CAA | GGT | GGT | GCA | ATC | GCT | ATG | GTT | GTT | GGT | 1680 |
|---|---|---|---|---|---|---|---|---|---|---|---|---|---|---|---|---|
| Glu | Glu | Leu | Phe | Glu | Leu | Gln | Gly | Gly | Ala | Ile | Ala | Met | Val | Val | Gly | |
| 545 | | | | | 550 | | | | | 555 | | | | | 560 | |

| TTT | GAA | TAC | CGT | GAA | GAA | ACG | TCT | GGT | TCA | ACA | ACC | GAT | GAA | TTT | ACT | 1728 |
|---|---|---|---|---|---|---|---|---|---|---|---|---|---|---|---|---|
| Phe | Glu | Tyr | Arg | Glu | Glu | Thr | Ser | Gly | Ser | Thr | Thr | Asp | Glu | Phe | Thr | |
| | | | 565 | | | | | 570 | | | | | 575 | | | |

| AAA | GCA | GGT | TTC | TTG | ACA | AGC | GCT | GCA | ACG | CCA | GAT | TCT | TAT | GGC | GAA | 1776 |
|---|---|---|---|---|---|---|---|---|---|---|---|---|---|---|---|---|
| Lys | Ala | Gly | Phe | Leu | Thr | Ser | Ala | Ala | Thr | Pro | Asp | Ser | Tyr | Gly | Glu | |
| | | | | 580 | | | | | 585 | | | | | 590 | | |

| TAC | GAC | GTG | ACT | GAG | TAT | TTT | GTT | GAG | GTG | AAC | ATC | CCA | GTA | CTA | AAA | 1824 |
|---|---|---|---|---|---|---|---|---|---|---|---|---|---|---|---|---|
| Tyr | Asp | Val | Thr | Glu | Tyr | Phe | Val | Glu | Val | Asn | Ile | Pro | Val | Leu | Lys | |
| | | | 595 | | | | | 600 | | | | | 605 | | | |

| GAA | TTA | CCT | TTT | GCA | CAT | GAG | TTG | AGC | TTT | GAC | GGT | GCA | TAC | CGT | AAT | 1872 |
|---|---|---|---|---|---|---|---|---|---|---|---|---|---|---|---|---|
| Glu | Leu | Pro | Phe | Ala | His | Glu | Leu | Ser | Phe | Asp | Gly | Ala | Tyr | Arg | Asn | |
| 610 | | | | | 615 | | | | | 620 | | | | | | |

| GCT | GAT | TAC | TCA | CAT | GCC | GGT | AAG | ACT | GAA | GCA | TGG | AAA | GCT | GGT | ATG | 1920 |
|---|---|---|---|---|---|---|---|---|---|---|---|---|---|---|---|---|
| Ala | Asp | Tyr | Ser | His | Ala | Gly | Lys | Thr | Glu | Ala | Trp | Lys | Ala | Gly | Met | |
| 625 | | | | | 630 | | | | | 635 | | | | | 640 | |

| TTC | TAC | TCA | CCA | TTA | GAG | CAA | CTT | GCA | TTA | CGT | GGT | ACG | GTA | GGT | GAA | 1968 |
|---|---|---|---|---|---|---|---|---|---|---|---|---|---|---|---|---|
| Phe | Tyr | Ser | Pro | Leu | Glu | Gln | Leu | Ala | Leu | Arg | Gly | Thr | Val | Gly | Glu | |
| | | | | 645 | | | | | 650 | | | | | 655 | | |

| GCA | GTA | CGA | GCA | CCA | AAC | ATT | GCA | GAA | GCC | TTT | AGT | CCA | CGC | TCT | CCT | 2016 |
|---|---|---|---|---|---|---|---|---|---|---|---|---|---|---|---|---|
| Ala | Val | Arg | Ala | Pro | Asn | Ile | Ala | Glu | Ala | Phe | Ser | Pro | Arg | Ser | Pro | |
| | | | 660 | | | | | 665 | | | | | 670 | | | |

| GGT | TTT | GGC | CGC | GTT | TCA | GAT | CCA | TGT | GAT | GCA | GAT | AAC | ATT | AAT | GAC | 2064 |
|---|---|---|---|---|---|---|---|---|---|---|---|---|---|---|---|---|
| Gly | Phe | Gly | Arg | Val | Ser | Asp | Pro | Cys | Asp | Ala | Asp | Asn | Ile | Asn | Asp | |
| | | 675 | | | | | 680 | | | | | 685 | | | | |

| GAT | CCG | GAT | CGC | GTG | TCA | AAC | TGT | GCA | GCA | TTG | GGG | ATC | CCT | CCA | GGA | 2112 |
|---|---|---|---|---|---|---|---|---|---|---|---|---|---|---|---|---|
| Asp | Pro | Asp | Arg | Val | Ser | Asn | Cys | Ala | Ala | Leu | Gly | Ile | Pro | Pro | Gly | |
| | 690 | | | | | 695 | | | | | 700 | | | | | |

| TTC | CAA | GCT | AAT | GAT | AAC | GTC | AGT | GTA | GAT | ACC | TTA | TCT | GGT | GGT | AAC | 2160 |
|---|---|---|---|---|---|---|---|---|---|---|---|---|---|---|---|---|
| Phe | Gln | Ala | Asn | Asp | Asn | Val | Ser | Val | Asp | Thr | Leu | Ser | Gly | Gly | Asn | |
| 705 | | | | | 710 | | | | | 715 | | | | | 720 | |

| CCA | GAT | CTA | AAA | CCT | GAA | ACA | TCA | ACA | TCC | TTT | ACA | GGT | GGT | CTT | GTT | 2208 |
|---|---|---|---|---|---|---|---|---|---|---|---|---|---|---|---|---|
| Pro | Asp | Leu | Lys | Pro | Glu | Thr | Ser | Thr | Ser | Phe | Thr | Gly | Gly | Leu | Val | |
| | | | | 725 | | | | | 730 | | | | | 735 | | |

| TGG | ACA | CCA | ACG | TTT | GCT | GAC | AAT | CTA | TCA | TTC | ACT | GTC | GAT | TAT | TAT | 2256 |
|---|---|---|---|---|---|---|---|---|---|---|---|---|---|---|---|---|
| Trp | Thr | Pro | Thr | Phe | Ala | Asp | Asn | Leu | Ser | Phe | Thr | Val | Asp | Tyr | Tyr | |
| | | | 740 | | | | | 745 | | | | | 750 | | | |

| GAT | ATT | CAA | ATT | GAG | GAT | GCT | ATT | TTG | TCA | GTA | GCC | ACC | CAG | ACT | GTG | 2304 |
|---|---|---|---|---|---|---|---|---|---|---|---|---|---|---|---|---|
| Asp | Ile | Gln | Ile | Glu | Asp | Ala | Ile | Leu | Ser | Val | Ala | Thr | Gln | Thr | Val | |
| | | 755 | | | | | 760 | | | | | 765 | | | | |

| GCT | GAT | AAC | TGT | GTT | GAC | TCA | ACT | GGC | GGA | CCT | GAC | ACC | GAC | TTC | TGT | 2352 |

| | | | | | | | | | | | | | | | |
|---|---|---|---|---|---|---|---|---|---|---|---|---|---|---|---|
| Ala | Asp | Asn | Cys | Val | Asp | Ser | Thr | Gly | Gly | Pro | Asp | Thr | Asp | Phe | Cys |
| | 770 | | | | 775 | | | | | 780 | | | | | |

| AGT | CAA | GTT | GAT | CGT | AAT | CCA | ACG | ACC | TAT | GAT | ATT | GAA | CTT | GTT | CGC | 2400 |
|---|---|---|---|---|---|---|---|---|---|---|---|---|---|---|---|---|
| Ser | Gln | Val | Asp | Arg | Asn | Pro | Thr | Thr | Tyr | Asp | Ile | Glu | Leu | Val | Arg | |
| 785 | | | | | 790 | | | | | 795 | | | | | 800 | |

| TCT | GGT | TAT | CTA | AAT | GCC | GCG | GCA | TTG | AAT | ACC | AAA | GGT | ATT | GAA | TTT | 2448 |
|---|---|---|---|---|---|---|---|---|---|---|---|---|---|---|---|---|
| Ser | Gly | Tyr | Leu | Asn | Ala | Ala | Ala | Leu | Asn | Thr | Lys | Gly | Ile | Glu | Phe | |
| | | | | 805 | | | | | 810 | | | | | 815 | | |

| CAA | GCT | GCA | TAC | TCA | TTA | GAT | CTA | GAG | TCT | TTC | AAC | GCG | CCT | GGT | GAA | 2496 |
|---|---|---|---|---|---|---|---|---|---|---|---|---|---|---|---|---|
| Gln | Ala | Ala | Tyr | Ser | Leu | Asp | Leu | Glu | Ser | Phe | Asn | Ala | Pro | Gly | Glu | |
| | | | 820 | | | | | 825 | | | | | 830 | | | |

| CTA | CGC | TTC | AAC | CTA | TTG | GGG | AAC | CAA | TTA | CTT | GAA | CTA | GAA | CGT | CTT | 2544 |
|---|---|---|---|---|---|---|---|---|---|---|---|---|---|---|---|---|
| Leu | Arg | Phe | Asn | Leu | Leu | Gly | Asn | Gln | Leu | Leu | Glu | Leu | Glu | Arg | Leu | |
| | | 835 | | | | | | 840 | | | | | 845 | | | |

| GAA | TTC | CAA | AAT | CGT | CCT | GAT | GAG | ATT | AAT | GAT | GAA | AAA | GGC | GAA | GTA | 2592 |
|---|---|---|---|---|---|---|---|---|---|---|---|---|---|---|---|---|
| Glu | Phe | Gln | Asn | Arg | Pro | Asp | Glu | Ile | Asn | Asp | Glu | Lys | Gly | Glu | Val | |
| | 850 | | | | | 855 | | | | | 860 | | | | | |

| GGT | GAT | CCA | GAG | CTG | CAG | TTC | CGC | CTA | GGC | ATC | GAT | TAC | CGT | CTA | GAT | 2640 |
|---|---|---|---|---|---|---|---|---|---|---|---|---|---|---|---|---|
| Gly | Asp | Pro | Glu | Leu | Gln | Phe | Arg | Leu | Gly | Ile | Asp | Tyr | Arg | Leu | Asp | |
| 865 | | | | | 870 | | | | | 875 | | | | | 880 | |

| GAT | CTA | AGT | GTT | AGC | TGG | AAC | ACG | CGT | TAT | ATT | GAT | AGC | GTA | GTA | ACT | 2688 |
|---|---|---|---|---|---|---|---|---|---|---|---|---|---|---|---|---|
| Asp | Leu | Ser | Val | Ser | Trp | Asn | Thr | Arg | Tyr | Ile | Asp | Ser | Val | Val | Thr | |
| | | | | 885 | | | | | 890 | | | | | 895 | | |

| TAT | GAT | GTC | TCT | GAA | AAT | GGT | GGC | TCT | CCT | GAA | GAT | TTA | TAT | CCA | GGC | 2736 |
|---|---|---|---|---|---|---|---|---|---|---|---|---|---|---|---|---|
| Tyr | Asp | Val | Ser | Glu | Asn | Gly | Gly | Ser | Pro | Glu | Asp | Leu | Tyr | Pro | Gly | |
| | | | 900 | | | | | 905 | | | | | 910 | | | |

| CAC | ATA | GGC | TCA | ATG | ACA | ACT | CAT | GAC | TTG | AGC | GCT | ACA | TAC | TAC | ATC | 2784 |
|---|---|---|---|---|---|---|---|---|---|---|---|---|---|---|---|---|
| His | Ile | Gly | Ser | Met | Thr | Thr | His | Asp | Leu | Ser | Ala | Thr | Tyr | Tyr | Ile | |
| | | 915 | | | | | 920 | | | | | 925 | | | | |

| AAT | GAG | AAC | TTC | ATG | ATT | AAC | GGT | GGT | GTA | CGT | AAC | CTA | TTT | GAC | GCA | 2832 |
|---|---|---|---|---|---|---|---|---|---|---|---|---|---|---|---|---|
| Asn | Glu | Asn | Phe | Met | Ile | Asn | Gly | Gly | Val | Arg | Asn | Leu | Phe | Asp | Ala | |
| | 930 | | | | | 935 | | | | | 940 | | | | | |

| CTT | CCA | CCT | GGA | TAC | ACT | AAC | GAT | GCG | CTA | TAT | GAT | CTA | GTT | GGT | CGC | 2880 |
|---|---|---|---|---|---|---|---|---|---|---|---|---|---|---|---|---|
| Leu | Pro | Pro | Gly | Tyr | Thr | Asn | Asp | Ala | Leu | Tyr | Asp | Leu | Val | Gly | Arg | |
| 945 | | | | | 950 | | | | | 955 | | | | | 960 | |

| CGT | GCA | TTC | CTA | GGT | ATT | AAG | GTA | ATG | ATG | | | | | | | 2910 |
|---|---|---|---|---|---|---|---|---|---|---|---|---|---|---|---|---|
| Arg | Ala | Phe | Leu | Gly | Ile | Lys | Val | Met | Met | | | | | | | |
| | | | | 965 | | | | | 970 | | | | | | | |

( 2 ) INFORMATION FOR SEQ ID NO:7:

( i ) SEQUENCE CHARACTERISTICS:
        ( A ) LENGTH: 970 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| Met | Ser | Met | Phe | Leu | Asn | Ser | Lys | Leu | Ser | Arg | Ser | Val | Lys | Leu | Ala |
|---|---|---|---|---|---|---|---|---|---|---|---|---|---|---|---|
| 1 | | | | 5 | | | | | 10 | | | | | 15 | |

| Ile | Ser | Ala | Gly | Leu | Thr | Ala | Ser | Leu | Ala | Met | Pro | Val | Phe | Ala | Glu |
|---|---|---|---|---|---|---|---|---|---|---|---|---|---|---|---|
| | | | 20 | | | | | 25 | | | | | 30 | | |

| Glu | Thr | Ala | Ala | Glu | Glu | Gln | Ile | Glu | Arg | Val | Ala | Val | Thr | Gly | Ser |
|---|---|---|---|---|---|---|---|---|---|---|---|---|---|---|---|
| | | | 35 | | | | | 40 | | | | | 45 | | |

| Arg | Ile | Ala | Lys | Ala | Glu | Leu | Thr | Gln | Pro | Ala | Pro | Val | Val | Ser | Leu |
|---|---|---|---|---|---|---|---|---|---|---|---|---|---|---|---|
| | | 50 | | | | | 55 | | | | | 60 | | | |

| Ser | Ala | Glu | Glu | Leu | Thr | Lys | Phe | Gly | Asn | Gln | Asp | Leu | Gly | Ser | Val |
|---|---|---|---|---|---|---|---|---|---|---|---|---|---|---|---|
| 65 | | | | | 70 | | | | | 75 | | | | | 80 |

| Leu | Ala | Glu | Leu | Pro | Ala | Ile | Gly | Ala | Thr | Asn | Thr | Ile | Ile | Gly | Asn |
|---|---|---|---|---|---|---|---|---|---|---|---|---|---|---|---|
| | | | | 85 | | | | | 90 | | | | | 95 | |

```
Asn Asn Ser Asn Ser Ser Ala Gly Val Ser Ser Ala Asp Leu Arg Arg
            100                 105                 110

Leu Gly Ala Asn Arg Thr Leu Val Leu Val Asn Gly Lys Arg Tyr Val
        115                 120                 125

Ala Gly Gln Pro Gly Ser Ala Glu Val Asp Leu Ser Thr Ile Pro Thr
    130                 135                 140

Ser Met Ile Ser Arg Val Glu Ile Val Thr Gly Gly Ala Ser Ala Ile
145                 150                 155                 160

Tyr Gly Ser Asp Ala Val Ser Gly Val Ile Asn Val Ile Leu Lys Glu
                165                 170                 175

Asp Phe Glu Gly Phe Glu Phe Asn Ala Arg Thr Ser Gly Ser Thr Glu
            180                 185                 190

Ser Val Gly Thr Gln Glu His Ser Phe Asp Ile Leu Gly Gly Ala Asn
        195                 200                 205

Val Ala Asp Gly Arg Gly Asn Val Thr Phe Tyr Ala Gly Tyr Glu Arg
    210                 215                 220

Thr Lys Glu Val Met Ala Thr Asp Ile Arg Gln Phe Asp Ala Trp Gly
225                 230                 235                 240

Thr Ile Lys Asn Glu Ala Asp Gly Gly Glu Asp Asp Gly Ile Pro Asp
                245                 250                 255

Arg Leu Arg Val Pro Arg Val Tyr Ser Glu Met Ile Asn Ala Thr Gly
            260                 265                 270

Val Ile Asn Ala Phe Gly Gly Ile Gly Arg Ser Thr Phe Asp Ser
    275                 280                 285

Asn Gly Asn Pro Ile Ala Gln Gln Glu Arg Asp Gly Thr Asn Ser Phe
    290                 295                 300

Ala Phe Gly Ser Phe Pro Asn Gly Cys Asp Thr Cys Phe Asn Thr Glu
305                 310                 315                 320

Ala Tyr Glu Asn Tyr Ile Pro Gly Val Glu Arg Ile Asn Val Gly Ser
                325                 330                 335

Ser Phe Asn Phe Asp Phe Thr Asp Asn Ile Gln Phe Tyr Thr Asp Phe
            340                 345                 350

Arg Tyr Val Lys Ser Asp Ile Gln Gln Phe Gln Pro Ser Phe Arg
        355                 360                 365

Phe Gly Asn Ile Asn Ile Asn Val Glu Asp Asn Ala Phe Leu Asn Asp
    370                 375                 380

Asp Leu Arg Gln Gln Met Leu Asp Ala Gly Gln Thr Asn Ala Ser Phe
385                 390                 395                 400

Ala Lys Phe Phe Asp Glu Leu Gly Asn Arg Ser Ala Glu Asn Lys Arg
            405                 410                 415

Glu Leu Phe Arg Tyr Val Gly Gly Phe Lys Gly Gly Phe Asp Ile Ser
        420                 425                 430

Glu Thr Ile Phe Asp Tyr Asp Leu Tyr Tyr Val Tyr Gly Glu Thr Asn
    435                 440                 445

Asn Arg Arg Lys Thr Leu Asn Asp Leu Ile Pro Asp Asn Phe Val Ala
    450                 455                 460

Ala Val Asp Ser Val Ile Asp Pro Asp Thr Gly Leu Ala Ala Cys Arg
465                 470                 475                 480

Ser Gln Val Ala Ser Ala Gln Gly Asp Tyr Thr Asp Pro Ala Ser
            485                 490                 495

Val Asn Gly Ser Asp Cys Val Ala Tyr Asn Pro Phe Gly Met Gly Gln
        500                 505                 510

Ala Ser Ala Glu Ala Arg Asp Trp Val Ser Ala Asp Val Thr Arg Glu
```

-continued

|   | 515 |   |   |   | 520 |   |   |   | 525 |   |   |   |
|---|---|---|---|---|---|---|---|---|---|---|---|---|
| Asp | Lys | Ile | Thr | Gln | Gln | Val | Ile | Gly | Gly | Thr | Leu | Gly | Thr | Asp | Ser |
|  | 530 |  |  |  | 535 |  |  |  | 540 |  |  |  |
| Glu | Glu | Leu | Phe | Glu | Leu | Gln | Gly | Gly | Ala | Ile | Ala | Met | Val | Val | Gly |
| 545 |  |  |  |  | 550 |  |  |  | 555 |  |  |  |  |  | 560 |
| Phe | Glu | Tyr | Arg | Glu | Thr | Ser | Gly | Ser | Thr | Thr | Asp | Glu | Phe | Thr |
|  |  |  |  | 565 |  |  |  | 570 |  |  |  | 575 |
| Lys | Ala | Gly | Phe | Leu | Thr | Ser | Ala | Ala | Thr | Pro | Asp | Ser | Tyr | Gly | Glu |
|  |  |  | 580 |  |  |  | 585 |  |  |  | 590 |
| Tyr | Asp | Val | Thr | Glu | Tyr | Phe | Val | Glu | Val | Asn | Ile | Pro | Val | Leu | Lys |
|  |  | 595 |  |  |  | 600 |  |  |  | 605 |
| Glu | Leu | Pro | Phe | Ala | His | Glu | Leu | Ser | Phe | Asp | Gly | Ala | Tyr | Arg | Asn |
| 610 |  |  |  |  | 615 |  |  |  | 620 |
| Ala | Asp | Tyr | Ser | His | Ala | Gly | Lys | Thr | Glu | Ala | Trp | Lys | Ala | Gly | Met |
| 625 |  |  |  | 630 |  |  |  | 635 |  |  |  | 640 |
| Phe | Tyr | Ser | Pro | Leu | Glu | Gln | Leu | Ala | Leu | Arg | Gly | Thr | Val | Gly | Glu |
|  |  |  | 645 |  |  |  | 650 |  |  |  | 655 |
| Ala | Val | Arg | Ala | Pro | Asn | Ile | Ala | Glu | Ala | Phe | Ser | Pro | Arg | Ser | Pro |
|  |  |  | 660 |  |  |  | 665 |  |  |  | 670 |
| Gly | Phe | Gly | Arg | Val | Ser | Asp | Pro | Cys | Asp | Ala | Asp | Asn | Ile | Asn | Asp |
|  |  | 675 |  |  |  | 680 |  |  |  | 685 |
| Asp | Pro | Asp | Arg | Val | Ser | Asn | Cys | Ala | Ala | Leu | Gly | Ile | Pro | Pro | Gly |
|  | 690 |  |  |  | 695 |  |  |  | 700 |
| Phe | Gln | Ala | Asn | Asp | Asn | Val | Ser | Val | Asp | Thr | Leu | Ser | Gly | Gly | Asn |
| 705 |  |  |  |  | 710 |  |  |  | 715 |  |  |  | 720 |
| Pro | Asp | Leu | Lys | Pro | Glu | Thr | Ser | Thr | Ser | Phe | Thr | Gly | Gly | Leu | Val |
|  |  |  |  | 725 |  |  |  | 730 |  |  |  | 735 |
| Trp | Thr | Pro | Thr | Phe | Ala | Asp | Asn | Leu | Ser | Phe | Thr | Val | Asp | Tyr | Tyr |
|  |  |  | 740 |  |  |  | 745 |  |  |  | 750 |
| Asp | Ile | Gln | Ile | Glu | Asp | Ala | Ile | Leu | Ser | Val | Ala | Thr | Gln | Thr | Val |
|  |  | 755 |  |  |  | 760 |  |  |  | 765 |
| Ala | Asp | Asn | Cys | Val | Asp | Ser | Thr | Gly | Gly | Pro | Asp | Thr | Asp | Phe | Cys |
| 770 |  |  |  |  | 775 |  |  |  | 780 |
| Ser | Gln | Val | Asp | Arg | Asn | Pro | Thr | Thr | Tyr | Asp | Ile | Glu | Leu | Val | Arg |
| 785 |  |  |  |  | 790 |  |  |  | 795 |  |  |  |  | 800 |
| Ser | Gly | Tyr | Leu | Asn | Ala | Ala | Ala | Leu | Asn | Thr | Lys | Gly | Ile | Glu | Phe |
|  |  |  |  | 805 |  |  |  | 810 |  |  |  | 815 |
| Gln | Ala | Ala | Tyr | Ser | Leu | Asp | Leu | Glu | Ser | Phe | Asn | Ala | Pro | Gly | Glu |
|  |  |  | 820 |  |  |  | 825 |  |  |  | 830 |
| Leu | Arg | Phe | Asn | Leu | Leu | Gly | Asn | Gln | Leu | Leu | Glu | Leu | Glu | Arg | Leu |
|  |  | 835 |  |  |  | 840 |  |  |  | 845 |
| Glu | Phe | Gln | Asn | Arg | Pro | Asp | Glu | Ile | Asn | Asp | Glu | Lys | Gly | Glu | Val |
|  | 850 |  |  |  | 855 |  |  |  | 860 |
| Gly | Asp | Pro | Glu | Leu | Gln | Phe | Arg | Leu | Gly | Ile | Asp | Tyr | Arg | Leu | Asp |
| 865 |  |  |  |  | 870 |  |  |  | 875 |  |  |  |  | 880 |
| Asp | Leu | Ser | Val | Ser | Trp | Asn | Thr | Arg | Tyr | Ile | Asp | Ser | Val | Val | Thr |
|  |  |  |  | 885 |  |  |  | 890 |  |  |  |  | 895 |
| Tyr | Asp | Val | Ser | Glu | Asn | Gly | Gly | Ser | Pro | Glu | Asp | Leu | Tyr | Pro | Gly |
|  |  |  | 900 |  |  |  | 905 |  |  |  | 910 |
| His | Ile | Gly | Ser | Met | Thr | Thr | His | Asp | Leu | Ser | Ala | Thr | Tyr | Tyr | Ile |
|  |  | 915 |  |  |  | 920 |  |  |  | 925 |
| Asn | Glu | Asn | Phe | Met | Ile | Asn | Gly | Gly | Val | Arg | Asn | Leu | Phe | Asp | Ala |
| 930 |  |  |  |  | 935 |  |  |  | 940 |

```
Leu  Pro  Pro  Gly  Tyr  Thr  Asn  Asp  Ala  Leu  Tyr  Asp  Leu  Val  Gly  Arg
945                      950                      955                      960

Arg  Ala  Phe  Leu  Gly  Ile  Lys  Val  Met  Met
                    965                      970
```

( 2 ) INFORMATION FOR SEQ ID NO:8:

( i ) SEQUENCE CHARACTERISTICS:
        ( A ) LENGTH: 864 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Shewanella putrefaciens SCRC-2874 (FERM BP- 1625)

( i x ) FEATURE:
        ( A ) NAME/KEY: CDS
        ( B ) LOCATION: 1..864

( i x ) FEATURE:
        ( A ) NAME/KEY: mat_peptide
        ( B ) LOCATION: 1..864

( x i ) SEQUENCE DESCRIPTION: SEQ ID NO:8:

```
ATG  GCA  AAA  ATA  AAT  AGT  GAA  CAC  TTG  GAT  GAA  GCT  ACT  ATT  ACT  TCG     48
Met  Ala  Lys  Ile  Asn  Ser  Glu  His  Leu  Asp  Glu  Ala  Thr  Ile  Thr  Ser
1                   5                        10                       15

AAT  AAG  TGT  ACG  CAA  ACA  GAG  ACT  GAG  GCT  CGG  CAT  AGA  AAT  GCC  ACT     96
Asn  Lys  Cys  Thr  Gln  Thr  Glu  Thr  Glu  Ala  Arg  His  Arg  Asn  Ala  Thr
               20                       25                       30

ACA  ACA  CCT  GAG  ATG  CGC  CGA  TTC  ATA  CAA  GAG  TCG  GAT  CTC  AGT  GTT    144
Thr  Thr  Pro  Glu  Met  Arg  Arg  Phe  Ile  Gln  Glu  Ser  Asp  Leu  Ser  Val
          35                       40                       45

AGC  CAA  CTG  TCT  AAA  ATA  TTA  AAT  ATC  AGT  GAA  GCT  ACC  GTA  CGT  AAG    192
Ser  Gln  Leu  Ser  Lys  Ile  Leu  Asn  Ile  Ser  Glu  Ala  Thr  Val  Arg  Lys
     50                       55                       60

TGG  CGC  AAG  CGT  GAC  TCT  GTC  GAA  AAC  TGT  CCT  AAT  ACC  CCG  CAC  CAT    240
Trp  Arg  Lys  Arg  Asp  Ser  Val  Glu  Asn  Cys  Pro  Asn  Thr  Pro  His  His
65                       70                       75                       80

CTC  AAT  ACC  ACG  CTA  ACC  CCT  TTG  CAA  GAA  TAT  GTG  GTT  GTG  GGC  CTG    288
Leu  Asn  Thr  Thr  Leu  Thr  Pro  Leu  Gln  Glu  Tyr  Val  Val  Val  Gly  Leu
                    85                       90                       95

CGT  TAT  CAA  TTG  AAA  ATG  CCA  TTA  GAC  AGA  TTG  CTC  AAA  GCA  ACC  CAA    336
Arg  Tyr  Gln  Leu  Lys  Met  Pro  Leu  Asp  Arg  Leu  Leu  Lys  Ala  Thr  Gln
               100                      105                      110

GAG  TTT  ATC  AAT  CCA  AAC  GTG  TCG  CGC  TCA  GGT  TTA  GCA  AGA  TGT  TTG    384
Glu  Phe  Ile  Asn  Pro  Asn  Val  Ser  Arg  Ser  Gly  Leu  Ala  Arg  Cys  Leu
          115                      120                      125

AAG  CGT  TAT  GGC  GTT  TCA  CGG  GTG  AGT  GAT  ATC  CAA  AGC  CCA  CAC  GTA    432
Lys  Arg  Tyr  Gly  Val  Ser  Arg  Val  Ser  Asp  Ile  Gln  Ser  Pro  His  Val
     130                      135                      140

CCA  ATG  CGC  TAC  TTT  AAT  CAA  ATT  CCA  GTC  ACT  CAA  GGC  AGC  GAT  GTG    480
Pro  Met  Arg  Tyr  Phe  Asn  Gln  Ile  Pro  Val  Thr  Gln  Gly  Ser  Asp  Val
145                      150                      155                      160

CAA  ACC  TAC  ACC  CTG  CAC  TAT  GAA  ACG  CTG  GCA  AAA  ACC  TTA  GCC  TTA    528
Gln  Thr  Tyr  Thr  Leu  His  Tyr  Glu  Thr  Leu  Ala  Lys  Thr  Leu  Ala  Leu
                    165                      170                      175

CCT  AGT  ACC  GAT  GGT  GAC  AAT  GTG  GTG  CAA  GTG  GTG  TCT  CTC  ACC  ATT    576
Pro  Ser  Thr  Asp  Gly  Asp  Asn  Val  Val  Gln  Val  Val  Ser  Leu  Thr  Ile
               180                      185                      190

CCA  CCA  AAG  TTA  ACC  GAA  GAA  GCA  CCC  AGT  TCA  ATT  TTG  CTC  GGC  ATT    624
```

|   |   |   |   |   |   |   |   |   |   |   |   |   |   |   |   |     |
|---|---|---|---|---|---|---|---|---|---|---|---|---|---|---|---|-----|
| Pro | Pro | Lys | Leu | Thr | Glu | Glu | Ala | Pro | Ser | Ser | Ile | Leu | Leu | Gly | Ile |  |
|  | | 195 | | | | | 200 | | | | 205 | | | | | |
| GAT | CCT | CAT | AGC | GAC | TGG | ATC | TAT | CTC | GAC | ATA | TAC | CAA | GAT | GGC | AAT | 672 |
| Asp | Pro | His | Ser | Asp | Trp | Ile | Tyr | Leu | Asp | Ile | Tyr | Gln | Asp | Gly | Asn |  |
| | 210 | | | | | 215 | | | | 220 | | | | | | |
| ACA | CAA | GCC | ACG | AAT | AGA | TAT | ATG | GCT | TAT | GTG | CTA | AAA | CAC | GGG | CCA | 720 |
| Thr | Gln | Ala | Thr | Asn | Arg | Tyr | Met | Ala | Tyr | Val | Leu | Lys | His | Gly | Pro |  |
| 225 | | | | | 230 | | | | 235 | | | | | | 240 | |
| TTC | CAT | TTA | CGA | AAG | TTA | CTC | GTG | CGT | AAC | TAT | CAC | ACC | TTT | TTA | CAG | 768 |
| Phe | His | Leu | Arg | Lys | Leu | Leu | Val | Arg | Asn | Tyr | His | Thr | Phe | Leu | Gln |  |
| | | | | 245 | | | | | 250 | | | | | 255 | | |
| CGC | TTT | CCT | GGA | GCG | ACG | CAA | AAT | CGC | CGC | CCC | TCT | AAA | GAT | ATG | CCT | 816 |
| Arg | Phe | Pro | Gly | Ala | Thr | Gln | Asn | Arg | Arg | Pro | Ser | Lys | Asp | Met | Pro |  |
| | | | 260 | | | | | 265 | | | | | 270 | | | |
| GAA | ACA | ATC | AAC | AAG | ACG | CCT | GAA | ACA | CAG | GCA | CCC | AGT | GGA | GAC | TCA | 864 |
| Glu | Thr | Ile | Asn | Lys | Thr | Pro | Glu | Thr | Gln | Ala | Pro | Ser | Gly | Asp | Ser |  |
| | | 275 | | | | | 280 | | | | | 285 | | | | |

( 2 ) INFORMATION FOR SEQ ID NO:9:

( i ) SEQUENCE CHARACTERISTICS:
        ( A ) LENGTH: 288 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

|   |   |   |   |   |   |   |   |   |   |   |   |   |   |   |
|---|---|---|---|---|---|---|---|---|---|---|---|---|---|---|
| Met | Ala | Lys | Ile | Asn | Ser | Glu | His | Leu | Asp | Glu | Ala | Thr | Ile | Thr | Ser |
| 1 | | | | 5 | | | | | 10 | | | | | 15 | |
| Asn | Lys | Cys | Thr | Gln | Thr | Glu | Thr | Glu | Ala | Arg | His | Arg | Asn | Ala | Thr |
| | | | 20 | | | | | 25 | | | | | 30 | | |
| Thr | Thr | Pro | Glu | Met | Arg | Arg | Phe | Ile | Gln | Glu | Ser | Asp | Leu | Ser | Val |
| | | 35 | | | | | 40 | | | | | 45 | | | |
| Ser | Gln | Leu | Ser | Lys | Ile | Leu | Asn | Ile | Ser | Glu | Ala | Thr | Val | Arg | Lys |
| | 50 | | | | | 55 | | | | | 60 | | | | |
| Trp | Arg | Lys | Arg | Asp | Ser | Val | Glu | Asn | Cys | Pro | Asn | Thr | Pro | His | His |
| 65 | | | | | 70 | | | | | 75 | | | | | 80 |
| Leu | Asn | Thr | Thr | Leu | Thr | Pro | Leu | Gln | Glu | Tyr | Val | Val | Val | Gly | Leu |
| | | | | 85 | | | | | 90 | | | | | 95 | |
| Arg | Tyr | Gln | Leu | Lys | Met | Pro | Leu | Asp | Arg | Leu | Leu | Lys | Ala | Thr | Gln |
| | | | 100 | | | | | 105 | | | | | 110 | | |
| Glu | Phe | Ile | Asn | Pro | Asn | Val | Ser | Arg | Ser | Gly | Leu | Ala | Arg | Cys | Leu |
| | | 115 | | | | | 120 | | | | | 125 | | | |
| Lys | Arg | Tyr | Gly | Val | Ser | Arg | Val | Ser | Asp | Ile | Gln | Ser | Pro | His | Val |
| | 130 | | | | | 135 | | | | | 140 | | | | |
| Pro | Met | Arg | Tyr | Phe | Asn | Gln | Ile | Pro | Val | Thr | Gln | Gly | Ser | Asp | Val |
| 145 | | | | | 150 | | | | | 155 | | | | | 160 |
| Gln | Thr | Tyr | Thr | Leu | His | Tyr | Glu | Thr | Leu | Ala | Lys | Thr | Leu | Ala | Leu |
| | | | | 165 | | | | | 170 | | | | | 175 | |
| Pro | Ser | Thr | Asp | Gly | Asp | Asn | Val | Val | Gln | Val | Val | Ser | Leu | Thr | Ile |
| | | | 180 | | | | | 185 | | | | | 190 | | |
| Pro | Pro | Lys | Leu | Thr | Glu | Glu | Ala | Pro | Ser | Ser | Ile | Leu | Leu | Gly | Ile |
| | | 195 | | | | | 200 | | | | | 205 | | | |
| Asp | Pro | His | Ser | Asp | Trp | Ile | Tyr | Leu | Asp | Ile | Tyr | Gln | Asp | Gly | Asn |
| | 210 | | | | | 215 | | | | | 220 | | | | |
| Thr | Gln | Ala | Thr | Asn | Arg | Tyr | Met | Ala | Tyr | Val | Leu | Lys | His | Gly | Pro |
| 225 | | | | | 230 | | | | | 235 | | | | | 240 |

5,683,898

69

70

-continued

| Phe | His | Leu | Arg | Lys<br>245 | Leu | Leu | Val | Arg | Asn<br>250 | Tyr | His | Thr | Phe | Leu<br>255 | Gln |
|---|---|---|---|---|---|---|---|---|---|---|---|---|---|---|---|
| Arg | Phe | Pro | Gly<br>260 | Ala | Thr | Gln | Asn | Arg<br>265 | Arg | Pro | Ser | Lys | Asp<br>270 | Met | Pro |
| Glu | Thr | Ile<br>275 | Asn | Lys | Thr | Pro | Glu<br>280 | Thr | Gln | Ala | Pro | Ser<br>285 | Gly | Asp | Ser |

( 2 ) INFORMATION FOR SEQ ID NO:10:

( i ) SEQUENCE CHARACTERISTICS:
        ( A ) LENGTH: 8268 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Shewanella putrefaciens SCRC-2874 (FERM
        BP- 1625)

( i x ) FEATURE:
        ( A ) NAME/KEY: CDS
        ( B ) LOCATION: 1..8268

( i x ) FEATURE:
        ( A ) NAME/KEY: mat_peptide
        ( B ) LOCATION: 1..8268

( x i ) SEQUENCE DESCRIPTION: SEQ ID NO:10:

| ATG | AGC | CAG | ACC | TCT | AAA | CCT | ACA | AAC | TCA | GCA | ACT | GAG | CAA | GCA | CAA | 48 |
|---|---|---|---|---|---|---|---|---|---|---|---|---|---|---|---|---|
| Met | Ser | Gln | Thr | Ser<br>5 | Lys | Pro | Thr | Asn | Ser<br>10 | Ala | Thr | Glu | Gln | Ala<br>15 | Gln | |
| GAC | TCA | CAA | GCT | GAC | TCT | CGT | TTA | AAT | AAA | CGA | CTA | AAA | GAT | ATG | CCA | 96 |
| Asp | Ser | Gln | Ala<br>20 | Asp | Ser | Arg | Leu | Asn<br>25 | Lys | Arg | Leu | Lys | Asp<br>30 | Met | Pro | |
| ATT | GCT | ATT | GTT | GGC | ATG | GCG | AGT | ATT | TTT | GCA | AAC | TCT | CGC | TAT | TTG | 144 |
| Ile | Ala | Ile | Val<br>35 | Gly | Met | Ala | Ser | Ile<br>40 | Phe | Ala | Asn | Ser | Arg<br>45 | Tyr | Leu | |
| AAT | AAG | TTT | TGG | GAC | TTA | ATC | AGC | GAA | AAA | ATT | GAT | GCG | ATT | ACT | GAA | 192 |
| Asn | Lys<br>50 | Phe | Trp | Asp | Leu | Ile<br>55 | Ser | Glu | Lys | Ile | Asp<br>60 | Ala | Ile | Thr | Glu | |
| TTA | CCA | TCA | ACT | CAC | TGG | CAG | CCT | GAA | GAA | TAT | TAC | GAC | GCA | GAT | AAA | 240 |
| Leu<br>65 | Pro | Ser | Thr | His | Trp<br>70 | Gln | Pro | Glu | Glu | Tyr<br>75 | Tyr | Asp | Ala | Asp | Lys<br>80 | |
| ACC | GCA | GCA | GAC | AAA | AGC | TAC | TGT | AAA | CGT | GGT | GGC | TTT | TTG | CCA | GAT | 288 |
| Thr | Ala | Ala | Asp | Lys<br>85 | Ser | Tyr | Cys | Lys | Arg<br>90 | Gly | Gly | Phe | Leu | Pro<br>95 | Asp | |
| GTA | GAC | TTC | AAC | CCA | ATG | GAG | TTT | GGC | CTG | CCG | CCA | AAC | ATT | TTG | GAA | 336 |
| Val | Asp | Phe | Asn | Pro<br>100 | Met | Glu | Phe | Gly | Leu<br>105 | Pro | Pro | Asn | Ile | Leu<br>110 | Glu | |
| CTG | ACC | GAT | TCA | TCG | CAA | CTA | TTA | TCA | CTC | ATC | GTT | GCT | AAA | GAA | GTG | 384 |
| Leu | Thr | Asp<br>115 | Ser | Ser | Gln | Leu | Leu<br>120 | Ser | Leu | Ile | Val | Ala<br>125 | Lys | Glu | Val | |
| TTG | GCT | GAT | GCT | AAC | TTA | CCT | GAG | AAT | TAC | GAC | CGC | GAT | AAA | ATT | GGT | 432 |
| Leu | Ala | Asp<br>130 | Ala | Asn | Leu | Pro | Glu<br>135 | Asn | Tyr | Asp | Arg | Asp<br>140 | Lys | Ile | Gly | |
| ATC | ACC | TTA | GGT | GTC | GGC | GGT | GGT | CAA | AAA | ATT | AGC | CAC | AGC | CTA | ACA | 480 |
| Ile | Thr | Leu | Gly<br>145 | Val | Gly | Gly<br>150 | Gly | Gln | Lys | Ile | Ser<br>155 | His | Ser | Leu | Thr<br>160 | |
| GCG | CGT | CTG | CAA | TAC | CCA | GTA | TTG | AAG | AAA | GTA | TTC | GCC | AAT | AGC | GGC | 528 |
| Ala | Arg | Leu | Gln | Tyr<br>165 | Pro | Val | Leu | Lys | Lys<br>170 | Val | Phe | Ala | Asn | Ser<br>175 | Gly | |
| ATT | AGT | GAC | ACC | GAC | AGC | GAA | ATG | CTT | ATC | AAG | AAA | TTC | CAA | GAC | CAA | 576 |
| Ile | Ser | Asp | Thr | Asp<br>180 | Ser | Glu | Met | Leu | Ile<br>185 | Lys | Lys | Phe | Gln | Asp<br>190 | Gln | |

-continued

| | | | | | | | | | | | | | | | | |
|---|---|---|---|---|---|---|---|---|---|---|---|---|---|---|---|---|
| | | | 180 | | | | | 185 | | | | | 190 | | | |
| TAT | GTA | CAC | TGG | GAA | GAA | AAC | TCG | TTC | CCA | GGT | TCA | CTT | GGT | AAC | GTT | 624 |
| Tyr | Val | His | Trp | Glu | Glu | Asn | Ser | Phe | Pro | Gly | Ser | Leu | Gly | Asn | Val | |
| | | 195 | | | | | 200 | | | | | 205 | | | | |
| ATT | GCG | GGC | CGT | ATC | GCC | AAC | CGC | TTC | GAT | TTT | GGC | GGC | ATG | AAC | TGT | 672 |
| Ile | Ala | Gly | Arg | Ile | Ala | Asn | Arg | Phe | Asp | Phe | Gly | Gly | Met | Asn | Cys | |
| | | 210 | | | | | 215 | | | | | 220 | | | | |
| GTG | GTT | GAT | GCT | GCC | TGT | GCT | GGA | TCA | CTT | GCT | GCT | ATG | CGT | ATG | GCG | 720 |
| Val | Val | Asp | Ala | Ala | Cys | Ala | Gly | Ser | Leu | Ala | Ala | Met | Arg | Met | Ala | |
| 225 | | | | | 230 | | | | | 235 | | | | | 240 | |
| CTA | ACA | GAG | CTA | ACT | GAA | GGT | CGC | TCT | GAA | ATG | ATG | ATC | ACC | GGT | GGT | 768 |
| Leu | Thr | Glu | Leu | Thr | Glu | Gly | Arg | Ser | Glu | Met | Met | Ile | Thr | Gly | Gly | |
| | | | | 245 | | | | | 250 | | | | | 255 | | |
| GTG | TGT | ACT | GAT | AAC | TCA | CCC | TCT | ATG | TAT | ATG | AGC | TTT | TCA | AAA | ACG | 816 |
| Val | Cys | Thr | Asp | Asn | Ser | Pro | Ser | Met | Tyr | Met | Ser | Phe | Ser | Lys | Thr | |
| | | | | 260 | | | | | 265 | | | | | 270 | | |
| CCC | GCC | TTT | ACC | ACT | AAC | GAA | ACC | ATT | CAG | CCA | TTT | GAT | ATC | GAC | TCA | 864 |
| Pro | Ala | Phe | Thr | Thr | Asn | Glu | Thr | Ile | Gln | Pro | Phe | Asp | Ile | Asp | Ser | |
| | | 275 | | | | | 280 | | | | | 285 | | | | |
| AAA | GGC | ATG | ATG | ATT | GGT | GAA | GGT | ATT | GGC | ATG | GTG | GCG | CTA | AAG | CGT | 912 |
| Lys | Gly | Met | Met | Ile | Gly | Glu | Gly | Ile | Gly | Met | Val | Ala | Leu | Lys | Arg | |
| | | 290 | | | | | 295 | | | | | 300 | | | | |
| CTT | GAA | GAT | GCA | GAG | CGC | GAT | GGC | GAC | CGC | ATT | TAC | TCT | GTA | ATT | AAA | 960 |
| Leu | Glu | Asp | Ala | Glu | Arg | Asp | Gly | Asp | Arg | Ile | Tyr | Ser | Val | Ile | Lys | |
| 305 | | | | | 310 | | | | | 315 | | | | | 320 | |
| GGT | GTG | GGT | GCA | TCA | TCT | GAC | GGT | AAG | TTT | AAA | TCA | ATC | TAT | GCC | CCT | 1008 |
| Gly | Val | Gly | Ala | Ser | Ser | Asp | Gly | Lys | Phe | Lys | Ser | Ile | Tyr | Ala | Pro | |
| | | | | 325 | | | | | 330 | | | | | 335 | | |
| CGC | CCA | TCA | GGC | CAA | GCT | AAA | GCA | CTT | AAC | CGT | GCC | TAT | GAT | GAC | GCA | 1056 |
| Arg | Pro | Ser | Gly | Gln | Ala | Lys | Ala | Leu | Asn | Arg | Ala | Tyr | Asp | Asp | Ala | |
| | | | 340 | | | | | 345 | | | | | 350 | | | |
| GGT | TTT | GCG | CCG | CAT | ACC | TTA | GGT | CTA | ATT | GAA | GCT | CAC | GGA | ACA | GGT | 1104 |
| Gly | Phe | Ala | Pro | His | Thr | Leu | Gly | Leu | Ile | Glu | Ala | His | Gly | Thr | Gly | |
| | | 355 | | | | | 360 | | | | | 365 | | | | |
| ACT | GCA | GCA | GGT | GAC | GCG | GCA | GAG | TTT | GCC | GGC | CTT | TGC | TCA | GTA | TTT | 1152 |
| Thr | Ala | Ala | Gly | Asp | Ala | Ala | Glu | Phe | Ala | Gly | Leu | Cys | Ser | Val | Phe | |
| | | 370 | | | | | 375 | | | | | 380 | | | | |
| GCT | GAA | GGC | AAC | GAT | ACC | AAG | CAA | CAC | ATT | GCG | CTA | GGT | TCA | GTT | AAA | 1200 |
| Ala | Glu | Gly | Asn | Asp | Thr | Lys | Gln | His | Ile | Ala | Leu | Gly | Ser | Val | Lys | |
| 385 | | | | | 390 | | | | | 395 | | | | | 400 | |
| TCA | CAA | ATT | GGT | CAT | ACT | AAA | TCA | ACT | GCA | GGT | ACA | GCA | GGT | TTA | ATT | 1248 |
| Ser | Gln | Ile | Gly | His | Thr | Lys | Ser | Thr | Ala | Gly | Thr | Ala | Gly | Leu | Ile | |
| | | | | 405 | | | | | 410 | | | | | 415 | | |
| AAA | GCT | GCT | CTT | GCT | TTG | CAT | CAC | AAG | GTA | CTG | CCG | CCG | ACC | ATT | AAC | 1296 |
| Lys | Ala | Ala | Leu | Ala | Leu | His | His | Lys | Val | Leu | Pro | Pro | Thr | Ile | Asn | |
| | | | 420 | | | | | 425 | | | | | 430 | | | |
| GTT | AGT | CAG | CCA | AGC | CCT | AAA | CTT | GAT | ATC | GAA | AAC | TCA | CCG | TTT | TAT | 1344 |
| Val | Ser | Gln | Pro | Ser | Pro | Lys | Leu | Asp | Ile | Glu | Asn | Ser | Pro | Phe | Tyr | |
| | | 435 | | | | | 440 | | | | | 445 | | | | |
| CTA | AAC | ACT | GAG | ACT | CGT | CCA | TGG | TTA | CCA | CGT | GTT | GAT | GGT | ACG | CCG | 1392 |
| Leu | Asn | Thr | Glu | Thr | Arg | Pro | Trp | Leu | Pro | Arg | Val | Asp | Gly | Thr | Pro | |
| | | 450 | | | | | 455 | | | | | 460 | | | | |
| CGC | CGC | GCG | GGT | ATT | AGC | TCA | TTT | GGT | TTT | GGT | GGC | ACT | AAC | TTC | CAT | 1440 |
| Arg | Arg | Ala | Gly | Ile | Ser | Ser | Phe | Gly | Phe | Gly | Gly | Thr | Asn | Phe | His | |
| 465 | | | | | 470 | | | | | 475 | | | | | 480 | |
| TTT | GTA | CTA | GAA | GAG | TAC | AAC | CAA | GAA | CAC | AGC | CGT | ACT | GAT | AGC | GAA | 1488 |
| Phe | Val | Leu | Glu | Glu | Tyr | Asn | Gln | Glu | His | Ser | Arg | Thr | Asp | Ser | Glu | |
| | | | | 485 | | | | | 490 | | | | | 495 | | |
| AAA | GCT | AAG | TAT | CGT | CAA | CGC | CAA | GTG | GCG | CAA | AGC | TTC | CTT | GTT | AGC | 1536 |
| Lys | Ala | Lys | Tyr | Arg | Gln | Arg | Gln | Val | Ala | Gln | Ser | Phe | Leu | Val | Ser | |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
|       |       | 500   |       |       |       |       | 505   |       |       |       |       | 510   |       |       |       |      |
| GCA   | AGC   | GAT   | AAA   | GCA   | TCG   | CTA   | ATT   | AAC   | GAG   | TTA   | AAC   | GTA   | CTA   | GCA   | GCA   | 1584 |
| Ala   | Ser   | Asp   | Lys   | Ala   | Ser   | Leu   | Ile   | Asn   | Glu   | Leu   | Asn   | Val   | Leu   | Ala   | Ala   |      |
|       |       | 515   |       |       |       |       | 520   |       |       |       |       | 525   |       |       |       |      |
| TCT   | GCA   | AGC   | CAA   | GCT   | GAG   | TTT   | ATC   | CTC   | AAA   | GAT   | GCA   | GCA   | GCA   | AAC   | TAT   | 1632 |
| Ser   | Ala   | Ser   | Gln   | Ala   | Glu   | Phe   | Ile   | Leu   | Lys   | Asp   | Ala   | Ala   | Ala   | Asn   | Tyr   |      |
|       | 530   |       |       |       |       | 535   |       |       |       |       | 540   |       |       |       |       |      |
| GGC   | GTA   | CGT   | GAG   | CTT   | GAT   | AAA   | AAT   | GCA   | CCA   | CGG   | ATC   | GGT   | TTA   | GTT   | GCA   | 1680 |
| Gly   | Val   | Arg   | Glu   | Leu   | Asp   | Lys   | Asn   | Ala   | Pro   | Arg   | Ile   | Gly   | Leu   | Val   | Ala   |      |
| 545   |       |       |       |       | 550   |       |       |       |       | 555   |       |       |       |       | 560   |      |
| AAC   | ACA   | GCT   | GAA   | GAG   | TTA   | GCA   | GGC   | CTA   | ATT   | AAG   | CAA   | GCA   | CTT   | GCC   | AAA   | 1728 |
| Asn   | Thr   | Ala   | Glu   | Glu   | Leu   | Ala   | Gly   | Leu   | Ile   | Lys   | Gln   | Ala   | Leu   | Ala   | Lys   |      |
|       |       |       |       | 565   |       |       |       |       | 570   |       |       |       |       | 575   |       |      |
| CTA   | GCA   | GCT   | AGC   | GAT   | GAT   | AAC   | GCA   | TGG   | CAG   | CTA   | CCT   | GGT   | GGC   | ACT   | AGC   | 1776 |
| Leu   | Ala   | Ala   | Ser   | Asp   | Asp   | Asn   | Ala   | Trp   | Gln   | Leu   | Pro   | Gly   | Gly   | Thr   | Ser   |      |
|       |       |       | 580   |       |       |       |       | 585   |       |       |       |       | 590   |       |       |      |
| TAC   | CGC   | GCC   | GCT   | GCA   | GTA   | GAA   | GGT   | AAA   | GTT   | GCC   | GCA   | CTG   | TTT   | GCT   | GGC   | 1824 |
| Tyr   | Arg   | Ala   | Ala   | Ala   | Val   | Glu   | Gly   | Lys   | Val   | Ala   | Ala   | Leu   | Phe   | Ala   | Gly   |      |
|       |       | 595   |       |       |       |       | 600   |       |       |       |       | 605   |       |       |       |      |
| CAA   | GGT   | TCA   | CAA   | TAT   | CTC   | AAT   | ATG   | GGC   | CGT   | GAC   | CTT   | ACT   | TGT   | TAT   | TAC   | 1872 |
| Gln   | Gly   | Ser   | Gln   | Tyr   | Leu   | Asn   | Met   | Gly   | Arg   | Asp   | Leu   | Thr   | Cys   | Tyr   | Tyr   |      |
|       | 610   |       |       |       |       | 615   |       |       |       |       | 620   |       |       |       |       |      |
| CCA   | GAG   | ATG   | CGT   | CAG   | CAA   | TTT   | GTA   | ACT   | GCA   | GAT   | AAA   | GTA   | TTT   | GCC   | GCA   | 1920 |
| Pro   | Glu   | Met   | Arg   | Gln   | Gln   | Phe   | Val   | Thr   | Ala   | Asp   | Lys   | Val   | Phe   | Ala   | Ala   |      |
| 625   |       |       |       | 630   |       |       |       |       | 635   |       |       |       |       | 640   |       |      |
| AAT   | GAT   | AAA   | ACG   | CCG   | TTA   | TCG   | CAA   | ACT   | CTG   | TAT   | CCA   | AAG   | CCT   | GTA   | TTT   | 1968 |
| Asn   | Asp   | Lys   | Thr   | Pro   | Leu   | Ser   | Gln   | Thr   | Leu   | Tyr   | Pro   | Lys   | Pro   | Val   | Phe   |      |
|       |       |       |       | 645   |       |       |       |       | 650   |       |       |       |       | 655   |       |      |
| AAT   | AAA   | GAT   | GAA   | TTA   | AAG   | GCT   | CAA   | GAA   | GCC   | ATT   | TTG   | ACC   | AAT   | ACC   | GCC   | 2016 |
| Asn   | Lys   | Asp   | Glu   | Leu   | Lys   | Ala   | Gln   | Glu   | Ala   | Ile   | Leu   | Thr   | Asn   | Thr   | Ala   |      |
|       |       |       | 660   |       |       |       |       | 665   |       |       |       |       | 670   |       |       |      |
| AAT   | GCC   | CAA   | AGC   | GCA   | ATT   | GGT   | GCG   | ATT   | TCA   | ATG   | GGT   | CAA   | TAC   | GAT   | TTG   | 2064 |
| Asn   | Ala   | Gln   | Ser   | Ala   | Ile   | Gly   | Ala   | Ile   | Ser   | Met   | Gly   | Gln   | Tyr   | Asp   | Leu   |      |
|       |       | 675   |       |       |       |       | 680   |       |       |       |       | 685   |       |       |       |      |
| TTT   | ACT   | GCG   | GCT   | GGC   | TTT   | AAT   | GCC   | GAC   | ATG   | GTT   | GCA   | GGC   | CAT   | AGC   | TTT   | 2112 |
| Phe   | Thr   | Ala   | Ala   | Gly   | Phe   | Asn   | Ala   | Asp   | Met   | Val   | Ala   | Gly   | His   | Ser   | Phe   |      |
|       | 690   |       |       |       |       | 695   |       |       |       |       | 700   |       |       |       |       |      |
| GGT   | GAG   | CTA   | AGT   | GCA   | CTG   | TGT   | GCT   | GCA   | GGT   | GTT   | ATT   | TCA   | GCT   | GAT   | GAC   | 2160 |
| Gly   | Glu   | Leu   | Ser   | Ala   | Leu   | Cys   | Ala   | Ala   | Gly   | Val   | Ile   | Ser   | Ala   | Asp   | Asp   |      |
| 705   |       |       |       |       | 710   |       |       |       |       | 715   |       |       |       |       | 720   |      |
| TAC   | TAC   | AAG   | CTG   | GCT   | TTT   | GCT   | CGT   | GGT   | GAG   | GCT   | ATG   | GCA   | ACA   | AAA   | GCA   | 2208 |
| Tyr   | Tyr   | Lys   | Leu   | Ala   | Phe   | Ala   | Arg   | Gly   | Glu   | Ala   | Met   | Ala   | Thr   | Lys   | Ala   |      |
|       |       |       |       | 725   |       |       |       |       | 730   |       |       |       |       | 735   |       |      |
| CCG   | GCT   | AAA   | GAC   | GGC   | GTT   | GAA   | GCA   | GAT   | GCA   | GGA   | GCA   | ATG   | TTT   | GCA   | ATC   | 2256 |
| Pro   | Ala   | Lys   | Asp   | Gly   | Val   | Glu   | Ala   | Asp   | Ala   | Gly   | Ala   | Met   | Phe   | Ala   | Ile   |      |
|       |       |       | 740   |       |       |       |       | 745   |       |       |       |       | 750   |       |       |      |
| ATA   | ACC   | AAG   | AGT   | GCT   | GCA   | GAC   | CTT   | GAA   | ACC   | GTT   | GAA   | GCC   | ACC   | ATC   | GCT   | 2304 |
| Ile   | Thr   | Lys   | Ser   | Ala   | Ala   | Asp   | Leu   | Glu   | Thr   | Val   | Glu   | Ala   | Thr   | Ile   | Ala   |      |
|       |       | 755   |       |       |       |       | 760   |       |       |       |       | 765   |       |       |       |      |
| AAA   | TTT   | GAT   | GGG   | GTG   | AAA   | GTC   | GCT   | AAC   | TAT   | AAC   | GCG   | CCA   | ACG   | CAA   | TCA   | 2352 |
| Lys   | Phe   | Asp   | Gly   | Val   | Lys   | Val   | Ala   | Asn   | Tyr   | Asn   | Ala   | Pro   | Thr   | Gln   | Ser   |      |
|       | 770   |       |       |       |       | 775   |       |       |       |       | 780   |       |       |       |       |      |
| GTA   | ATT   | GCA   | GGC   | CCA   | ACA   | GCA   | ACT   | ACC   | GCT   | GAT   | GCG   | GCT   | AAA   | GCG   | CTA   | 2400 |
| Val   | Ile   | Ala   | Gly   | Pro   | Thr   | Ala   | Thr   | Thr   | Ala   | Asp   | Ala   | Ala   | Lys   | Ala   | Leu   |      |
| 785   |       |       |       |       | 790   |       |       |       |       | 795   |       |       |       |       | 800   |      |
| ACT   | GAG   | CTT   | GGT   | TAC   | AAA   | GCG   | ATT   | AAC   | CTG   | CCA   | GTA   | TCA   | GGT   | GCA   | TTC   | 2448 |
| Thr   | Glu   | Leu   | Gly   | Tyr   | Lys   | Ala   | Ile   | Asn   | Leu   | Pro   | Val   | Ser   | Gly   | Ala   | Phe   |      |
|       |       |       |       | 805   |       |       |       |       | 810   |       |       |       |       | 815   |       |      |
| CAC   | ACT   | GAA   | CTT   | GTT   | GGT   | CAC   | GCT   | CAA   | GCG   | CCA   | TTT   | GCT   | AAA   | GCG   | ATT   | 2496 |
| His   | Thr   | Glu   | Leu   | Val   | Gly   | His   | Ala   | Gln   | Ala   | Pro   | Phe   | Ala   | Lys   | Ala   | Ile   |      |

-continued

|  |  |  | 820 |  |  |  | 825 |  |  |  | 830 |  |  |  |  |
|---|---|---|---|---|---|---|---|---|---|---|---|---|---|---|---|
| GAC | GCA | GCC | AAA | TTT | ACT | AAA | ACA | AGC | CGA | GCA | CTT | TAC | TCA | AAT | GCA | 2544 |
| Asp | Ala | Ala | Lys | Phe | Thr | Lys | Thr | Ser | Arg | Ala | Leu | Tyr | Ser | Asn | Ala |
|  |  | 835 |  |  |  | 840 |  |  |  |  | 845 |  |  |  |  |
| ACT | GGC | GGA | CTT | TAT | GAA | AGC | ACT | GCT | GCA | AAG | ATT | AAA | GCC | TCG | TTT | 2592 |
| Thr | Gly | Gly | Leu | Tyr | Glu | Ser | Thr | Ala | Ala | Lys | Ile | Lys | Ala | Ser | Phe |
|  | 850 |  |  |  |  | 855 |  |  |  |  | 860 |  |  |  |  |
| AAG | AAA | CAT | ATG | CTT | CAA | TCA | GTG | CGC | TTT | ACT | AGC | CAG | CTA | GAA | GCC | 2640 |
| Lys | Lys | His | Met | Leu | Gln | Ser | Val | Arg | Phe | Thr | Ser | Gln | Leu | Glu | Ala |
| 865 |  |  |  |  | 870 |  |  |  |  | 875 |  |  |  |  | 880 |
| ATG | TAC | AAC | GAC | GGC | GCC | CGT | GTA | TTT | GTT | GAA | TTT | GGT | CCA | AAG | AAC | 2688 |
| Met | Tyr | Asn | Asp | Gly | Ala | Arg | Val | Phe | Val | Glu | Phe | Gly | Pro | Lys | Asn |
|  |  |  |  | 885 |  |  |  |  | 890 |  |  |  |  | 895 |  |
| ATC | TTA | CAA | AAA | TTA | GTT | CAA | GGC | ACG | CTT | GTC | AAC | ACT | GAA | AAT | GAA | 2736 |
| Ile | Leu | Gln | Lys | Leu | Val | Gln | Gly | Thr | Leu | Val | Asn | Thr | Glu | Asn | Glu |
|  |  | 900 |  |  |  |  | 905 |  |  |  |  | 910 |  |  |  |
| GTT | TGC | ACT | ATC | TCT | ATC | AAC | CCT | AAT | CCT | AAA | GTT | GAT | AGT | GAT | CTG | 2784 |
| Val | Cys | Thr | Ile | Ser | Ile | Asn | Pro | Asn | Pro | Lys | Val | Asp | Ser | Asp | Leu |
|  | 915 |  |  |  |  | 920 |  |  |  |  | 925 |  |  |  |  |
| CAG | CTT | AAG | CAA | GCA | GCA | ATG | CAG | CTA | GCG | GTT | ACT | GGT | GTG | GTA | CTC | 2832 |
| Gln | Leu | Lys | Gln | Ala | Ala | Met | Gln | Leu | Ala | Val | Thr | Gly | Val | Val | Leu |
| 930 |  |  |  |  | 935 |  |  |  |  | 940 |  |  |  |  |  |
| AGT | GAA | ATT | GAC | CCA | TAC | CAA | GCC | GAT | ATT | GCC | GCA | CCA | GCG | AAA | AAG | 2880 |
| Ser | Glu | Ile | Asp | Pro | Tyr | Gln | Ala | Asp | Ile | Ala | Ala | Pro | Ala | Lys | Lys |
| 945 |  |  |  |  | 950 |  |  |  |  | 955 |  |  |  |  | 960 |
| TCG | CCA | ATG | AGC | ATT | TCG | CTT | AAT | GCT | GCT | AAC | CAT | ATC | AGC | AAA | GCA | 2928 |
| Ser | Pro | Met | Ser | Ile | Ser | Leu | Asn | Ala | Ala | Asn | His | Ile | Ser | Lys | Ala |
|  |  |  |  | 965 |  |  |  |  | 970 |  |  |  |  | 975 |  |
| ACT | CGC | GCT | AAG | ATG | GCC | AAG | TCT | TTA | GAG | ACA | GGT | ATC | GTC | ACC | TCG | 2976 |
| Thr | Arg | Ala | Lys | Met | Ala | Lys | Ser | Leu | Glu | Thr | Gly | Ile | Val | Thr | Ser |
|  |  |  | 980 |  |  |  |  | 985 |  |  |  |  | 990 |  |  |
| CAA | ATA | GAA | CAT | GTT | ATT | GAA | GAA | AAA | ATC | GTT | GAA | GTT | GAG | AAA | CTG | 3024 |
| Gln | Ile | Glu | His | Val | Ile | Glu | Glu | Lys | Ile | Val | Glu | Val | Glu | Lys | Leu |
|  |  | 995 |  |  |  |  | 1000 |  |  |  |  | 1005 |  |  |  |
| GTT | GAA | GTC | GAA | AAG | ATC | GTC | GAA | AAA | GTG | GTT | GAA | GTA | GAG | AAA | GTT | 3072 |
| Val | Glu | Val | Glu | Lys | Ile | Val | Glu | Lys | Val | Val | Glu | Val | Glu | Lys | Val |
| 1010 |  |  |  |  | 1015 |  |  |  |  | 1020 |  |  |  |  |  |
| GTT | GAG | GTT | GAA | GCT | CCT | GTT | AAT | TCA | GTG | CAA | GCC | AAT | GCA | ATT | CAA | 3120 |
| Val | Glu | Val | Glu | Ala | Pro | Val | Asn | Ser | Val | Gln | Ala | Asn | Ala | Ile | Gln |
| 1025 |  |  |  |  | 1030 |  |  |  |  | 1035 |  |  |  |  | 1040 |
| ACC | CGT | TCA | GTT | GTC | GCT | CCA | GTA | ATA | GAG | AAC | CAA | GTC | GTG | TCT | AAA | 3168 |
| Thr | Arg | Ser | Val | Val | Ala | Pro | Val | Ile | Glu | Asn | Gln | Val | Val | Ser | Lys |
|  |  |  |  | 1045 |  |  |  |  | 1050 |  |  |  |  | 1055 |  |
| AAC | AGT | AAG | CCA | GCA | GTC | CAG | AGC | ATT | AGT | GGT | GAT | GCA | CTC | AGC | AAC | 3216 |
| Asn | Ser | Lys | Pro | Ala | Val | Gln | Ser | Ile | Ser | Gly | Asp | Ala | Leu | Ser | Asn |
|  |  |  | 1060 |  |  |  |  | 1065 |  |  |  |  | 1070 |  |  |
| TTT | TTT | GCT | GCA | CAG | CAG | CAA | ACC | GCA | CAG | TTG | CAT | CAG | CAG | TTC | TTA | 3264 |
| Phe | Phe | Ala | Ala | Gln | Gln | Gln | Thr | Ala | Gln | Leu | His | Gln | Gln | Phe | Leu |
|  |  | 1075 |  |  |  |  | 1080 |  |  |  |  | 1085 |  |  |  |
| GCT | ATT | CCG | CAG | CAA | TAT | GGT | GAG | ACG | TTC | ACT | ACG | CTG | ATG | ACC | GAG | 3312 |
| Ala | Ile | Pro | Gln | Gln | Tyr | Gly | Glu | Thr | Phe | Thr | Thr | Leu | Met | Thr | Glu |
|  |  | 1090 |  |  |  |  | 1095 |  |  |  |  | 1100 |  |  |  |
| CAA | GCT | AAA | CTG | GCA | AGT | TCT | GGT | GTT | GCA | ATT | CCA | GAG | AGT | CTG | CAA | 3360 |
| Gln | Ala | Lys | Leu | Ala | Ser | Ser | Gly | Val | Ala | Ile | Pro | Glu | Ser | Leu | Gln |
| 1105 |  |  |  |  | 1110 |  |  |  |  | 1115 |  |  |  |  | 1120 |
| CGC | TCA | ATG | GAG | CAA | TTC | CAC | CAA | CTA | CAA | GCG | CAA | ACA | CTA | CAA | AGC | 3408 |
| Arg | Ser | Met | Glu | Gln | Phe | His | Gln | Leu | Gln | Ala | Gln | Thr | Leu | Gln | Ser |
|  |  |  |  | 1125 |  |  |  |  | 1130 |  |  |  |  | 1135 |  |
| CAC | ACC | CAG | TTC | CTT | GAG | ATG | CAA | GCG | GGT | AGC | AAC | ATT | GCA | GCG | TTA | 3456 |
| His | Thr | Gln | Phe | Leu | Glu | Met | Gln | Ala | Gly | Ser | Asn | Ile | Ala | Ala | Leu |

```
                1140                         1145                         1150
AAC  CTA  CTC  AAT  AGC  AGC  CAA  GCA  ACT  TAC  GCT  CCA  GCC  ATT  CAC  AAT    3504
Asn  Leu  Leu  Asn  Ser  Ser  Gln  Ala  Thr  Tyr  Ala  Pro  Ala  Ile  His  Asn
               1155                         1160                         1165

GAA  GCG  ATT  CAA  AGC  CAA  GTG  GTT  CAA  AGC  CAA  ACT  GCA  GTC  CAG  CCA    3552
Glu  Ala  Ile  Gln  Ser  Gln  Val  Val  Gln  Ser  Gln  Thr  Ala  Val  Gln  Pro
     1170                         1175                         1180

GTA  ATT  TCA  ACA  CAA  GTT  AAC  CAT  GTG  TCA  GAG  CAG  CCA  ACT  CAA  GCT    3600
Val  Ile  Ser  Thr  Gln  Val  Asn  His  Val  Ser  Glu  Gln  Pro  Thr  Gln  Ala
1185                         1190                         1195                1200

CCA  GCT  CCA  AAA  GCG  CAG  CCA  GCA  CCT  GTG  ACA  ACT  GCA  GTT  CAA  ACT    3648
Pro  Ala  Pro  Lys  Ala  Gln  Pro  Ala  Pro  Val  Thr  Thr  Ala  Val  Gln  Thr
                    1205                         1210                         1215

GCT  CCG  GCA  CAA  GTT  GTT  CGT  CAA  GCC  GCA  CCA  GTT  CAA  GCC  GCT  ATT    3696
Ala  Pro  Ala  Gln  Val  Val  Arg  Gln  Ala  Ala  Pro  Val  Gln  Ala  Ala  Ile
               1220                         1225                         1230

GAA  CCG  ATT  AAT  ACA  AGT  GTT  GCG  ACT  ACA  ACG  CCT  TCA  GCC  TTC  AGC    3744
Glu  Pro  Ile  Asn  Thr  Ser  Val  Ala  Thr  Thr  Thr  Pro  Ser  Ala  Phe  Ser
     1235                         1240                         1245

GCC  GAA  ACA  GCC  CTG  AGC  GCA  ACA  AAA  GTC  CAA  GCC  ACT  ATG  CTT  GAA    3792
Ala  Glu  Thr  Ala  Leu  Ser  Ala  Thr  Lys  Val  Gln  Ala  Thr  Met  Leu  Glu
1250                         1255                         1260

GTG  GTT  GCT  GAG  AAA  ACC  GGT  TAC  CCA  ACT  GAA  ATG  CTA  GAG  CTT  GAA    3840
Val  Val  Ala  Glu  Lys  Thr  Gly  Tyr  Pro  Thr  Glu  Met  Leu  Glu  Leu  Glu
1265                         1270                         1275                1280

ATG  GAT  ATG  GAA  GCC  GAT  TTA  GGC  ATC  GAT  TCT  ATC  AAG  CGT  GTA  GAA    3888
Met  Asp  Met  Glu  Ala  Asp  Leu  Gly  Ile  Asp  Ser  Ile  Lys  Arg  Val  Glu
                    1285                         1290                         1295

ATT  CTT  GGC  ACA  GTA  CAA  GAT  GAG  CTA  CCG  GGT  CTA  CCT  GAG  CTT  AGC    3936
Ile  Leu  Gly  Thr  Val  Gln  Asp  Glu  Leu  Pro  Gly  Leu  Pro  Glu  Leu  Ser
               1300                         1305                         1310

CCT  GAA  GAT  CTA  GCT  GAG  TGT  CGA  ACG  CTA  GGC  GAA  ATC  GTT  GAC  TAT    3984
Pro  Glu  Asp  Leu  Ala  Glu  Cys  Arg  Thr  Leu  Gly  Glu  Ile  Val  Asp  Tyr
     1315                         1320                         1325

ATG  GGC  AGT  AAA  CTG  CCG  GCT  GAA  GGC  TCT  ATG  AAT  TCT  CAG  CTG  TCT    4032
Met  Gly  Ser  Lys  Leu  Pro  Ala  Glu  Gly  Ser  Met  Asn  Ser  Gln  Leu  Ser
1330                         1335                         1340

ACA  GGT  TCC  GCA  GCT  GCG  ACT  CCT  GCA  GCG  AAT  GGT  CTT  TCT  GCG  GAG    4080
Thr  Gly  Ser  Ala  Ala  Ala  Thr  Pro  Ala  Ala  Asn  Gly  Leu  Ser  Ala  Glu
1345                         1350                         1355                1360

AAA  GTT  CAA  GCG  ACT  ATG  ATG  TCT  GTG  GTT  GCC  GAA  AAG  ACT  GGC  TAC    4128
Lys  Val  Gln  Ala  Thr  Met  Met  Ser  Val  Val  Ala  Glu  Lys  Thr  Gly  Tyr
                    1365                         1370                         1375

CCA  ACT  GAA  ATG  CTA  GAG  CTT  GAA  ATG  GAT  ATG  GAA  GCC  GAT  TTA  GGC    4176
Pro  Thr  Glu  Met  Leu  Glu  Leu  Glu  Met  Asp  Met  Glu  Ala  Asp  Leu  Gly
               1380                         1385                         1390

ATA  GAT  TCT  ATC  AAG  CGC  GTT  GAA  ATT  CTT  GGC  ACA  GTA  CAA  GAT  GAG    4224
Ile  Asp  Ser  Ile  Lys  Arg  Val  Glu  Ile  Leu  Gly  Thr  Val  Gln  Asp  Glu
     1395                         1400                         1405

CTA  CCG  GGT  CTA  CCT  GAG  CTT  AGC  CCT  GAA  GAT  CTA  GCT  GAG  TGT  CGT    4272
Leu  Pro  Gly  Leu  Pro  Glu  Leu  Ser  Pro  Glu  Asp  Leu  Ala  Glu  Cys  Arg
1410                         1415                         1420

ACT  CTA  GGC  GAA  ATC  GTT  GAC  TAT  ATG  AAC  TCT  AAA  CTC  GCT  GAC  GGC    4320
Thr  Leu  Gly  Glu  Ile  Val  Asp  Tyr  Met  Asn  Ser  Lys  Leu  Ala  Asp  Gly
1425                         1430                         1435                1440

TCT  AAG  CTG  CCG  GCT  GAA  GGC  TCT  ATG  AAT  TCT  CAG  CTG  TCT  ACA  AGT    4368
Ser  Lys  Leu  Pro  Ala  Glu  Gly  Ser  Met  Asn  Ser  Gln  Leu  Ser  Thr  Ser
                    1445                         1450                         1455

GCC  GCA  GCT  GCG  ACT  CCT  GCA  GCG  AAT  GGT  CTC  TCT  GCG  GAG  AAA  GTT    4416
Ala  Ala  Ala  Ala  Thr  Pro  Ala  Ala  Asn  Gly  Leu  Ser  Ala  Glu  Lys  Val
```

|   |   |   |   |   |   |   |   |   |   |   |   |   |   |   |   |
|---|---|---|---|---|---|---|---|---|---|---|---|---|---|---|---|

```
                     1460                          1465                          1470
CAA  GCG  ACT  ATG  ATG  TCT  GTG  GTT  GCC  GAA  AAG  ACT  GGC  TAC  CCA  ACT         4464
Gln  Ala  Thr  Met  Met  Ser  Val  Val  Ala  Glu  Lys  Thr  Gly  Tyr  Pro  Thr
          1475                          1480                          1485

GAA  ATG  CTA  GAA  CTT  GAA  ATG  GAT  ATG  GAA  GCT  GAC  CTT  GGC  ATC  GAT         4512
Glu  Met  Leu  Glu  Leu  Glu  Met  Asp  Met  Glu  Ala  Asp  Leu  Gly  Ile  Asp
     1490                          1495                          1500

TCA  ATC  AAG  CGC  GTT  GAA  ATT  CTT  GGC  ACA  GTA  CAA  GAT  GAG  CTA  CCG         4560
Ser  Ile  Lys  Arg  Val  Glu  Ile  Leu  Gly  Thr  Val  Gln  Asp  Glu  Leu  Pro
1505                          1510                          1515                1520

GGT  TTA  CCT  GAG  CTA  AAT  CCA  GAA  GAT  TTG  GCA  GAG  TGT  CGT  ACT  CTT         4608
Gly  Leu  Pro  Glu  Leu  Asn  Pro  Glu  Asp  Leu  Ala  Glu  Cys  Arg  Thr  Leu
                    1525                          1530                      1535

GGC  GAA  ATC  GTG  ACT  TAT  ATG  AAC  TCT  AAA  CTC  GCT  GAC  GGC  TCT  AAG         4656
Gly  Glu  Ile  Val  Thr  Tyr  Met  Asn  Ser  Lys  Leu  Ala  Asp  Gly  Ser  Lys
               1540                          1545                     1550

CTG  CCA  GCT  GAA  GGC  TCT  ATG  CAC  TAT  CAG  CTG  TCT  ACA  AGT  ACC  GCT         4704
Leu  Pro  Ala  Glu  Gly  Ser  Met  His  Tyr  Gln  Leu  Ser  Thr  Ser  Thr  Ala
     1555                          1560                          1565

GCT  GCG  ACT  CCT  GTA  GCG  AAT  GGT  CTC  TCT  GCA  GAA  AAA  GTT  CAA  GCG         4752
Ala  Ala  Thr  Pro  Val  Ala  Asn  Gly  Leu  Ser  Ala  Glu  Lys  Val  Gln  Ala
1570                          1575                          1580

ACC  ATG  ATG  TCT  GTA  GTT  GCA  GAT  AAA  ACT  GGC  TAC  CCA  ACT  GAA  ATG         4800
Thr  Met  Met  Ser  Val  Val  Ala  Asp  Lys  Thr  Gly  Tyr  Pro  Thr  Glu  Met
1585                          1590                          1595                1600

CTT  GAA  CTT  GAA  ATG  GAT  ATG  GAA  GCC  GAT  TTA  GGT  ATC  GAT  TCT  ATC         4848
Leu  Glu  Leu  Glu  Met  Asp  Met  Glu  Ala  Asp  Leu  Gly  Ile  Asp  Ser  Ile
                         1605                          1610                1615

AAG  CGC  GTT  GAA  ATT  CTT  GGC  ACA  GTA  CAA  GAT  GAG  CTA  CCG  GGT  TTA         4896
Lys  Arg  Val  Glu  Ile  Leu  Gly  Thr  Val  Gln  Asp  Glu  Leu  Pro  Gly  Leu
               1620                          1625                     1630

CCT  GAG  CTA  AAT  CCA  GAA  GAT  CTA  GCA  GAG  TGT  CGC  ACC  CTA  GGC  GAA         4944
Pro  Glu  Leu  Asn  Pro  Glu  Asp  Leu  Ala  Glu  Cys  Arg  Thr  Leu  Gly  Glu
          1635                          1640                          1645

ATC  GTT  GAC  TAT  ATG  GGC  AGT  AAA  CTG  CCG  GCT  GAA  GGC  TCT  GCT  AAT         4992
Ile  Val  Asp  Tyr  Met  Gly  Ser  Lys  Leu  Pro  Ala  Glu  Gly  Ser  Ala  Asn
     1650                          1655                          1660

ACA  AGT  GCC  GCT  GCG  TCT  CTT  AAT  GTT  AGT  GCC  GTT  GCG  GCG  CCT  CAA         5040
Thr  Ser  Ala  Ala  Ala  Ser  Leu  Asn  Val  Ser  Ala  Val  Ala  Ala  Pro  Gln
1665                          1670                          1675                1680

GCT  GCT  GCG  ACT  CCT  GTA  TCG  AAC  GGT  CTC  TCT  GCA  GAG  AAA  GTG  CAA         5088
Ala  Ala  Ala  Thr  Pro  Val  Ser  Asn  Gly  Leu  Ser  Ala  Glu  Lys  Val  Gln
                    1685                          1690                     1695

AGC  ACT  ATG  ATG  TCA  GTA  GTT  GCA  GAA  AAG  ACC  GGC  TAC  CCA  ACT  GAA         5136
Ser  Thr  Met  Met  Ser  Val  Val  Ala  Glu  Lys  Thr  Gly  Tyr  Pro  Thr  Glu
          1700                          1705                          1710

ATG  CTA  GAA  CTT  GGC  ATG  GAT  ATG  GAA  GCC  GAT  TTA  GGT  ATC  GAC  TCA         5184
Met  Leu  Glu  Leu  Gly  Met  Asp  Met  Glu  Ala  Asp  Leu  Gly  Ile  Asp  Ser
               1715                          1720                     1725

ATT  AAA  CGC  GTT  GAG  ATT  CTT  GGC  ACA  GTA  CAA  GAT  GAG  CTA  CCG  GGT         5232
Ile  Lys  Arg  Val  Glu  Ile  Leu  Gly  Thr  Val  Gln  Asp  Glu  Leu  Pro  Gly
     1730                          1735                          1740

CTA  CCA  GAG  CTT  AAT  CCT  GAA  GAT  TTA  GCT  GAG  TGC  CGT  ACG  CTG  GGC         5280
Leu  Pro  Glu  Leu  Asn  Pro  Glu  Asp  Leu  Ala  Glu  Cys  Arg  Thr  Leu  Gly
1745                          1750                          1755                1760

GAA  ATC  GTT  GAC  TAT  ATG  AAC  TCT  AAG  CTG  GCT  GAC  GGC  TCT  AAG  CTT         5328
Glu  Ile  Val  Asp  Tyr  Met  Asn  Ser  Lys  Leu  Ala  Asp  Gly  Ser  Lys  Leu
                    1765                          1770                     1775

CCA  GCT  GAA  GGC  TCT  GCT  AAT  ACA  AGT  GCC  ACT  GCT  GCG  ACT  CCT  GCA         5376
Pro  Ala  Glu  Gly  Ser  Ala  Asn  Thr  Ser  Ala  Thr  Ala  Ala  Thr  Pro  Ala
```

|   |   |   |   |   |   |   |   |   |   |   |   |   |   |   |   |
|---|---|---|---|---|---|---|---|---|---|---|---|---|---|---|---|
| GTG | AAT | GGT | CTT | TCT | GCT | GAC | AAG | GTA | CAG | GCG | ACT | ATG | ATG | TCT | GTA | 5424
| Val | Asn | Gly | Leu | Ser | Ala | Asp | Lys | Val | Gln | Ala | Thr | Met | Met | Ser | Val |
|  | 1795 |  |  |  | 1800 |  |  |  |  | 1805 |  |  |  |  |  |

```
                       1780                         1785                         1790
GTG  AAT  GGT  CTT  TCT  GCT  GAC  AAG  GTA  CAG  GCG  ACT  ATG  ATG  TCT  GTA          5424
Val  Asn  Gly  Leu  Ser  Ala  Asp  Lys  Val  Gln  Ala  Thr  Met  Met  Ser  Val
     1795                1800                1805

GTT  GCT  GAA  AAG  ACC  GGC  TAC  CCA  ACT  GAA  ATG  CTA  GAA  CTT  GGC  ATG          5472
Val  Ala  Glu  Lys  Thr  Gly  Tyr  Pro  Thr  Glu  Met  Leu  Glu  Leu  Gly  Met
1810                1815                1820

GAT  ATG  GAA  GCA  GAC  CTT  GGT  ATT  GAT  TCT  ATT  AAG  CGC  GTT  GAA  ATT          5520
Asp  Met  Glu  Ala  Asp  Leu  Gly  Ile  Asp  Ser  Ile  Lys  Arg  Val  Glu  Ile
1825                1830                1835                1840

CTT  GGC  ACA  GTA  CAA  GAT  GAG  CTC  CCA  GGT  TTA  CCT  GAG  CTT  AAT  CCT          5568
Leu  Gly  Thr  Val  Gln  Asp  Glu  Leu  Pro  Gly  Leu  Pro  Glu  Leu  Asn  Pro
          1845                1850                1855

GAA  GAT  CTC  GCT  GAG  TGC  CGC  ACG  CTT  GGC  GAA  ATC  GTT  AGC  TAT  ATG          5616
Glu  Asp  Leu  Ala  Glu  Cys  Arg  Thr  Leu  Gly  Glu  Ile  Val  Ser  Tyr  Met
1860                1865                1870

AAC  TCT  CAA  CTG  GCT  GAT  GGC  TCT  AAA  CTT  TCT  ACA  AGT  GCG  GCT  GAA          5664
Asn  Ser  Gln  Leu  Ala  Asp  Gly  Ser  Lys  Leu  Ser  Thr  Ser  Ala  Ala  Glu
          1875                1880                1885

GGC  TCT  GCT  GAT  ACA  AGT  GCT  GCA  AAT  GCT  GCA  AAG  CCG  GCA  GCA  ATT          5712
Gly  Ser  Ala  Asp  Thr  Ser  Ala  Ala  Asn  Ala  Ala  Lys  Pro  Ala  Ala  Ile
1890                1895                1900

TCG  GCA  GAA  CCA  AGT  GTT  GAG  CTT  CCT  CCT  CAT  AGC  GAG  GTA  GCG  CTA          5760
Ser  Ala  Glu  Pro  Ser  Val  Glu  Leu  Pro  Pro  His  Ser  Glu  Val  Ala  Leu
1905                1910                1915                1920

AAA  AAG  CTT  AAT  GCG  GCG  AAC  AAG  CTA  GAA  AAT  TGT  TTC  GCC  GCA  GAC          5808
Lys  Lys  Leu  Asn  Ala  Ala  Asn  Lys  Leu  Glu  Asn  Cys  Phe  Ala  Ala  Asp
          1925                1930                1935

GCA  AGT  GTT  GTG  ATT  AAC  GAT  GAT  GGT  CAC  AAC  GCA  GGC  GTT  TTA  GCT          5856
Ala  Ser  Val  Val  Ile  Asn  Asp  Asp  Gly  His  Asn  Ala  Gly  Val  Leu  Ala
               1940                1945                1950

GAG  AAA  CTT  ATT  AAA  CAA  GGC  CTA  AAA  GTA  GCC  GTT  GTG  CGT  TTA  CCG          5904
Glu  Lys  Leu  Ile  Lys  Gln  Gly  Leu  Lys  Val  Ala  Val  Val  Arg  Leu  Pro
          1955                1960                1965

AAA  GGT  CAG  CCT  CAA  TCG  CCA  CTT  TCA  AGC  GAT  GTT  GCT  AGC  TTT  GAG          5952
Lys  Gly  Gln  Pro  Gln  Ser  Pro  Leu  Ser  Ser  Asp  Val  Ala  Ser  Phe  Glu
     1970                1975                1980

CTT  GCC  TCA  AGC  CAA  GAA  TCT  GAG  CTT  GAA  GCC  AGT  ATC  ACT  GCA  GTT          6000
Leu  Ala  Ser  Ser  Gln  Glu  Ser  Glu  Leu  Glu  Ala  Ser  Ile  Thr  Ala  Val
1985                1990                1995                2000

ATC  GCG  CAG  ATT  GAA  ACT  CAG  GTT  GGC  GCT  ATT  GGT  GGC  TTT  ATT  CAC          6048
Ile  Ala  Gln  Ile  Glu  Thr  Gln  Val  Gly  Ala  Ile  Gly  Gly  Phe  Ile  His
                2005                2010                2015

TTG  CAA  CCA  GAA  GCG  AAT  ACA  GAA  GAG  CAA  ACG  GCA  GTA  AAC  CTA  GAT          6096
Leu  Gln  Pro  Glu  Ala  Asn  Thr  Glu  Glu  Gln  Thr  Ala  Val  Asn  Leu  Asp
               2020                2025                2030

GCG  CAA  AGT  TTT  ACT  CAC  GTT  AGC  AAT  GCG  TTC  TTG  TGG  GCC  AAA  TTA          6144
Ala  Gln  Ser  Phe  Thr  His  Val  Ser  Asn  Ala  Phe  Leu  Trp  Ala  Lys  Leu
          2035                2040                2045

TTG  CAA  CCA  AAG  CTC  GTT  GCT  GGA  GCA  GAT  GCG  CGT  CGC  TGT  TTT  GTA          6192
Leu  Gln  Pro  Lys  Leu  Val  Ala  Gly  Ala  Asp  Ala  Arg  Arg  Cys  Phe  Val
     2050                2055                2060

ACA  GTA  AGC  CGT  ATC  GAC  GGT  GGC  TTT  GGT  TAC  CTA  AAT  ACT  GAC  GCC          6240
Thr  Val  Ser  Arg  Ile  Asp  Gly  Gly  Phe  Gly  Tyr  Leu  Asn  Thr  Asp  Ala
2065                2070                2075                2080

CTA  AAA  GAT  GCT  GAG  CTA  AAC  CAA  GCA  GCA  TTA  GCT  GGT  TTA  ACT  AAA          6288
Leu  Lys  Asp  Ala  Glu  Leu  Asn  Gln  Ala  Ala  Leu  Ala  Gly  Leu  Thr  Lys
                2085                2090                2095

ACC  TTA  AGC  CAT  GAA  TGG  CCA  CAA  GTG  TTC  TGT  CGC  GCG  CTA  GAT  ATT          6336
Thr  Leu  Ser  His  Glu  Trp  Pro  Gln  Val  Phe  Cys  Arg  Ala  Leu  Asp  Ile
```

-continued

```
              2100                      2105                      2110
GCA  ACA  GAT  GTT  GAT  GCA  ACC  CAT  CTT  GCT  GAT  GCA  ATC  ACC  AGT  GAA         6384
Ala  Thr  Asp  Val  Asp  Ala  Thr  His  Leu  Ala  Asp  Ala  Ile  Thr  Ser  Glu
          2115                     2120                     2125

CTA  TTT  GAT  AGC  CAA  GCT  CAG  CTA  CCT  GAA  GTG  GGC  TTA  AGC  TTA  ATT         6432
Leu  Phe  Asp  Ser  Gln  Ala  Gln  Leu  Pro  Glu  Val  Gly  Leu  Ser  Leu  Ile
     2130                     2135                     2140

GAT  GGC  AAA  GTT  AAC  CGC  GTA  ACT  CTA  GTT  GCT  GCT  GAA  GCT  GCA  GAT         6480
Asp  Gly  Lys  Val  Asn  Arg  Val  Thr  Leu  Val  Ala  Ala  Glu  Ala  Ala  Asp
2145                     2150                     2155                     2160

AAA  ACA  GCA  AAA  GCA  GAG  CTT  AAC  AGC  ACA  GAT  AAA  ATC  TTA  GTG  ACT         6528
Lys  Thr  Ala  Lys  Ala  Glu  Leu  Asn  Ser  Thr  Asp  Lys  Ile  Leu  Val  Thr
               2165                     2170                     2175

GGT  GGG  GCA  AAA  GGG  GTG  ACA  TTT  GAA  TGT  GCA  CTG  GCA  TTA  GCA  TCT         6576
Gly  Gly  Ala  Lys  Gly  Val  Thr  Phe  Glu  Cys  Ala  Leu  Ala  Leu  Ala  Ser
          2180                     2185                     2190

CGC  AGC  CAG  TCT  CAC  TTT  ATC  TTA  GCT  GGG  CGC  AGT  GAA  TTA  CAA  GCT         6624
Arg  Ser  Gln  Ser  His  Phe  Ile  Leu  Ala  Gly  Arg  Ser  Glu  Leu  Gln  Ala
     2195                     2200                     2205

TTA  CCA  AGC  TGG  GCT  GAG  GGT  AAG  CAA  ACT  AGC  GAG  CTA  AAA  TCA  GCT         6672
Leu  Pro  Ser  Trp  Ala  Glu  Gly  Lys  Gln  Thr  Ser  Glu  Leu  Lys  Ser  Ala
2210                     2215                     2220

GCA  ATC  GCA  CAT  ATT  ATT  TCT  ACT  GGT  CAA  AAG  CCA  ACG  CCT  AAG  CAA         6720
Ala  Ile  Ala  His  Ile  Ile  Ser  Thr  Gly  Gln  Lys  Pro  Thr  Pro  Lys  Gln
2225                     2230                     2235                     2240

GTT  GAA  GCC  GCT  GTG  TGG  CCA  GTG  CAA  AGC  AGC  ATT  GAA  ATT  AAT  GCC         6768
Val  Glu  Ala  Ala  Val  Trp  Pro  Val  Gln  Ser  Ser  Ile  Glu  Ile  Asn  Ala
                    2245                     2250                     2255

GCC  CTA  GCC  GCC  TTT  AAC  AAA  GTT  GGC  GCC  TCA  GCT  GAA  TAC  GTC  AGC         6816
Ala  Leu  Ala  Ala  Phe  Asn  Lys  Val  Gly  Ala  Ser  Ala  Glu  Tyr  Val  Ser
               2260                     2265                     2270

ATG  GAT  GTT  ACC  GAT  AGC  GCC  GCA  ATC  ACA  GCA  GCA  CTT  AAT  GGT  CGC         6864
Met  Asp  Val  Thr  Asp  Ser  Ala  Ala  Ile  Thr  Ala  Ala  Leu  Asn  Gly  Arg
          2275                     2280                     2285

TCA  AAT  GAG  ATC  ACC  GGT  CTT  ATT  CAT  GGC  GCA  GGT  GTA  CTA  GCC  GAC         6912
Ser  Asn  Glu  Ile  Thr  Gly  Leu  Ile  His  Gly  Ala  Gly  Val  Leu  Ala  Asp
     2290                     2295                     2300

AAG  CAT  ATT  CAA  GAC  AAG  ACT  CTT  GCT  GAA  CTT  GCT  AAA  GTT  TAT  GGC         6960
Lys  His  Ile  Gln  Asp  Lys  Thr  Leu  Ala  Glu  Leu  Ala  Lys  Val  Tyr  Gly
2305                     2310                     2315                     2320

ACT  AAA  GTC  AAC  GGC  CTA  AAA  GCG  CTG  CTC  GCG  GCA  CTT  GAG  CCA  AGC         7008
Thr  Lys  Val  Asn  Gly  Leu  Lys  Ala  Leu  Leu  Ala  Ala  Leu  Glu  Pro  Ser
                    2325                     2330                     2335

AAA  ATT  AAA  TTA  CTT  GCT  ATG  TTC  TCA  TCT  GCA  GCA  GGT  TTT  TAC  GGT         7056
Lys  Ile  Lys  Leu  Leu  Ala  Met  Phe  Ser  Ser  Ala  Ala  Gly  Phe  Tyr  Gly
               2340                     2345                     2350

AAT  ATC  GGC  CAA  AGC  GAT  TAC  GCG  ATG  TCG  AAC  GAT  ATT  CTT  AAC  AAG         7104
Asn  Ile  Gly  Gln  Ser  Asp  Tyr  Ala  Met  Ser  Asn  Asp  Ile  Leu  Asn  Lys
          2355                     2360                     2365

GCA  GCG  CTG  CAG  TTC  ACC  GCT  CGC  AAC  CCA  CAA  GCT  AAA  GTC  ATG  AGC         7152
Ala  Ala  Leu  Gln  Phe  Thr  Ala  Arg  Asn  Pro  Gln  Ala  Lys  Val  Met  Ser
     2370                     2375                     2380

TTT  AAC  TGG  GGT  CCT  TGG  GAT  GGC  GGC  ATG  GTT  AAC  CCA  GCG  CTT  AAA         7200
Phe  Asn  Trp  Gly  Pro  Trp  Asp  Gly  Gly  Met  Val  Asn  Pro  Ala  Leu  Lys
2385                     2390                     2395                     2400

AAG  ATG  TTT  ACC  GAG  CGT  GGT  GTG  TAC  GTT  ATT  CCA  CTA  AAA  GCA  GGT         7248
Lys  Met  Phe  Thr  Glu  Arg  Gly  Val  Tyr  Val  Ile  Pro  Leu  Lys  Ala  Gly
               2405                     2410                     2415

GCA  GAG  CTA  TTT  GCC  ACT  CAG  CTA  TTG  GCT  GAA  ACT  GGC  GTG  CAG  TTG         7296
Ala  Glu  Leu  Phe  Ala  Thr  Gln  Leu  Leu  Ala  Glu  Thr  Gly  Val  Gln  Leu
```

```
      2420                         2425                        2430
CTC ATT GGT ACG TCA ATG CAA GGT GGC AGC GAC ACT AAA GCA ACT GAG    7344
Leu Ile Gly Thr Ser Met Gln Gly Gly Ser Asp Thr Lys Ala Thr Glu
        2435                        2440                    2445

ACT GCT TCT GTA AAA AAG CTT AAT GCG GGT GAG GTG CTA AGT GCA TCG    7392
Thr Ala Ser Val Lys Lys Leu Asn Ala Gly Glu Val Leu Ser Ala Ser
2450                    2455                    2460

CAT CCG CGT GCT GGT GCA CAA AAA ACA CCA CTA CAA GCT GTC ACT GCA    7440
His Pro Arg Ala Gly Ala Gln Lys Thr Pro Leu Gln Ala Val Thr Ala
2465                    2470                    2475                2480

ACG CGT CTG TTA ACC CCA AGT GCC ATG GTC TTC ATT GAA GAT CAC CGC    7488
Thr Arg Leu Leu Thr Pro Ser Ala Met Val Phe Ile Glu Asp His Arg
            2485                    2490                    2495

ATT GGC GGT AAC AGT GTG TTG CCA ACG GTA TGC GCC ATC GAC TGG ATG    7536
Ile Gly Gly Asn Ser Val Leu Pro Thr Val Cys Ala Ile Asp Trp Met
        2500                    2505                    2510

CGT GAA GCG GCA AGC GAC ATG CTT GGC GCT CAA GTT AAG GTA CTT GAT    7584
Arg Glu Ala Ala Ser Asp Met Leu Gly Ala Gln Val Lys Val Leu Asp
            2515                    2520                    2525

TAC AAG CTA TTA AAA GGC ATT GTA TTT GAG ACT GAT GAG CCG CAA GAG    7632
Tyr Lys Leu Leu Lys Gly Ile Val Phe Glu Thr Asp Glu Pro Gln Glu
2530                    2535                    2540

TTA ACA CTT GAG CTA ACG CCA GAC GAT TCA GAC GAA GCT ACG CTA CAA    7680
Leu Thr Leu Glu Leu Thr Pro Asp Asp Ser Asp Glu Ala Thr Leu Gln
2545                    2550                    2555                2560

GCA TTA ATC AGC TGT AAT GGG CGT CCG CAA TAC AAG GCG ACG CTT ATC    7728
Ala Leu Ile Ser Cys Asn Gly Arg Pro Gln Tyr Lys Ala Thr Leu Ile
            2565                    2570                    2575

AGT GAT AAT GCC GAT ATT AAG CAA CTT AAC AAG CAG TTT GAT TTA AGC    7776
Ser Asp Asn Ala Asp Ile Lys Gln Leu Asn Lys Gln Phe Asp Leu Ser
        2580                    2585                    2590

GCT AAG GCG ATT ACC ACA GCA AAA GAG CTT TAT AGC AAC GGC ACC TTG    7824
Ala Lys Ala Ile Thr Thr Ala Lys Glu Leu Tyr Ser Asn Gly Thr Leu
        2595                    2600                    2605

TTC CAC GGT CCG CGT CTA CAA GGG ATC CAA TCT GTA GTG CAG TTC GAT    7872
Phe His Gly Pro Arg Leu Gln Gly Ile Gln Ser Val Val Gln Phe Asp
2610                    2615                    2620

GAT CAA GGC TTA ATT GCT AAA GTC GCT CTG CCT AAG GTT GAA CTT AGC    7920
Asp Gln Gly Leu Ile Ala Lys Val Ala Leu Pro Lys Val Glu Leu Ser
2625                    2630                    2635                2640

GAT TGT GGT GAG TTC TTG CCG CAA ACC CAC ATG GGT GGC AGT CAA CCT    7968
Asp Cys Gly Glu Phe Leu Pro Gln Thr His Met Gly Gly Ser Gln Pro
            2645                    2650                    2655

TTT GCT GAG GAC TTG CTA TTA CAA GCT ATG CTG GTT TGG GCT CGC CTT    8016
Phe Ala Glu Asp Leu Leu Leu Gln Ala Met Leu Val Trp Ala Arg Leu
        2660                    2665                    2670

AAA ACT GGC TCG GCA AGT TTG CCA TCA AGC ATT GGT GAG TTT ACC TCA    8064
Lys Thr Gly Ser Ala Ser Leu Pro Ser Ser Ile Gly Glu Phe Thr Ser
        2675                    2680                    2685

TAC CAA CCA ATG GCC TTT GGT GAA ACT GGT ACC ATA GAG CTT GAA GTG    8112
Tyr Gln Pro Met Ala Phe Gly Glu Thr Gly Thr Ile Glu Leu Glu Val
    2690                    2695                    2700

ATT AAG CAC AAC AAA CGC TCA CTT GAA GCG AAT GTT GCG CTA TAT CGT    8160
Ile Lys His Asn Lys Arg Ser Leu Glu Ala Asn Val Ala Leu Tyr Arg
2705                    2710                    2715                2720

GAC AAC GGC GAG TTA AGT GCC ATG TTT AAG TCA GCT AAA ATC ACC ATT    8208
Asp Asn Gly Glu Leu Ser Ala Met Phe Lys Ser Ala Lys Ile Thr Ile
            2725                    2730                    2735

AGC AAA AGC TTA AAT TCA GCA TTT TTA CCT GCT GTC TTA GCA AAC GAC    8256
Ser Lys Ser Leu Asn Ser Ala Phe Leu Pro Ala Val Leu Ala Asn Asp
```

|     |     | 2740 |     |     | 2745 |     |     | 2750 |     |      |
| --- | --- | ---  | --- | --- | ---  | --- | --- | ---  | --- | ---  |
| AGT | GAG | GCG  | AAT |     |      |     |     |      |     | 8268 |
| Ser | Glu | Ala  | Asn |     |      |     |     |      |     |      |
|     |     | 2755 |     |     |      |     |     |      |     |      |

( 2 ) INFORMATION FOR SEQ ID NO:11:

( i ) SEQUENCE CHARACTERISTICS:
        ( A ) LENGTH: 2756 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| Met | Ser | Gln | Thr | Ser | Lys | Pro | Thr | Asn | Ser | Ala | Thr | Glu | Gln | Ala | Gln |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Asp | Ser | Gln | Ala | Asp | Ser | Arg | Leu | Asn | Lys | Arg | Leu | Lys | Asp | Met | Pro |
|     |     |     | 20  |     |     |     |     | 25  |     |     |     |     | 30  |     |     |
| Ile | Ala | Ile | Val | Gly | Met | Ala | Ser | Ile | Phe | Ala | Asn | Ser | Arg | Tyr | Leu |
|     |     | 35  |     |     |     |     | 40  |     |     |     |     | 45  |     |     |     |
| Asn | Lys | Phe | Trp | Asp | Leu | Ile | Ser | Glu | Lys | Ile | Asp | Ala | Ile | Thr | Glu |
|     | 50  |     |     |     |     | 55  |     |     |     |     | 60  |     |     |     |     |
| Leu | Pro | Ser | Thr | His | Trp | Gln | Pro | Glu | Glu | Tyr | Tyr | Asp | Ala | Asp | Lys |
| 65  |     |     |     | 70  |     |     |     |     | 75  |     |     |     |     | 80  |     |
| Thr | Ala | Ala | Asp | Lys | Ser | Tyr | Cys | Lys | Arg | Gly | Gly | Phe | Leu | Pro | Asp |
|     |     |     |     | 85  |     |     |     |     | 90  |     |     |     |     | 95  |     |
| Val | Asp | Phe | Asn | Pro | Met | Glu | Phe | Gly | Leu | Pro | Pro | Asn | Ile | Leu | Glu |
|     |     |     | 100 |     |     |     |     | 105 |     |     |     |     | 110 |     |     |
| Leu | Thr | Asp | Ser | Ser | Gln | Leu | Leu | Ser | Leu | Ile | Val | Ala | Lys | Glu | Val |
|     |     | 115 |     |     |     |     | 120 |     |     |     |     | 125 |     |     |     |
| Leu | Ala | Asp | Ala | Asn | Leu | Pro | Glu | Asn | Tyr | Asp | Arg | Asp | Lys | Ile | Gly |
|     | 130 |     |     |     |     | 135 |     |     |     |     | 140 |     |     |     |     |
| Ile | Thr | Leu | Gly | Val | Gly | Gly | Gln | Lys | Ile | Ser | His | Ser | Leu | Thr |     |
| 145 |     |     |     | 150 |     |     |     |     | 155 |     |     |     |     | 160 |     |
| Ala | Arg | Leu | Gln | Tyr | Pro | Val | Leu | Lys | Lys | Val | Phe | Ala | Asn | Ser | Gly |
|     |     |     |     | 165 |     |     |     |     | 170 |     |     |     |     | 175 |     |
| Ile | Ser | Asp | Thr | Asp | Ser | Glu | Met | Leu | Ile | Lys | Lys | Phe | Gln | Asp | Gln |
|     |     |     | 180 |     |     |     |     | 185 |     |     |     |     | 190 |     |     |
| Tyr | Val | His | Trp | Glu | Glu | Asn | Ser | Phe | Pro | Gly | Ser | Leu | Gly | Asn | Val |
|     |     | 195 |     |     |     |     | 200 |     |     |     |     | 205 |     |     |     |
| Ile | Ala | Gly | Arg | Ile | Ala | Asn | Arg | Phe | Asp | Phe | Gly | Gly | Met | Asn | Cys |
|     | 210 |     |     |     |     | 215 |     |     |     |     | 220 |     |     |     |     |
| Val | Val | Asp | Ala | Ala | Cys | Ala | Gly | Ser | Leu | Ala | Ala | Met | Arg | Met | Ala |
| 225 |     |     |     |     | 230 |     |     |     |     | 235 |     |     |     |     | 240 |
| Leu | Thr | Glu | Leu | Thr | Glu | Gly | Arg | Ser | Glu | Met | Met | Ile | Thr | Gly | Gly |
|     |     |     |     | 245 |     |     |     |     | 250 |     |     |     |     | 255 |     |
| Val | Cys | Thr | Asp | Asn | Ser | Pro | Ser | Met | Tyr | Met | Ser | Phe | Ser | Lys | Thr |
|     |     |     | 260 |     |     |     |     | 265 |     |     |     |     | 270 |     |     |
| Pro | Ala | Phe | Thr | Thr | Asn | Glu | Thr | Ile | Gln | Pro | Phe | Asp | Ile | Asp | Ser |
|     |     | 275 |     |     |     |     | 280 |     |     |     |     | 285 |     |     |     |
| Lys | Gly | Met | Met | Ile | Gly | Glu | Gly | Ile | Gly | Met | Val | Ala | Leu | Lys | Arg |
|     | 290 |     |     |     |     | 295 |     |     |     |     | 300 |     |     |     |     |
| Leu | Glu | Asp | Ala | Glu | Arg | Asp | Gly | Asp | Arg | Ile | Tyr | Ser | Val | Ile | Lys |
| 305 |     |     |     |     | 310 |     |     |     |     | 315 |     |     |     |     | 320 |
| Gly | Val | Gly | Ala | Ser | Ser | Asp | Gly | Lys | Phe | Lys | Ser | Ile | Tyr | Ala | Pro |
|     |     |     |     | 325 |     |     |     |     | 330 |     |     |     |     | 335 |     |

```
Arg Pro Ser Gly Gln Ala Lys Ala Leu Asn Arg Ala Tyr Asp Asp Ala
            340                 345                 350

Gly Phe Ala Pro His Thr Leu Gly Leu Ile Glu Ala His Gly Thr Gly
        355                 360             365

Thr Ala Ala Gly Asp Ala Ala Glu Phe Ala Gly Leu Cys Ser Val Phe
370                 375                 380

Ala Glu Gly Asn Asp Thr Lys Gln His Ile Ala Leu Gly Ser Val Lys
385                 390                 395                 400

Ser Gln Ile Gly His Thr Lys Ser Thr Ala Gly Thr Ala Gly Leu Ile
                405                 410                 415

Lys Ala Ala Leu Ala Leu His His Lys Val Leu Pro Pro Thr Ile Asn
            420                 425                 430

Val Ser Gln Pro Ser Pro Lys Leu Asp Ile Glu Asn Ser Pro Phe Tyr
        435                 440                 445

Leu Asn Thr Glu Thr Arg Pro Trp Leu Pro Arg Val Asp Gly Thr Pro
450                 455                 460

Arg Arg Ala Gly Ile Ser Ser Phe Gly Phe Gly Gly Thr Asn Phe His
465             470                 475                 480

Phe Val Leu Glu Glu Tyr Asn Gln Glu His Ser Arg Thr Asp Ser Glu
                485                 490                 495

Lys Ala Lys Tyr Arg Gln Arg Gln Val Ala Gln Ser Phe Leu Val Ser
            500                 505                 510

Ala Ser Asp Lys Ala Ser Leu Ile Asn Glu Leu Asn Val Leu Ala Ala
        515                 520                 525

Ser Ala Ser Gln Ala Glu Phe Ile Leu Lys Asp Ala Ala Ala Asn Tyr
530                 535                 540

Gly Val Arg Glu Leu Asp Lys Asn Ala Pro Arg Ile Gly Leu Val Ala
545                 550                 555                 560

Asn Thr Ala Glu Glu Leu Ala Gly Leu Ile Lys Gln Ala Leu Ala Lys
                565                 570                 575

Leu Ala Ala Ser Asp Asp Asn Ala Trp Gln Leu Pro Gly Gly Thr Ser
            580                 585                 590

Tyr Arg Ala Ala Ala Val Glu Gly Lys Val Ala Ala Leu Phe Ala Gly
        595                 600                 605

Gln Gly Ser Gln Tyr Leu Asn Met Gly Arg Asp Leu Thr Cys Tyr Tyr
610                 615                 620

Pro Glu Met Arg Gln Gln Phe Val Thr Ala Asp Lys Val Phe Ala Ala
625                 630                 635                 640

Asn Asp Lys Thr Pro Leu Ser Gln Thr Leu Tyr Pro Lys Pro Val Phe
                645                 650                 655

Asn Lys Asp Glu Leu Lys Ala Gln Glu Ala Ile Leu Thr Asn Thr Ala
            660                 665                 670

Asn Ala Gln Ser Ala Ile Gly Ala Ile Ser Met Gly Gln Tyr Asp Leu
        675                 680                 685

Phe Thr Ala Ala Gly Phe Asn Ala Asp Met Val Ala Gly His Ser Phe
690                 695                 700

Gly Glu Leu Ser Ala Leu Cys Ala Ala Gly Val Ile Ser Ala Asp Asp
705                 710                 715                 720

Tyr Tyr Lys Leu Ala Phe Ala Arg Gly Glu Ala Met Ala Thr Lys Ala
                725                 730                 735

Pro Ala Lys Asp Gly Val Glu Ala Asp Ala Gly Ala Met Phe Ala Ile
            740                 745                 750

Ile Thr Lys Ser Ala Ala Asp Leu Glu Thr Val Glu Ala Thr Ile Ala
```

-continued

|     |     |     | 755 |     |     |     | 760 |     |     |     | 765 |     |     |     |
|-----|-----|-----|-----|-----|-----|-----|-----|-----|-----|-----|-----|-----|-----|-----|
| Lys | Phe | Asp | Gly | Val | Lys | Val | Ala | Asn | Tyr | Asn | Ala | Pro | Thr | Gln | Ser |
|     | 770 |     |     |     | 775 |     |     |     |     | 780 |     |     |     |     |
| Val | Ile | Ala | Gly | Pro | Thr | Ala | Thr | Thr | Ala | Asp | Ala | Ala | Lys | Ala | Leu |
| 785 |     |     |     |     | 790 |     |     |     |     | 795 |     |     |     |     | 800 |
| Thr | Glu | Leu | Gly | Tyr | Lys | Ala | Ile | Asn | Leu | Pro | Val | Ser | Gly | Ala | Phe |
|     |     |     |     | 805 |     |     |     |     | 810 |     |     |     | 815 |     |     |
| His | Thr | Glu | Leu | Val | Gly | His | Ala | Gln | Ala | Pro | Phe | Ala | Lys | Ala | Ile |
|     |     |     | 820 |     |     |     |     | 825 |     |     |     |     | 830 |     |     |
| Asp | Ala | Ala | Lys | Phe | Thr | Lys | Thr | Ser | Arg | Ala | Leu | Tyr | Ser | Asn | Ala |
|     |     | 835 |     |     |     |     | 840 |     |     |     |     | 845 |     |     |     |
| Thr | Gly | Gly | Leu | Tyr | Glu | Ser | Thr | Ala | Ala | Lys | Ile | Lys | Ala | Ser | Phe |
|     | 850 |     |     |     |     | 855 |     |     |     |     | 860 |     |     |     |     |
| Lys | Lys | His | Met | Leu | Gln | Ser | Val | Arg | Phe | Thr | Ser | Gln | Leu | Glu | Ala |
| 865 |     |     |     |     | 870 |     |     |     |     | 875 |     |     |     |     | 880 |
| Met | Tyr | Asn | Asp | Gly | Ala | Arg | Val | Phe | Val | Glu | Phe | Gly | Pro | Lys | Asn |
|     |     |     |     | 885 |     |     |     |     | 890 |     |     |     |     | 895 |     |
| Ile | Leu | Gln | Lys | Leu | Val | Gln | Gly | Thr | Leu | Val | Asn | Thr | Glu | Asn | Glu |
|     |     |     | 900 |     |     |     |     | 905 |     |     |     |     | 910 |     |     |
| Val | Cys | Thr | Ile | Ser | Ile | Asn | Pro | Asn | Pro | Lys | Val | Asp | Ser | Asp | Leu |
|     |     | 915 |     |     |     |     | 920 |     |     |     |     | 925 |     |     |     |
| Gln | Leu | Lys | Gln | Ala | Ala | Met | Gln | Leu | Ala | Val | Thr | Gly | Val | Val | Leu |
|     | 930 |     |     |     |     | 935 |     |     |     |     | 940 |     |     |     |     |
| Ser | Glu | Ile | Asp | Pro | Tyr | Gln | Ala | Asp | Ile | Ala | Ala | Pro | Ala | Lys | Lys |
| 945 |     |     |     |     | 950 |     |     |     |     | 955 |     |     |     |     | 960 |
| Ser | Pro | Met | Ser | Ile | Ser | Leu | Asn | Ala | Ala | Asn | His | Ile | Ser | Lys | Ala |
|     |     |     |     | 965 |     |     |     |     | 970 |     |     |     | 975 |     |     |
| Thr | Arg | Ala | Lys | Met | Ala | Lys | Ser | Leu | Glu | Thr | Gly | Ile | Val | Thr | Ser |
|     |     |     | 980 |     |     |     |     | 985 |     |     |     |     | 990 |     |     |
| Gln | Ile | Glu | His | Val | Ile | Glu | Glu | Lys | Ile | Val | Glu | Val | Glu | Lys | Leu |
|     |     | 995 |     |     |     |     | 1000|     |     |     |     | 1005|     |     |     |
| Val | Glu | Val | Glu | Lys | Ile | Val | Glu | Lys | Val | Val | Glu | Val | Glu | Lys | Val |
|     | 1010|     |     |     |     | 1015|     |     |     |     | 1020|     |     |     |     |
| Val | Glu | Val | Glu | Ala | Pro | Val | Asn | Ser | Val | Gln | Ala | Asn | Ala | Ile | Gln |
| 1025|     |     |     |     | 1030|     |     |     |     | 1035|     |     |     |     | 1040|
| Thr | Arg | Ser | Val | Val | Ala | Pro | Val | Ile | Glu | Asn | Gln | Val | Val | Ser | Lys |
|     |     |     |     | 1045|     |     |     |     | 1050|     |     |     |     | 1055|     |
| Asn | Ser | Lys | Pro | Ala | Val | Gln | Ser | Ile | Ser | Gly | Asp | Ala | Leu | Ser | Asn |
|     |     |     | 1060|     |     |     |     | 1065|     |     |     |     | 1070|     |     |
| Phe | Phe | Ala | Ala | Gln | Gln | Gln | Thr | Ala | Gln | Leu | His | Gln | Gln | Phe | Leu |
|     |     |     | 1075|     |     |     |     | 1080|     |     |     |     | 1085|     |     |
| Ala | Ile | Pro | Gln | Gln | Tyr | Gly | Glu | Thr | Phe | Thr | Thr | Leu | Met | Thr | Glu |
|     |     |     | 1090|     |     |     |     | 1095|     |     |     |     | 1100|     |     |
| Gln | Ala | Lys | Leu | Ala | Ser | Ser | Gly | Val | Ala | Ile | Pro | Glu | Ser | Leu | Gln |
| 1105|     |     |     |     | 1110|     |     |     |     | 1115|     |     |     |     | 1120|
| Arg | Ser | Met | Glu | Gln | Phe | His | Gln | Leu | Gln | Ala | Gln | Thr | Leu | Gln | Ser |
|     |     |     |     | 1125|     |     |     |     | 1130|     |     |     |     | 1135|     |
| His | Thr | Gln | Phe | Leu | Glu | Met | Gln | Ala | Gly | Ser | Asn | Ile | Ala | Ala | Leu |
|     |     |     |     | 1140|     |     |     |     | 1145|     |     |     |     | 1150|     |
| Asn | Leu | Leu | Asn | Ser | Ser | Gln | Ala | Thr | Tyr | Ala | Pro | Ala | Ile | His | Asn |
|     |     |     |     | 1155|     |     |     |     | 1160|     |     |     |     | 1165|     |
| Glu | Ala | Ile | Gln | Ser | Gln | Val | Val | Gln | Ser | Gln | Thr | Ala | Val | Gln | Pro |
|     | 1170|     |     |     |     | 1175|     |     |     |     | 1180|     |     |     |     |

```
Val Ile Ser Thr Gln Val Asn His Val Ser Glu Gln Pro Thr Gln Ala
1185                1190                1195                1200

Pro Ala Pro Lys Ala Gln Pro Ala Pro Val Thr Thr Ala Val Gln Thr
                1205                1210                1215

Ala Pro Ala Gln Val Val Arg Gln Ala Ala Pro Val Gln Ala Ala Ile
            1220                1225                1230

Glu Pro Ile Asn Thr Ser Val Ala Thr Thr Pro Ser Ala Phe Ser
        1235                1240                1245

Ala Glu Thr Ala Leu Ser Ala Thr Lys Val Gln Ala Thr Met Leu Glu
            1250                1255                1260

Val Val Ala Glu Lys Thr Gly Tyr Pro Thr Glu Met Leu Glu Leu Glu
1265                1270                1275                1280

Met Asp Met Glu Ala Asp Leu Gly Ile Asp Ser Ile Lys Arg Val Glu
                1285                1290                1295

Ile Leu Gly Thr Val Gln Asp Glu Leu Pro Gly Leu Pro Glu Leu Ser
            1300                1305                1310

Pro Glu Asp Leu Ala Glu Cys Arg Thr Leu Gly Glu Ile Val Asp Tyr
        1315                1320                1325

Met Gly Ser Lys Leu Pro Ala Glu Gly Ser Met Asn Ser Gln Leu Ser
    1330                1335                1340

Thr Gly Ser Ala Ala Ala Thr Pro Ala Ala Asn Gly Leu Ser Ala Glu
1345                1350                1355                1360

Lys Val Gln Ala Thr Met Met Ser Val Val Ala Glu Lys Thr Gly Tyr
                1365                1370                1375

Pro Thr Glu Met Leu Glu Leu Glu Met Asp Met Glu Ala Asp Leu Gly
        1380                1385                1390

Ile Asp Ser Ile Lys Arg Val Glu Ile Leu Gly Thr Val Gln Asp Glu
        1395                1400                1405

Leu Pro Gly Leu Pro Glu Leu Ser Pro Glu Asp Leu Ala Glu Cys Arg
    1410                1415                1420

Thr Leu Gly Glu Ile Val Asp Tyr Met Asn Ser Lys Leu Ala Asp Gly
1425                1430                1435                1440

Ser Lys Leu Pro Ala Glu Gly Ser Met Asn Ser Gln Leu Ser Thr Ser
                1445                1450                1455

Ala Ala Ala Ala Thr Pro Ala Ala Asn Gly Leu Ser Ala Glu Lys Val
            1460                1465                1470

Gln Ala Thr Met Met Ser Val Val Ala Glu Lys Thr Gly Tyr Pro Thr
        1475                1480                1485

Glu Met Leu Glu Leu Glu Met Asp Met Glu Ala Asp Leu Gly Ile Asp
    1490                1495                1500

Ser Ile Lys Arg Val Glu Ile Leu Gly Thr Val Gln Asp Glu Leu Pro
1505                1510                1515                1520

Gly Leu Pro Glu Leu Asn Pro Glu Asp Leu Ala Glu Cys Arg Thr Leu
                1525                1530                1535

Gly Glu Ile Val Thr Tyr Met Asn Ser Lys Leu Ala Asp Gly Ser Lys
            1540                1545                1550

Leu Pro Ala Glu Gly Ser Met His Tyr Gln Leu Ser Thr Ser Thr Ala
        1555                1560                1565

Ala Ala Thr Pro Val Ala Asn Gly Leu Ser Ala Glu Lys Val Gln Ala
    1570                1575                1580

Thr Met Met Ser Val Val Ala Asp Lys Thr Gly Tyr Pro Thr Glu Met
1585                1590                1595                1600

Leu Glu Leu Glu Met Asp Met Glu Ala Asp Leu Gly Ile Asp Ser Ile
                1605                1610                1615
```

-continued

Lys Arg Val Glu Ile Leu Gly Thr Val Gln Asp Glu Leu Pro Gly Leu
                1620                    1625                1630

Pro Glu Leu Asn Pro Glu Asp Leu Ala Glu Cys Arg Thr Leu Gly Glu
                1635                1640                1645

Ile Val Asp Tyr Met Gly Ser Lys Leu Pro Ala Glu Gly Ser Ala Asn
                1650                1655                1660

Thr Ser Ala Ala Ala Ser Leu Asn Val Ser Ala Val Ala Ala Pro Gln
1665                1670                1675                1680

Ala Ala Ala Thr Pro Val Ser Asn Gly Leu Ser Ala Glu Lys Val Gln
                1685                1690                1695

Ser Thr Met Met Ser Val Val Ala Glu Lys Thr Gly Tyr Pro Thr Glu
                1700                1705                1710

Met Leu Glu Leu Gly Met Asp Met Glu Ala Asp Leu Gly Ile Asp Ser
                1715                1720                1725

Ile Lys Arg Val Glu Ile Leu Gly Thr Val Gln Asp Glu Leu Pro Gly
                1730                1735                1740

Leu Pro Glu Leu Asn Pro Glu Asp Leu Ala Glu Cys Arg Thr Leu Gly
1745                1750                1755                1760

Glu Ile Val Asp Tyr Met Asn Ser Lys Leu Ala Asp Gly Ser Lys Leu
                1765                1770                1775

Pro Ala Glu Gly Ser Ala Asn Thr Ser Ala Thr Ala Ala Thr Pro Ala
                1780                1785                1790

Val Asn Gly Leu Ser Ala Asp Lys Val Gln Ala Thr Met Met Ser Val
                1795                1800                1805

Val Ala Glu Lys Thr Gly Tyr Pro Thr Glu Met Leu Glu Leu Gly Met
                1810                1815                1820

Asp Met Glu Ala Asp Leu Gly Ile Asp Ser Ile Lys Arg Val Glu Ile
1825                1830                1835                1840

Leu Gly Thr Val Gln Asp Glu Leu Pro Gly Leu Pro Glu Leu Asn Pro
                1845                1850                1855

Glu Asp Leu Ala Glu Cys Arg Thr Leu Gly Glu Ile Val Ser Tyr Met
                1860                1865                1870

Asn Ser Gln Leu Ala Asp Gly Ser Lys Leu Ser Thr Ser Ala Ala Glu
                1875                1880                1885

Gly Ser Ala Asp Thr Ser Ala Ala Asn Ala Ala Lys Pro Ala Ala Ile
                1890                1895                1900

Ser Ala Glu Pro Ser Val Glu Leu Pro Pro His Ser Glu Val Ala Leu
1905                1910                1915                1920

Lys Lys Leu Asn Ala Ala Asn Lys Leu Glu Asn Cys Phe Ala Ala Asp
                1925                1930                1935

Ala Ser Val Val Ile Asn Asp Asp Gly His Asn Ala Gly Val Leu Ala
                1940                1945                1950

Glu Lys Leu Ile Lys Gln Gly Leu Lys Val Ala Val Val Arg Leu Pro
                1955                1960                1965

Lys Gly Gln Pro Gln Ser Pro Leu Ser Ser Asp Val Ala Ser Phe Glu
                1970                1975                1980

Leu Ala Ser Ser Gln Glu Ser Glu Leu Glu Ala Ser Ile Thr Ala Val
1985                1990                1995                2000

Ile Ala Gln Ile Glu Thr Gln Val Gly Ala Ile Gly Gly Phe Ile His
                2005                2010                2015

Leu Gln Pro Glu Ala Asn Thr Glu Glu Gln Thr Ala Val Asn Leu Asp
                2020                2025                2030

Ala Gln Ser Phe Thr His Val Ser Asn Ala Phe Leu Trp Ala Lys Leu

```
                2035                    2040                    2045
Leu Gln Pro Lys Leu Val Ala Gly Ala Asp Ala Arg Arg Cys Phe Val
        2050                    2055                2060
Thr Val Ser Arg Ile Asp Gly Gly Phe Gly Tyr Leu Asn Thr Asp Ala
2065                    2070                    2075                    2080
Leu Lys Asp Ala Glu Leu Asn Gln Ala Ala Leu Ala Gly Leu Thr Lys
                    2085                    2090                2095
Thr Leu Ser His Glu Trp Pro Gln Val Phe Cys Arg Ala Leu Asp Ile
            2100                    2105                2110
Ala Thr Asp Val Asp Ala Thr His Leu Ala Asp Ala Ile Thr Ser Glu
        2115                    2120                    2125
Leu Phe Asp Ser Gln Ala Gln Leu Pro Glu Val Gly Leu Ser Leu Ile
        2130                    2135                    2140
Asp Gly Lys Val Asn Arg Val Thr Leu Val Ala Ala Glu Ala Ala Asp
2145                    2150                    2155                    2160
Lys Thr Ala Lys Ala Glu Leu Asn Ser Thr Asp Lys Ile Leu Val Thr
                    2165                    2170                2175
Gly Gly Ala Lys Gly Val Thr Phe Glu Cys Ala Leu Ala Leu Ala Ser
            2180                    2185                2190
Arg Ser Gln Ser His Phe Ile Leu Ala Gly Arg Ser Glu Leu Gln Ala
        2195                    2200                    2205
Leu Pro Ser Trp Ala Glu Gly Lys Gln Thr Ser Glu Leu Lys Ser Ala
        2210                    2215                    2220
Ala Ile Ala His Ile Ile Ser Thr Gly Gln Lys Pro Thr Pro Lys Gln
2225                    2230                    2235                    2240
Val Glu Ala Ala Val Trp Pro Val Gln Ser Ser Ile Glu Ile Asn Ala
                    2245                    2250                2255
Ala Leu Ala Ala Phe Asn Lys Val Gly Ala Ser Ala Glu Tyr Val Ser
            2260                    2265                2270
Met Asp Val Thr Asp Ser Ala Ala Ile Thr Ala Ala Leu Asn Gly Arg
        2275                    2280                    2285
Ser Asn Glu Ile Thr Gly Leu Ile His Gly Ala Gly Val Leu Ala Asp
        2290                    2295                    2300
Lys His Ile Gln Asp Lys Thr Leu Ala Glu Leu Ala Lys Val Tyr Gly
2305                    2310                    2315                    2320
Thr Lys Val Asn Gly Leu Lys Ala Leu Ala Ala Leu Glu Pro Ser
                    2325                    2330                2335
Lys Ile Lys Leu Leu Ala Met Phe Ser Ser Ala Ala Gly Phe Tyr Gly
            2340                    2345                2350
Asn Ile Gly Gln Ser Asp Tyr Ala Met Ser Asn Asp Ile Leu Asn Lys
        2355                    2360                    2365
Ala Ala Leu Gln Phe Thr Ala Arg Asn Pro Gln Ala Lys Val Met Ser
2370                    2375                    2380
Phe Asn Trp Gly Pro Trp Asp Gly Gly Met Val Asn Pro Ala Leu Lys
2385                    2390                    2395                    2400
Lys Met Phe Thr Glu Arg Gly Val Tyr Val Ile Pro Leu Lys Ala Gly
            2405                    2410                2415
Ala Glu Leu Phe Ala Thr Gln Leu Leu Ala Glu Thr Gly Val Gln Leu
            2420                    2425                2430
Leu Ile Gly Thr Ser Met Gln Gly Gly Ser Asp Thr Lys Ala Thr Glu
            2435                    2440                2445
Thr Ala Ser Val Lys Lys Leu Asn Ala Gly Glu Val Leu Ser Ala Ser
        2450                    2455                    2460
```

```
His Pro Arg Ala Gly Ala Gln Lys Thr Pro Leu Gln Ala Val Thr Ala
2465                 2470                2475                2480

Thr Arg Leu Leu Thr Pro Ser Ala Met Val Phe Ile Glu Asp His Arg
            2485                2490                2495

Ile Gly Gly Asn Ser Val Leu Pro Thr Val Cys Ala Ile Asp Trp Met
                2500                2505                2510

Arg Glu Ala Ala Ser Asp Met Leu Gly Ala Gln Val Lys Val Leu Asp
            2515                2520                2525

Tyr Lys Leu Leu Lys Gly Ile Val Phe Glu Thr Asp Glu Pro Gln Glu
            2530                2535                2540

Leu Thr Leu Glu Leu Thr Pro Asp Asp Ser Asp Glu Ala Thr Leu Gln
2545                2550                2555                2560

Ala Leu Ile Ser Cys Asn Gly Arg Pro Gln Tyr Lys Ala Thr Leu Ile
                2565                2570                2575

Ser Asp Asn Ala Asp Ile Lys Gln Leu Asn Lys Gln Phe Asp Leu Ser
                2580                2585                2590

Ala Lys Ala Ile Thr Thr Ala Lys Glu Leu Tyr Ser Asn Gly Thr Leu
            2595                2600                2605

Phe His Gly Pro Arg Leu Gln Gly Ile Gln Ser Val Val Gln Phe Asp
            2610                2615                2620

Asp Gln Gly Leu Ile Ala Lys Val Ala Leu Pro Lys Val Glu Leu Ser
2625                2630                2635                2640

Asp Cys Gly Glu Phe Leu Pro Gln Thr His Met Gly Gly Ser Gln Pro
                2645                2650                2655

Phe Ala Glu Asp Leu Leu Leu Gln Ala Met Leu Val Trp Ala Arg Leu
                2660                2665                2670

Lys Thr Gly Ser Ala Ser Leu Pro Ser Ser Ile Gly Glu Phe Thr Ser
            2675                2680                2685

Tyr Gln Pro Met Ala Phe Gly Glu Thr Gly Thr Ile Glu Leu Glu Val
            2690                2695                2700

Ile Lys His Asn Lys Arg Ser Leu Glu Ala Asn Val Ala Leu Tyr Arg
2705                2710                2715                2720

Asp Asn Gly Glu Leu Ser Ala Met Phe Lys Ser Ala Lys Ile Thr Ile
                2725                2730                2735

Ser Lys Ser Leu Asn Ser Ala Phe Leu Pro Ala Val Leu Ala Asn Asp
            2740                2745                2750

Ser Glu Ala Asn
            2755
```

( 2 ) INFORMATION FOR SEQ ID NO:12:

( i ) SEQUENCE CHARACTERISTICS:
        ( A ) LENGTH: 2340 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Shewanella putrefaciens SCRC-2874 (FERM BP- 1625)

( i x ) FEATURE:
        ( A ) NAME/KEY: CDS
        ( B ) LOCATION: 1..2340

( i x ) FEATURE:
        ( A ) NAME/KEY: mat_peptide
        ( B ) LOCATION: 1..2340

( x i ) SEQUENCE DESCRIPTION: SEQ ID NO:12:

| | | | | | | | | | | | | | | | | |
|---|---|---|---|---|---|---|---|---|---|---|---|---|---|---|---|---|
| GTG | GAA | CAA | ACG | CCT | AAA | GCT | AGT | GCG | ATG | CCG | CTG | CGC | ATC | GCA | CTT | 48 |
| Val | Glu | Gln | Thr | Pro | Lys | Ala | Ser | Ala | Met | Pro | Leu | Arg | Ile | Ala | Leu | |
| 1 | | | | 5 | | | | | 10 | | | | | 15 | | |
| ATC | TTA | CTG | CCA | ACA | CCG | CAG | TTT | GAA | GTT | AAC | TCT | GTC | GAC | CAG | TCA | 96 |
| Ile | Leu | Leu | Pro | Thr | Pro | Gln | Phe | Glu | Val | Asn | Ser | Val | Asp | Gln | Ser | |
| | | | 20 | | | | | 25 | | | | | 30 | | | |
| GTA | TTA | GCC | AGC | TAT | CAA | ACA | CTG | CAG | CCT | GAG | CTA | AAT | GCC | CTG | CTT | 144 |
| Val | Leu | Ala | Ser | Tyr | Gln | Thr | Leu | Gln | Pro | Glu | Leu | Asn | Ala | Leu | Leu | |
| | | | 35 | | | | | 40 | | | | | 45 | | | |
| AAT | AGT | GCG | CCG | ACA | CCT | GAA | ATG | CTC | AGC | ATC | ACT | ATC | TCA | GAT | GAT | 192 |
| Asn | Ser | Ala | Pro | Thr | Pro | Glu | Met | Leu | Ser | Ile | Thr | Ile | Ser | Asp | Asp | |
| | 50 | | | | | 55 | | | | | 60 | | | | | |
| AGC | GAT | GCA | AAC | AGC | TTT | GAG | TCG | CAG | CTA | AAT | GCT | GCG | ACC | AAC | GCA | 240 |
| Ser | Asp | Ala | Asn | Ser | Phe | Glu | Ser | Gln | Leu | Asn | Ala | Ala | Thr | Asn | Ala | |
| 65 | | | | | 70 | | | | | 75 | | | | | 80 | |
| ATT | AAC | AAT | GGC | TAT | ATC | GTC | AAG | CTT | GCT | ACG | GCA | ACT | CAC | GCT | TTG | 288 |
| Ile | Asn | Asn | Gly | Tyr | Ile | Val | Lys | Leu | Ala | Thr | Ala | Thr | His | Ala | Leu | |
| | | | | 85 | | | | | 90 | | | | | 95 | | |
| TTA | ATG | CTG | CCT | GCA | TTA | AAA | GCG | GCG | CAA | ATG | CGG | ATC | CAT | CCT | CAT | 336 |
| Leu | Met | Leu | Pro | Ala | Leu | Lys | Ala | Ala | Gln | Met | Arg | Ile | His | Pro | His | |
| | | | 100 | | | | | 105 | | | | | 110 | | | |
| GCG | CAG | CTT | GCC | GCT | ATG | CAG | CAA | GCT | AAA | TCG | ACG | CCA | ATG | AGT | CAA | 384 |
| Ala | Gln | Leu | Ala | Ala | Met | Gln | Gln | Ala | Lys | Ser | Thr | Pro | Met | Ser | Gln | |
| | | | 115 | | | | | 120 | | | | | 125 | | | |
| GTA | TCT | GGT | GAG | CTA | AAG | CTT | GGC | GCT | AAT | GCG | CTA | AGC | CTA | GCT | CAG | 432 |
| Val | Ser | Gly | Glu | Leu | Lys | Leu | Gly | Ala | Asn | Ala | Leu | Ser | Leu | Ala | Gln | |
| | 130 | | | | | 135 | | | | | 140 | | | | | |
| ACT | AAT | GCG | CTG | TCT | CAT | GCT | TTA | AGC | CAA | GCC | AAG | CGT | AAC | TTA | ACT | 480 |
| Thr | Asn | Ala | Leu | Ser | His | Ala | Leu | Ser | Gln | Ala | Lys | Arg | Asn | Leu | Thr | |
| 145 | | | | | 150 | | | | | 155 | | | | | 160 | |
| GAT | GTC | AGC | GTG | AAT | GAG | TGT | TTT | GAG | AAC | CTC | AAA | AGT | GAA | CAG | CAG | 528 |
| Asp | Val | Ser | Val | Asn | Glu | Cys | Phe | Glu | Asn | Leu | Lys | Ser | Glu | Gln | Gln | |
| | | | | 165 | | | | | 170 | | | | | 175 | | |
| TTC | ACA | GAG | GTT | TAT | TCG | CTT | ATT | CAG | CAA | CTT | GCT | AGC | CGC | ACC | CAT | 576 |
| Phe | Thr | Glu | Val | Tyr | Ser | Leu | Ile | Gln | Gln | Leu | Ala | Ser | Arg | Thr | His | |
| | | | 180 | | | | | 185 | | | | | 190 | | | |
| GTG | AGA | AAA | GAG | GTT | AAT | CAA | GGT | GTG | GAA | CTT | GGC | CCT | AAA | CAA | GCC | 624 |
| Val | Arg | Lys | Glu | Val | Asn | Gln | Gly | Val | Glu | Leu | Gly | Pro | Lys | Gln | Ala | |
| | | 195 | | | | | 200 | | | | | 205 | | | | |
| AAA | AGC | CAC | TAT | TGG | TTT | AGC | GAA | TTT | CAC | CAA | AAC | CGT | GTT | GCT | GCC | 672 |
| Lys | Ser | His | Tyr | Trp | Phe | Ser | Glu | Phe | His | Gln | Asn | Arg | Val | Ala | Ala | |
| | 210 | | | | | 215 | | | | | 220 | | | | | |
| ATC | AAC | TTT | ATT | AAT | GGC | CAA | CAA | GCA | ACC | AGC | TAT | GTG | CTT | ACT | CAA | 720 |
| Ile | Asn | Phe | Ile | Asn | Gly | Gln | Gln | Ala | Thr | Ser | Tyr | Val | Leu | Thr | Gln | |
| 225 | | | | | 230 | | | | | 235 | | | | | 240 | |
| GGT | TCA | GGA | TTG | TTA | GCT | GCG | AAA | TCA | ATG | CTA | AAC | CAG | CAA | AGA | TTA | 768 |
| Gly | Ser | Gly | Leu | Leu | Ala | Ala | Lys | Ser | Met | Leu | Asn | Gln | Gln | Arg | Leu | |
| | | | | 245 | | | | | 250 | | | | | 255 | | |
| ATG | TTT | ATC | TTG | CCG | GGT | AAC | AGT | CAG | CAA | CAA | ATA | ACC | GCA | TCA | ATA | 816 |
| Met | Phe | Ile | Leu | Pro | Gly | Asn | Ser | Gln | Gln | Gln | Ile | Thr | Ala | Ser | Ile | |
| | | | | 260 | | | | | 265 | | | | | 270 | | |
| ACT | CAG | TTA | ATG | CAG | CAA | TTA | GAG | CGT | TTG | CAG | GTA | ACT | GAG | GTT | AAT | 864 |
| Thr | Gln | Leu | Met | Gln | Gln | Leu | Glu | Arg | Leu | Gln | Val | Thr | Glu | Val | Asn | |
| | | | 275 | | | | | 280 | | | | | 285 | | | |
| GAG | CTT | TCT | CTA | GAA | TGC | CAA | CTA | GAG | CTG | CTC | AGC | ATA | ATG | TAT | GAC | 912 |
| Glu | Leu | Ser | Leu | Glu | Cys | Gln | Leu | Glu | Leu | Leu | Ser | Ile | Met | Tyr | Asp | |
| | | | 290 | | | | | 295 | | | | | 300 | | | |
| AAC | TTA | GTC | AAC | GCA | GAC | AAA | CTC | ACT | ACT | CGC | GAT | AGT | AAG | CCC | GCT | 960 |
| Asn | Leu | Val | Asn | Ala | Asp | Lys | Leu | Thr | Thr | Arg | Asp | Ser | Lys | Pro | Ala | |

-continued

| 305 | | | | 310 | | | | 315 | | | | 320 | | | | |
|---|---|---|---|---|---|---|---|---|---|---|---|---|---|---|---|---|
| TAT | CAG | GCT | GTG | ATT | CAA | GCA | AGC | TCT | GTT | AGC | GCT | GCA | AAG | CAA | GAG | 1008 |
| Tyr | Gln | Ala | Val | Ile | Gln | Ala | Ser | Ser | Val | Ser | Ala | Ala | Lys | Gln | Glu | |
| | | | | 325 | | | | | 330 | | | | | 335 | | |
| TTA | AGC | GCG | CTT | AAC | GAT | GCA | CTC | ACA | GCG | CTG | TTT | GCT | GAG | CAA | ACA | 1056 |
| Leu | Ser | Ala | Leu | Asn | Asp | Ala | Leu | Thr | Ala | Leu | Phe | Ala | Glu | Gln | Thr | |
| | | | 340 | | | | | 345 | | | | | 350 | | | |
| AAC | GCC | ACA | TCA | ACG | AAT | AAA | GGC | TTA | ATC | CAA | TAC | AAA | ACA | CCG | GCG | 1104 |
| Asn | Ala | Thr | Ser | Thr | Asn | Lys | Gly | Leu | Ile | Gln | Tyr | Lys | Thr | Pro | Ala | |
| | | 355 | | | | | 360 | | | | | 365 | | | | |
| GGC | AGT | TAC | TTA | ACC | CTA | ACA | CCG | CTT | GGC | AGC | AAC | AAT | GAC | AAC | GCC | 1152 |
| Gly | Ser | Tyr | Leu | Thr | Leu | Thr | Pro | Leu | Gly | Ser | Asn | Asn | Asp | Asn | Ala | |
| | 370 | | | | | 375 | | | | | 380 | | | | | |
| CAA | GCG | GGT | CTT | GCT | TTT | GTC | TAT | CCG | GGT | GTG | GGA | ACG | GTT | TAC | GCC | 1200 |
| Gln | Ala | Gly | Leu | Ala | Phe | Val | Tyr | Pro | Gly | Val | Gly | Thr | Val | Tyr | Ala | |
| 385 | | | | | 390 | | | | | 395 | | | | | 400 | |
| GAT | ATG | CTT | AAT | GAG | CTG | CAT | CAG | TAC | TTC | CCT | GCG | CTT | TAC | GCC | AAA | 1248 |
| Asp | Met | Leu | Asn | Glu | Leu | His | Gln | Tyr | Phe | Pro | Ala | Leu | Tyr | Ala | Lys | |
| | | | | 405 | | | | | 410 | | | | | 415 | | |
| CTT | GAG | CGT | GAA | GGC | GAT | TTA | AAG | GCG | ATG | CTA | CAA | GCA | GAA | GAT | ATC | 1296 |
| Leu | Glu | Arg | Glu | Gly | Asp | Leu | Lys | Ala | Met | Leu | Gln | Ala | Glu | Asp | Ile | |
| | | | 420 | | | | | 425 | | | | | 430 | | | |
| TAT | CAT | CTT | GAC | CCT | AAA | CAT | GCT | GCC | CAA | ATG | AGC | TTA | GGT | GAC | TTA | 1344 |
| Tyr | His | Leu | Asp | Pro | Lys | His | Ala | Ala | Gln | Met | Ser | Leu | Gly | Asp | Leu | |
| | | 435 | | | | | 440 | | | | | 445 | | | | |
| GCC | ATT | GCT | GGC | GTG | GGG | AGC | AGC | TAC | CTG | TTA | ACT | CAG | CTG | CTC | ACC | 1392 |
| Ala | Ile | Ala | Gly | Val | Gly | Ser | Ser | Tyr | Leu | Leu | Thr | Gln | Leu | Leu | Thr | |
| | 450 | | | | | 455 | | | | | 460 | | | | | |
| GAT | GAG | TTT | AAT | ATT | AAG | CCT | AAT | TTT | GCA | TTA | GGT | TAC | TCA | ATG | GGT | 1440 |
| Asp | Glu | Phe | Asn | Ile | Lys | Pro | Asn | Phe | Ala | Leu | Gly | Tyr | Ser | Met | Gly | |
| 465 | | | | | 470 | | | | | 475 | | | | | 480 | |
| GAA | GCA | TCA | ATG | TGG | GCA | AGC | TTA | GGC | GTA | TGG | CAA | AAC | CCG | CAT | GCG | 1488 |
| Glu | Ala | Ser | Met | Trp | Ala | Ser | Leu | Gly | Val | Trp | Gln | Asn | Pro | His | Ala | |
| | | | | 485 | | | | | 490 | | | | | 495 | | |
| CTG | ATC | AGC | AAA | ACC | CAA | ACC | GAC | CCG | CTA | TTT | ACT | TCT | GCT | ATT | TCC | 1536 |
| Leu | Ile | Ser | Lys | Thr | Gln | Thr | Asp | Pro | Leu | Phe | Thr | Ser | Ala | Ile | Ser | |
| | | | 500 | | | | | 505 | | | | | 510 | | | |
| GGC | AAA | TTG | ACC | GCG | GTT | AGA | CAA | GCT | TGG | CAG | CTT | GAT | GAT | ACC | GCA | 1584 |
| Gly | Lys | Leu | Thr | Ala | Val | Arg | Gln | Ala | Trp | Gln | Leu | Asp | Asp | Thr | Ala | |
| | | 515 | | | | | 520 | | | | | 525 | | | | |
| GCG | GAA | ATC | CAG | TGG | AAT | AGC | TTT | GTG | GTT | AGA | AGT | GAA | GCA | GCG | CCG | 1632 |
| Ala | Glu | Ile | Gln | Trp | Asn | Ser | Phe | Val | Val | Arg | Ser | Glu | Ala | Ala | Pro | |
| | 530 | | | | | 535 | | | | | 540 | | | | | |
| ATT | GAA | GCC | TTG | CTA | AAA | GAT | TAC | CCA | CAC | GCT | TAC | CTC | GCG | ATT | ATT | 1680 |
| Ile | Glu | Ala | Leu | Leu | Lys | Asp | Tyr | Pro | His | Ala | Tyr | Leu | Ala | Ile | Ile | |
| 545 | | | | | 550 | | | | | 555 | | | | | 560 | |
| CAA | GGG | GAT | ACC | TGC | GTA | ATC | GCT | GGC | TGT | GAA | ATC | CAA | TGT | AAA | GCG | 1728 |
| Gln | Gly | Asp | Thr | Cys | Val | Ile | Ala | Gly | Cys | Glu | Ile | Gln | Cys | Lys | Ala | |
| | | | | 565 | | | | | 570 | | | | | 575 | | |
| CTA | CTT | GCA | GCA | CTG | GGT | AAA | CGC | GGT | ATT | GCA | GCT | AAT | CGT | GTA | ACG | 1776 |
| Leu | Leu | Ala | Ala | Leu | Gly | Lys | Arg | Gly | Ile | Ala | Ala | Asn | Arg | Val | Thr | |
| | | | 580 | | | | | 585 | | | | | 590 | | | |
| GCG | ATG | CAT | ACG | CAG | CCT | GCG | ATG | CAA | GAG | CAT | CAA | AAT | GTG | ATG | GAT | 1824 |
| Ala | Met | His | Thr | Gln | Pro | Ala | Met | Gln | Glu | His | Gln | Asn | Val | Met | Asp | |
| | | 595 | | | | | 600 | | | | | 605 | | | | |
| TTT | TAT | CTG | CAA | CCG | TTA | AAA | GCA | GAG | CTT | CCT | AGT | GAA | ATA | AGC | TTT | 1872 |
| Phe | Tyr | Leu | Gln | Pro | Leu | Lys | Ala | Glu | Leu | Pro | Ser | Glu | Ile | Ser | Phe | |
| | 610 | | | | | 615 | | | | | 620 | | | | | |
| ATC | AGC | GCC | GCT | GAT | TTA | ACT | GCC | AAG | CAA | ACG | GTG | AGT | GAG | CAA | GCA | 1920 |
| Ile | Ser | Ala | Ala | Asp | Leu | Thr | Ala | Lys | Gln | Thr | Val | Ser | Glu | Gln | Ala | |

-continued

```
625                     630                     635                     640
CTT AGC AGC CAA GTC GTT GCT CAG TCT ATT GCC GAC ACC TTC TGC CAA         1968
Leu Ser Ser Gln Val Val Ala Gln Ser Ile Ala Asp Thr Phe Cys Gln
                645                     650                     655

ACC TTG GAC TTT ACC GCG CTA GTA CAT CAC GCC CAA CAT CAA GGC GCT         2016
Thr Leu Asp Phe Thr Ala Leu Val His His Ala Gln His Gln Gly Ala
            660                     665                     670

AAG CTG TTT GTT GAA ATT GGC GCG GAT AGA CAA AAC TGC ACC TTG ATA         2064
Lys Leu Phe Val Glu Ile Gly Ala Asp Arg Gln Asn Cys Thr Leu Ile
        675                     680                     685

GAC AAG ATT GTT AAA CAA GAT GGT GCC AGC AGT GTA CAA CAT CAA CCT         2112
Asp Lys Ile Val Lys Gln Asp Gly Ala Ser Ser Val Gln His Gln Pro
    690                     695                     700

TGT TGC ACA GTG CCT ATG AAC GCA AAA GGT AGC CAA GAT ATT ACC AGC         2160
Cys Cys Thr Val Pro Met Asn Ala Lys Gly Ser Gln Asp Ile Thr Ser
705                     710                     715                     720

GTG ATT AAA GCG CTT GGC CAA TTA ATT AGC CAT CAG GTG CCA TTA TCG         2208
Val Ile Lys Ala Leu Gly Gln Leu Ile Ser His Gln Val Pro Leu Ser
                725                     730                     735

GTG CAA CCA TTT ATT GAT GGA CTC AAG CGC GAG CTA ACA CTT TGC CAA         2256
Val Gln Pro Phe Ile Asp Gly Leu Lys Arg Glu Leu Thr Leu Cys Gln
            740                     745                     750

TTG ACC AGC CAA CAG CTG GCA GCA CAT GCA AAT GTT GAC AGC AAG TTT         2304
Leu Thr Ser Gln Gln Leu Ala Ala His Ala Asn Val Asp Ser Lys Phe
        755                     760                     765

GAG TCT AAC CAA GAC CAT TTA CTT CAA GGG GAA GTC                         2340
Glu Ser Asn Gln Asp His Leu Leu Gln Gly Glu Val
    770                     775                     780
```

( 2 ) INFORMATION FOR SEQ ID NO:13:

( i ) SEQUENCE CHARACTERISTICS:
        ( A ) LENGTH: 780 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Val Glu Gln Thr Pro Lys Ala Ser Ala Met Pro Leu Arg Ile Ala Leu
 1               5                  10                  15

Ile Leu Leu Pro Thr Pro Gln Phe Glu Val Asn Ser Val Asp Gln Ser
                20                  25                  30

Val Leu Ala Ser Tyr Gln Thr Leu Gln Pro Glu Leu Asn Ala Leu Leu
            35                  40                  45

Asn Ser Ala Pro Thr Pro Glu Met Leu Ser Ile Thr Ile Ser Asp Asp
        50                  55                  60

Ser Asp Ala Asn Ser Phe Glu Ser Gln Leu Asn Ala Ala Thr Asn Ala
65                  70                  75                  80

Ile Asn Asn Gly Tyr Ile Val Lys Leu Ala Thr Ala Thr His Ala Leu
                85                  90                  95

Leu Met Leu Pro Ala Leu Lys Ala Ala Gln Met Arg Ile His Pro His
                100                 105                 110

Ala Gln Leu Ala Ala Met Gln Gln Ala Lys Ser Thr Pro Met Ser Gln
            115                 120                 125

Val Ser Gly Glu Leu Lys Leu Gly Ala Asn Ala Leu Ser Leu Ala Gln
        130                 135                 140

Thr Asn Ala Leu Ser His Ala Leu Ser Gln Ala Lys Arg Asn Leu Thr
145                 150                 155                 160
```

-continued

| | | | | | | | | | | | | | | |
|---|---|---|---|---|---|---|---|---|---|---|---|---|---|---|
| Asp | Val | Ser | Val 165 | Asn | Glu | Cys | Phe | Glu | Asn 170 | Leu | Lys | Ser | Glu | Gln Gln 175 |
| Phe | Thr | Glu | Val 180 | Tyr | Ser | Leu | Ile | Gln 185 | Gln | Leu | Ala | Ser | Arg | Thr His 190 |
| Val | Arg | Lys 195 | Glu | Val | Asn | Gln | Gly 200 | Val | Glu | Leu | Gly | Pro 205 | Lys | Gln Ala |
| Lys | Ser 210 | His | Tyr | Trp | Phe | Ser 215 | Glu | Phe | His | Gln | Asn 220 | Arg | Val | Ala Ala |
| Ile 225 | Asn | Phe | Ile | Asn | Gly 230 | Gln | Gln | Ala | Thr | Ser 235 | Tyr | Val | Leu | Thr Gln 240 |
| Gly | Ser | Gly | Leu | Leu 245 | Ala | Ala | Lys | Ser | Met 250 | Leu | Asn | Gln | Gln | Arg Leu 255 |
| Met | Phe | Ile | Leu 260 | Pro | Gly | Asn | Ser | Gln 265 | Gln | Gln | Ile | Thr | Ala 270 | Ser Ile |
| Thr | Gln | Leu 275 | Met | Gln | Gln | Leu | Glu 280 | Arg | Leu | Gln | Val | Thr 285 | Glu | Val Asn |
| Glu | Leu 290 | Ser | Leu | Glu | Cys | Gln 295 | Leu | Glu | Leu | Leu | Ser 300 | Ile | Met | Tyr Asp |
| Asn 305 | Leu | Val | Asn | Ala | Asp 310 | Lys | Leu | Thr | Thr | Arg 315 | Asp | Ser | Lys | Pro Ala 320 |
| Tyr | Gln | Ala | Val | Ile 325 | Gln | Ala | Ser | Ser | Val 330 | Ser | Ala | Ala | Lys | Gln Glu 335 |
| Leu | Ser | Ala | Leu 340 | Asn | Asp | Ala | Leu | Thr 345 | Ala | Leu | Phe | Ala | Glu 350 | Gln Thr |
| Asn | Ala | Thr 355 | Ser | Thr | Asn | Lys | Gly 360 | Leu | Ile | Gln | Tyr | Lys 365 | Thr | Pro Ala |
| Gly | Ser 370 | Tyr | Leu | Thr | Leu | Thr 375 | Pro | Leu | Gly | Ser | Asn 380 | Asn | Asp | Asn Ala |
| Gln 385 | Ala | Gly | Leu | Ala | Phe 390 | Val | Tyr | Pro | Gly | Val 395 | Gly | Thr | Val | Tyr Ala 400 |
| Asp | Met | Leu | Asn | Glu 405 | Leu | His | Gln | Tyr | Phe 410 | Pro | Ala | Leu | Tyr | Ala Lys 415 |
| Leu | Glu | Arg | Glu 420 | Gly | Asp | Leu | Lys | Ala 425 | Met | Leu | Gln | Ala | Glu 430 | Asp Ile |
| Tyr | His | Leu 435 | Asp | Pro | Lys | His | Ala 440 | Ala | Gln | Met | Ser | Leu 445 | Gly | Asp Leu |
| Ala | Ile 450 | Ala | Gly | Val | Gly | Ser 455 | Ser | Tyr | Leu | Leu | Thr 460 | Gln | Leu | Leu Thr |
| Asp 465 | Glu | Phe | Asn | Ile | Lys 470 | Pro | Asn | Phe | Ala | Leu 475 | Gly | Tyr | Ser | Met Gly 480 |
| Glu | Ala | Ser | Met | Trp 485 | Ala | Ser | Leu | Gly | Val 490 | Trp | Gln | Asn | Pro | His Ala 495 |
| Leu | Ile | Ser | Lys 500 | Thr | Gln | Thr | Asp | Pro 505 | Leu | Phe | Thr | Ser | Ala 510 | Ile Ser |
| Gly | Lys | Leu 515 | Thr | Ala | Val | Arg | Gln 520 | Ala | Trp | Gln | Leu | Asp 525 | Thr | Ala |
| Ala | Glu 530 | Ile | Gln | Trp | Asn | Ser 535 | Phe | Val | Val | Arg | Ser 540 | Glu | Ala | Ala Pro |
| Ile 545 | Glu | Ala | Leu | Leu | Lys 550 | Asp | Tyr | Pro | His | Ala 555 | Tyr | Leu | Ala | Ile Ile 560 |
| Gln | Gly | Asp | Thr | Cys 565 | Val | Ile | Ala | Gly | Cys 570 | Glu | Ile | Gln | Cys | Lys Ala 575 |
| Leu | Leu | Ala | Ala | Leu 580 | Gly | Lys | Arg | Gly | Ile 585 | Ala | Ala | Asn | Arg | Val Thr 590 |

```
Ala Met His Thr Gln Pro Ala Met Gln Glu His Gln Asn Val Met Asp
    595             600                 605
Phe Tyr Leu Gln Pro Leu Lys Ala Glu Leu Pro Ser Glu Ile Ser Phe
    610             615                 620
Ile Ser Ala Ala Asp Leu Thr Ala Lys Gln Thr Val Ser Glu Gln Ala
625                 630                 635                 640
Leu Ser Ser Gln Val Val Ala Gln Ser Ile Ala Asp Thr Phe Cys Gln
                645                 650                 655
Thr Leu Asp Phe Thr Ala Leu Val His His Ala Gln His Gln Gly Ala
            660                 665                 670
Lys Leu Phe Val Glu Ile Gly Ala Asp Arg Gln Asn Cys Thr Leu Ile
        675                 680                 685
Asp Lys Ile Val Lys Gln Asp Gly Ala Ser Ser Val Gln His Gln Pro
    690                 695                 700
Cys Cys Thr Val Pro Met Asn Ala Lys Gly Ser Gln Asp Ile Thr Ser
705                 710                 715                 720
Val Ile Lys Ala Leu Gly Gln Leu Ile Ser His Gln Val Pro Leu Ser
                725                 730                 735
Val Gln Pro Phe Ile Asp Gly Leu Lys Arg Glu Leu Thr Leu Cys Gln
            740                 745                 750
Leu Thr Ser Gln Gln Leu Ala Ala His Ala Asn Val Asp Ser Lys Phe
        755                 760                 765
Glu Ser Asn Gln Asp His Leu Leu Gln Gly Glu Val
    770                 775                 780
```

( 2 ) INFORMATION FOR SEQ ID NO:14:

( i ) SEQUENCE CHARACTERISTICS:
        ( A ) LENGTH: 6012 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Shewanella putrefaciens SCRC-2874 (FERM
            BP- 1625)

( i x ) FEATURE:
        ( A ) NAME/KEY: CDS
        ( B ) LOCATION: 1..6012

( i x ) FEATURE:
        ( A ) NAME/KEY: mat_peptide
        ( B ) LOCATION: 1..6012

( x i ) SEQUENCE DESCRIPTION: SEQ ID NO:14:

```
ATG TCA TTA CCA GAC AAT GCT TCT AAC CAC CTT TCT GCC AAC CAG AAA        48
Met Ser Leu Pro Asp Asn Ala Ser Asn His Leu Ser Ala Asn Gln Lys
 1               5                  10                  15

GGC GCA TCT CAG GCA AGT AAA ACC AGT AAG CAA AGC AAA ATC GCC ATT        96
Gly Ala Ser Gln Ala Ser Lys Thr Ser Lys Gln Ser Lys Ile Ala Ile
                20                  25                  30

GTC GGT TTA GCC ACT CTG TAT CCA GAC GCT AAA ACC CCG CAA GAA TTT       144
Val Gly Leu Ala Thr Leu Tyr Pro Asp Ala Lys Thr Pro Gln Glu Phe
                35                  40                  45

TGG CAG AAT TTG CTG GAT AAA CGC GAC TCT CGC AGC ACC TTA ACT AAC       192
Trp Gln Asn Leu Leu Asp Lys Arg Asp Ser Arg Ser Thr Leu Thr Asn
        50                  55                  60

GAA AAA CTC GGC GCT AAC AGC CAA GAT TAT CAA GGT GTG CAA GGC CAA       240
Glu Lys Leu Gly Ala Asn Ser Gln Asp Tyr Gln Gly Val Gln Gly Gln
```

-continued

|  |  |  |  |  |  |  |  |  |  |  |  |  |  |  |  |  |
|---|---|---|---|---|---|---|---|---|---|---|---|---|---|---|---|---|
| 65 | | | | | 70 | | | | | 75 | | | | | 80 | |

```
TCT  GAC  CGT  TTT  TAT  TGT  AAT  AAA  GGC  GGC  TAC  ATT  GAG  AAC  TTC  AGC       288
Ser  Asp  Arg  Phe  Tyr  Cys  Asn  Lys  Gly  Gly  Tyr  Ile  Glu  Asn  Phe  Ser
                         85                      90                       95

TTT  AAT  GCT  GCA  GGC  TAC  AAA  TTG  CCG  GAG  CAA  AGC  TTA  AAT  GGC  TTG       336
Phe  Asn  Ala  Ala  Gly  Tyr  Lys  Leu  Pro  Glu  Gln  Ser  Leu  Asn  Gly  Leu
              100                      105                     110

GAC  GAC  AGC  TTC  CTT  TGG  GCG  CTC  GAT  ACT  AGC  CGT  AAC  GCA  CTA  ATT       384
Asp  Asp  Ser  Phe  Leu  Trp  Ala  Leu  Asp  Thr  Ser  Arg  Asn  Ala  Leu  Ile
              115                      120                     125

GAT  GCT  GGT  ATT  GAT  ATC  AAC  GGC  GCT  GAT  TTA  AGC  CGC  GCA  GGT  GTA       432
Asp  Ala  Gly  Ile  Asp  Ile  Asn  Gly  Ala  Asp  Leu  Ser  Arg  Ala  Gly  Val
         130                      135                     140

GTC  ATG  GGC  GCG  CTG  TCG  TTC  CCA  ACT  ACC  CGC  TCA  AAC  GAT  CTG  TTT       480
Val  Met  Gly  Ala  Leu  Ser  Phe  Pro  Thr  Thr  Arg  Ser  Asn  Asp  Leu  Phe
145                      150                     155                     160

TTG  CCA  ATT  TAT  CAC  AGC  GCC  GTT  GAA  AAA  GCC  CTG  CAA  GAT  AAA  CTA       528
Leu  Pro  Ile  Tyr  His  Ser  Ala  Val  Glu  Lys  Ala  Leu  Gln  Asp  Lys  Leu
                         165                     170                     175

GGC  GTA  AAG  GCA  TTT  AAG  CTA  AGC  CCA  ACT  AAT  GCT  CAT  ACC  GCT  CGC       576
Gly  Val  Lys  Ala  Phe  Lys  Leu  Ser  Pro  Thr  Asn  Ala  His  Thr  Ala  Arg
              180                      185                     190

GCG  GCA  AAT  GAG  AGC  AGC  CTA  AAT  GCA  GCC  AAT  GGT  GCC  ATT  GCC  CAT       624
Ala  Ala  Asn  Glu  Ser  Ser  Leu  Asn  Ala  Ala  Asn  Gly  Ala  Ile  Ala  His
              195                      200                     205

AAC  AGC  TCA  AAA  GTG  GTG  GCC  GAT  GCA  CTT  GGC  CTT  GGC  GGC  GCA  CAA       672
Asn  Ser  Ser  Lys  Val  Val  Ala  Asp  Ala  Leu  Gly  Leu  Gly  Gly  Ala  Gln
         210                      215                     220

CTA  AGC  CTA  GAT  GCT  GCC  TGT  GCT  AGT  TCG  GTT  TAC  TCA  TTA  AAG  CTT       720
Leu  Ser  Leu  Asp  Ala  Ala  Cys  Ala  Ser  Ser  Val  Tyr  Ser  Leu  Lys  Leu
225                      230                     235                     240

GCC  TGC  GAT  TAC  CTA  AGC  ACT  GGC  AAA  GCC  GAT  ATC  ATG  CTA  GCA  GGC       768
Ala  Cys  Asp  Tyr  Leu  Ser  Thr  Gly  Lys  Ala  Asp  Ile  Met  Leu  Ala  Gly
                         245                     250                     255

GCA  GTA  TCT  GGC  GCG  GAT  CCT  TTC  TTT  ATT  AAT  ATG  GGA  TTC  TCA  ATC       816
Ala  Val  Ser  Gly  Ala  Asp  Pro  Phe  Phe  Ile  Asn  Met  Gly  Phe  Ser  Ile
              260                      265                     270

TTC  CAC  GCC  TAC  CCA  GAC  CAT  GGT  ATC  TCA  GTA  CCG  TTT  GAT  GCC  AGC       864
Phe  His  Ala  Tyr  Pro  Asp  His  Gly  Ile  Ser  Val  Pro  Phe  Asp  Ala  Ser
              275                      280                     285

AGT  AAA  GGT  TTG  TTT  GCT  GGC  GAA  GGC  GCT  GGC  GTA  TTA  GTG  CTT  AAA       912
Ser  Lys  Gly  Leu  Phe  Ala  Gly  Glu  Gly  Ala  Gly  Val  Leu  Val  Leu  Lys
290                      295                     300

CGT  CTT  GAA  GAT  GCC  GAG  CGC  GAC  AAT  GAC  AAA  ATC  TAT  GCG  GTT  GTT       960
Arg  Leu  Glu  Asp  Ala  Glu  Arg  Asp  Asn  Asp  Lys  Ile  Tyr  Ala  Val  Val
305                      310                     315                     320

AGC  GGC  GTA  GGT  CTA  TCA  AAC  GAC  GGT  AAA  GGC  CAG  TTT  GTA  TTA  AGC      1008
Ser  Gly  Val  Gly  Leu  Ser  Asn  Asp  Gly  Lys  Gly  Gln  Phe  Val  Leu  Ser
              325                      330                     335

CCT  AAT  CCA  AAA  GGT  CAG  GTG  AAG  GCC  TTT  GAA  CGT  GCT  TAT  GCT  GCC      1056
Pro  Asn  Pro  Lys  Gly  Gln  Val  Lys  Ala  Phe  Glu  Arg  Ala  Tyr  Ala  Ala
              340                      345                     350

AGT  GAC  ATT  GAG  CCA  AAA  GAC  ATT  GAA  GTG  ATT  GAG  TGC  CAC  GCA  ACA      1104
Ser  Asp  Ile  Glu  Pro  Lys  Asp  Ile  Glu  Val  Ile  Glu  Cys  His  Ala  Thr
              355                      360                     365

GGC  ACA  CCG  CTT  GGC  GAT  AAA  ATT  GAG  CTC  ACT  TCA  ATG  GAA  ACC  TTC      1152
Gly  Thr  Pro  Leu  Gly  Asp  Lys  Ile  Glu  Leu  Thr  Ser  Met  Glu  Thr  Phe
         370                      375                     380

TTT  GAA  GAC  AAG  CTG  CAA  GGC  ACC  GAT  GCA  CCG  TTA  ATT  GGC  TCA  GCT      1200
Phe  Glu  Asp  Lys  Leu  Gln  Gly  Thr  Asp  Ala  Pro  Leu  Ile  Gly  Ser  Ala
```

-continued

| | | | | | | | | | | | | | | | | |
|---|---|---|---|---|---|---|---|---|---|---|---|---|---|---|---|---|
| 385 | | | | | 390 | | | | | 395 | | | | | 400 | |
| AAG | TCT | AAC | TTA | GGC | CAC | CTA | TTA | ACT | GCA | GCG | CAT | GCG | GGG | ATC | ATG | 1248 |
| Lys | Ser | Asn | Leu | Gly | His | Leu | Leu | Thr | Ala | Ala | His | Ala | Gly | Ile | Met | |
| | | | | 405 | | | | | 410 | | | | | 415 | | |
| AAG | ATG | ATC | TTC | GCC | ATG | AAA | GAA | GGT | TAC | CTG | CCG | CCA | AGT | ATC | AAT | 1296 |
| Lys | Met | Ile | Phe | Ala | Met | Lys | Glu | Gly | Tyr | Leu | Pro | Pro | Ser | Ile | Asn | |
| | | | | 420 | | | | | 425 | | | | | 430 | | |
| ATT | AGT | GAT | GCT | ATC | GCT | TCG | CCG | AAA | AAA | CTC | TTC | GGT | AAA | CCA | ACC | 1344 |
| Ile | Ser | Asp | Ala | Ile | Ala | Ser | Pro | Lys | Lys | Leu | Phe | Gly | Lys | Pro | Thr | |
| | | | | 435 | | | | | 440 | | | | | 445 | | |
| CTG | CCT | AGC | ATG | GTT | CAA | GGC | TGG | CCA | GAT | AAG | CCA | TCG | AAT | AAT | CAT | 1392 |
| Leu | Pro | Ser | Met | Val | Gln | Gly | Trp | Pro | Asp | Lys | Pro | Ser | Asn | Asn | His | |
| | | | | 450 | | | | | 455 | | | | | 460 | | |
| TTT | GGT | GTA | AGA | ACC | CGT | CAC | GCA | GGC | GTA | TCG | GTA | TTT | GGC | TTT | GGT | 1440 |
| Phe | Gly | Val | Arg | Thr | Arg | His | Ala | Gly | Val | Ser | Val | Phe | Gly | Phe | Gly | |
| 465 | | | | | 470 | | | | | 475 | | | | | 480 | |
| GGC | TGT | AAC | GCC | CAT | CTG | TTG | CTT | GAG | TCA | TAC | AAC | GGC | AAA | GGA | ACA | 1488 |
| Gly | Cys | Asn | Ala | His | Leu | Leu | Leu | Glu | Ser | Tyr | Asn | Gly | Lys | Gly | Thr | |
| | | | | 485 | | | | | 490 | | | | | 495 | | |
| GTA | AAG | GCA | GAA | GCC | ACT | CAA | GTA | CCG | CGT | CAA | GCT | GAG | CCG | CTA | AAA | 1536 |
| Val | Lys | Ala | Glu | Ala | Thr | Gln | Val | Pro | Arg | Gln | Ala | Glu | Pro | Leu | Lys | |
| | | | 500 | | | | | 505 | | | | | 510 | | | |
| GTG | GTT | GGC | CTT | GCC | TCG | CAC | TTT | GGG | CCT | CTT | AGC | AGC | ATT | AAT | GCA | 1584 |
| Val | Val | Gly | Leu | Ala | Ser | His | Phe | Gly | Pro | Leu | Ser | Ser | Ile | Asn | Ala | |
| | | 515 | | | | | 520 | | | | | 525 | | | | |
| CTC | AAC | AAT | GCT | GTG | ACC | CAA | GAT | GGG | AAT | GGC | TTT | ATC | GAA | CTG | CCG | 1632 |
| Leu | Asn | Asn | Ala | Val | Thr | Gln | Asp | Gly | Asn | Gly | Phe | Ile | Glu | Leu | Pro | |
| | 530 | | | | | 535 | | | | | 540 | | | | | |
| AAA | AAG | CGC | TGG | AAA | GGC | CTT | GAA | AAG | CAC | AGT | GAA | CTG | TTA | GCT | GAA | 1680 |
| Lys | Lys | Arg | Trp | Lys | Gly | Leu | Glu | Lys | His | Ser | Glu | Leu | Leu | Ala | Glu | |
| 545 | | | | 550 | | | | | 555 | | | | | 560 | | |
| TTT | GGC | TTA | GCA | TCT | GCG | CCA | AAA | GGT | GCT | TAT | GTT | GAT | AAC | TTC | GAG | 1728 |
| Phe | Gly | Leu | Ala | Ser | Ala | Pro | Lys | Gly | Ala | Tyr | Val | Asp | Asn | Phe | Glu | |
| | | | | 565 | | | | | 570 | | | | | 575 | | |
| CTG | GAC | TTT | TTA | CGC | TTT | AAA | CTG | CCG | CCA | AAC | GAA | GAT | GAC | CGT | TTG | 1776 |
| Leu | Asp | Phe | Leu | Arg | Phe | Lys | Leu | Pro | Pro | Asn | Glu | Asp | Asp | Arg | Leu | |
| | | | 580 | | | | | 585 | | | | | 590 | | | |
| ATC | TCA | CAG | CAG | CTA | ATG | CTA | ATG | CGA | GTA | ACA | GAC | GAA | GCC | ATT | CGT | 1824 |
| Ile | Ser | Gln | Gln | Leu | Met | Leu | Met | Arg | Val | Thr | Asp | Glu | Ala | Ile | Arg | |
| | | 595 | | | | | 600 | | | | | 605 | | | | |
| GAT | GCC | AAG | CTT | GAG | CCG | GGG | CAA | AAA | GTA | GCT | GTA | TTA | GTG | GCA | ATG | 1872 |
| Asp | Ala | Lys | Leu | Glu | Pro | Gly | Gln | Lys | Val | Ala | Val | Leu | Val | Ala | Met | |
| | 610 | | | | | 615 | | | | | 620 | | | | | |
| GAA | ACT | GAG | CTT | GAA | CTG | CAT | CAG | TTC | CGC | GGC | CGG | GTT | AAC | TTG | CAT | 1920 |
| Glu | Thr | Glu | Leu | Glu | Leu | His | Gln | Phe | Arg | Gly | Arg | Val | Asn | Leu | His | |
| 625 | | | | | 630 | | | | | 635 | | | | | 640 | |
| ACT | CAA | TTA | GCG | CAA | AGT | CTT | GCC | GCC | ATG | GGC | GTG | AGT | TTA | TCA | ACG | 1968 |
| Thr | Gln | Leu | Ala | Gln | Ser | Leu | Ala | Ala | Met | Gly | Val | Ser | Leu | Ser | Thr | |
| | | | | 645 | | | | | 650 | | | | | 655 | | |
| GAT | GAA | TAC | CAA | GCG | CTT | GAA | GCC | ATC | GCC | ATG | GAC | AGC | GTG | CTT | GAT | 2016 |
| Asp | Glu | Tyr | Gln | Ala | Leu | Glu | Ala | Ile | Ala | Met | Asp | Ser | Val | Leu | Asp | |
| | | | 660 | | | | | 665 | | | | | 670 | | | |
| GCT | GCC | AAG | CTC | AAT | CAG | TAC | ACC | AGC | TTT | ATT | GGT | AAT | ATT | ATG | GCG | 2064 |
| Ala | Ala | Lys | Leu | Asn | Gln | Tyr | Thr | Ser | Phe | Ile | Gly | Asn | Ile | Met | Ala | |
| | | 675 | | | | | 680 | | | | | 685 | | | | |
| TCA | CGC | GTG | GCG | TCA | CTA | TGG | GAC | TTT | AAT | GGC | CCA | GCC | TTC | ACT | ATT | 2112 |
| Ser | Arg | Val | Ala | Ser | Leu | Trp | Asp | Phe | Asn | Gly | Pro | Ala | Phe | Thr | Ile | |
| | 690 | | | | | 695 | | | | | 700 | | | | | |
| TCA | GCA | GCA | GAG | CAA | TCT | GTG | AGC | CGC | TGT | ATC | GAT | GTG | GCG | CAA | AAC | 2160 |
| Ser | Ala | Ala | Glu | Gln | Ser | Val | Ser | Arg | Cys | Ile | Asp | Val | Ala | Gln | Asn | |

```
                                                         -continued
705                       710                       715                       720
CTC ATC ATG GAG GAT AAC CTA GAT GCG GTG GTG ATT GCA GCG GTC GAT          2208
Leu Ile Met Glu Asp Asn Leu Asp Ala Val Val Ile Ala Ala Val Asp
            725                       730                       735

CTC TCT GGT AGC TTT GAG CAA GTC ATT CTT AAA AAT GCC ATT GCA CCT          2256
Leu Ser Gly Ser Phe Glu Gln Val Ile Leu Lys Asn Ala Ile Ala Pro
        740                       745                       750

GTA GCC ATT GAG CCA AAC CTC GAA GCA AGC CTT AAT CCA ACA TCA GCA          2304
Val Ala Ile Glu Pro Asn Leu Glu Ala Ser Leu Asn Pro Thr Ser Ala
            755                       760                       765

AGC TGG AAT GTC GGT GAA GGT GCT GGC GCG GTC GTG CTT GTT AAA AAT          2352
Ser Trp Asn Val Gly Glu Gly Ala Gly Ala Val Val Leu Val Lys Asn
        770                       775                       780

GAA GCT ACA TCG GGC TGC TCA TAC GGC CAA ATT GAT GCA CTT GGC TTT          2400
Glu Ala Thr Ser Gly Cys Ser Tyr Gly Gln Ile Asp Ala Leu Gly Phe
785                       790                       795                       800

GCT AAA ACT GCC GAA ACA GCG TTG GCT ACC GAC AAG CTA CTG AGC CAA          2448
Ala Lys Thr Ala Glu Thr Ala Leu Ala Thr Asp Lys Leu Leu Ser Gln
            805                       810                       815

ACT GCC ACA GAC TTT AAT AAG GTT AAA GTG ATT GAA ACT ATG GCA GCG          2496
Thr Ala Thr Asp Phe Asn Lys Val Lys Val Ile Glu Thr Met Ala Ala
        820                       825                       830

CCT GCT AGC CAA ATT CAA TTA GCG CCA ATA GTT AGC TCT CAA GTG ACT          2544
Pro Ala Ser Gln Ile Gln Leu Ala Pro Ile Val Ser Ser Gln Val Thr
            835                       840                       845

CAC ACT GCT GCA GAG CAG CGT GTT GGT CAC TGC TTT GCT GCA GCG GGT          2592
His Thr Ala Ala Glu Gln Arg Val Gly His Cys Phe Ala Ala Ala Gly
        850                       855                       860

ATG GCA AGC CTA TTA CAC GGC TTA CTT AAC TTA AAT ACT GTA GCC CAA          2640
Met Ala Ser Leu Leu His Gly Leu Leu Asn Leu Asn Thr Val Ala Gln
865                       870                       875                       880

ACC AAT AAA GCC AAT TGC GCG CTT ATC AAC AAT ATC AGT GAA AAC CAA          2688
Thr Asn Lys Ala Asn Cys Ala Leu Ile Asn Asn Ile Ser Glu Asn Gln
            885                       890                       895

TTA TCA CAG CTG TTG ATT AGC CAA ACA GCG AGC GAA CAA CAA GCA TTA          2736
Leu Ser Gln Leu Leu Ile Ser Gln Thr Ala Ser Glu Gln Gln Ala Leu
        900                       905                       910

ACC GCG CGT TTA AGC AAT GAG CTT AAA TCC GAT GCT AAA CAC CAA CTG          2784
Thr Ala Arg Leu Ser Asn Glu Leu Lys Ser Asp Ala Lys His Gln Leu
            915                       920                       925

GTT AAG CAA GTC ACC TTA GGT GGC CGT GAT ATC TAC CAG CAT ATT GTT          2832
Val Lys Gln Val Thr Leu Gly Gly Arg Asp Ile Tyr Gln His Ile Val
        930                       935                       940

GAT ACA CCG CTT GCA AGC CTT GAA AGC ATT ACT CAG AAA TTG GCG CAA          2880
Asp Thr Pro Leu Ala Ser Leu Glu Ser Ile Thr Gln Lys Leu Ala Gln
945                       950                       955                       960

GCG ACA GCA TCG ACA GTG GTC AAC CAA GTT AAA CCT ATT AAG GCC GCT          2928
Ala Thr Ala Ser Thr Val Val Asn Gln Val Lys Pro Ile Lys Ala Ala
            965                       970                       975

GGC TCA GTC GAA ATG GCT AAC TCA TTC GAA ACG GAA AGC TCA GCA GAG          2976
Gly Ser Val Glu Met Ala Asn Ser Phe Glu Thr Glu Ser Ser Ala Glu
        980                       985                       990

CCA CAA ATA ACA ATT GCA GCA CAA CAG ACT GCA AAC ATT GGC GTC ACC          3024
Pro Gln Ile Thr Ile Ala Ala Gln Gln Thr Ala Asn Ile Gly Val Thr
            995                       1000                      1005

GCT CAG GCA ACC AAA CGT GAA TTA GGT ACC CCA CCA ATG ACA ACA AAT          3072
Ala Gln Ala Thr Lys Arg Glu Leu Gly Thr Pro Pro Met Thr Thr Asn
        1010                      1015                      1020

ACC ATT GCT AAT ACA GCA AAT AAT TTA GAC AAG ACT CTT GAG ACT GTT          3120
Thr Ile Ala Asn Thr Ala Asn Asn Leu Asp Lys Thr Leu Glu Thr Val
```

|  |  |  |  |  |  |  |  |  |  |  |  |  |  |  |  |
|---|---|---|---|---|---|---|---|---|---|---|---|---|---|---|---|
| GCT | GGC | AAT | ACT | GTT | GCT | AGC | AAG | GTT | GGC | TCT | GGC | GAC | ATA | GTC | AAT | 3168 |
| Ala | Gly | Asn | Thr | Val | Ala | Ser | Lys | Val | Gly | Ser | Gly | Asp | Ile | Val | Asn |
|  |  |  | 1045 |  |  |  |  | 1050 |  |  |  |  | 1055 |

```
GCT GGC AAT ACT GTT GCT AGC AAG GTT GGC TCT GGC GAC ATA GTC AAT    3168
Ala Gly Asn Thr Val Ala Ser Lys Val Gly Ser Gly Asp Ile Val Asn
            1045                    1050                1055

TTT CAA CAG AAC CAA CAA TTG GCT CAA CAA GCT CAC CTC GCC TTT CTT    3216
Phe Gln Gln Asn Gln Gln Leu Ala Gln Gln Ala His Leu Ala Phe Leu
            1060                    1065                1070

GAA AGC CGC AGT GCG GGT ATG AAG GTG GCT GAT GCT TTA TTG AAG CAA    3264
Glu Ser Arg Ser Ala Gly Met Lys Val Ala Asp Ala Leu Leu Lys Gln
            1075                    1080                1085

CAG CTA GCT CAA GTA ACA GGC CAA ACT ATC GAT AAT CAG GCC CTC GAT    3312
Gln Leu Ala Gln Val Thr Gly Gln Thr Ile Asp Asn Gln Ala Leu Asp
            1090                    1095                1100

ACT CAA GCC GTC GAT ACT CAA ACA AGC GAG AAT GTA GCG ATT GCC GCA    3360
Thr Gln Ala Val Asp Thr Gln Thr Ser Glu Asn Val Ala Ile Ala Ala
1105                1110                1115                1120

GAA TCA CCA GTT CAA GTT ACA ACA CCT GTT CAA GTT ACA ACA CCT GTT    3408
Glu Ser Pro Val Gln Val Thr Thr Pro Val Gln Val Thr Thr Pro Val
            1125                    1130                1135

CAA ATC AGT GTT GTG GAG TTA AAA CCA GAT CAC GCT AAT GTG CCA CCA    3456
Gln Ile Ser Val Val Glu Leu Lys Pro Asp His Ala Asn Val Pro Pro
            1140                    1145                1150

TAC ACG CCG CCA GTG CCT GCA TTA AAG CCG TGT ATC TGG AAC TAT GCC    3504
Tyr Thr Pro Pro Val Pro Ala Leu Lys Pro Cys Ile Trp Asn Tyr Ala
            1155                    1160                1165

GAT TTA GTT GAG TAC GCA GAA GGC GAT ATC GCC AAG GTA TTT GGC AGT    3552
Asp Leu Val Glu Tyr Ala Glu Gly Asp Ile Ala Lys Val Phe Gly Ser
            1170                    1175                1180

GAT TAT GCC ATT ATC GAC AGC TAC TCG CGC CGC GTA CGT CTA CCG ACC    3600
Asp Tyr Ala Ile Ile Asp Ser Tyr Ser Arg Arg Val Arg Leu Pro Thr
1185                1190                1195                1200

ACT GAC TAC CTG TTG GTA TCG CGC GTG ACC AAA CTT GAT GCG ACC ATC    3648
Thr Asp Tyr Leu Leu Val Ser Arg Val Thr Lys Leu Asp Ala Thr Ile
            1205                    1210                1215

AAT CAA TTT AAG CCA TGC TCA ATG ACC ACT GAG TAC GAC ATC CCT GTT    3696
Asn Gln Phe Lys Pro Cys Ser Met Thr Thr Glu Tyr Asp Ile Pro Val
            1220                    1225                1230

GAT GCG CCG TAC TTA GTA GAC GGA CAA ATC CCT TGG GCG GTA GCA GTA    3744
Asp Ala Pro Tyr Leu Val Asp Gly Gln Ile Pro Trp Ala Val Ala Val
            1235                    1240                1245

GAA TCA GGC CAA TGT GAC TTG ATG CTT ATT AGC TAT CTC GGT ATC GAC    3792
Glu Ser Gly Gln Cys Asp Leu Met Leu Ile Ser Tyr Leu Gly Ile Asp
            1250                    1255                1260

TTT GAG AAC AAA GGC GAG CGG GTT TAT CGA CTA CTC GAT TGT ACC CTC    3840
Phe Glu Asn Lys Gly Glu Arg Val Tyr Arg Leu Leu Asp Cys Thr Leu
1265                1270                1275                1280

ACC TTC CTA GGC GAC TTG CCA CGT GGA GAT ACC CTA CGT TAC GAC        3888
Thr Phe Leu Gly Asp Leu Pro Arg Gly Gly Asp Thr Leu Arg Tyr Asp
            1285                    1290                1295

ATT AAG ATC AAT AAC TAT GCT CGC AAC GGC GAC ACC TTG CTG TTC TTC    3936
Ile Lys Ile Asn Asn Tyr Ala Arg Asn Gly Asp Thr Leu Leu Phe Phe
            1300                    1305                1310

TTC TCG TAT GAG TGT TTT GTT GGC GAC AAG ATG ATC CTC AAG ATG GAT    3984
Phe Ser Tyr Glu Cys Phe Val Gly Asp Lys Met Ile Leu Lys Met Asp
            1315                    1320                1325

GGC GGC TGC GCT GGC TTC TTC ACT GAT GAA GAG CTT GCC GAC GGT AAA    4032
Gly Gly Cys Ala Gly Phe Phe Thr Asp Glu Glu Leu Ala Asp Gly Lys
            1330                    1335                1340

GGC GTG ATT CGC ACA GAA GAA GAG ATT AAA GCT CGC AGC CTA GTG CAA    4080
Gly Val Ile Arg Thr Glu Glu Glu Ile Lys Ala Arg Ser Leu Val Gln
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| AAG | CAA | CGC | TTT | AAT | CCG | TTA | CTA | GAT | TGT | CCT | AAA | ACC | CAA | TTT | AGT | 4128 |
| Lys | Gln | Arg | Phe | Asn | Pro | Leu | Leu | Asp | Cys | Pro | Lys | Thr | Gln | Phe | Ser |      |
|     |     |     |     | 1365|     |     |     | 1370|     |     |     |     | 1375|     |     |      |
| TAT | GGT | GAT | ATT | CAT | AAG | CTA | TTA | ACT | GCT | GAT | ATT | GAG | GGT | TGT | TTT | 4176 |
| Tyr | Gly | Asp | Ile | His | Lys | Leu | Leu | Thr | Ala | Asp | Ile | Glu | Gly | Cys | Phe |      |
|     |     |     | 1380|     |     |     |     | 1385|     |     |     |     | 1390|     |     |      |
| GGC | CCA | AGC | CAC | AGT | GGC | GTC | CAC | CAG | CCG | TCA | CTT | TGT | TTC | GCA | TCT | 4224 |
| Gly | Pro | Ser | His | Ser | Gly | Val | His | Gln | Pro | Ser | Leu | Cys | Phe | Ala | Ser |      |
|     |     | 1395|     |     |     |     | 1400|     |     |     |     | 1405|     |     |     |      |
| GAA | AAA | TTC | TTG | ATG | ATT | GAA | CAA | GTC | AGC | AAG | GTT | GAT | CGC | ACT | GGC | 4272 |
| Glu | Lys | Phe | Leu | Met | Ile | Glu | Gln | Val | Ser | Lys | Val | Asp | Arg | Thr | Gly |      |
|     | 1410|     |     |     |     | 1415|     |     |     |     | 1420|     |     |     |     |      |
| GGT | ACT | TGG | GGA | CTT | GGC | TTA | ATT | GAG | GGT | CAT | AAG | CAG | CTT | GAA | GCA | 4320 |
| Gly | Thr | Trp | Gly | Leu | Gly | Leu | Ile | Glu | Gly | His | Lys | Gln | Leu | Glu | Ala |      |
| 1425|     |     |     |     | 1430|     |     |     |     | 1435|     |     |     |     | 1440|      |
| GAC | CAC | TGG | TAC | TTC | CCA | TGT | CAT | TTC | AAG | GGC | GAC | CAA | GTG | ATG | GCT | 4368 |
| Asp | His | Trp | Tyr | Phe | Pro | Cys | His | Phe | Lys | Gly | Asp | Gln | Val | Met | Ala |      |
|     |     |     |     |     | 1445|     |     |     |     | 1450|     |     |     |     | 1455|      |
| GGC | TCG | CTA | ATG | GCT | GAA | GGT | TGT | GGC | CAG | TTA | TTG | CAG | TTC | TAT | ATG | 4416 |
| Gly | Ser | Leu | Met | Ala | Glu | Gly | Cys | Gly | Gln | Leu | Leu | Gln | Phe | Tyr | Met |      |
|     |     |     | 1460|     |     |     |     | 1465|     |     |     |     | 1470|     |     |      |
| CTG | CAC | CTT | GGT | ATG | CAT | ACC | CAA | ACT | AAA | AAT | GGT | CGT | TTC | CAA | CCT | 4464 |
| Leu | His | Leu | Gly | Met | His | Thr | Gln | Thr | Lys | Asn | Gly | Arg | Phe | Gln | Pro |      |
|     |     | 1475|     |     |     |     | 1480|     |     |     |     | 1485|     |     |     |      |
| CTT | GAA | AAC | GCC | TCA | CAG | CAA | GTA | CGC | TGT | CGC | GGT | CAA | GTG | CTG | CCA | 4512 |
| Leu | Glu | Asn | Ala | Ser | Gln | Gln | Val | Arg | Cys | Arg | Gly | Gln | Val | Leu | Pro |      |
|     | 1490|     |     |     |     | 1495|     |     |     |     | 1500|     |     |     |     |      |
| CAA | TCA | GGC | GTG | CTA | ACT | TAC | CGT | ATG | GAA | GTG | ACT | GAA | ATC | GGT | TTC | 4560 |
| Gln | Ser | Gly | Val | Leu | Thr | Tyr | Arg | Met | Glu | Val | Thr | Glu | Ile | Gly | Phe |      |
| 1505|     |     |     |     | 1510|     |     |     |     | 1515|     |     |     |     | 1520|      |
| AGT | CCA | CGC | CCA | TAT | GCT | AAA | GCT | AAC | ATC | GAT | ATC | TTG | CTT | AAT | GGC | 4608 |
| Ser | Pro | Arg | Pro | Tyr | Ala | Lys | Ala | Asn | Ile | Asp | Ile | Leu | Leu | Asn | Gly |      |
|     |     |     |     | 1525|     |     |     |     | 1530|     |     |     |     | 1535|     |      |
| AAA | GCG | GTA | GTG | GAT | TTC | CAA | AAC | CTA | GGG | GTG | ATG | ATA | AAA | GAG | GAA | 4656 |
| Lys | Ala | Val | Val | Asp | Phe | Gln | Asn | Leu | Gly | Val | Met | Ile | Lys | Glu | Glu |      |
|     |     |     | 1540|     |     |     |     | 1545|     |     |     |     | 1550|     |     |      |
| GAT | GAG | TGT | ACT | CGT | TAT | CCA | CTT | TTG | ACT | GAA | TCA | ACA | ACG | GCT | AGC | 4704 |
| Asp | Glu | Cys | Thr | Arg | Tyr | Pro | Leu | Leu | Thr | Glu | Ser | Thr | Thr | Ala | Ser |      |
|     |     | 1555|     |     |     |     | 1560|     |     |     |     | 1565|     |     |     |      |
| ACT | GCA | CAA | GTA | AAC | GCT | CAA | ACA | AGT | GCG | AAA | AAG | GTA | TAC | AAG | CCA | 4752 |
| Thr | Ala | Gln | Val | Asn | Ala | Gln | Thr | Ser | Ala | Lys | Lys | Val | Tyr | Lys | Pro |      |
|     | 1570|     |     |     |     | 1575|     |     |     |     | 1580|     |     |     |     |      |
| GCA | TCA | GTC | AAT | GCG | CCA | TTA | ATG | GCA | CAA | ATT | CCT | GAT | CTG | ACT | AAA | 4800 |
| Ala | Ser | Val | Asn | Ala | Pro | Leu | Met | Ala | Gln | Ile | Pro | Asp | Leu | Thr | Lys |      |
| 1585|     |     |     |     | 1590|     |     |     |     | 1595|     |     |     |     | 1600|      |
| GAG | CCA | AAC | AAG | GGC | GTT | ATT | CCG | ATT | TCC | CAT | GTT | GAA | GCA | CCA | ATT | 4848 |
| Glu | Pro | Asn | Lys | Gly | Val | Ile | Pro | Ile | Ser | His | Val | Glu | Ala | Pro | Ile |      |
|     |     |     |     | 1605|     |     |     |     | 1610|     |     |     |     | 1615|     |      |
| ACG | CCA | GAC | TAC | CCG | AAC | CGT | GTA | CCT | GAT | ACA | GTG | CCA | TTC | ACG | CCG | 4896 |
| Thr | Pro | Asp | Tyr | Pro | Asn | Arg | Val | Pro | Asp | Thr | Val | Pro | Phe | Thr | Pro |      |
|     |     |     | 1620|     |     |     |     | 1625|     |     |     |     | 1630|     |     |      |
| TAT | CAC | ATG | TTT | GAG | TTT | GCT | ACA | GGC | AAT | ATC | GAA | AAC | TGT | TTC | GGG | 4944 |
| Tyr | His | Met | Phe | Glu | Phe | Ala | Thr | Gly | Asn | Ile | Glu | Asn | Cys | Phe | Gly |      |
|     |     | 1635|     |     |     |     | 1640|     |     |     |     | 1645|     |     |     |      |
| CCA | GAG | TTC | TCA | ATC | TAT | CGC | GGC | ATG | ATC | CCA | CCA | CGT | ACA | CCA | TGC | 4992 |
| Pro | Glu | Phe | Ser | Ile | Tyr | Arg | Gly | Met | Ile | Pro | Pro | Arg | Thr | Pro | Cys |      |
|     | 1650|     |     |     |     | 1655|     |     |     |     | 1660|     |     |     |     |      |
| GGT | GAC | TTA | CAA | GTG | ACC | ACA | CGT | GTG | ATT | GAA | GTT | AAC | GGT | AAG | CGT | 5040 |
| Gly | Asp | Leu | Gln | Val | Thr | Thr | Arg | Val | Ile | Glu | Val | Asn | Gly | Lys | Arg |      |

```
                                                    -continued
1665                    1670                    1675                    1680

GGC GAC TTT AAA AAG CCA TCA TCG TGT ATC GCT GAA TAT GAA GTG CCT    5088
Gly Asp Phe Lys Lys Pro Ser Ser Cys Ile Ala Glu Tyr Glu Val Pro
                1685                    1690                    1695

GCA GAT GCG TGG TAT TTC GAT AAA AAC AGC CAC GGC GCA GTG ATG CCA    5136
Ala Asp Ala Trp Tyr Phe Asp Lys Asn Ser His Gly Ala Val Met Pro
1700                    1705                    1710

TAT TCA ATT TTA ATG GAG ATC TCA CTG CAA CCT AAC GGC TTT ATC TCA    5184
Tyr Ser Ile Leu Met Glu Ile Ser Leu Gln Pro Asn Gly Phe Ile Ser
        1715                    1720                    1725

GGT TAC ATG GGC ACA ACC CTA GGC TTC CCT GGC CTT GAG CTG TTC TTC    5232
Gly Tyr Met Gly Thr Thr Leu Gly Phe Pro Gly Leu Glu Leu Phe Phe
                1730                    1735                    1740

CGT AAC TTA GAC GGT AGC GGT GAG TTA CTA CGT GAA GTA GAT TTA CGT    5280
Arg Asn Leu Asp Gly Ser Gly Glu Leu Leu Arg Glu Val Asp Leu Arg
1745                    1750                    1755                    1760

GGT AAA ACC ATC CGT AAC GAC TCA CGT TTA TTA TCA ACA GTG ATG GCC    5328
Gly Lys Thr Ile Arg Asn Asp Ser Arg Leu Leu Ser Thr Val Met Ala
                1765                    1770                    1775

GGC ACT AAC ATC ATC CAA AGC TTT AGC TTC GAG CTA AGC ACT GAC GGT    5376
Gly Thr Asn Ile Ile Gln Ser Phe Ser Phe Glu Leu Ser Thr Asp Gly
                1780                    1785                    1790

GAG CCT TTC TAT CGC GGC ACT GCG GTA TTT GGC TAT TTT AAA GGT GAC    5424
Glu Pro Phe Tyr Arg Gly Thr Ala Val Phe Gly Tyr Phe Lys Gly Asp
        1795                    1800                    1805

GCA CTT AAA GAT CAG CTA GGC CTA GAT AAC GGT AAA GTC ACT CAG CCA    5472
Ala Leu Lys Asp Gln Leu Gly Leu Asp Asn Gly Lys Val Thr Gln Pro
1810                    1815                    1820

TGG CAT GTA GCT AAC GGC GTT GCT GCA AGC ACT AAG GTG AAC CTG CTT    5520
Trp His Val Ala Asn Gly Val Ala Ala Ser Thr Lys Val Asn Leu Leu
1825                    1830                    1835                    1840

GAT AAG AGC TGC CGT CAC TTT AAT GCG CCA GCT AAC CAG CCA CAC TAT    5568
Asp Lys Ser Cys Arg His Phe Asn Ala Pro Ala Asn Gln Pro His Tyr
                1845                    1850                    1855

CGT CTA GCC GGT GGT CAG CTG AAC TTT ATC GAC AGT GTT GAA ATT GTT    5616
Arg Leu Ala Gly Gly Gln Leu Asn Phe Ile Asp Ser Val Glu Ile Val
                1860                    1865                    1870

GAT AAT GGC GGC ACC GAA GGT TTA GGT TAC TTG TAT GCC GAG CGC ACC    5664
Asp Asn Gly Gly Thr Glu Gly Leu Gly Tyr Leu Tyr Ala Glu Arg Thr
        1875                    1880                    1885

ATT GAC CCA AGT GAT TGG TTC TTC CAG TTC CAC TTC CAC CAA GAT CCG    5712
Ile Asp Pro Ser Asp Trp Phe Phe Gln Phe His Phe His Gln Asp Pro
                1890                    1895                    1900

GTT ATG CCA GGC TCC TTA GGT GTT GAA GCA ATT ATT GAA ACC ATG CAA    5760
Val Met Pro Gly Ser Leu Gly Val Glu Ala Ile Ile Glu Thr Met Gln
1905                    1910                    1915                    1920

GCT TAC GCT ATT AGT AAA GAC TTG GGC GCA GAT TTC AAA AAT CCT AAG    5808
Ala Tyr Ala Ile Ser Lys Asp Leu Gly Ala Asp Phe Lys Asn Pro Lys
                1925                    1930                    1935

TTT GGT CAG ATT TTA TCG AAC ATC AAG TGG AAG TAT CGC GGT CAA ATC    5856
Phe Gly Gln Ile Leu Ser Asn Ile Lys Trp Lys Tyr Arg Gly Gln Ile
                1940                    1945                    1950

AAT CCG CTG AAC AAG CAG ATG TCT ATG GAT GTC AGC ATT ACT TCA ATC    5904
Asn Pro Leu Asn Lys Gln Met Ser Met Asp Val Ser Ile Thr Ser Ile
        1955                    1960                    1965

AAA GAT GAA GAC GGT AAG AAA GTC ATC ACA GGT AAT GCC AGC TTG AGT    5952
Lys Asp Glu Asp Gly Lys Lys Val Ile Thr Gly Asn Ala Ser Leu Ser
1970                    1975                    1980

AAA GAT GGT CTG CGC ATA TAC GAG GTC TTC GAT ATA GCT ATC AGC ATC    6000
Lys Asp Gly Leu Arg Ile Tyr Glu Val Phe Asp Ile Ala Ile Ser Ile
```

```
                               1985                  1990                  1995                  2000
GAA GAA TCT GTA                                                                                                          6012
Glu Glu Ser Val
```

( 2 ) INFORMATION FOR SEQ ID NO:15:

( i ) SEQUENCE CHARACTERISTICS:
        ( A ) LENGTH: 2004 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met Ser Leu Pro Asp Asn Ala Ser Asn His Leu Ser Ala Asn Gln Lys
 1               5                  10                  15
Gly Ala Ser Gln Ala Ser Lys Thr Ser Lys Gln Ser Lys Ile Ala Ile
             20                  25                  30
Val Gly Leu Ala Thr Leu Tyr Pro Asp Ala Lys Thr Pro Gln Glu Phe
             35                  40                  45
Trp Gln Asn Leu Leu Asp Lys Arg Asp Ser Arg Ser Thr Leu Thr Asn
     50                  55                  60
Glu Lys Leu Gly Ala Asn Ser Gln Asp Tyr Gln Gly Val Gln Gly Gln
 65                  70                  75                  80
Ser Asp Arg Phe Tyr Cys Asn Lys Gly Gly Tyr Ile Glu Asn Phe Ser
                 85                  90                  95
Phe Asn Ala Ala Gly Tyr Lys Leu Pro Glu Gln Ser Leu Asn Gly Leu
             100                 105                 110
Asp Asp Ser Phe Leu Trp Ala Leu Asp Thr Ser Arg Asn Ala Leu Ile
             115                 120                 125
Asp Ala Gly Ile Asp Ile Asn Gly Ala Asp Leu Ser Arg Ala Gly Val
     130                 135                 140
Val Met Gly Ala Leu Ser Phe Pro Thr Thr Arg Ser Asn Asp Leu Phe
145                 150                 155                 160
Leu Pro Ile Tyr His Ser Ala Val Glu Lys Ala Leu Gln Asp Lys Leu
                 165                 170                 175
Gly Val Lys Ala Phe Lys Leu Ser Pro Thr Asn Ala His Thr Ala Arg
             180                 185                 190
Ala Ala Asn Glu Ser Ser Leu Asn Ala Ala Asn Gly Ala Ile Ala His
             195                 200                 205
Asn Ser Ser Lys Val Val Ala Asp Ala Leu Gly Leu Gly Gly Ala Gln
     210                 215                 220
Leu Ser Leu Asp Ala Ala Cys Ala Ser Ser Val Tyr Ser Leu Lys Leu
225                 230                 235                 240
Ala Cys Asp Tyr Leu Ser Thr Gly Lys Ala Asp Ile Met Leu Ala Gly
                 245                 250                 255
Ala Val Ser Gly Ala Asp Pro Phe Phe Ile Asn Met Gly Phe Ser Ile
             260                 265                 270
Phe His Ala Tyr Pro Asp His Gly Ile Ser Val Pro Phe Asp Ala Ser
             275                 280                 285
Ser Lys Gly Leu Phe Ala Gly Glu Gly Ala Gly Val Leu Val Leu Lys
     290                 295                 300
Arg Leu Glu Asp Ala Glu Arg Asp Asn Asp Lys Ile Tyr Ala Val Val
305                 310                 315                 320
Ser Gly Val Gly Leu Ser Asn Asp Gly Lys Gln Phe Val Leu Ser
                 325                 330                 335
```

| | | | | | | | | | | | | | | |
|---|---|---|---|---|---|---|---|---|---|---|---|---|---|---|
| Pro | Asn | Pro | Lys 340 | Gly | Gln | Val | Lys 345 | Ala | Phe | Glu | Arg | Ala 350 | Tyr | Ala | Ala |
| Ser | Asp | Ile 355 | Glu | Pro | Lys | Asp 360 | Ile | Glu | Val | Ile | Glu 365 | Cys | His | Ala | Thr |
| Gly | Thr 370 | Pro | Leu | Gly | Asp 375 | Lys | Ile | Glu | Leu | Thr 380 | Ser | Met | Glu | Thr | Phe |
| Phe 385 | Glu | Asp | Lys | Leu 390 | Gln | Gly | Thr | Asp | Ala 395 | Pro | Leu | Ile | Gly | Ser | Ala 400 |
| Lys | Ser | Asn | Leu | Gly 405 | His | Leu | Leu | Thr 410 | Ala | Ala | His | Ala | Gly 415 | Ile | Met |
| Lys | Met | Ile | Phe 420 | Ala | Met | Lys | Glu | Gly 425 | Tyr | Leu | Pro | Pro 430 | Ser | Ile | Asn |
| Ile | Ser | Asp 435 | Ala | Ile | Ala | Ser | Pro 440 | Lys | Lys | Leu | Phe | Gly 445 | Lys | Pro | Thr |
| Leu | Pro 450 | Ser | Met | Val | Gln | Gly 455 | Trp | Pro | Asp | Lys | Pro 460 | Ser | Asn | Asn | His |
| Phe 465 | Gly | Val | Arg | Thr | Arg 470 | His | Ala | Gly | Val | Ser 475 | Val | Phe | Gly | Phe | Gly 480 |
| Gly | Cys | Asn | Ala | His 485 | Leu | Leu | Leu | Glu | Ser 490 | Tyr | Asn | Gly | Lys | Gly 495 | Thr |
| Val | Lys | Ala | Glu 500 | Ala | Thr | Gln | Val | Pro 505 | Arg | Gln | Ala | Glu | Pro 510 | Leu | Lys |
| Val | Val | Gly 515 | Leu | Ala | Ser | His | Phe 520 | Gly | Pro | Leu | Ser | Ser 525 | Ile | Asn | Ala |
| Leu | Asn 530 | Asn | Ala | Val | Thr | Gln 535 | Asp | Gly | Asn | Gly | Phe 540 | Ile | Glu | Leu | Pro |
| Lys 545 | Lys | Arg | Trp | Lys | Gly 550 | Leu | Glu | Lys | His | Ser 555 | Glu | Leu | Leu | Ala | Glu 560 |
| Phe | Gly | Leu | Ala | Ser 565 | Ala | Pro | Lys | Gly | Ala 570 | Tyr | Val | Asp | Asn | Phe 575 | Glu |
| Leu | Asp | Phe | Leu 580 | Arg | Phe | Lys | Leu | Pro 585 | Pro | Asn | Glu | Asp | Asp 590 | Arg | Leu |
| Ile | Ser | Gln 595 | Gln | Leu | Met | Leu | Met 600 | Arg | Val | Thr | Asp | Glu 605 | Ala | Ile | Arg |
| Asp | Ala 610 | Lys | Leu | Glu | Pro | Gly 615 | Gln | Lys | Val | Ala | Val 620 | Leu | Val | Ala | Met |
| Glu 625 | Thr | Glu | Leu | Glu | Leu 630 | His | Gln | Phe | Arg | Gly 635 | Arg | Val | Asn | Leu | His 640 |
| Thr | Gln | Leu | Ala | Gln 645 | Ser | Leu | Ala | Ala | Met 650 | Gly | Val | Ser | Leu | Ser 655 | Thr |
| Asp | Glu | Tyr | Gln 660 | Ala | Leu | Glu | Ala | Ile 665 | Ala | Met | Asp | Ser | Val 670 | Leu | Asp |
| Ala | Ala | Lys 675 | Leu | Asn | Gln | Tyr | Thr 680 | Ser | Phe | Ile | Gly | Asn 685 | Ile | Met | Ala |
| Ser | Arg 690 | Val | Ala | Ser | Leu | Trp 695 | Asp | Phe | Asn | Gly | Pro 700 | Ala | Phe | Thr | Ile |
| Ser 705 | Ala | Ala | Glu | Gln | Ser 710 | Val | Ser | Arg | Cys | Ile 715 | Asp | Val | Ala | Gln | Asn 720 |
| Leu | Ile | Met | Glu | Asp 725 | Asn | Leu | Asp | Ala | Val 730 | Val | Ile | Ala | Ala | Val 735 | Asp |
| Leu | Ser | Gly 740 | Ser | Phe | Glu | Gln | Val 745 | Ile | Leu | Lys | Asn | Ala 750 | Ile | Ala | Pro |
| Val | Ala 755 | Ile | Glu | Pro | Asn | Leu 760 | Glu | Ala | Ser | Leu | Asn 765 | Pro | Thr | Ser | Ala |

-continued

| | | | | | | | | | | | | | |
|---|---|---|---|---|---|---|---|---|---|---|---|---|---|
| Ser | Trp | Asn | Val | Gly | Glu | Gly | Ala | Gly | Ala | Val | Val | Leu | Val | Lys | Asn |
| | 770 | | | | 775 | | | | 780 | | | | |
| Glu | Ala | Thr | Ser | Gly | Cys | Ser | Tyr | Gly | Gln | Ile | Asp | Ala | Leu | Gly | Phe |
| 785 | | | | | 790 | | | | 795 | | | | | | 800 |
| Ala | Lys | Thr | Ala | Glu | Thr | Ala | Leu | Ala | Thr | Asp | Lys | Leu | Leu | Ser | Gln |
| | | | | 805 | | | | | 810 | | | | | 815 | |
| Thr | Ala | Thr | Asp | Phe | Asn | Lys | Val | Lys | Val | Ile | Glu | Thr | Met | Ala | Ala |
| | | | 820 | | | | | 825 | | | | | 830 | | |
| Pro | Ala | Ser | Gln | Ile | Gln | Leu | Ala | Pro | Ile | Val | Ser | Ser | Gln | Val | Thr |
| | | 835 | | | | | 840 | | | | | 845 | | | |
| His | Thr | Ala | Ala | Glu | Gln | Arg | Val | Gly | His | Cys | Phe | Ala | Ala | Ala | Gly |
| | 850 | | | | | 855 | | | | | 860 | | | | |
| Met | Ala | Ser | Leu | Leu | His | Gly | Leu | Leu | Asn | Leu | Asn | Thr | Val | Ala | Gln |
| 865 | | | | | 870 | | | | | 875 | | | | | 880 |
| Thr | Asn | Lys | Ala | Asn | Cys | Ala | Leu | Ile | Asn | Asn | Ile | Ser | Glu | Asn | Gln |
| | | | | 885 | | | | | 890 | | | | | 895 | |
| Leu | Ser | Gln | Leu | Leu | Ile | Ser | Gln | Thr | Ala | Ser | Glu | Gln | Gln | Ala | Leu |
| | | | 900 | | | | | 905 | | | | | 910 | | |
| Thr | Ala | Arg | Leu | Ser | Asn | Glu | Leu | Lys | Ser | Asp | Ala | Lys | His | Gln | Leu |
| | | 915 | | | | | 920 | | | | | 925 | | | |
| Val | Lys | Gln | Val | Thr | Leu | Gly | Gly | Arg | Asp | Ile | Tyr | Gln | His | Ile | Val |
| | 930 | | | | | 935 | | | | | 940 | | | | |
| Asp | Thr | Pro | Leu | Ala | Ser | Leu | Glu | Ser | Ile | Thr | Gln | Lys | Leu | Ala | Gln |
| 945 | | | | | 950 | | | | | 955 | | | | | 960 |
| Ala | Thr | Ala | Ser | Thr | Val | Val | Asn | Gln | Val | Lys | Pro | Ile | Lys | Ala | Ala |
| | | | | 965 | | | | | 970 | | | | | 975 | |
| Gly | Ser | Val | Glu | Met | Ala | Asn | Ser | Phe | Glu | Thr | Glu | Ser | Ser | Ala | Glu |
| | | | 980 | | | | | 985 | | | | | 990 | | |
| Pro | Gln | Ile | Thr | Ile | Ala | Ala | Gln | Gln | Thr | Ala | Asn | Ile | Gly | Val | Thr |
| | | 995 | | | | | 1000 | | | | | 1005 | | | |
| Ala | Gln | Ala | Thr | Lys | Arg | Glu | Leu | Gly | Thr | Pro | Pro | Met | Thr | Thr | Asn |
| | 1010 | | | | | 1015 | | | | | 1020 | | | | |
| Thr | Ile | Ala | Asn | Thr | Ala | Asn | Asn | Leu | Asp | Lys | Thr | Leu | Glu | Thr | Val |
| 1025 | | | | | 1030 | | | | | 1035 | | | | | 1040 |
| Ala | Gly | Asn | Thr | Val | Ala | Ser | Lys | Val | Gly | Ser | Gly | Asp | Ile | Val | Asn |
| | | | | 1045 | | | | | 1050 | | | | | 1055 | |
| Phe | Gln | Gln | Asn | Gln | Gln | Leu | Ala | Gln | Gln | Ala | His | Leu | Ala | Phe | Leu |
| | | | | 1060 | | | | | 1065 | | | | | 1070 | |
| Glu | Ser | Arg | Ser | Ala | Gly | Met | Lys | Val | Ala | Asp | Ala | Leu | Leu | Lys | Gln |
| | | | 1075 | | | | 1080 | | | | | 1085 | | | |
| Gln | Leu | Ala | Gln | Val | Thr | Gly | Gln | Thr | Ile | Asp | Asn | Gln | Ala | Leu | Asp |
| | 1090 | | | | | 1095 | | | | | 1100 | | | | |
| Thr | Gln | Ala | Val | Asp | Thr | Gln | Thr | Ser | Glu | Asn | Val | Ala | Ile | Ala | Ala |
| 1105 | | | | | 1110 | | | | | 1115 | | | | | 1120 |
| Glu | Ser | Pro | Val | Gln | Val | Thr | Thr | Pro | Val | Gln | Val | Thr | Thr | Pro | Val |
| | | | | 1125 | | | | | 1130 | | | | | 1135 | |
| Gln | Ile | Ser | Val | Val | Glu | Leu | Lys | Pro | Asp | His | Ala | Asn | Val | Pro | Pro |
| | | | | 1140 | | | | | 1145 | | | | | 1150 | |
| Tyr | Thr | Pro | Pro | Val | Pro | Ala | Leu | Lys | Pro | Cys | Ile | Trp | Asn | Tyr | Ala |
| | | | 1155 | | | | | 1160 | | | | | 1165 | | |
| Asp | Leu | Val | Glu | Tyr | Ala | Glu | Gly | Asp | Ile | Ala | Lys | Val | Phe | Gly | Ser |
| | | | 1170 | | | | | 1175 | | | | | 1180 | | |
| Asp | Tyr | Ala | Ile | Ile | Asp | Ser | Tyr | Ser | Arg | Arg | Val | Arg | Leu | Pro | Thr |

|  |  |  |  |
|---|---|---|---|
| 1185 | 1190 | 1195 | 1200 |

Thr Asp Tyr Leu Leu Val Ser Arg Val Thr Lys Leu Asp Ala Thr Ile
                1205                    1210                   1215

Asn Gln Phe Lys Pro Cys Ser Met Thr Thr Glu Tyr Asp Ile Pro Val
                1220                    1225                   1230

Asp Ala Pro Tyr Leu Val Asp Gly Gln Ile Pro Trp Ala Val Ala Val
                1235                    1240                   1245

Glu Ser Gly Gln Cys Asp Leu Met Leu Ile Ser Tyr Leu Gly Ile Asp
            1250                    1255                   1260

Phe Glu Asn Lys Gly Glu Arg Val Tyr Arg Leu Leu Asp Cys Thr Leu
1265                1270                    1275                   1280

Thr Phe Leu Gly Asp Leu Pro Arg Gly Gly Asp Thr Leu Arg Tyr Asp
                1285                    1290                   1295

Ile Lys Ile Asn Asn Tyr Ala Arg Asn Gly Asp Thr Leu Leu Phe Phe
                1300                    1305                   1310

Phe Ser Tyr Glu Cys Phe Val Gly Asp Lys Met Ile Leu Lys Met Asp
            1315                    1320                   1325

Gly Gly Cys Ala Gly Phe Phe Thr Asp Glu Glu Leu Ala Asp Gly Lys
1330                1335                    1340

Gly Val Ile Arg Thr Glu Glu Glu Ile Lys Ala Arg Ser Leu Val Gln
1345                1350                    1355                   1360

Lys Gln Arg Phe Asn Pro Leu Leu Asp Cys Pro Lys Thr Gln Phe Ser
                1365                    1370                   1375

Tyr Gly Asp Ile His Lys Leu Leu Thr Ala Asp Ile Glu Gly Cys Phe
            1380                    1385                   1390

Gly Pro Ser His Ser Gly Val His Gln Pro Ser Leu Cys Phe Ala Ser
            1395                    1400                   1405

Glu Lys Phe Leu Met Ile Glu Gln Val Ser Lys Val Asp Arg Thr Gly
        1410                    1415                   1420

Gly Thr Trp Gly Leu Gly Leu Ile Glu Gly His Lys Gln Leu Glu Ala
1425                1430                    1435                   1440

Asp His Trp Tyr Phe Pro Cys His Phe Lys Gly Asp Gln Val Met Ala
                1445                    1450                   1455

Gly Ser Leu Met Ala Glu Gly Cys Gly Gln Leu Leu Gln Phe Tyr Met
            1460                    1465                   1470

Leu His Leu Gly Met His Thr Gln Thr Lys Asn Gly Arg Phe Gln Pro
            1475                    1480                   1485

Leu Glu Asn Ala Ser Gln Gln Val Arg Cys Arg Gly Gln Val Leu Pro
        1490                    1495                   1500

Gln Ser Gly Val Leu Thr Tyr Arg Met Glu Val Thr Glu Ile Gly Phe
1505                1510                    1515                   1520

Ser Pro Arg Pro Tyr Ala Lys Ala Asn Ile Asp Ile Leu Leu Asn Gly
                1525                    1530                   1535

Lys Ala Val Val Asp Phe Gln Asn Leu Gly Val Met Ile Lys Glu Glu
                1540                    1545                   1550

Asp Glu Cys Thr Arg Tyr Pro Leu Leu Thr Glu Ser Thr Thr Ala Ser
            1555                    1560                   1565

Thr Ala Gln Val Asn Ala Gln Thr Ser Ala Lys Lys Val Tyr Lys Pro
        1570                    1575                   1580

Ala Ser Val Asn Ala Pro Leu Met Ala Gln Ile Pro Asp Leu Thr Lys
1585                1590                    1595                   1600

Glu Pro Asn Lys Gly Val Ile Pro Ile Ser His Val Glu Ala Pro Ile
                1605                    1610                   1615

-continued

```
Thr Pro Asp Tyr Pro Asn Arg Val Pro Asp Thr Val Pro Phe Thr Pro
        1620                1625                1630

Tyr His Met Phe Glu Phe Ala Thr Gly Asn Ile Glu Asn Cys Phe Gly
        1635                1640                1645

Pro Glu Phe Ser Ile Tyr Arg Gly Met Ile Pro Pro Arg Thr Pro Cys
        1650                1655                1660

Gly Asp Leu Gln Val Thr Thr Arg Val Ile Glu Val Asn Gly Lys Arg
1665                1670                1675                1680

Gly Asp Phe Lys Lys Pro Ser Ser Cys Ile Ala Glu Tyr Glu Val Pro
        1685                1690                1695

Ala Asp Ala Trp Tyr Phe Asp Lys Asn Ser His Gly Ala Val Met Pro
        1700                1705                1710

Tyr Ser Ile Leu Met Glu Ile Ser Leu Gln Pro Asn Gly Phe Ile Ser
        1715                1720                1725

Gly Tyr Met Gly Thr Thr Leu Gly Phe Pro Gly Leu Glu Leu Phe Phe
        1730                1735                1740

Arg Asn Leu Asp Gly Ser Gly Glu Leu Leu Arg Glu Val Asp Leu Arg
1745                1750                1755                1760

Gly Lys Thr Ile Arg Asn Asp Ser Arg Leu Leu Ser Thr Val Met Ala
        1765                1770                1775

Gly Thr Asn Ile Ile Gln Ser Phe Ser Phe Glu Leu Ser Thr Asp Gly
        1780                1785                1790

Glu Pro Phe Tyr Arg Gly Thr Ala Val Phe Gly Tyr Phe Lys Gly Asp
        1795                1800                1805

Ala Leu Lys Asp Gln Leu Gly Leu Asp Asn Gly Lys Val Thr Gln Pro
        1810                1815                1820

Trp His Val Ala Asn Gly Val Ala Ala Ser Thr Lys Val Asn Leu Leu
1825                1830                1835                1840

Asp Lys Ser Cys Arg His Phe Asn Ala Pro Ala Asn Gln Pro His Tyr
        1845                1850                1855

Arg Leu Ala Gly Gly Gln Leu Asn Phe Ile Asp Ser Val Glu Ile Val
        1860                1865                1870

Asp Asn Gly Gly Thr Glu Gly Leu Gly Tyr Leu Tyr Ala Glu Arg Thr
        1875                1880                1885

Ile Asp Pro Ser Asp Trp Phe Phe Gln Phe His Phe His Gln Asp Pro
        1890                1895                1900

Val Met Pro Gly Ser Leu Gly Val Glu Ala Ile Ile Glu Thr Met Gln
1905                1910                1915                1920

Ala Tyr Ala Ile Ser Lys Asp Leu Gly Ala Asp Phe Lys Asn Pro Lys
        1925                1930                1935

Phe Gly Gln Ile Leu Ser Asn Ile Lys Trp Lys Tyr Arg Gly Gln Ile
        1940                1945                1950

Asn Pro Leu Asn Lys Gln Met Ser Met Asp Val Ser Ile Thr Ser Ile
        1955                1960                1965

Lys Asp Glu Asp Gly Lys Lys Val Ile Thr Gly Asn Ala Ser Leu Ser
1970                1975                1980

Lys Asp Gly Leu Arg Ile Tyr Glu Val Phe Asp Ile Ala Ile Ser Ile
1985                1990                1995                2000

Glu Glu Ser Val
```

( 2 ) INFORMATION FOR SEQ ID NO:16:

( i ) SEQUENCE CHARACTERISTICS:
        ( A ) LENGTH: 1629 base pairs
        ( B ) TYPE: nucleic acid ( C ) STRANDEDNESS: double
( D ) TOPOLOGY: linear ( i i ) MOLECULE TYPE: DNA (genomic)

( v i ) ORIGINAL SOURCE:
 ( A ) ORGANISM: Shewanella putrefaciens SCRC-2874 (FERM BP- 1625)

( i x ) FEATURE:
 ( A ) NAME/KEY: CDS
 ( B ) LOCATION: 1..1629

( i x ) FEATURE:
 ( A ) NAME/KEY: mat_peptide
 ( B ) LOCATION: 1..1629

( x i ) SEQUENCE DESCRIPTION: SEQ ID NO:16:

| | | | | | | | | | | | | | | | | |
|---|---|---|---|---|---|---|---|---|---|---|---|---|---|---|---|---|
| ATG | AAT | CCT | ACA | GCA | ACT | AAC | GAA | ATG | CTT | TCT | CCG | TGG | CCA | TGG | GCT | 48 |
| Met | Asn | Pro | Thr | Ala | Thr | Asn | Glu | Met | Leu | Ser | Pro | Trp | Pro | Trp | Ala | |
| 1 | | | | 5 | | | | | 10 | | | | | 15 | | |
| GTG | ACA | GAG | TCA | AAT | ATC | AGT | TTT | GAC | GTG | CAA | GTG | ATG | GAA | CAA | CAA | 96 |
| Val | Thr | Glu | Ser | Asn | Ile | Ser | Phe | Asp | Val | Gln | Val | Met | Glu | Gln | Gln | |
| | | | 20 | | | | | 25 | | | | | 30 | | | |
| CTT | AAA | GAT | TTT | AGC | CGG | GCA | TGT | TAC | GTG | GTC | AAT | CAT | GCC | GAC | CAC | 144 |
| Leu | Lys | Asp | Phe | Ser | Arg | Ala | Cys | Tyr | Val | Val | Asn | His | Ala | Asp | His | |
| | | | 35 | | | | | 40 | | | | | 45 | | | |
| GGC | TTT | GGT | ATT | GCG | CAA | ACT | GCC | GAT | ATC | GTG | ACT | GAA | CAA | GCG | GCA | 192 |
| Gly | Phe | Gly | Ile | Ala | Gln | Thr | Ala | Asp | Ile | Val | Thr | Glu | Gln | Ala | Ala | |
| | | 50 | | | | | 55 | | | | | 60 | | | | |
| AAC | AGC | ACA | GAT | TTA | CCT | GTT | AGT | GCT | TTT | ACT | CCT | GCA | TTA | GGT | ACC | 240 |
| Asn | Ser | Thr | Asp | Leu | Pro | Val | Ser | Ala | Phe | Thr | Pro | Ala | Leu | Gly | Thr | |
| 65 | | | | | 70 | | | | | 75 | | | | | 80 | |
| GAA | AGC | CTA | GGC | GAC | AAT | AAT | TTC | CGC | CGC | GTT | CAC | GGC | GTT | AAA | TAC | 288 |
| Glu | Ser | Leu | Gly | Asp | Asn | Asn | Phe | Arg | Arg | Val | His | Gly | Val | Lys | Tyr | |
| | | | | 85 | | | | | 90 | | | | | 95 | | |
| GCT | TAT | TAC | GCA | GGC | GCT | ATG | GCA | AAC | GGT | ATT | TCA | TCT | GAA | GAG | CTA | 336 |
| Ala | Tyr | Tyr | Ala | Gly | Ala | Met | Ala | Asn | Gly | Ile | Ser | Ser | Glu | Glu | Leu | |
| | | | 100 | | | | | 105 | | | | | 110 | | | |
| GTG | ATT | GCC | CTA | GGT | CAA | GCT | GGC | ATT | TTG | TGT | GGT | TCG | TTT | GGA | GCA | 384 |
| Val | Ile | Ala | Leu | Gly | Gln | Ala | Gly | Ile | Leu | Cys | Gly | Ser | Phe | Gly | Ala | |
| | | | 115 | | | | | 120 | | | | | 125 | | | |
| GCC | GGT | CTT | ATT | CCA | AGT | CGC | GTT | GAA | GCG | GCA | ATT | AAC | CGT | ATT | CAA | 432 |
| Ala | Gly | Leu | Ile | Pro | Ser | Arg | Val | Glu | Ala | Ala | Ile | Asn | Arg | Ile | Gln | |
| | | 130 | | | | | 135 | | | | | 140 | | | | |
| GCA | GCG | CTG | CCA | AAT | GGC | CCT | TAT | ATG | TTT | AAC | CTT | ATC | CAT | AGT | CCT | 480 |
| Ala | Ala | Leu | Pro | Asn | Gly | Pro | Tyr | Met | Phe | Asn | Leu | Ile | His | Ser | Pro | |
| 145 | | | | | 150 | | | | | 155 | | | | | 160 | |
| AGC | GAG | CCA | GCA | TTA | GAG | CGT | GGC | AGC | GTA | GAG | CTA | TTT | TTA | AAG | CAT | 528 |
| Ser | Glu | Pro | Ala | Leu | Glu | Arg | Gly | Ser | Val | Glu | Leu | Phe | Leu | Lys | His | |
| | | | | 165 | | | | | 170 | | | | | 175 | | |
| AAG | GTA | CGC | ACC | GTT | GAA | GCA | TCA | GCT | TTC | TTA | GGT | CTA | ACA | CCA | CAA | 576 |
| Lys | Val | Arg | Thr | Val | Glu | Ala | Ser | Ala | Phe | Leu | Gly | Leu | Thr | Pro | Gln | |
| | | | 180 | | | | | 185 | | | | | 190 | | | |
| ATC | GTC | TAT | TAC | CGT | GCA | GCA | GGA | TTG | AGC | CGA | GAC | GCA | CAA | GGT | AAA | 624 |
| Ile | Val | Tyr | Tyr | Arg | Ala | Ala | Gly | Leu | Ser | Arg | Asp | Ala | Gln | Gly | Lys | |
| | | | 195 | | | | | 200 | | | | | 205 | | | |
| GTT | GTG | GTT | GGT | AAC | AAG | GTT | ATC | GCT | AAA | GTA | AGT | CGC | ACC | GAA | GTG | 672 |
| Val | Val | Val | Gly | Asn | Lys | Val | Ile | Ala | Lys | Val | Ser | Arg | Thr | Glu | Val | |
| | | | 210 | | | | | 215 | | | | | 220 | | | |
| GCT | GAA | AAG | TTT | ATG | ATG | CCA | GCG | CCC | GCA | AAA | ATG | CTA | CAA | AAA | CTA | 720 |
| Ala | Glu | Lys | Phe | Met | Met | Pro | Ala | Pro | Ala | Lys | Met | Leu | Gln | Lys | Leu | |
| 225 | | | | | 230 | | | | | 235 | | | | | 240 | |
| GTT | GAT | GAC | GGT | TCA | ATT | ACC | GCT | GAG | CAA | ATG | GAG | CTG | GCG | CAA | CTT | 768 |

```
           Val  Asp  Asp  Gly  Ser  Ile  Thr  Ala  Glu  Gln  Met  Glu  Leu  Ala  Gln  Leu
                              245                      250                     255

GTA  CCT  ATG  GCT  GAC  GAC  ATC  ACT  GCA  GAG  GCC  GAT  TCA  GGT  GGC  CAT           816
Val  Pro  Met  Ala  Asp  Asp  Ile  Thr  Ala  Glu  Ala  Asp  Ser  Gly  Gly  His
               260                     265                     270

ACT  GAT  AAC  CGT  CCA  TTA  GTA  ACA  TTG  CTG  CCA  ACC  ATT  TTA  GCG  CTG           864
Thr  Asp  Asn  Arg  Pro  Leu  Val  Thr  Leu  Leu  Pro  Thr  Ile  Leu  Ala  Leu
               275                     280                     285

AAA  GAA  GAA  ATT  CAA  GCT  AAA  TAC  CAA  TAC  GAC  ACT  CCT  ATT  CGT  GTC           912
Lys  Glu  Glu  Ile  Gln  Ala  Lys  Tyr  Gln  Tyr  Asp  Thr  Pro  Ile  Arg  Val
     290                     295                     300

GGT  TGT  GGT  GGC  GGT  GTG  GGT  ACG  CCT  GAT  GCA  GCG  CTG  GCA  ACG  TTT           960
Gly  Cys  Gly  Gly  Gly  Val  Gly  Thr  Pro  Asp  Ala  Ala  Leu  Ala  Thr  Phe
305                     310                     315                     320

AAC  ATG  GGC  GCG  GCG  TAT  ATT  GTT  ACC  GGC  TCT  ATC  AAC  CAA  GCT  TGT          1008
Asn  Met  Gly  Ala  Ala  Tyr  Ile  Val  Thr  Gly  Ser  Ile  Asn  Gln  Ala  Cys
               325                     330                     335

GTT  GAA  GCG  GGC  GCA  AGT  GAT  CAC  ACT  CGT  AAA  TTA  CTT  GCC  ACC  ACT          1056
Val  Glu  Ala  Gly  Ala  Ser  Asp  His  Thr  Arg  Lys  Leu  Leu  Ala  Thr  Thr
               340                     345                     350

GAA  ATG  GCC  GAT  GTG  ACT  ATG  GCA  CCA  GCT  GCA  GAT  ATG  TTC  GAG  ATG          1104
Glu  Met  Ala  Asp  Val  Thr  Met  Ala  Pro  Ala  Ala  Asp  Met  Phe  Glu  Met
               355                     360                     365

GGC  GTA  AAA  CTG  CAG  GTG  GTT  AAG  CGC  GGC  ACG  CTA  TTC  CCA  ATG  CGC          1152
Gly  Val  Lys  Leu  Gln  Val  Val  Lys  Arg  Gly  Thr  Leu  Phe  Pro  Met  Arg
     370                     375                     380

GCT  AAC  AAG  CTA  TAT  GAG  ATC  TAC  ACC  CGT  TAC  GAT  TCA  ATC  GAA  GCG          1200
Ala  Asn  Lys  Leu  Tyr  Glu  Ile  Tyr  Thr  Arg  Tyr  Asp  Ser  Ile  Glu  Ala
385                     390                     395                     400

ATC  CCA  TTA  GAC  GAG  CGT  GAA  AAG  CTT  GAG  AAA  CAA  GTA  TTC  CGC  TCA          1248
Ile  Pro  Leu  Asp  Glu  Arg  Glu  Lys  Leu  Glu  Lys  Gln  Val  Phe  Arg  Ser
                         405                     410                     415

AGC  CTA  GAT  GAA  ATA  TGG  GCA  GGT  ACA  GTG  GCG  CAC  TTT  AAC  GAG  CGC          1296
Ser  Leu  Asp  Glu  Ile  Trp  Ala  Gly  Thr  Val  Ala  His  Phe  Asn  Glu  Arg
               420                     425                     430

GAC  CCT  AAG  CAA  ATC  GAA  CGC  GCA  GAG  GGT  AAC  CCT  AAG  CGT  AAA  ATG          1344
Asp  Pro  Lys  Gln  Ile  Glu  Arg  Ala  Glu  Gly  Asn  Pro  Lys  Arg  Lys  Met
          435                     440                     445

GCA  TTG  ATT  TTC  CGT  TGG  TAC  TTA  GGT  CTT  TCT  AGT  CGC  TGG  TCA  AAC          1392
Ala  Leu  Ile  Phe  Arg  Trp  Tyr  Leu  Gly  Leu  Ser  Ser  Arg  Trp  Ser  Asn
     450                     455                     460

TCA  GGC  GAA  GTG  GGT  CGT  GAA  ATG  GAT  TAT  CAA  ATT  TGG  GCT  GGC  CCT          1440
Ser  Gly  Glu  Val  Gly  Arg  Glu  Met  Asp  Tyr  Gln  Ile  Trp  Ala  Gly  Pro
465                     470                     475                     480

GCT  CTC  GGT  GCA  TTT  AAC  CAA  TGG  GCA  AAA  GGC  AGT  TAC  TTA  GAT  AAC          1488
Ala  Leu  Gly  Ala  Phe  Asn  Gln  Trp  Ala  Lys  Gly  Ser  Tyr  Leu  Asp  Asn
               485                     490                     495

TAT  CAA  GAC  CGA  AAT  GCC  GTC  GAT  TTG  GCA  AAG  CAC  TTA  ATG  TAC  GGC          1536
Tyr  Gln  Asp  Arg  Asn  Ala  Val  Asp  Leu  Ala  Lys  His  Leu  Met  Tyr  Gly
               500                     505                     510

GCG  GCT  TAC  TTA  AAT  CGT  ATT  AAC  TCG  CTA  ACG  GCT  CAA  GGC  GTT  AAA          1584
Ala  Ala  Tyr  Leu  Asn  Arg  Ile  Asn  Ser  Leu  Thr  Ala  Gln  Gly  Val  Lys
               515                     520                     525

GTG  CCA  GCA  CAG  TTA  CTT  CGC  TGG  AAG  CCA  AAC  CAA  AGA  ATG  GCC               1629
Val  Pro  Ala  Gln  Leu  Leu  Arg  Trp  Lys  Pro  Asn  Gln  Arg  Met  Ala
     530                     535                     540
```

( 2 ) INFORMATION FOR SEQ ID NO:17:

( i ) SEQUENCE CHARACTERISTICS:

( A ) LENGTH: 543 amino acids (B) TYPE: amino acid
(D) TOPOLOGY: linear (ii) MOLECULE TYPE: protein (xi) SEQUENCE DESCRIPTION: SEQ ID NO:17:

| Met | Asn | Pro | Thr | Ala | Thr | Asn | Glu | Met | Leu | Ser | Pro | Trp | Pro | Trp | Ala |
|---|---|---|---|---|---|---|---|---|---|---|---|---|---|---|---|
| 1 | | | | 5 | | | | | 10 | | | | | 15 | |
| Val | Thr | Glu | Ser | Asn | Ile | Ser | Phe | Asp | Val | Gln | Val | Met | Glu | Gln | Gln |
| | | | 20 | | | | | 25 | | | | | 30 | | |
| Leu | Lys | Asp | Phe | Ser | Arg | Ala | Cys | Tyr | Val | Val | Asn | His | Ala | Asp | His |
| | | 35 | | | | | 40 | | | | | 45 | | | |
| Gly | Phe | Gly | Ile | Ala | Gln | Thr | Ala | Asp | Ile | Val | Thr | Glu | Gln | Ala | Ala |
| | 50 | | | | | 55 | | | | | 60 | | | | |
| Asn | Ser | Thr | Asp | Leu | Pro | Val | Ser | Ala | Phe | Thr | Pro | Ala | Leu | Gly | Thr |
| 65 | | | | | 70 | | | | | 75 | | | | | 80 |
| Glu | Ser | Leu | Gly | Asp | Asn | Asn | Phe | Arg | Arg | Val | His | Gly | Val | Lys | Tyr |
| | | | | 85 | | | | | 90 | | | | | 95 | |
| Ala | Tyr | Tyr | Ala | Gly | Ala | Met | Ala | Asn | Gly | Ile | Ser | Ser | Glu | Glu | Leu |
| | | | | 100 | | | | | 105 | | | | | 110 | |
| Val | Ile | Ala | Leu | Gly | Gln | Ala | Gly | Ile | Leu | Cys | Gly | Ser | Phe | Gly | Ala |
| | | | 115 | | | | | 120 | | | | | 125 | | |
| Ala | Gly | Leu | Ile | Pro | Ser | Arg | Val | Glu | Ala | Ala | Ile | Asn | Arg | Ile | Gln |
| | 130 | | | | | 135 | | | | | 140 | | | | |
| Ala | Ala | Leu | Pro | Asn | Gly | Pro | Tyr | Met | Phe | Asn | Leu | Ile | His | Ser | Pro |
| 145 | | | | | 150 | | | | | 155 | | | | | 160 |
| Ser | Glu | Pro | Ala | Leu | Glu | Arg | Gly | Ser | Val | Glu | Leu | Phe | Leu | Lys | His |
| | | | | 165 | | | | | 170 | | | | | 175 | |
| Lys | Val | Arg | Thr | Val | Glu | Ala | Ser | Ala | Phe | Leu | Gly | Leu | Thr | Pro | Gln |
| | | | 180 | | | | | 185 | | | | | 190 | | |
| Ile | Val | Tyr | Tyr | Arg | Ala | Ala | Gly | Leu | Ser | Arg | Asp | Ala | Gln | Gly | Lys |
| | | | 195 | | | | | 200 | | | | | 205 | | |
| Val | Val | Val | Gly | Asn | Lys | Val | Ile | Ala | Lys | Val | Ser | Arg | Thr | Glu | Val |
| | | 210 | | | | | 215 | | | | | 220 | | | |
| Ala | Glu | Lys | Phe | Met | Met | Pro | Ala | Pro | Ala | Lys | Met | Leu | Gln | Lys | Leu |
| 225 | | | | | 230 | | | | | 235 | | | | | 240 |
| Val | Asp | Asp | Gly | Ser | Ile | Thr | Ala | Glu | Gln | Met | Glu | Leu | Ala | Gln | Leu |
| | | | | 245 | | | | | 250 | | | | | 255 | |
| Val | Pro | Met | Ala | Asp | Asp | Ile | Thr | Ala | Glu | Ala | Asp | Ser | Gly | Gly | His |
| | | | 260 | | | | | 265 | | | | | 270 | | |
| Thr | Asp | Asn | Arg | Pro | Leu | Val | Thr | Leu | Leu | Pro | Thr | Ile | Leu | Ala | Leu |
| | | 275 | | | | | 280 | | | | | 285 | | | |
| Lys | Glu | Glu | Ile | Gln | Ala | Lys | Tyr | Gln | Tyr | Asp | Thr | Pro | Ile | Arg | Val |
| 290 | | | | | 295 | | | | | 300 | | | | | |
| Gly | Cys | Gly | Gly | Gly | Val | Gly | Thr | Pro | Asp | Ala | Ala | Leu | Ala | Thr | Phe |
| 305 | | | | | 310 | | | | | 315 | | | | | 320 |
| Asn | Met | Gly | Ala | Ala | Tyr | Ile | Val | Thr | Gly | Ser | Ile | Asn | Gln | Ala | Cys |
| | | | | 325 | | | | | 330 | | | | | 335 | |
| Val | Glu | Ala | Gly | Ala | Ser | Asp | His | Thr | Arg | Lys | Leu | Leu | Ala | Thr | Thr |
| | | | 340 | | | | | 345 | | | | | 350 | | |
| Glu | Met | Ala | Asp | Val | Thr | Met | Ala | Pro | Ala | Ala | Asp | Met | Phe | Glu | Met |
| | | 355 | | | | | 360 | | | | | 365 | | | |
| Gly | Val | Lys | Leu | Gln | Val | Val | Lys | Arg | Gly | Thr | Leu | Phe | Pro | Met | Arg |
| | 370 | | | | | 375 | | | | | 380 | | | | |
| Ala | Asn | Lys | Leu | Tyr | Glu | Ile | Tyr | Thr | Arg | Tyr | Asp | Ser | Ile | Glu | Ala |

-continued

```
              385                      390                      395                      400
Ile   Pro   Leu   Asp   Glu   Arg   Glu   Lys   Leu   Glu   Lys   Gln   Val   Phe   Arg   Ser
                        405                            410                      415

Ser   Leu   Asp   Glu   Ile   Trp   Ala   Gly   Thr   Val   Ala   His   Phe   Asn   Glu   Arg
                  420                            425                      430

Asp   Pro   Lys   Gln   Ile   Glu   Arg   Ala   Glu   Gly   Asn   Pro   Lys   Arg   Lys   Met
                  435                      440                      445

Ala   Leu   Ile   Phe   Arg   Trp   Tyr   Leu   Gly   Leu   Ser   Ser   Arg   Trp   Ser   Asn
      450                            455                      460

Ser   Gly   Glu   Val   Gly   Arg   Glu   Met   Asp   Tyr   Gln   Ile   Trp   Ala   Gly   Pro
465                           470                      475                            480

Ala   Leu   Gly   Ala   Phe   Asn   Gln   Trp   Ala   Lys   Gly   Ser   Tyr   Leu   Asp   Asn
                        485                      490                            495

Tyr   Gln   Asp   Arg   Asn   Ala   Val   Asp   Leu   Ala   Lys   His   Leu   Met   Tyr   Gly
                  500                      505                      510

Ala   Ala   Tyr   Leu   Asn   Arg   Ile   Asn   Ser   Leu   Thr   Ala   Gln   Gly   Val   Lys
            515                      520                            525

Val   Pro   Ala   Gln   Leu   Leu   Arg   Trp   Lys   Pro   Asn   Gln   Arg   Met   Ala
530                           535                            540
```

( 2 ) INFORMATION FOR SEQ ID NO:18:

( i ) SEQUENCE CHARACTERISTICS:
        ( A ) LENGTH: 1575 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Shewanella putrefaciens SCRC-2874 (FERM BP- 1625)

( i x ) FEATURE:
        ( A ) NAME/KEY: CDS
        ( B ) LOCATION: 1..1575

( i x ) FEATURE:
        ( A ) NAME/KEY: mat_peptide
        ( B ) LOCATION: 1..1575

( x i ) SEQUENCE DESCRIPTION: SEQ ID NO:18:

```
GTG   CAA   CTA   CCA   TTA   ATT   GAG   GCC   TCA   TTA   GTT   AAA   TTA   TCT   GAG   CAA        48
Val   Gln   Leu   Pro   Leu   Ile   Glu   Ala   Ser   Leu   Val   Lys   Leu   Ser   Glu   Gln
  1                     5                           10                          15

GAG   CTC   ACC   TCT   TTA   AAT   TAC   GCT   TTT   CAG   CAA   ATG   AGA   AAG   CCA   CTA        96
Glu   Leu   Thr   Ser   Leu   Asn   Tyr   Ala   Phe   Gln   Gln   Met   Arg   Lys   Pro   Leu
                  20                          25                          30

CAA   ACC   ATT   AAT   TAC   GAC   TAT   GCG   GTG   TGG   GAC   AGA   ACC   TAC   AGC   TAT       144
Gln   Thr   Ile   Asn   Tyr   Asp   Tyr   Ala   Val   Trp   Asp   Arg   Thr   Tyr   Ser   Tyr
            35                          40                          45

ATG   AAA   TCA   AAC   TCA   GCG   AGC   GCT   AAA   AGG   TAC   TAT   GAA   AAA   CAT   GAG       192
Met   Lys   Ser   Asn   Ser   Ala   Ser   Ala   Lys   Arg   Tyr   Tyr   Glu   Lys   His   Glu
      50                          55                          60

TAC   CCA   GAT   GAT   ACG   TTC   AAG   AGT   TTA   AAA   GTC   GAC   GGA   GTA   TTT   ATA       240
Tyr   Pro   Asp   Asp   Thr   Phe   Lys   Ser   Leu   Lys   Val   Asp   Gly   Val   Phe   Ile
65                          70                          75                          80

TTC   AAC   CGT   ACA   AAT   CAG   CCA   GTT   TTT   AGT   AAA   GGT   TTT   AAT   CAT   AGA       288
Phe   Asn   Arg   Thr   Asn   Gln   Pro   Val   Phe   Ser   Lys   Gly   Phe   Asn   His   Arg
                        85                          90                          95

AAT   GAT   ATA   CCG   CTG   GTC   TTT   GAA   TTA   ACT   GAC   TTT   AAA   CAA   CAT   CCA       336
Asn   Asp   Ile   Pro   Leu   Val   Phe   Glu   Leu   Thr   Asp   Phe   Lys   Gln   His   Pro
```

|     |     |     |     |     | 100 |     |     |     | 105 |     |     |     | 110 |     |     |      |
|-----|-----|-----|-----|-----|-----|-----|-----|-----|-----|-----|-----|-----|-----|-----|-----|------|

```
CAA  AAC  ATC  GCA  TTA  TCT  CCA  CAA  ACC  AAA  CAG  GCA  CAC  CCA  CCG  GCA      384
Gln  Asn  Ile  Ala  Leu  Ser  Pro  Gln  Thr  Lys  Gln  Ala  His  Pro  Pro  Ala
          115                      120                      125

AGT  AAG  CCG  TTA  GAC  TCC  CCT  GAT  GAT  GTG  CCT  TCT  ACC  CAT  GGG  GTT      432
Ser  Lys  Pro  Leu  Asp  Ser  Pro  Asp  Asp  Val  Pro  Ser  Thr  His  Gly  Val
     130                      135                      140

ATC  GCC  ACA  CGA  TAC  GGT  CCA  GCA  ATT  TAT  AGC  TCT  ACC  AGC  ATT  TTA      480
Ile  Ala  Thr  Arg  Tyr  Gly  Pro  Ala  Ile  Tyr  Ser  Ser  Thr  Ser  Ile  Leu
145                      150                      155                      160

AAA  TCT  GAT  CGT  AGC  GGC  TCC  CAA  CTT  GGT  TAT  TTA  GTC  TTC  ATT  AGG      528
Lys  Ser  Asp  Arg  Ser  Gly  Ser  Gln  Leu  Gly  Tyr  Leu  Val  Phe  Ile  Arg
               165                      170                      175

TTA  ATT  GAT  GAA  TGG  TTC  ATC  GCT  GAG  CTA  TCG  CAA  TAC  ACT  GCC  GCA      576
Leu  Ile  Asp  Glu  Trp  Phe  Ile  Ala  Glu  Leu  Ser  Gln  Tyr  Thr  Ala  Ala
          180                      185                      190

GGT  GTT  GAA  ATC  GCT  ATG  GCT  GAT  GCC  GCA  GAC  GCA  CAA  TTA  GCG  AGA      624
Gly  Val  Glu  Ile  Ala  Met  Ala  Asp  Ala  Ala  Asp  Ala  Gln  Leu  Ala  Arg
     195                      200                      205

TTA  GGC  GCA  AAC  ACT  AAG  CTT  AAT  AAA  GTA  ACC  GCT  ACA  TCC  GAA  CGG      672
Leu  Gly  Ala  Asn  Thr  Lys  Leu  Asn  Lys  Val  Thr  Ala  Thr  Ser  Glu  Arg
210                      215                      220

TTA  ATA  ACT  AAT  GTC  GAT  GGT  AAG  CCT  CTG  TTG  AAG  TTA  GTG  CTT  TAC      720
Leu  Ile  Thr  Asn  Val  Asp  Gly  Lys  Pro  Leu  Leu  Lys  Leu  Val  Leu  Tyr
225                      230                      235                      240

CAT  ACC  AAT  AAC  CAA  CCG  CCG  CCG  ATG  CTA  GAT  TAC  AGT  ATA  ATA  ATT      768
His  Thr  Asn  Asn  Gln  Pro  Pro  Pro  Met  Leu  Asp  Tyr  Ser  Ile  Ile  Ile
               245                      250                      255

CTA  TTA  GTT  GAG  ATG  TCA  TTT  TTA  CTG  ATC  CTC  GCT  TAT  TTC  CTT  TAC      816
Leu  Leu  Val  Glu  Met  Ser  Phe  Leu  Leu  Ile  Leu  Ala  Tyr  Phe  Leu  Tyr
          260                      265                      270

TCC  TAC  TTC  TTA  GTC  AGG  CCA  GTT  AGA  AAG  CTG  GCT  TCA  GAT  ATT  AAA      864
Ser  Tyr  Phe  Leu  Val  Arg  Pro  Val  Arg  Lys  Leu  Ala  Ser  Asp  Ile  Lys
     275                      280                      285

AAA  ATG  GAT  AAA  AGT  CGT  GAA  ATT  AAA  AAG  CTA  AGG  TAT  CAC  TAC  CCT      912
Lys  Met  Asp  Lys  Ser  Arg  Glu  Ile  Lys  Lys  Leu  Arg  Tyr  His  Tyr  Pro
290                      295                      300

ATT  ACT  GAG  CTA  GTC  AAA  GTT  GCG  ACT  CAC  TTC  AAC  GCC  CTA  ATG  GGG      960
Ile  Thr  Glu  Leu  Val  Lys  Val  Ala  Thr  His  Phe  Asn  Ala  Leu  Met  Gly
305                      310                      315                      320

ACG  ATT  CAG  GAA  CAA  ACT  AAA  CAG  CTT  AAT  GAA  CAA  GTT  TTT  ATT  GAT     1008
Thr  Ile  Gln  Glu  Gln  Thr  Lys  Gln  Leu  Asn  Glu  Gln  Val  Phe  Ile  Asp
          325                      330                      335

AAA  TTA  ACC  AAT  ATT  CCC  AAT  CGT  CGC  GCT  TTT  GAG  CAG  CGA  CTT  GAA     1056
Lys  Leu  Thr  Asn  Ile  Pro  Asn  Arg  Arg  Ala  Phe  Glu  Gln  Arg  Leu  Glu
               340                      345                      350

ACC  TAT  TGC  CAA  CTG  CTA  GCC  CGG  CAA  CAA  ATT  GGC  TTT  ACT  CTC  ATC     1104
Thr  Tyr  Cys  Gln  Leu  Leu  Ala  Arg  Gln  Gln  Ile  Gly  Phe  Thr  Leu  Ile
     355                      360                      365

ATT  GCC  GAT  GTG  GAT  CAT  TTT  AAA  GAG  TAC  AAC  GAT  ACT  CTT  GGG  CAC     1152
Ile  Ala  Asp  Val  Asp  His  Phe  Lys  Glu  Tyr  Asn  Asp  Thr  Leu  Gly  His
370                      375                      380

CTT  GCT  GGG  GAT  GAA  GCA  TTA  ATA  AAA  GTG  GCA  CAA  ACA  CTA  TCG  CAA     1200
Leu  Ala  Gly  Asp  Glu  Ala  Leu  Ile  Lys  Val  Ala  Gln  Thr  Leu  Ser  Gln
385                      390                      395                      400

CAG  TTT  TAC  CGT  GCA  GAA  GAT  ATT  TGT  GCC  CGT  TTT  GGT  GGT  GAA  GAA     1248
Gln  Phe  Tyr  Arg  Ala  Glu  Asp  Ile  Cys  Ala  Arg  Phe  Gly  Gly  Glu  Glu
          405                      410                      415

TTT  ATT  ATG  TTA  TTT  CGA  GAC  ATA  CCT  GAT  GAG  CCC  TTG  CAG  AGA  AAG     1296
Phe  Ile  Met  Leu  Phe  Arg  Asp  Ile  Pro  Asp  Glu  Pro  Leu  Gln  Arg  Lys
```

```
                    420                        425                        430
CTC  GAT  GCG  ATG  CTG  CAC  TCT  TTT  GCA  GAG  CTC  AAC  CTA  CCT  CAT  CCA    1344
Leu  Asp  Ala  Met  Leu  His  Ser  Phe  Ala  Glu  Leu  Asn  Leu  Pro  His  Pro
          435                      440                      445

AAC  TCA  TCA  ACC  GCT  AAT  TAC  GTT  ACT  GTG  AGC  CTT  GGG  GTT  TGC  ACA    1392
Asn  Ser  Ser  Thr  Ala  Asn  Tyr  Val  Thr  Val  Ser  Leu  Gly  Val  Cys  Thr
450                          455                      460

GTT  GTT  GCT  GTT  GAT  GAT  TTT  GAA  TTT  AAA  AGT  GAG  TCG  CAT  ATT  ATT    1440
Val  Val  Ala  Val  Asp  Asp  Phe  Glu  Phe  Lys  Ser  Glu  Ser  His  Ile  Ile
465                          470                      475                      480

GGC  AGT  CAG  GCT  GCA  TTA  ATC  GCA  GAT  AAG  GCG  CTT  TAT  CAT  GCT  AAA    1488
Gly  Ser  Gln  Ala  Ala  Leu  Ile  Ala  Asp  Lys  Ala  Leu  Tyr  His  Ala  Lys
                    485                      490                      495

GCC  TGT  GGT  CGT  AAC  CAG  TTG  TCA  AAA  ACT  ACT  ATT  ACT  GTT  GAT  GAG    1536
Ala  Cys  Gly  Arg  Asn  Gln  Leu  Ser  Lys  Thr  Thr  Ile  Thr  Val  Asp  Glu
               500                      505                      510

ATT  GAG  CAA  TTA  GAA  GCA  AAT  AAA  ATC  GGT  CAT  CAA  GCC                    1575
Ile  Glu  Gln  Leu  Glu  Ala  Asn  Lys  Ile  Gly  His  Gln  Ala
          515                      520                      525
```

( 2 ) INFORMATION FOR SEQ ID NO:19:

( i ) SEQUENCE CHARACTERISTICS:
        ( A ) LENGTH: 525 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Val  Gln  Leu  Pro  Leu  Ile  Glu  Ala  Ser  Leu  Val  Lys  Leu  Ser  Glu  Gln
1                    5                    10                       15

Glu  Leu  Thr  Ser  Leu  Asn  Tyr  Ala  Phe  Gln  Gln  Met  Arg  Lys  Pro  Leu
               20                       25                  30

Gln  Thr  Ile  Asn  Tyr  Asp  Tyr  Ala  Val  Trp  Asp  Arg  Thr  Tyr  Ser  Tyr
          35                       40                       45

Met  Lys  Ser  Asn  Ser  Ala  Ser  Ala  Lys  Arg  Tyr  Tyr  Glu  Lys  His  Glu
     50                       55                       60

Tyr  Pro  Asp  Asp  Thr  Phe  Lys  Ser  Leu  Lys  Val  Asp  Gly  Val  Phe  Ile
65                            70                       75                      80

Phe  Asn  Arg  Thr  Asn  Gln  Pro  Val  Phe  Ser  Lys  Gly  Phe  Asn  His  Arg
                    85                       90                       95

Asn  Asp  Ile  Pro  Leu  Val  Phe  Glu  Leu  Thr  Asp  Phe  Lys  Gln  His  Pro
               100                      105                      110

Gln  Asn  Ile  Ala  Leu  Ser  Pro  Gln  Thr  Lys  Gln  Ala  His  Pro  Pro  Ala
          115                      120                      125

Ser  Lys  Pro  Leu  Asp  Ser  Pro  Asp  Val  Pro  Ser  Thr  His  Gly  Val
     130                      135                      140

Ile  Ala  Thr  Arg  Tyr  Gly  Pro  Ala  Ile  Tyr  Ser  Ser  Thr  Ser  Ile  Leu
145                      150                      155                      160

Lys  Ser  Asp  Arg  Ser  Gly  Ser  Gln  Leu  Gly  Tyr  Leu  Val  Phe  Ile  Arg
                    165                      170                      175

Leu  Ile  Asp  Glu  Trp  Phe  Ile  Ala  Glu  Leu  Ser  Gln  Tyr  Thr  Ala  Ala
               180                      185                      190

Gly  Val  Glu  Ile  Ala  Met  Ala  Asp  Ala  Ala  Asp  Ala  Gln  Leu  Ala  Arg
          195                      200                      205

Leu  Gly  Ala  Asn  Thr  Lys  Leu  Asn  Lys  Val  Thr  Ala  Thr  Ser  Glu  Arg
210                      215                      220
```

-continued

```
Leu  Ile  Thr  Asn  Val  Asp  Gly  Lys  Pro  Leu  Leu  Lys  Leu  Val  Leu  Tyr
225                      230                      235                     240

His  Thr  Asn  Asn  Gln  Pro  Pro  Pro  Met  Leu  Asp  Tyr  Ser  Ile  Ile  Ile
                    245                      250                          255

Leu  Leu  Val  Glu  Met  Ser  Phe  Leu  Leu  Ile  Leu  Ala  Tyr  Phe  Leu  Tyr
               260                      265                     270

Ser  Tyr  Phe  Leu  Val  Arg  Pro  Val  Arg  Lys  Leu  Ala  Ser  Asp  Ile  Lys
          275                      280                     285

Lys  Met  Asp  Lys  Ser  Arg  Glu  Ile  Lys  Lys  Leu  Arg  Tyr  His  Tyr  Pro
     290                      295                     300

Ile  Thr  Glu  Leu  Val  Lys  Val  Ala  Thr  His  Phe  Asn  Ala  Leu  Met  Gly
305                      310                      315                     320

Thr  Ile  Gln  Glu  Gln  Thr  Lys  Gln  Leu  Asn  Glu  Gln  Val  Phe  Ile  Asp
                    325                      330                          335

Lys  Leu  Thr  Asn  Ile  Pro  Asn  Arg  Arg  Ala  Phe  Glu  Gln  Arg  Leu  Glu
               340                      345                     350

Thr  Tyr  Cys  Gln  Leu  Leu  Ala  Arg  Gln  Gln  Ile  Gly  Phe  Thr  Leu  Ile
          355                      360                     365

Ile  Ala  Asp  Val  Asp  His  Phe  Lys  Glu  Tyr  Asn  Asp  Thr  Leu  Gly  His
     370                      375                     380

Leu  Ala  Gly  Asp  Glu  Ala  Leu  Ile  Lys  Val  Ala  Gln  Thr  Leu  Ser  Gln
385                      390                      395                     400

Gln  Phe  Tyr  Arg  Ala  Glu  Asp  Ile  Cys  Ala  Arg  Phe  Gly  Gly  Glu  Glu
                    405                      410                          415

Phe  Ile  Met  Leu  Phe  Arg  Asp  Ile  Pro  Asp  Glu  Pro  Leu  Gln  Arg  Lys
               420                      425                     430

Leu  Asp  Ala  Met  Leu  His  Ser  Phe  Ala  Glu  Leu  Asn  Leu  Pro  His  Pro
          435                      440                     445

Asn  Ser  Ser  Thr  Ala  Asn  Tyr  Val  Thr  Val  Ser  Leu  Gly  Val  Cys  Thr
     450                      455                     460

Val  Val  Ala  Val  Asp  Asp  Phe  Glu  Phe  Lys  Ser  Glu  Ser  His  Ile  Ile
465                      470                      475                     480

Gly  Ser  Gln  Ala  Ala  Leu  Ile  Ala  Asp  Lys  Ala  Leu  Tyr  His  Ala  Lys
                    485                      490                          495

Ala  Cys  Gly  Arg  Asn  Gln  Leu  Ser  Lys  Thr  Thr  Ile  Thr  Val  Asp  Glu
               500                      505                     510

Ile  Glu  Gln  Leu  Glu  Ala  Asn  Lys  Ile  Gly  His  Gln  Ala
          515                      520                     525
```

GENE CODING FOR EICOSAPENTAENOIC ACID SYNTHESIZING ENZYMES AND PROCESS FOR PRODUCTION OF EICOSAPENTAENOIC ACID

CROSS REFERENCE TO RELATED APPLICATION

This application is a continuation-in-part application of Ser. No. 08/178,251 filed on Jan. 10, 1994, now abandoned.

FIELD OF THE ART

The present invention relates to genes coding for eicosapentaenoic acid (designated EPA hereinafter) synthesizing enzymes, plasmids containing these genes, microorganisms transformed with the plasmid, and a process for production of eicosapentaenoic acid using the microorganism. The EPA is useful as a starting material for pharmaceuticals, foods, feeds and the like.

BACKGROUND ART

Polyunsaturated fatty acids represented by eicosapentaenoic acid (EPA) play an important roll as a component of a biomembrane. So far, the following pharmacological actions of EPA are known. (1) Platelet coagulation inhibitory action (thrombolytic action), (2) blood neutral fat-lowering action, (3) actions for lowering blood VLDL-cholesterol and LDL-cholesterol and increasing HDL-cholesterol (anti-arterial sclerosis action), (4) blood viscosity-lowering action, (5) blood pressure lowering action, (7) anti-inflammatory action, (8) anti-tumor action.

In addition, EPA is a substrate for biosynthesis of prostaglandins and exhibits an essential function in vivo in higher mammals including humans. In particular EPA is important as a substrate for production of three types of prostaglandins, has platelet coagulation inhibitory action and is studied for applications to treatment and prophylactic agents for thrombosis. In addition EPA has especially high activity for lowering plasma cholesterol level among polyunsaturated fatty acids having said action, and is highly effective in comparison with linoleic acid and the like usually contained in plant oil. Additionally, EPA is known as an essential nutrient for fish.

Thus, epidemiological research by Dyerberg, Denmark (Am. J. Clin. Nutur, 28, 959, 1975) showed a possibility for use as health foods or pharmaceuticals on the basis of thrombosis inhibitory action or lipid-lowering actions of EPA. However, as can be seen from its chemical structure, the chemical synthesis of EPA is very difficult. Accordingly, in Japan, it is recommended to eat blue back fish such as sardine, salmon, saury, and the like.

At present, most commercially available EPA products are fractionation products from fish oil obtained by a boiling process, and the EPA content thereof is about 10 to 30%. Fish oil extracted by a boiling process is a mixed glyceride containing various kind of fatty acids as component fatty acids, and not only is isolation and purification of each component difficult, but also since EPA is a polyunsaturated fatty acid having 20 carbon atoms and five double bonds all of which are cis-type, EPA is also a unstable and highly oxidation-liable fatty acid. Therefore, it is necessary for EPA to be concentrated from fish oil with prevention of oxygen, light, heat and the like. In addition, since fish oil contains various fatty acids in addition to EPA, their fractionation is difficult. Moreover, although various organic solvents used for fractionation of EPA are eliminated under a reduced pressure, complete elimination of the organic solvents is difficult from a technical and economical point of view.

Most EPA preparations used for pharmaceuticals are those having at least 90% EPA concentration, produced by extracting fish oil by various processes, hydrolysing the fish oil enzymatically or under an alkaline condition to generate free fatty acids, optionally converting the free fatty acids to corresponding methyl or ethyl esters, and further purifying by fractional crystallization at a low temperature, applying a urea-addition method, distillation under a reduced pressure, reverse phase chromatography, or the like. However, since these processes use many organic solvents and heating to near 200° C., it is possible that an EPA concentrate obtained by using such process may be denaturated by residual organic solvent, and polymerization, isomerization or oxidation of EPA. Moreover, where a fish oil is used as a starting material for production of EPA, it is difficult to eliminate docosenoic acid or the like which is considered to be a cause of cardiodiseases, and therefore problems remain in the use for health foods, pharmaceuticals or the like.

On the other hand, recently, processes for production of EPA using microorganisms such as chlorella, unicellular algae Monodus, Euqrena or Diatomaceae have been studied in place of extraction methods from fish oil having drawbacks such as residual fish odor due to incomplete purification and concentration, and the production of EPA using microorganisms has been considered. Recently, fungi producing EPA were reported by Gellerman and Schlenk (J. L. Gellerman and H. Schlenk, BBA, 573, 23, 1979) and Yamada et al. (Meeting of The society of Fermentation Technology, Japan, 1986).

The present inventors sought marine bacteria having an ability to produce EPA to find a new fermentation process for production of EPA using bacteria from which genes can be easily obtained, and which can be cultured in a short time and be easily controlled, and as a result, the present inventors found a new bacteria belonging to the genus Pseudomonas, Alteromonas or Shewanella (K. Yazawa et al., J. Biochem., 103, 5 (1988); K. Yazawa et al., Nippon Suisan Gakkai shi, 54, 1835 (1988)).

It has been suggested that biosynthesis of polyunsaturated fatty acids including EPA works by site-specific aerobic unsaturation of corresponding saturated fatty acids (for example, R. Jeffcoat and A. T. James (1984) in: S. Numa (Ed.): Fatty acid metabolism and its regulation, Elsevier, Amsterdam, pp85–112). However, there is no report relating to biosynthetic enzymes which participate in EPA synthesis, and gene coding therefor.

DISCLOSURE OF THE INVENTION

Generally, the ability of a wild strain to produce a useful substance is low, and therefore where it is intended that the ability of the microorganism is industrially used, an improvement, i.e., an increase of productivity of the microorganism is carried out by various methods. The present inventors intended to carry out research for increasing an EPA productivity by finding genes not described in literature for EPA biosynthetic enzymes using gene recombination techniques and introducing the same into another organism, to impart an EPA biosynthesis ability to an organism not having an EPA biosynthesis ability, and eventually to establish an advantageous process for production of EPA.

Accordingly, the present invention provides genes for EPA biosynthetic enzymes, expression plasmids containing said genes, organisms transformed with said plasmid, and a process for production of EPA using said organism.

Figure 1:
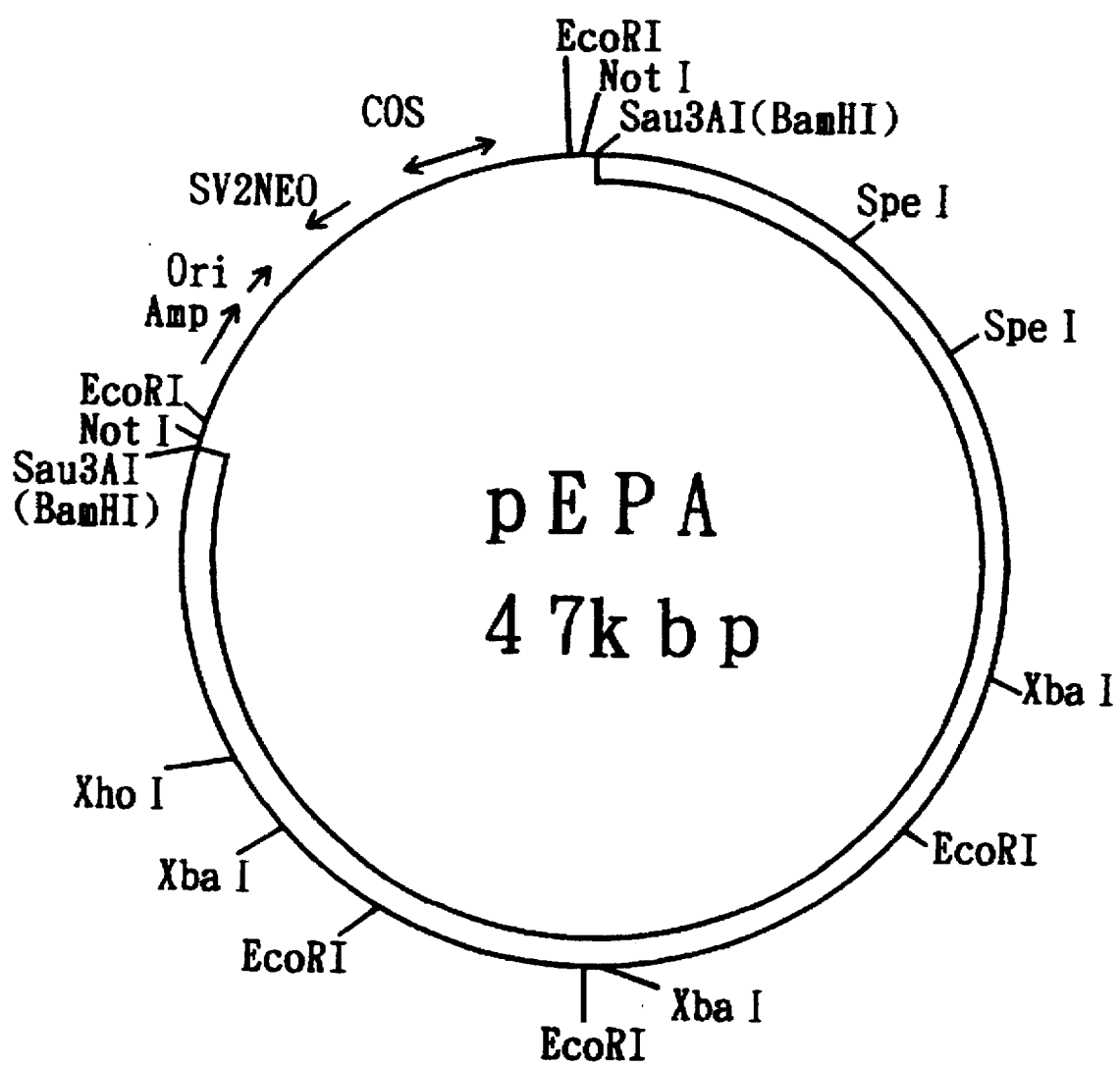
FIG. 1 represents the structure of the plasmid pEPA containing a group of the present genes.

Best Mode for Carrying Out the Invention

According to the present invention, an EPA producing strain is constructed by extracting DNA from a microorganism having an ability to produce EPA (microbial origin of genes), cutting this DNA with restriction enzymes to excise genes coded for a group of EPA biosynthesis enzymes, introducing the genes into an appropriate vector to construct an expression plasmid, and transforming a host organism with the plasmid to construct an EPA producing strain. EPA can be produced by this organism.

Gene source

Although organisms which can be used as a gene source according to the present invention are not limited to specific genera, species or strains, usually, microorganisms classified to the genus Pseudomonas, Alteromonas, Shewanella or the like can be used. These microorganisms can be easily obtained from official or public depository institutes for microorganisms.

As examples of microorganisms belonging to the genus Pseudomonas, *Pseudomonas putrefaciens* SCRC-2181 (FERM BP-2917), SCRC-2201 (FERM BP-2916), SCRC-2271 (FERM BP-2195), SCRC-2341 (FERM BP-2918), SCRC-2451 (FERM BP-2919), SCRC-2642 (FERM BP-2920), SCRC-2792 (FERM BP-2921), SCRC-2878 (FERM BP-1623), SCRC-3011 (FERM BP-2913), and SCRC-3022 (FERM BP-2914) may be mentioned.

As example of microorganisms belonging to the genus Alteromonas, *Alteromonas putrefaciens* SCRC-2871 (FERM BP-1624) and *Alteromonas putrefaciens* subspecies *sagamifaciens* SCRC-1162 (FERM BP-1626) may be mentioned.

As an example of microorganism belonging to the genus Shewanella, *Shewanella putrefaciens* SCRC-2874 (FERM BP-1625) may be mentioned.

Cloning of Genes Coding for a Group of EPA Biosynthesis Enzymes and Construction of Expression Plasmid In the present invention, the case wherein *Shewanella putrefaciens* SCRC-2874 (FERM BP-1625) was used as a source of genes for a group of EPA biosynthesis enzymes is concretely explained. However, as described above, various EPA producing microorganisms can be similarly used as a gene source. A process for cloning genes is described in the Examples of the present invention.

According to the present invention, EPA producing strains can be artificially generated by transforming an heterogeneous host such as *Escherichia coli* or a homogeneous host such as Shewanella, or further yeast, fungus or the like. In addition, EPA producing plants can be generated by introducing the present genes into a higher plant such as soybean, sunflower, rape, or the like. As a region for expression of a group of EPA biosynthesis genes, although a control region natively accompanying these enzymes can be used, it is advantageous to prepare another promoter/operator system for increasing an amount of expression or allowing inducible expression. Where *E. coli* is used as a host, as the promoter/operator system, trp, tac, lavUV5, $P_L$, $P_R$ or lpp promoter/operator system and the like can be used, and as an SD sequence, an SD sequence of trp leader peptide, lacZ, metapyrocatechase or cII gene can be used. In addition, a transcriptional terminator, for example, rrnBT$_1$T$_2$ terminator of *E. coli* ribosome gene or the like can be provided downstream of a coding region. In addition, for expression of the above-mentioned gene, a host/vector system of *Saccharomyces cerevisiae* can be used, wherein as a promoter there can be used a promoter of alcohol dehydrogenase gene, a promoter of acid phosphatase gene, a promoter of glycelaldehyde-3-phosphate dehydrogenase gene, a promoter of enolase gene or the like can be used, wherein a plasmid preferably contains a sequence for replication in yeast, and an auxotrophic marker as a selectable maker for selection of yeast containing said plasmid, such as Leu, Trp, His or the like.

For introduction of the genes into a plant, there are a method using a vector, and a direct introduction method. As vectors, Ti plasmid; DNA viruses such as cauliflower mosaic virus (CaMV), Geminivirus, cassava roten virus, tomato golden mosaic virus, and the like; and RNA viruses such as brome mosaic virus (BMV), and tobacco mosaic virus (TMV) can be used, wherein as a promoter, 35S promoter of CaMV or the like may be mentioned. On the other hand, as direct protoplast introduction methods there can be mentioned a calcium phosphate method, polyethylene glycol method, microinjection, electroporation, liposome method and the like. Moreover, as a direct plant cell introduction method, there may be mentioned a particle gun method.

In addition, a fatty acid composition in a host plant can be changed by using a part of the group of the genes.

Note, that generally, an amount of expression of a particular protein in *E. coli* is affected by the number of copies of the genes, an efficiency of transcription, stability of mRNA, efficiency of translation, and stability of the protein. To modify control regions such as a promoter, SD region, terminator and the like, a smaller plasmid can be easily treated. The number of copies of the genes depends on the size of the plasmid, and there is a tendency for the plasmid to be smaller as the number of copies increases. For this purpose, a smaller plasmid can be obtained by inserting a DNA fragment containing a group of genes for EPA biosynthesis described in the Examples of the present invention into a plasmid, and repeating subcloning of the plasmid to cut off unnecessary portions of the gene DNA fragment. Smaller EPA biosynthesis enzyme genes thus obtained are included in the present invention. In addition, to enhance stability or activity of the enzyme, the nucleotide sequence of the gene (amino acid sequence) can be modified by a known technique, and the present invention includes such a modified gene.

As a host *E. coli* of the present invention, any strain derived from *E. coli* K12 may be used. For example, JM83, JM101, JM103, JM105, JM109, RR1, RB791, W3110, C600, HB101, DH1, AG1, NM554 or the like can be used. As a yeast host, AH22, DC5, D-13-1A, YNN144 or the like can be mentioned.

Note, that a group of the enzymes encoded by the present genes can convert higher fatty acids synthesized by a biosynthetic system natively possessed by the host organism to eicosapentaenoic acid.

In practicing the present invention, an organism such as a microorganism transformed with the present genes is cultured in a medium according to a conventional procedure to obtain microbial cells. In this case, for example, a medium having a composition shown in Table 1 is prepared.

TABLE 1

| | |
|---|---|
| Yeast extract | 0.5% |
| Pepton | 1.0% |
| Sea water | ½ concentration | pH 7.0

From the microbial cells thus obtained, EPA can be obtained according to a conventional procedure such as extraction with an organic solvent. The details are described in the following Examples.

EXAMPLES

Next, the present invention is explained in more detail by way of Examples.

Example 1—1 Preparation of Genomic DNA Containing Genes Coding for a Group of PEA Biosynthesis Enzymes Shewanella putrefaciens SCRC-2874 (FERM BP-1625) was inoculated in 125 ml of a medium (1% pepton, 0.5% yeast extract, ½ concentration artificial sea water), and cultured at 15° C. for 18 hours with shaking (OD610=8.6). The resulting microbial cells were washed once with 1M NaCl, and suspended in 20 ml of 1M NaCl. The suspension was allowed to stand at 55° C. for 30 minutes, 20 ml of 0.1M EDTA was added thereto, and after being allowed to stand at 55° C. for 15 minutes, the suspension was centrifuged at 10,000 rpm for 10 minutes. To the precipitate, was added 10 ml of TES buffer (1 mM EDTA, 0.1 mM NaCl, 10 mM Tris-HCl, pH 8.0) containing 100 mg of lysozyme, and the cells were suspended. After being allowed to stand at 37° C. for an hour, 1 ml of 10% SDS was added to the suspension, which was then allowed to stand at 60° C. for an hour. 11 ml of neutralized phenol was added to the suspension, which was then gently shaken for 5 minutes and centrifuged at 6,500 rpm for 5 minutes to obtain the upper layer. 20 ml of ethanol was added to the layer and the mixture was gently shaken. Precipitated DNA was wound onto a glass bar, washed in ethanol, dissolved in 10 ml of TES buffer, and the solution was allowed to stand at 4° C. of overnight. 0.5 mg of RNase A was added to the solution, which was then gently shaken at 37° C. for 3 hours, and after 1 mg of proteinse K was added thereto, the solution was further shaken for 4.5 hours; 5 ml each of neutralized phenol and chloroform were gradually added to the mixture, which was then gently shaken for 5 minutes and centrifuged to recover the upper layer. 10 ml of chloroform was added to the layer, which was then gently shaken and centrifuged to obtain the upper layer. 20 ml of ethanol was added to the layer, which was then gently shaken, and precipitated DNA was wound onto a glass bar. The DNA was washed in ethanol, and dissolved in 3 ml of TES buffer. An amount of DNA thus obtained was about 2.8 mg. Next, 200 µg of the DNA was partially digested with restriction enzyme Sau3Al and subjected to electrophoresis on 0.3% agarose, and DNA fragments larger than about 20 Kb were isolated by electroelusion. The DNA fragments were extracted with phenol/chloroform, and precipitated with ethanol, and the precipitate was dissolved in 500 µl of TE buffer (1 mM EDTA, 10 mM Tris-HCl, pH 7.4).

Example 1-2 Insertion of Chromosomal DNA Fragments into Vector

As a vector, cosmid pWE15 (STRATAGENE) was used. 10 µg of pWE15 was completely digested with restriction enzyme BamHI, treated with calf intestine alkaline phosphatase at 37° C. for an hour, extracted with phenol/chloroform, and precipitated with ethanol, and the precipitate was dissolved in 10 µl of TE buffer. 1.5 µg of the vector DNA thus obtained was mixed with 1 µg of the chromosomal DNA prepared in Example 1 and partially digested with restriction enzyme Sau3Al, and these DNA were ligated using T4 DNA ligase at 26° C. for 10 minutes. One fourth of the reaction mixture was packaged according to a conventional method to form phage, which was then infected to E. coli K12/AG-1.

Example 1-3 Screening of Recombinant EPA Producing Strain

The E. coli suspension infected with the phage of Example 1-2 was plated on an LB agar medium (trypton 1%, yeast extract 0.5%, NaCl 1%, Agar 2%) containing 50 µg/ml ampicillin and cultured at 37° C. overnight. The developed colony was inoculated in 1.5 ml of LB medium containing 50 µg/ml ampicillin, and cultured at 25° C. for 1 to 7 days with shaking. The culture was centrifuged to collect the microbial cells, and after removing the medium, the cells were suspended in 0.5 ml of methanol saturated with hydrogen chloride. The cell suspension was sealed and incubated at 80° C. for an hour to methyl-esterify fatty acids. After allowing the suspension to cool, it was extracted three times with 0.3 ml hexane, the hexane layer was dried and the residue was dissolved in 20 µl of methanol. 2 µl of the solution was spotted on a silica gel plate which was then developed three times with a developing solvent of hexane and ether 19:1, dried in air, and colored with iodine.

In this way, as a result of tests of about 390 recombinant clones, one clone showing a thin layer chromatography spot at the same position as a standard methyl ester of EPA was obtained. From the clone, cosmid was extracted using an alkali/SDS method. This cosmid was designated as pEPA. The pEPA is a cosmid wherein a San3A1 fragment of about 37 Kbp was inserted into BamHI site of pWE15.

Example 1—4 Preparation of Restriction Enzyme Map of pEPA

Comsmid pEPA was prepared from transformant AG-1/pEPA. The pEPA was cleaved with various restriction enzymes, and a restriction enzyme map was prepared (FIG. 1).

Example 1-5 Analysis of Sequence

An entire nucleotide sequence of a Sau3Al-Sau3Al fragment containing a genomic DNA insert in the cosmid pEPA is shown in SEQ ID NO: 1. In the nucleotide sequence, 9 open reading frames, ORFs 2 to 10, can be identified, and these nucleotide sequences and corresponding amino acid sequences are shown in SEQ ID NOs: 2 to 19 respectively. The relationship between the entire nucleotide sequence (SEQ ID NO: 1) and ORFs 2 to 10 (SEQ ID NOs: 2 to 19, respectively) is shown in Table 2.

TABLE 2

| SEQ ID NO | Length of sequence | Positions on SEQ ID NO: 1 |
|---|---|---|
| 2 | 1983 | 6121–8103 |
| 4 | 831 | 8186–9016* |
| 6 | 2910 | 9681–12590 |
| 8 | 864 | 13040–13903 |

TABLE 2-continued

| SEQ ID NO | Length of sequence | Positions on SEQ ID NO: 1 |
|---|---|---|
| 10 | 8268 | 13906–22173 |
| 12 | 2340 | 22176–24515 |
| 14 | 6012 | 24518–30529 |
| 16 | 1629 | 30730–32358 |
| 18 | 1575 | 32753–34327 |

*Reversed sequence extending from the position No. 9016 to the position No. 8186 in the nucleotide sequence shown in SEQ ID NO: 1.

Figure 2:
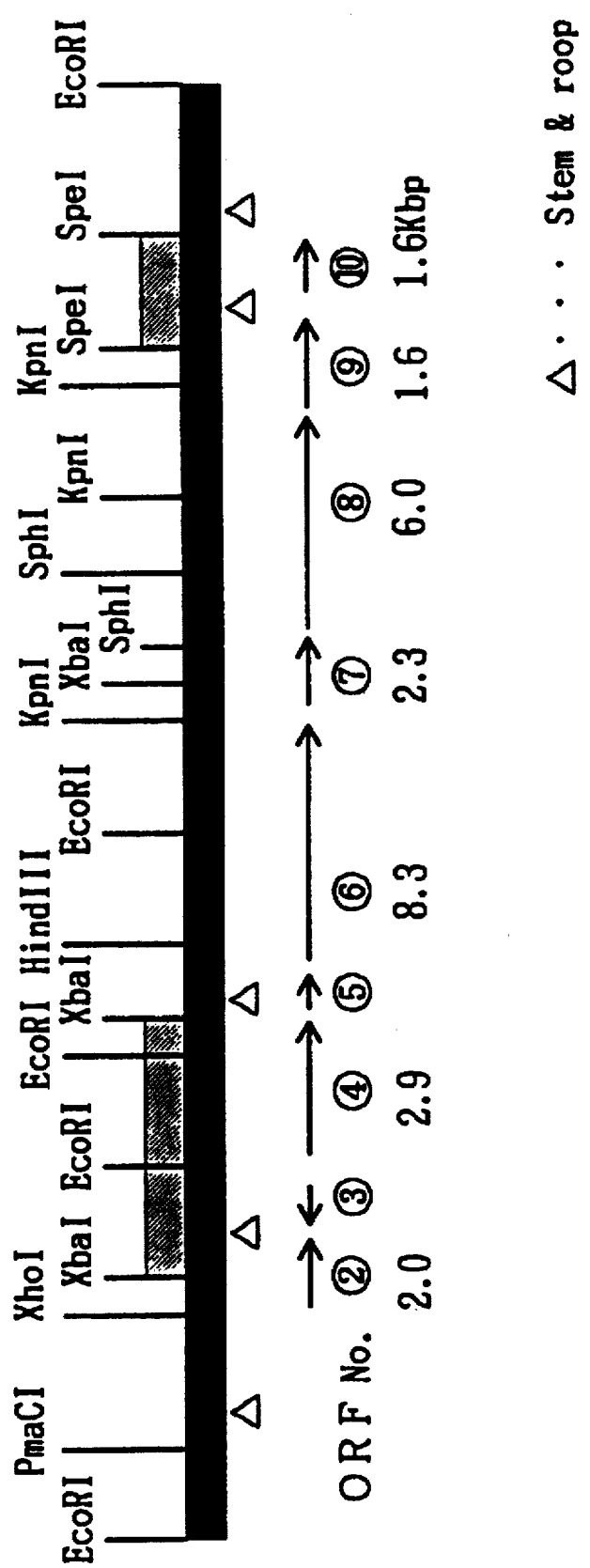
FIG. 2 represents a restriction enzyme map of a DNA fragment containing a group of the present genes.

A restriction enzyme map of the above-mentioned genomic DNA insert and positions of the ORFs 2 to 10 on the map are shown in FIG. 2. In FIG. 2, the symbols Δ show the sites at which mRNA forms a hair pin structure (stem and roop structure). The pEPA was cleaved with different restriction enzymes to remove a part of the sequence of SEQ ID NO: 1, and the cleaved pEPA was re-ligated, and used to transform E. coli. Next, the transformants were tested for the productivity of eicosapentaenoic acid. As a result, in the case where the parts shown by hatching in FIG. 2 were deleted, the production of eicosapentaenoic acid was not observed. Accordingly, it is considered that for the production of eicosapentaenoic acid in E. coli, at least one of ORFs 2, and 4, and at least one of ORFs 9 and 10 is essential.

By comparison of the amino acid sequences of various ORFs with known amino acid sequences, it was found that five regions in the ORF 6, and 2 regions in the ORF 8 have homology to some extent with amino acid sequences of enzymes participating in fatty acid synthesis. The results are shown in Table 3.

TABLE 3

| SEQ ID NO (ORF No.) | Position of amino acid sequence | Similar enzyme and position | References |
|---|---|---|---|
| 10 (6) | 668(Leu)-930(Leu) | MalonylCoA—ACP transferase 56(Leu)-309(Leu) | (1) |
| 10 (6) | 189(Phe)-424(His) | Fatty acid synthetase-120(Phe)-350(His) | (2) |
| 10 (6) | 200(Ser)-483(Leu) | Fatty acid synthetase (3-ketoacyl-ACP synthetase domain) 137(Ala)-406(Asp) | (3) |
| 10 (6) | 204(Ser)-488(Gln) | 3-Ketoacyl-ACP synthetase 137(Ala)-406(Asp) | (4) |
| 10 (6) | 2261(Phe)-2392(Gly) | 2-Oxoacylreductase 1470(Leu)-1604(Gly) | (5) |
| 14 (8) | 205(Ala)-442(Lys) | 3-Ketoacyl-ACP synthetase 187(Ala)-416(Asn) | (6) |
| 14 (8) | 1373(Thr)-1547(Val) | 3-Hydroxydecanoyl-ACP dehydratase 29(Leu)-163(Val) | (7) |

References
(1) Magnuson K. et al., FEBS Lett. (1992) 299:262–266
(2) Kameda K. et al., J. Biol. Chem. (1991) 266:419–426
(3) Huang W. Y. et al., Arch. Biochem. Biophys. (1989) 270:92–98
(4) Kauppinen S. et al., Carlsberg Res. Commun. (1988) 53:357–370
(5) Beck J. et al., Eur. J. Biochem. (1990) 192:487–498
(6) Siggaard-Andersen M. et al., Proc. Natl. Acad. Sci. U.S.A. (1991) 88:4114–4118
(7) Cronan Jr. J. E. et al., J. Biol. Chem. (1988) 263:4641–4646

Accordingly, the present invention provides genes coding for amino acid sequences shown in SEQ ID NOs 3 to 19, and further provides DNAs coding for amino acid sequence region having a homology with amino acid sequences of known enzymes or amino acid sequences containing the same. The present invention further includes nucleotide sequences which can hybridize with one of the nucleotide sequences shown in SEQ ID NOs: 1 to 10 or a part thereof and coding for a useful activity, and polypeptides encoded by one of these nucleotide sequences and having a useful activity.

Example 2 Production of EPA by Transformant GA-1/pEPA

Transformant AG-1/pEPA was inoculated in 100 ml of LB medium containing 50 μl/ml ampicillin, and cultured at 25° C. for 48 hours. The cells were obtained by centrifugation, washed once and suspended in 2 ml of pure water, and the suspension was extracted three times with 12 ml of a solvent composed of chloroform and methanol 2:1. The solvent layer was dried, and the residue was dissolved in 1.5 ml of methanol saturated with hydrogen chloride, and the solution was sealed and incubated at 80° C. for an hour to methyl-esterify fatty acids. After allowing the solution to cool, it was extracted three times with 2 ml of hexane, and after the hexane layer was dried, the residue was dissolved in 20 μl of methanol. A part of the solution was analyzed by gas chromatography. As a result, a peak of EPA was observed, and a ratio of EPA relating to total fatty acid esters was calculated as about 1.36% from the area of peaks. The amount of EPA per culture volume was about 0.5 mg/l. The ester mixture thus obtained was spotted on a silver nitrate silica gel plate, which was then developed by a solvent composed of hexane and ether at a ratio of 3:1. The plate was colored with fluorescein and ultraviolet light, the spot of the ester of the polyunsaturated fatty acid was scraped off, 1.8 ml of methanol and 0.2 ml of 10% NaCl were added thereto, and the mixture was shaken at room temperature for 30 minutes. The mixture was extracted three times with 2 ml of hexane, the hexane layer was dried, the residue was dissolved in 40 μl of hexane, and GC-MS analysis was carried out. As a result, molecular weight of the substance of the desired peak on the chromatography was 316, and the peak of the fragment conformed to that of an authentic sample, and the substance was identified as EPA. Note that MS fragment peaks were as follow:

Mass: 316 ($M^+$), 287, 273, 262, 247, 234, 220, 201, 180, 161, 148, 133, 119, 108, 93, 79, 67, 55, 41, 28.

Example 3 Production of EPA by Transformant JM109/pEPA

According to a conventional procedure the cosmid pEPA was used to transform E. coli K12/JM109. JM109/pEPA (FERM BP-4257) was obtained by selection using an LB agar medium containing 50 μl/ml ampicillin. According to the same procedure as described in Example 2, extraction of lipid from the cells, methyl-esterification and analysis by gas chromatography were carried out and a peak of EPA was detected. A ratio of EPA relating to a total of esters of fatty acids was calculated as about 1.43% on the basis of the area of peaks. An amount of EPA per culture volume was about 0.6 mg/l.

Reference to deposited microorganisms and the depository authority under the Rule 13-2

Depository authority: National Institute of Bioscience and Human-Technology Agency of Industrial Science and Technology Deposition Number and Deposition Date:
May 14, 1992 FERM BP-4257

We claim:

1. An isolated DNA encoding a group of eicosapentaenoic acid synthesis enzymes derived from a microorganism belonging to the genus Shewanella.

2. An isolated DNA encoding a group of eicosapentaenoic acid synthesis enzymes having the nucleotide sequence shown in SEQ ID NO: 1.

3. A plasmid comprising the isolated DNA of claim 1.

4. A plasmid comprising the isolated DNA of claim 2.

5. A bacterium transformed with a plasmid according to claim 3.

6. A bacterium transformed with a plasmid according claim 4.

7. A process for producing eicosapentaenoic acid, comprising the step of culturing a bacterium according to claim 5.

8. A process for producing eicosapentaenoic acid, comprising the step of culturing a bacterium according to claim 6.

9. A DNA encoding a group of eicosapentaenoic acid synthesis enzymes, which is obtainable by the steps of:

(1) culturing a microorganism belonging to the genus Shewanella capable of producing eicosapentaenoic acid to obtain cultured cells;

(2) extracting chromosomal DNA from the cultured cells;

(3) partially digesting the chromosomal DNA with restriction enzyme Sau3A1 to obtain DNA fragments;

(4) inserting the DNA fragments into cosmid pWE15 completely digested with restriction enzyme BamH1 to obtain recombinant expression vectors;

(5) transforming *Escherichia coli* cells with the recombinant expression vectors to obtain transformants;

(6) culturing the transformants to obtain cultured transformed cells;

(7) detecting eicosapentaenoic acid in the cultured transformed cells to select a positive transformed cell capable of producing eicosapentaenoic acid; and (8) recovering a DNA encoding a group of eicosapentaenoic acid synthesis enzymes by cleaving the recombinant expression vector extracted from the positive transformant with restriction enzyme Sau3A1.

* * * * *